US011440921B2

(12) United States Patent
Bauer et al.

(10) Patent No.: US 11,440,921 B2
(45) Date of Patent: *Sep. 13, 2022

(54) SALTS, CRYSTAL FORMS, AND PRODUCTION METHODS THEREOF

(71) Applicant: Sunovion Pharmaceuticals Inc., Marlborough, MA (US)

(72) Inventors: Andrea Bauer, North Reading, MA (US); Nandkumar Nivritti Bhogle, Shrewsbury, MA (US); Xiaoxia Chen, Acton, MA (US); Shahla Jamzad, Belmont, MA (US); Robert Joseph Prytko, Millbury, MA (US); Kostas Saranteas, Littleton, MA (US); Michael Joseph Sizensky, South Grafton, MA (US); Harold Scott Wilkinson, Westboro, MA (US); Haitao Zhang, Shrewsbury, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/006,101

(22) Filed: Aug. 28, 2020

(65) Prior Publication Data

US 2021/0053983 A1 Feb. 25, 2021

Related U.S. Application Data

(63) Continuation of application No. 16/277,443, filed on Feb. 15, 2019, now Pat. No. 10,815,249.

(60) Provisional application No. 62/710,416, filed on Feb. 16, 2018.

(51) Int. Cl.
| | |
|---|---|
| *C07D 495/04* | (2006.01) |
| *A61K 9/20* | (2006.01) |
| *A61K 45/06* | (2006.01) |
| *A61K 31/381* | (2006.01) |
| *A61P 25/18* | (2006.01) |
| *A61P 25/00* | (2006.01) |

(52) U.S. Cl.
CPC .......... *C07D 495/04* (2013.01); *A61K 9/2018* (2013.01); *A61K 9/2054* (2013.01); *A61K 9/2059* (2013.01); *A61K 31/381* (2013.01); *A61K 45/06* (2013.01); *A61P 25/00* (2018.01); *A61P 25/18* (2018.01); *C07B 2200/13* (2013.01)

(58) Field of Classification Search
CPC ..... C07D 495/04; A61K 31/381; A61P 25/00; A61P 25/18
See application file for complete search history.

(56) References Cited

U.S. PATENT DOCUMENTS

| | | | |
|---|---|---|---|
| 4,021,451 A | 5/1977 | Dobson et al. | |
| 4,021,452 A | 5/1977 | Floyd, Jr. | |
| 4,036,842 A | 7/1977 | Dobson et al. | |
| 4,127,665 A | 11/1978 | Sarges et al. | |
| 4,337,343 A | 6/1982 | Maillard et al. | |
| 5,532,233 A | 7/1996 | Weber et al. | |
| 6,262,044 B1 | 7/2001 | Moller et al. | |
| 6,313,309 B1 | 11/2001 | Baxter et al. | |
| 7,019,026 B1 | 3/2006 | Andersen et al. | |
| 8,710,245 B2 * | 4/2014 | Shao .................. | A61P 9/12 549/50 |
| 9,351,954 B2 | 5/2016 | Shao et al. | |
| 10,085,968 B2 | 10/2018 | Shao et al. | |
| 10,815,249 B2 * | 10/2020 | Bauer .................. | C07D 495/04 |
| 10,894,033 B2 | 1/2021 | Shao et al. | |
| 11,129,807 B2 * | 9/2021 | Hopkins ................ | A61K 31/55 |
| 2004/0180883 A1 | 9/2004 | Gilmore | |
| 2004/0220402 A1 | 11/2004 | Chow et al. | |
| 2005/0075366 A1 | 4/2005 | Heidelbaugh et al. | |
| 2005/0187281 A1 | 8/2005 | Hinze et al. | |
| 2006/0047127 A1 | 3/2006 | Arjona | |
| 2006/0148872 A1 | 7/2006 | Chow et al. | |
| 2007/0072926 A1 | 3/2007 | Chow et al. | |
| 2007/0154534 A1 | 7/2007 | Sheitman et al. | |
| 2008/0081910 A1 | 4/2008 | Sabb et al. | |
| 2008/0113961 A1 | 5/2008 | Nishi et al. | |
| 2008/0255239 A1 | 10/2008 | Chow et al. | |

(Continued)

FOREIGN PATENT DOCUMENTS

| | | |
|---|---|---|
| AU | 2010325925 A1 | 6/2011 |
| AU | 2016200448 A1 | 2/2016 |

(Continued)

OTHER PUBLICATIONS

Bengi et al. "Towards Novel Treatments for Schizophrenia: Molecular and Behavioural Signatures of the Psychotropic Agent SEP-363856", Interational Journal of Molecular Sciences, vol. 22, No. 4119, 19 pages. 2021.

(Continued)

*Primary Examiner* — Theodore R. Howell
*Assistant Examiner* — George W Kosturko
(74) *Attorney, Agent, or Firm* — Heslin Rothenberg Farley & Mesiti, P.C.

(57) ABSTRACT

Provided are salts of (S)-(4,5-dihydro-7H-thieno[2,3-c] pyran-7-yl)-N-methylmethanamine and various of crystal forms thereof, and compositions, medicaments, pharmaceutically acceptable formulations thereof, and methods of making same. In addition, provided are compounds comprising specific particle size distributions of crystalline (S)-(4,5-dihydro-7H-thieno[2,3-c]pyran-7-yl)-N-methylmethanamine HCl and methods of making and modulating the particle size distributions.

21 Claims, 43 Drawing Sheets

(56) References Cited

U.S. PATENT DOCUMENTS

| | | |
|---|---|---|
| 2009/0318690 A1 | 12/2009 | Sasaki et al. |
| 2010/0035887 A1 | 2/2010 | Ricciardi |
| 2012/0295881 A1 | 11/2012 | Lange et al. |
| 2019/0125722 A1 | 5/2019 | Shao et al. |
| 2019/0256525 A1 | 8/2019 | Bauer et al. |
| 2020/0129477 A1 | 4/2020 | Hopkins et al. |
| 2020/0179336 A1 | 6/2020 | Hopkins |
| 2021/0008030 A1 | 1/2021 | Blum |
| 2021/0267938 A1 | 9/2021 | Shao et al. |
| 2021/0315859 A1 | 10/2021 | Bowen et al. |

FOREIGN PATENT DOCUMENTS

| | | |
|---|---|---|
| CA | 2031684 A1 | 6/1991 |
| CA | 2781716 A1 | 6/2011 |
| CN | 1300291 A | 6/2001 |
| CN | 101759710 A | 6/2010 |
| CN | 102731574 A | 10/2012 |
| CN | 104193761 A | 12/2014 |
| DE | 3827727 A1 | 2/1990 |
| DE | 4104257 A1 | 8/1992 |
| EP | 333427 A1 | 9/1989 |
| EP | 366327 A1 | 5/1990 |
| EP | 0368175 A1 | 5/1990 |
| EP | 370732 A2 | 5/1990 |
| EP | 416740 A2 | 3/1991 |
| EP | 431945 A2 | 6/1991 |
| EP | 483647 A1 | 5/1992 |
| EP | 0518805 A1 | 12/1992 |
| EP | 555824 A1 | 8/1993 |
| EP | 574313 A1 | 12/1993 |
| EP | 600836 A2 | 6/1994 |
| EP | 745598 A1 | 12/1996 |
| EP | 1634873 A1 | 3/2006 |
| EP | 1829869 A1 | 9/2007 |
| EP | 1982714 A1 | 10/2008 |
| EP | 1982987 A1 | 10/2008 |
| EP | 2377850 A1 | 10/2011 |
| FR | 2875230 A1 | 3/2017 |
| JP | 54109975 A | 8/1979 |
| JP | S567772 A | 1/1981 |
| JP | 2243691 A | 9/1990 |
| JP | 4009367 A | 1/1992 |
| JP | 03163068 B2 | 5/2001 |
| JP | 03223277 B2 | 10/2001 |
| JP | 2003261566 A | 9/2003 |
| JP | 2004269449 A | 9/2004 |
| JP | 2005145859 A | 6/2005 |
| JP | 2005523925 A | 8/2005 |
| JP | 2006117568 A | 5/2006 |
| JP | 2008530229 A | 8/2008 |
| JP | 2009505948 A | 2/2009 |
| JP | 2015227348 A | 12/2015 |
| JP | 6333382 B2 | 5/2018 |
| MX | 2012006326 A | 10/2012 |
| RU | 2128649 C1 | 4/1999 |
| SG | 181498 A1 | 7/2012 |
| WO | 9108205 A1 | 6/1991 |
| WO | 9203434 A1 | 3/1992 |
| WO | 9215592 A1 | 9/1992 |
| WO | 9400441 A1 | 1/1994 |
| WO | 9604287 A1 | 2/1996 |
| WO | 9946237 A1 | 9/1999 |
| WO | 9946267 A1 | 9/1999 |
| WO | 0023445 A1 | 4/2000 |
| WO | 2000023445 | 4/2000 |
| WO | 0035915 A1 | 6/2000 |
| WO | 2000035915 | 6/2000 |
| WO | 0043397 A1 | 7/2000 |
| WO | 2000043397 | 7/2000 |
| WO | 0068230 A1 | 11/2000 |
| WO | 2000068230 | 11/2000 |
| WO | 0117516 A2 | 3/2001 |
| WO | 0119831 A1 | 3/2001 |
| WO | 2001017516 | 3/2001 |
| WO | 2001019831 | 3/2001 |
| WO | 0132610 A1 | 5/2001 |
| WO | 0132655 A2 | 5/2001 |
| WO | 2001032610 | 5/2001 |
| WO | 0212189 A1 | 2/2002 |
| WO | 2002012189 | 2/2002 |
| WO | 0222614 A1 | 3/2002 |
| WO | 2002022614 | 3/2002 |
| WO | 02102387 A1 | 12/2002 |
| WO | 03006455 A1 | 1/2003 |
| WO | 03035065 A1 | 5/2003 |
| WO | 03092374 A2 | 11/2003 |
| WO | 2004004726 A1 | 1/2004 |
| WO | 2004035812 A2 | 4/2004 |
| WO | 2004066912 A2 | 8/2004 |
| WO | 2004078723 A1 | 9/2004 |
| WO | 2004082687 A1 | 9/2004 |
| WO | 2004087680 A1 | 10/2004 |
| WO | 2005072412 A2 | 8/2005 |
| WO | 2005073236 A2 | 8/2005 |
| WO | 2005087779 A1 | 9/2005 |
| WO | 2006014135 A1 | 2/2006 |
| WO | 2006014136 A1 | 2/2006 |
| WO | 2006015259 A2 | 2/2006 |
| WO | 2006030124 A1 | 3/2006 |
| WO | 2006053274 A2 | 5/2006 |
| WO | 2006089053 A2 | 8/2006 |
| WO | 2007001939 A1 | 1/2007 |
| WO | 2007002681 A2 | 1/2007 |
| WO | 2007006546 A1 | 1/2007 |
| WO | 2007095586 A2 | 8/2007 |
| WO | 2007102999 A2 | 9/2007 |
| WO | 2007126041 A1 | 11/2007 |
| WO | 2008042422 A2 | 4/2008 |
| WO | 2008048981 A2 | 4/2008 |
| WO | 2008058342 A1 | 5/2008 |
| WO | 2008155132 A1 | 12/2008 |
| WO | 2009009550 A1 | 1/2009 |
| WO | 2009067202 A1 | 5/2009 |
| WO | 2009068467 A1 | 6/2009 |
| WO | 2009072621 A1 | 6/2009 |
| WO | 2009085256 A1 | 7/2009 |
| WO | 2010053583 A2 | 5/2010 |
| WO | 2010092180 A1 | 8/2010 |
| WO | 2010092181 A1 | 8/2010 |
| WO | 2011036889 A1 | 3/2011 |
| WO | 2011060035 A1 | 5/2011 |
| WO | 2011060217 A1 | 5/2011 |
| WO | 2011069063 A2 | 6/2011 |
| WO | WO-2011069063 A2 * | 6/2011 ........... A61K 31/435 |
| WO | 2011081205 A1 | 7/2011 |
| WO | 2011133729 A2 | 10/2011 |
| WO | 2012016879 A1 | 2/2012 |
| WO | 2012020133 A1 | 2/2012 |
| WO | 2012122340 A1 | 9/2012 |
| WO | 2013010453 A1 | 1/2013 |
| WO | 2018151861 A1 | 8/2018 |
| WO | 2019161236 A1 | 8/2019 |
| WO | 2019161238 A1 | 8/2019 |
| WO | 2020118032 A1 | 6/2020 |
| ZA | 9102744 A | 2/1992 |

OTHER PUBLICATIONS

Chen et al., "No Chiral Inversion for SEP-363856 in Humans by A Novel Chiral LC-MS/MS Analysis of Human Plasma from Clinical Trials", Poster, American Society for Mass Spectrometry. 2020.

Dworak, "SEP-363856: A Compound with a Non-D2 Receptor Mechanism of Action for the Treatment of Schizophrenia: Update", Poster, American Society of Clinical Psychpharmacology Annual Meeting. 2021.

Dworak et al., "Effects of SEP-363856, A Novel TAAR1 Agonist, On Negative Symptoms in Schizophrenia: Results Across An Initial Double-Blind Acute Study, And A 6-Month, Open-Label Extension Study", Poster, The American College of Neuropsychopharmacology 59th Annual Meeting. 2020.

(56) References Cited

OTHER PUBLICATIONS

Hopkins et al., "Characterization of Specific and Distinct Patient Types in Clinical Trails of Acute Schizophrenia Using an Uncorrelated PANSS Score Matrix Transform (UPSM)", Psychiatry Research, vol. 294, 7 pages. 2020.

Hopkins et al., "The Safety Profile of the TAAR1 Agonist, SEP-363856, Is Distinct From Atypical Antipsychotics", Poster, American Psychiatric Association Annual Meeting. 2021.

Isaacson et al., "Efficacy and Safety of SEP-363856, A Non-D2-Receptor-Binding Drug With Antipsychotic Activity, in Patients with Parkinson's Disease Psychosis", American Academy of Neurology, Virtual Annual Meeting, 18 pages. 2021.

Koblan, "SEP-363856, A Novel Non-D2, TAAR1 Agonist for the Treatment of Schizophrenia: Current Development Status", American Society of Clinical Psychopharmacology, Annual Meeting, 15 pages. 2020.

Hopkins et al., "Effect of TAAR1/5-HT1A Agonist SEP-363856 on REM Sleep in Humans", Translational Psychiatry, vol. 11, No. 228, 10 pages. 2021.

Koblan, "SEP-363856: A Compound with a Non-D2 Receptor Mechanism of Action for the Treatment of Schizophrenia: Update", Schizophrenia International Research Society Annual Congress, Poster. 2020.

Kokkinou et al., "Reproducing the Dopamine Pathophysiology of Schizophrenia and Approaches to Ameliorate It: A Translational Imaging Study with Ketamine", Molecular Psychiatry, 15 pages. May 7, 2020.

Milanovic et al., "Measures of Cognition and Social Functioning in Schizophrenia Patients Receiving SEP-363856", Poster, Schizophrenia International Research Society Congress. 2020.

Synan et al., "Preclinical Abuse Liability Assessment of SEP-363856, A Compound with a Non-D2 Receptor Mechanism of Action", Poster, College on Problems of Drug Dependence. 2020.

Synan et al., "SEP-363856, A Novel TAAR1 Agonist, Lacks Abuse Liability in Preclinical Models and Attenuates Concaine Cue-Induced Relaps in Rats", Poster, The American College of Neuropsuchopharmacology. 2020.

Sheitman et al., "Secretin for refractory schizophrenia" Elsevier, Science Direct, Schizophrenia Research 66 (2004) 177-181 2004 2004.

Hopkins et al., "Transformed PANSS Factors Intended to Reduce Pseudospecificity Among Domains and Enhancing Understanding of Symptom Change in Antipsychotic-Treated Patients with Schizophrenia", The International Society for CNS Clinical Trials and Methodology (ISCTM) 13th Annual Scientific Meeting; Feb. 21-23, 2017 (The Fairmont, Washington DC), https://isctm.org/meeting/13th-annual-scientific-meeting/ Feb. 21, 2017.

Hopkins et al., "Transformed PANSS Factors Intended to Reduce Pseudospecificity Among Symptom Domains and Enhance Understanding of Symptom Change in Antipsychotic-Treated Patients With Schizophrenia", Schizophrenia Bulletin vol. 44 No. 3 pp. 593-602, 2018,doi:10.1093/schbul/sbx101, https://pubmed.ncbi.nlm.nih.gov/28981857/, https://academic.oup.com/schizophreniabulletin/article/44/3/593/4110338 2018.

Hopkins, "Improving the Specificity and Precision of PANSS Factors: One Approach to Facilitate Development of Novel Treatments in Schizophrenia", The International Society for CNS Clinical Trials and Methodology, (ISCTM) 14th Annual Scientific Meeting; Feb. 20-22, 2018 (The Fairmont, Washington DC), https://isctm.org/meeting/14th-annual-scientific-meeting/ Feb. 20, 2018.

Galluppi et al., "Population Pharmacokinetic Analysis of Ulotaront in Subjects with Schizophrenia", CPT Pharmacometrics Syst Pharmacol, pp. 1-10. Jul. 22, 2021.

Fujima, et al., Synthesis of (S)-3-(N-Methylamino)-1-(2-thienyl)propan-1-ol: Revisiting Eli Lilly's Resolulion-Racemization-Recycle Synthesis of Duloxetine for Its Robust Processes, Organic Process Research & Development, vol. 10, No. 5 2006.

Caira, Mino R., Crystalline Polymorphism of Organic Compounds, Topics in Current Chemistry, vol. 198 1998.

International Search Report and Written Opinion issued in PCT/US2019/018265 dated Jun. 18, 2019.

Kay et al., Schizophrenia Bulletin, 1987, vol. 13(2), pp. 261-276 (Year: 1987) 1987.

Mahableshwarkar et. al., "Replication of a statistical method to reduce pseudospecificity and enhance understanding of score changes among PANSS factors", poster presented at meeting for Int. Soc. For CNS clinical trials and methodology, presented between Aug. 31, 2017-Sep. 2, 2017 (Year: 2017) 2017.

Singapore Search Report and Written Opinion issued in Singapore Application No. 10201401661, 10 pages, dated Jun. 15, 2015.

Singapore Written Opinion issued in Singapore Application No. 201204089-5, 12 pages, dated Sep. 20, 2013.

Swerdlow et al. "Seroquel Restores Sensorimotor Gating in Phencyclidine-Treated Rats", Journal of Pharmacology and Experimental Therapeutics, vol. 279, No. 3, pp. 1290-1299. Dec. 1996.

Torrado et al. "Novel Selective and Potent 5-HT Reuptake Inhibitors with 5-HT1D Antagonist Activity: Chemistry and Pharmacological Evaluation of a Series of Thienopyran Derivatives", Bioorganic & Medicinial Chemistry, 12(20), pp. 5277-5295. Oct. 15, 2004.

Vecchietti et al. "(1 S)-1-(Aminomethyl)-2-(arylacetyl)-1,2,3,4-tetrahydroisoquinoline and Heterocycle-Condensed Tetrahydropyridine Derivatives: Members of a Novel Class of Very Potent K Opioid Analgesics", Journal of Medicinal Chemistry, vol. 34, No. 8, pp. 2624-2633. 1991.

PubChem CID 4878038 (search date Feb. 22, 2019). Sep. 17, 2005.
PubChem CID 4878041 (search date Feb. 22, 2019). Sep. 17, 2005.

Ross et al., "α2 Adrenoceptor Agonists as Potential Analgesic Agents. 2. Discovery of 4-(4-Imidazo)-1,3-dimethyl-6,7-dihydrothianaphthene as a High-Affinity Ligand for the α2D Adrenergic Receptor", J. Med. Chem., vol. 43, pp. 1423-1426. 2000.

Frohlich et al., "A Novel Synthesis of 3,3-(Spiro)Substituted Azetidines", Heterocycles, vol. 37, No. 3, pp. 1897-1891. 1994.

Datta et al., "Studies in Sulphur Heterocycles. Part 5. Further Use of 6,7-Dihydribenzo[b]thiphen-4[5H]-one in the Synthesis of Substitited Benzo[b]thiophene Derivatives", J. Chem. Research (S), pp. 72-73. 1988.

Stanetty et al., "Heterocyclische Spiroverbindungen Spiroverbindungen: Spiro [benzo[b]thiophen-4(5H),3'-pyrrolidine]", Arch. Pharm. vol. 317, pp. 168-176. 1984.

Devani et al., "Synthesis of 2-Aminothiophenes & Thieno[2,3-d]pyrimidines", Indian Journal of Chemistry, vol. 14B, pp. 357-360. May 1976.

Caira "Crystalline Polymorphism of Organic Compounds" Topics in Current Chemistry, vol. 198. Jan. 1, 1998.

Fujima et al. "Synthesis of (S)-3-(N-Methylamino)-1-(2-thienyl)propan-1-ol: Revisiting Eli Lilly's Resolution-Racemization-Recycle Synthesis of Duloxetine for its Robust Processes", Organic Process Research and Development, vol. 10, No. 5. Jan. 1, 2006.

International Search Report in International Application No. PCT/US2019/018265, dated May 29, 2019.

International Searech Report in International Application No. PCT/US2019/018263 dated Apr. 2, 2019.

Written Opinion in International Application No. PCT/US2019/018263, dated Apr. 2, 2019.

International Search Report in International Application No. PCT/US2018/000078, dated Mar. 25, 2018.

Written Opinion in International Application No. PCT/US2018/000078, dated May 25, 2018.

Unpublished U.S. Appl. No. 16/486,257 to Hopkins et al., filed Aug. 15, 2019.

Unpublished U.S. Appl. No. 16/704,202 to Hopkins, filed Dec. 5, 2019.

Unpublished International Application No. PCT/US2019/064646 to Hopkins. Dec. 5, 2019.

Deakin et al. "A Phase 1 Functional Neuroimaging Study Of Sep 363856 In Healthy Volunteers With High Or Low Schizotype", American College of Neuropsychopharmacology, Poster. Dec. 2016.

Koblan et al. "A Phase 1 Open Label Safety And Tolerability Study Of Sep-363856, A Novel Non-D2 Mechanism Of Action Molecule, In Patients With Schizophrenia", American College of Neuropsychopharmacology, Poster. Dec. 2016.

(56) References Cited

OTHER PUBLICATIONS

Poola et al. "Pharmacokinetics, Safety, And Tolerability Of Sep-363856 In Healthy Adult Male Subjects And In Adult Patients With Schizophrenia Following Oral Administration", American College of Clinical Pharmacology, Poster. Sep. 2018.
Koblan et al. "Efficacy And Safety Of Sep-363856 In The Treatment Of Schizophrenia: A 4-Week, Randomized, Placebo-Controlled Trial Of A Novel Compound With A Non-D2 Mechanism Of Action", American College of Neuropsychopharmacology, Poster. Dec. 2018.
Koblan, "SEP-363856, A Candidate Antipsychotic And Antidepressant Compound With A Noval Non-D2 Mechanism Of Action", Schizophrenia International Research Society, Oral Presentation. Apr. 2018.
Koblan et al. "SEP-363856, A Novel Psychotropic Agent With A Non-D2 Mechanism Of Action, For The Treatment Of Schizophrenia", Schizophrenia International Research Society, Oral Presentation. Apr. 2019.
Koblan et al. "Efficacy And Safety Of SEP-363856, A Novel Psychotropic Agent With A Non-D2 Mechanism Of Action, In The Treatment Of Schizophrenia: A 4-Week, Randomized, Placebo-Controlled Trial", American Psychiatric Association, Poster. Oct. 2019.
Koblan et al. "Efficacy And Safety Of SEP-363856, A Novel Psychotropic Agent With A Non-D2 Mechanism Of Action, In The Treatment Of Schizophrenia: A 4-Week, Randomized, Placebo-Controlled Trial", American Society of Clinical Psychopharmacology, Poster. May 2019.
Jones et al. "SEP-0363856, A Novel Psychotropic Agent With A Unique, Non-D2 Mechanism Of Action", European College of Neuropsychopharmacology, Poster. Sep. 2019.
Koblan et al. "Efficacy And Safety Of SEP-363856, A Novel Non-D2 Agent, In The Treatment Of Schizophrenia: A 4-Week, Randomized, Placebo-Controlled Trial", European College of Neuropsychopharmacology, Poster. Sep. 2019.
Koblan et al. "Efficacy And Safety Of SEP-363856, A Novel Psychotropic Agent With A Non-D2 Mechanism Of Action, In The Treatment Of Schizophrenia: A 4-Week, Randomized, Placebo-Controlled Trial", US Psychiatric and Mental Health Congress, Poster. May 2019.
Koblan et al. "Efficacy And Safety Of SEP-363856, A Novel Psychotropic Agent With A Non-D2 Mechanism Of Action, In The Treatment Of Schizophrenia: A Randomized, Placebo-Controlled Trial", Neuroscience Education Institute, Poster. Nov. 2019.
Correll et al. "Safety And Effectiveness Of SEP-363856 In Schizophrenia: Results Of A 6-Month, Open-Label Extension Study", American College of Neuropsychopharmacology, Poster. Dec. 2019.
Hopkins et al. "Effects Of SEP-363856 On Negative Symptoms In Schizophrenia: Analysis Of An Acute, Placebo-Controlled Trial Of A Novel Psychotropic Agent With No Dopamine-D2/5-Ht2a Antagonist Activity", American College of Neuropsychopharmacology, Poster. Dec. 2019.
Dedic et al. "The Novel, Non-D2 Psychotropic Agent SEP-363856 Modulates Presynaptic Dopamine Function In Mice", American College of Neuropsychopharmacology, Poster. Dec. 9, 2019.
Dedic et al. "SEP-363856, A Novel Psychotropic Agent With A Unique, Non-D2 Receptor Mechanism Of Action", The Journal of Pharmacology and Experimental Therapeutics, Manuscript. Oct. 2019.
Written Opinion in International Application No. PCT/US2019/064646, dated Mar. 9, 2020.
International Search Report in International Application No. PCT/US2019/064646, dated Mar. 9, 2020.
Fujima, et al., Synthesis of (S)-3-(N-Methylamino)-1-(2-thienyl)propan-1-ol: Revisiting Eli Lilly's Resolution-Racemization-Recycle Synthesis of Duloxetine for Its Robust Processes, Organic Process Research & Development, vol. 10, No. 5 2006.
Karran et al. "The Amyloid Cascade Hypothesis for Alzheimer's Disease: an Appraisal for the Development of Therapeutics", Nature, vol. 10, p. 698. 2011.

Schmitz et al. "Hippocampal Neuron Loss Exceeds Amyloid Plaque Load in a Transgenic Mouse Model of Alzheimer's Disease", American Journal of Pathology, vol. 164, p. 1495. 2004.
Hejl et al. "Prepulse Inhibition in Patients with Alzheimer's Disease", Neurobiology of Aging, vol. 25, p. 1045. 2004.
Trehan "A New Synthesis of 13-aza-18-nor-17-oxo-A-nor-3-thiaestra-1,5(10), 9(11)-triene", retrieved from STN Database Accession No. 1986:225089 and Indian Journal of Chemistry, Section 6: Organic Chemistry Including Medicinal Chemistry, vol. 24B(6), pp. 659-661. 1985.
Trehan "Synthesis of 2, 3, 13-Triaza-18-nor-17-oxo-3-phenyl-A-nor-estra-1,5(10), 9(11)-triene & 2, 3, 13-Triaza-7,7-dimethyl-18-nor-17-oxo-3-phenyl-A-nor=estra-1,5(10), 9(11)-triene", Indian Journal of Chemistry, vol. 19B, pp. 243-245. 1980.
Mashkovskiy "Drugs", Moscow, New Wave, LLC, vol. 1, p. 11 with translation. 2002.
Berardi et al. "A Multireceptorial Binding Reinvestigation on an Extended Class of s Ligands: N-[w-(Indan-1-yl and Tetralin-1-yl)alkyl] Derivatives of 3,3-Dimethylpiperidine Reveal High Affinities Towards s1 and EBP Sites", Bioorganic & Medicinial Chemistry, vol. 9, No. 5, pp. 1325-1335. 2001.
Berardi et al. "Novel Potent s1 Ligands: N-[w-(Tetralin-1-yl)alkyl] piperidine Derivatives" Journal of Medicinal Chemistry, American Chemical Society, vol. 39, No. 21, pp. 4255-4260. 1996.
Berardi et al. "4-(Tetralin-1-yl)-and 4-(Naphthalen-1-yl) alkyl Derivatives Ligands with Agonist s2 Activity", Journal of Medicinal Chemistry, American Chemical Society, vol. 47, No. 9, pp. 2308-2317. 2004.
Chihara et al. "Preparation of Benzothiophene Derivatives as Blood Platelet Aggregation Inhibitors", Retrieved from STN Database Accession No. 1992:128652 and JP03223277A, Yoshitomi Pharmaceutical Industries Ltd. Oct. 2, 1991.
Corbera et al. "A Medicinal-Chemistry-Guided Approach to Selective and Druglike Sigma 1 Ligands", Chemmedchem, vol. 1, No. 1, pp. 140-154. Jan. 2006.
Dehaven-Hudkins et al. "Characterization of the Binding of [3H](+)pentazocine to O'Recognition Sites in Guinea Pig Brain" Eur. Journal Pharmacol., vol. 277, pp. 371-378. 1992.
Hanner et al. "Purification, Molecular Cloning, and Expression of the Mammalian Sigma1-Binding Site", Proc. Natl. Aca. Sci, vol. 93, pp. 8072-8077. 1996.
Krogsgaard-Larsen et al. "Textbook of Drug Design and Discovery", Taylor & Francis. Apr. 2002.
Langa et al. "Generation and Phenotypic Analysis of Sigma Receptor Type 1 (Sigma1) Knockout Mice", European Journal of Neuroscience, vol. 18, pp. 2188-2196. 2003.
Lowry et al. "Protein Measurement with the Folin Phenol Reagent", Journal Bio. Chem., vol. 193, p. 265. 1951.
Maier et al., "Novel Spiropiperidines as Highly Potent and Subtype Selective σ-Receptor Ligands. Part 1", Journal Med. Chem., vol. 45, pp. 438-448. 2002.
Maier et al., "Novel σ Receptor Ligands. Part 2. SAR of Spiro[[2]benzopyran-1,4'-piperidines] and Spiro [[2] benzofuran-1,4'-piperidines] with Carbon Substituents in Position 3", Journal Med. Chem., vol. 45, pp. 4923-4930. 2002.
Quirion et al. "A Proposal for the Classification of Sigma Binding Sites", Trends Pharmacol. Sci., vol. 13, pp. 86-86. Mar. 1992.
Radesca "Synthesis adn Receptor Binding EnantiomericN-Substitutedcis-N-[2-(3,4-Dichloroph-enyl)ethyl]-2-(1-pyrrolidiny) Cyclohexylamines as High-Affinity O' Receptor Ligands", Journal Med. Chem., vol. 34, pp. 3065-3074. 1991.
Schow "Novel Sigma Receptor Ligands 2", Bioorganic and Medicinal Chemistry Letters, No. 2, pp. 221-224. 1993.
Snyder et al. "Receptor Mechanisms in Antipsychotic Drug Action: Focus on Sigma Receptors", Journal Neuropsychiatry, vol. 1, pp. 7-15. 1989.
Extended European Search Report for EP Application No. 10835185.9, pp. 1-15, dated Apr. 4, 2013.
Walker: Pharmacological Reviews, "Sigma Receptors: Biology and Function", vol. 42, No. 4, pp. 355-402. 1990.
Bakshi et al. "Antagonism of Phencyclidine-Induced Deficits in Prepulse Inhibition by the Putative Aytpical Antipsychotic Olanzapine", Psychopharmacology, vol. 122, No. 2, pp. 198-201. Nov. 1995.

(56) References Cited

OTHER PUBLICATIONS

First Examination Report Issued in New Zealand Application No. 600008, 3 pages, dated Mar. 11, 2013.
Ghaemi et al. "Does Olanzapine have Antidepressant Properties? A Retrospective Preliminary Study", Bipolar Disorders, vol. 2, pp. 196-199. 2000.
Ghasemi et al. "The Role of NMDA Receptors in teh Pathophysiology and Treatment of Mood Disorders", Neuroscience and Biobehavioral Reviews, vol. 47, pp. 336-358. Sep. 16, 2014.
Gleason et al. "Blockade of Phencyclidine-Induced Hyperlocomotion by Olanzapine, Clozapine adn Serotonin Receptor Subtype Selective Antagonists in Mice", Psyhopharmacology, vol. 129, pp. 79-84. 1997.
International Search Report and Written Opinion issued in PCT/US2010/05884, 10 pages, dated Aug. 25, 2011.
Jacobs et al. "1-Imidazolyl(alkyl)-Substituted Di- and Tetrahydroquinolines and Analogues: Syntheses and Evaluation of Dual Inhibitors of Thromboxane A2 Synthase and Aromatase", Journal of Medicinal Chemistry, vol. 43, No. 9, pp. 1841-1851. Apr. 12, 2000.
Jentsch et al., "The Neuropsychopharmacology of Phencyclidine: From NMDA Receptor Hypofunction to the Dopamine Hypothesis of Schizophrenia", Neuropsychopharmacology, vol. 20, No. 3, pp. 201-225. 1999.
Jobson et al. "Pyrano Heterocycles. I. The Syntheses of Isochromans and the Novel thieno[3,2-c]pyran, benzothieno[3,2-c]pyran, benzothieno[2,3-c]pyran, and pyrano[4,3-b] benzofuran Systems", Journal of Heterocyclic Chemistry, 12(3), pp. 591-594. Jan. 1, 1975.
Kapur et al. "NMDA Receptor Antagonist Ketamine and PCP Have Direct Effects on the Dopamine D2 adn Serotonin 5-HT2 Receptors-Implications for Models of Schizophrenia", Molecular Psychiatry, vol. 7, pp. 837-844. 2002.
Katsuki et al., "Excitotoxic Degeneration of Hypothalamic Orexin Neurons in Slice Culture", Neurobiology of Disease, vol. 15, pp. 61-69. 2004.
Kostin et al. "Lack of Hypocretin Attenuates Behavioral Changes Produced by Glutamatergic Activation of the Perifornical-Lateral Hypothalamic Area", Sleep, vol. 37, No. 5, pp. 1011-1020. 2014.
Marcus et al. "The Efficacy and Safety of Aripiprazole as Adjunctive Therapy in Major Depressive Disorder. A second Multicenterm Randomized, Double-Blind, Pacebo-Controlled Study", Journal of Clinical Psychopharmacology, vol. 28, No. 2, pp. 15-165. Apr. 2008.
Moreno et al. "Preclinical Models of Antipsychotic Drug Action", International Journal of Neuropsychopharmacology, vol. 16, pp. 2131-2144. Jun. 10, 2013.
Nordquist et al. "Effects of Aripiprazole/OPC-14597 on Motor Activity, Pharmacological Models of Psychosis, and Brain Activity in Rats", Neuropharmacology, vol. 54, pp. 405-416. 2008.
Pittenger et al. "The NMDA Receptor as a Therapeutic Target in Major Depressive Disorder", CNS & Neurological Disorders—Drug Targets, vol. 6, No. 2, pp. 101-115. Feb. 19, 2007.
Registry (STN) [online] CAS Registry No. 933704-21-3, 1 page. Apr. 30, 2007.
Koblan, A Non-D2-Receptor-Binding Drug for the Treatment of Schizophrenia, The New England Journal of Medicine, vol. 382, No. 16 Apr. 16, 2020.
Dedic, Sep-363856, a Novel Psychotropic Agent with the Unique, Non-D2 Receptor Mechanism of Action, The Journal of Pharmacology and Experimental Therapeutics, htt://jpet.aspetjournals.org/content/suppl/2019/08/01/pet.119.260281.DC1 Oct. 2019.
International Search Report adn Written Opinion in International Application No. PCT/US2019/064646 dated Mar. 9, 2020.
Hopkins et al., "Depicting Safety Proile of TAAR1 Agonist Ulotaront Relative to Reactions Anticipated for a Dopamine D2-Based Pharmacological Class in FAERS", Clinical Drug Investigation, vol. 41, pp. 1067-1073. 2021.
Revel et al., "A New Perspective for Schizophrenia: TAAR1 Agonists Reveal Antipyschotic- and Antidepressant-like Activity, Improve Cognition and Control Body Weight", Molecular Psychiatry, vol. 18, pp. 543-556. 2013.
Raab et al., "Incretin-like Effects of Small Molecule Trace Amine-Associated Receptor 1 Agonists", Molecular Metabolism, vol. 5, pp. 47-56. (available online Nov. 1, 2015) 2016.
Heffernan et al., "Ulotaront: A TAAR1 Agonist for the Treatment of Schizophrenia", ACS Medical Chemistry Letters, vol. 13, pp. 92-98. 2022.
Dedic et al., "Therapeutic Potential of TAAR1 Agonists in Schizophrenia: Evidence from Preclinical Models and Clinical Studies", International Journal of Molecular Sciences, vol. 22, 23 pages. 2021.
Correll et al., "Safety and Effectiveness of Ulotaront (SEP-363856) in Schizophrenia: Results of a 6-month, Open-Label Extension Study", NPJ Schizophrenia, vol. 7, No. 63, 9 pages. 2021.
Synan et al., "Ulotaront, a Novel TAAR1 Agonist with 5-HT1A Agonist Activity, Lacks Abuse Liability and Attenuates Cocaine Cue-Induced Relapse in Rats", Drug and Alcohol Dependence, 39 pages. 2021.
Koblan et al., "Understanding Negative Symptoms in Clinical Trials of Acute Schizophrenia", Neuropsychopharmacology, vol. 46, 1 page. 2021.

\* cited by examiner

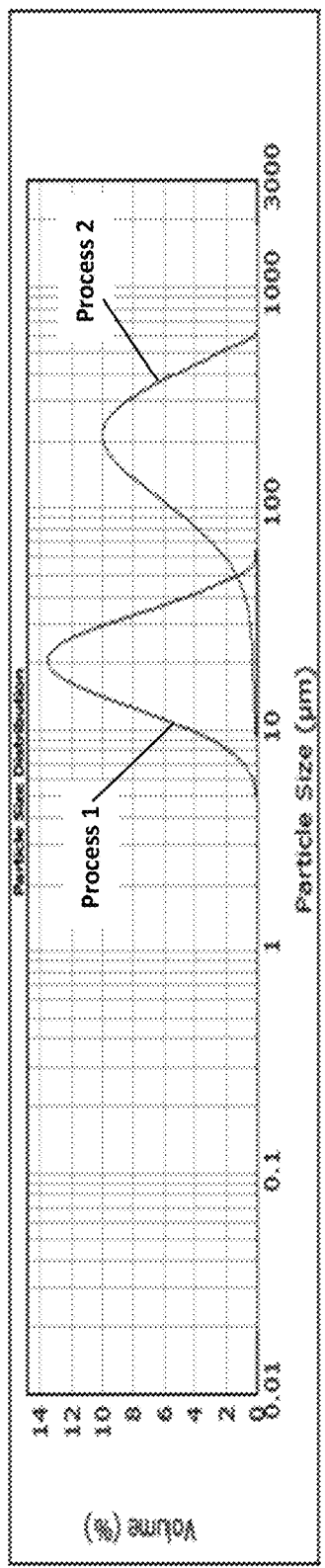
FIG. 9A
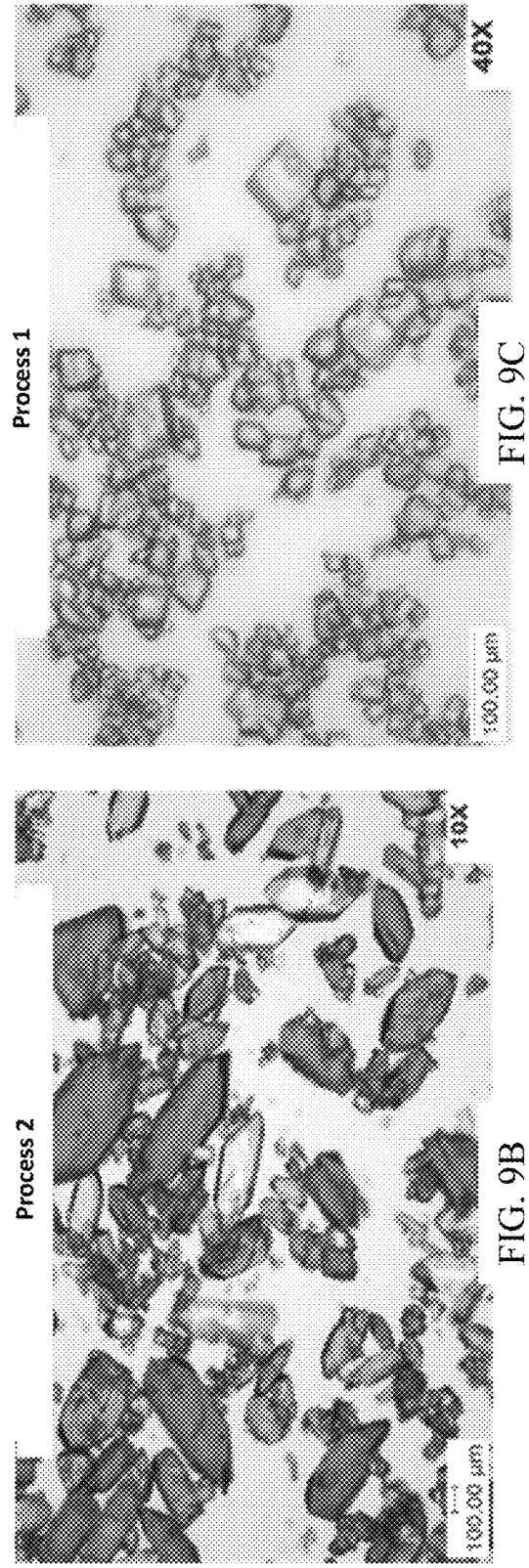
FIG. 9C
FIG. 9B

SALTS, CRYSTAL FORMS, AND PRODUCTION METHODS THEREOF

CROSS-REFERENCE TO RELATED APPLICATIONS

This application is a continuation of U.S. application Ser. No. 16/277,443, filed Feb. 15, 2019. U.S. Ser. No. 16/277,443 claimed priority to U.S. Provisional Application No. 62/710,416, filed Feb. 16, 2018, the contents of both of which are incorporated by reference herein in their entirety.

FIELD

Provided herein are (S)-(4,5-dihydro-7H-thieno[2,3-c]pyran-7-yl)-N-methylmethanamine salts and polymorphic forms of thereof, formulations comprising them, methods of making them, and methods for their use for the treatment of various diseases and disorders. Provided herein are pharmaceutical compositions comprising (S)-(4,5-dihydro-7H-thieno[2,3-c]pyran-7-yl)-N-methylmethanamine hydrochloride and polymorphic forms of thereof, methods of making the compositions, and methods for their use for the treatment of various diseases and disorders.

BACKGROUND (S)-(4,5-Dihydro-7H-thieno[2,3-c]pyran-7-yl)-N-methylmethanamine is described in U.S. Pat. No. 8,710,245 (the '245 patent). It has the following chemical structure:

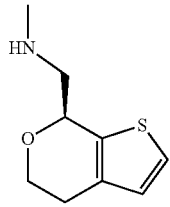

Uses of (S)-(4,5-Dihydro-7H-thieno[2,3-c]pyran-7-yl)-N-methylmethanamine in the treatment, prevention, or management of affective disorders and other various CNS disorders are also disclosed in the '245 patent.

Drug substances are most frequently administered orally by means of solid dosage forms such as tablets and capsules. Tablets remain popular as a dosage form because of the advantages afforded both to the manufacturer (e.g., simplicity and economy of preparation, stability and convenience in packaging, shipping and dispensing) and to the subject (e.g., accuracy of dosage, compactness, portability, blandness of taste and ease of administration). The preparation of tablets almost universally requires that the active pharmaceutical ingredient (API) be a solid. In the manufacture of solid APIs, it is necessary to obtain products with reproducible properties, including chemical purity and composition. For crystalline solid APIs that exhibit polymorphism, it is important to produce the desired polymorph to assure the bioavailability and stability of the drug substance. In addition to considerations of polymorphism, the manufacture of tablets is often sensitive to crystal size and morphology. While the target of many crystallization operations is to produce crystals large enough to be isolated easily on standard filtration equipment, smaller particle sizes are often desired to enhance the dissolution rate, improve bioavailability, and facilitate tablet formation. A reliable, reproducible process for preparing shelf-stable, readily bioavailable, pharmaceutical dosage forms for (S)-(4,5-Dihydro-7H-thieno[2,3-c]pyran-7-yl)-N-methylmethanamine would be highly desirable.

SUMMARY

The present disclosure provides salts of (S)-(4,5-dihydro-7H-thieno[2,3-c]pyran-7-yl)-N-methylmethanamine, formulations or compositions comprising these salts, method of preparing the compound, salts, formulations or compositions thereof, as well as polymorphs of the salts. In various aspects, the present inventions relate to substantially pure crystalline forms of (S)-(4,5-dihydro-7H-thieno[2,3-c]pyran-7-yl)-N-methylmethanamine hydrochloride, methods of producing same, compositions, medicaments and formulations including same, and methods of treating various diseases and disorders using same.

In various aspects, provided are crystalline forms of (S)-(4,5-dihydro-7H-thieno[2,3-c]pyran-7-yl)-N-methylmethanamine hydrochloride, ((S)-TPMA HCl). In various embodiments, provided are crystalline forms of (S)-(4,5-dihydro-7H-thieno[2,3-c]pyran-7-yl)-N-methylmethanamine hydrochloride of crystalline Form A. In various embodiments, crystalline (S)-(4,5-dihydro-7H-thieno[2,3-c]pyran-7-yl)-N-methylmethanamine hydrochloride of Form A is characterized by a powder x-ray diffraction pattern comprising peaks, in terms of 2-theta, at 9.6±0.2°, 14.9±0.2°, 20.5±0.2°, and 25.1±0.2°, in various embodiments further comprising peaks at 20.2±0.2° and 20.8±0.2°, and in various embodiments further comprising peaks at 20.2±0.2° and 20.8±0.2° and a prominent peak at two or more of 17.9±0.2°, 24.8±0.2° and 27.1±0.2°.

In various embodiments, the present inventions provide substantially enantiomerically pure crystalline forms of (S)-TPMA HCl of Form A. For example, in various embodiments, the present inventions provide crystalline forms of TPMA HCl that contain greater than about 90% (S)-TPMA HCl and less than about 10% of (R)-TPMA HCl, greater than about 95% (S)-TPMA HCl and less than about 5% of (R)-TPMA HCl, greater than about 97% (S)-TPMA HCl and less than about 3% of (R)-TPMA HCl, greater than about 99% (S)-TPMA HCl and less than about 1% of (R)-TPMA HCl, greater than about 99.5% (S)-TPMA HCl and less than about 0.5% of (R)-TPMA HCl, greater than about 99.7% (S)-TPMA HCl and less than about 0.3% of (R)-TPMA HCl, or greater than about 99.9% (S)-TPMA HCl and less than about 0.1% of (R)-TPMA HCl.

In various embodiments, the present inventions provide substantially chemically pure crystalline forms of (S)-TPMA HCl of Form A. For example, in various embodiments, the present inventions provide crystalline (S)-TPMA HCl of Form A that has a greater than about 80% chemical purity, greater than about 90% chemical purity, greater than about 95% chemical purity, greater than about 97% chemical purity, greater than about 99% chemical purity, greater than about 99.5% chemical purity, greater than about 99.7% chemical purity, or greater than about 99.9% chemical purity. In various embodiments, provided is crystalline (S)-TPMA HCl of Form A that has less than about 8000 ppm residual solvents, less than about 6000 ppm residual solvents, less than about 4000 ppm residual solvents, less than about 2000 ppm residual solvents, less than about 1000 ppm residual solvents, less than about 800 ppm residual solvents, or less than about 500 ppm residual solvents. Parts per million (ppm) are based on the weight of solvent as a proportion of the weight of compound plus solvent, as is commonly understood. (See USP 40, section <467>.)

In various aspects, provided are methods for preparing (S)-(4,5-dihydro-7H-thieno[2,3-c]pyran-7-yl)-N-methylmethanamine hydrochloride as crystalline Form A.

In various embodiments, the method comprises:

(a) dissolving (S)-(4,5-dihydro-7H-thieno[2,3-c]pyran-7-yl)-N-methylmethanamine free base in a solvent system comprising an alkyl alcohol of 4 carbons or less;

(b) adding excess HCl in an alkyl alcohol of 4 carbons or less; and (c) isolating crystalline (S)-(4,5-dihydro-7H-thieno[2,3-c]pyran-7-yl)-N-methylmethanamine hydrochloride. In various embodiments, the alkyl alcohol is one or more of n-propanol, isopropanol, and n-butanol, and in various embodiments, the alkyl alcohol is preferably isopropanol.

In various embodiments of methods for preparing (S)-(4,5-dihydro-7H-thieno[2,3-c]pyran-7-yl)-N-methylmethanamine hydrochloride as Form A, the method comprises:

(a) combining racemic-(4,5-dihydro-7H-thieno[2,3-c]pyran-7-yl)-N-methylmethanamine with a stoichiometric excess of (R)-mandelic acid in a solvent;

(b) isolating (S)-(4,5-dihydro-7H-thieno[2,3-c]pyran-7-yl)-N-methylmethanamine R-mandelate salt;

(c) freeing (S)-(4,5-dihydro-7H-thieno[2,3-c]pyran-7-yl)-N-methylmethanamine from the (R)-mandelate salt;

(d) dissolving the (S)-(4,5-dihydro-7H-thieno[2,3-c]pyran-7-yl)-N-methylmethanamine in a solvent system comprising an alkyl alcohol of 4 carbons or less;

(e) adding HCl in an alkyl alcohol of 4 carbons or less;

(f) isolating crystalline (S)-(4,5-dihydro-7H-thieno[2,3-c]pyran-7-yl)-N-methylmethanamine hydrochloride. In various embodiments, the alkyl alcohol is one or more of n-propanol, isopropanol, and n-butanol, and in various embodiments, the alkyl alcohol is preferably isopropanol.

In various aspects, provided are solid oral dosage forms comprising a tablet core and an optional coating. The tablet core comprising: from about 30 mg to about 120 mg of crystalline (S)-(4,5-dihydro-7H-thieno[2,3-c]pyran-7-yl)-N-methylmethanamine hydrochloride of Form A; and one or more of: (a) one or more fillers, such as, e.g., mannitol, and microcrystalline cellulose, and the like; (b) a disintegrant; and (c) a lubricant. In various embodiments, the optional tablet coating comprises one or more of (a) a polymer coating system; and (b) a polishing agent, such as, e.g., carnauba wax.

In various aspects, the present disclosure relates to methods of treating neurological diseases or disorders with a composition, formulation and/or medicament comprising (S)-TPMA, salts, and polymorphs thereof. In various aspects, the present inventions relate to methods of treating neurological diseases or disorders with a composition, formulation and/or medicament comprising crystalline (S)-TPMA HCl. In various preferred embodiments, the crystalline (S)-TPMA HCl comprises crystalline (S)-TPMA HCl of Form A. The neurological diseases and disorders include, but are not limited to: schizophrenia spectrum disorder, schizophrenia negative symptoms, prodromal schizophrenia, delusional disorder, psychosis, attenuated psychosis syndrome, Parkinson's disease psychosis, psychotic disorder, delirium, Tourette's syndrome, post-traumatic stress disorder, behavior disorder, affective disorder, depression, bipolar depression, major depressive disorder, dysthymia, bipolar disorder, manic disorder, seasonal affective disorder, obsessive-compulsive disorder, narcolepsy, REM behavior disorder, substance abuse or dependency, Lesch-Nyhan disease, Wilson's disease, autism, Alzheimer's disease with agitation and/or psychosis, and Huntington's chorea.

These and other objects, features, and advantages of the present inventions will become apparent from the following detailed description of the various aspects and embodiments of the inventions taken in conjunction with the accompanying tables and drawings.

BRIEF DESCRIPTION OF THE DRAWINGS

In the accompanying drawings like reference numerals indicate like elements and features in the various figures. For clarity, not every element may be labeled in every figure. In addition, the drawings are not necessarily complete when viewed without reference to the text, emphasis instead being placed upon illustrating the principles of the inventions.

The following abbreviations are used herein. The abbreviation DSC refers to differential scanning calorimetry; the abbreviation XRD refers to x-ray diffraction; the abbreviation XRPD refers to x-ray powder diffraction; the abbreviation NMR refers to nuclear magnetic resonance; the abbreviation DVS refers to dynamic vapor sorption; the abbreviation FBRM refers to focused beam reflectance measurement; the abbreviation HPLC refers to high performance liquid chromatography; and the abbreviation GC refers to gas chromatography; the abbreviation PSD refers to particle size distribution; the abbreviations D4,3 and D(4,3) refer to the volume mean diameter of a volume percent PSD; the abbreviation D50 refers to the median of a distribution where half the population resides above this value and half resides below; the abbreviation D10 refers to the point on a distribution where 10% of the population resides below this value; the abbreviation D90 refers to the point on a distribution where 90% of the population resides below this value; the abbreviation PVM refers to particle vision and measurement; the abbreviation TPMA refers to (4,5-dihydro-7H-thieno[2,3-c]pyran-7-yl)-N-methylmethanamine. Other abbreviations not explicitly described herein have their normal meanings in the art.

FIG. 2A is the XRPD measured in transmission mode and FIG. 2B in reflection mode.

FIG. 4A presents Raman spectra of Form A; where FIG. 4B presents Raman spectra of Form B; where FIG. 4C presents Raman spectra of both Form A (lower trace) and Form B (upper trace); FIG. 4D presents a Terahertz (THz) Raman spectra of Form A peak at 1089 cm$^{-1}$ (wavenumbers); and FIG. 4E presents a Terahertz (THz) Raman spectra of Form B peak at 1162 cm$^{-1}$ (wavenumbers).

FIG. 9A presents various PSD (particle size distribution) data of Example 2 for (S)-(4,5-dihydro-7H-thieno[2,3-c]pyran-7-yl)-N-methylmethanamine hydrochloride, of polymorph Form A.

FIG. 9B and FIG. 9C present SEM images of crystalline (S)-(4,5-dihydro-7H-thieno[2,3-c]pyran-7-yl)-N-methylmethanamine hydrochloride, of polymorph Form A.

DETAILED DESCRIPTION

Figure 1B:
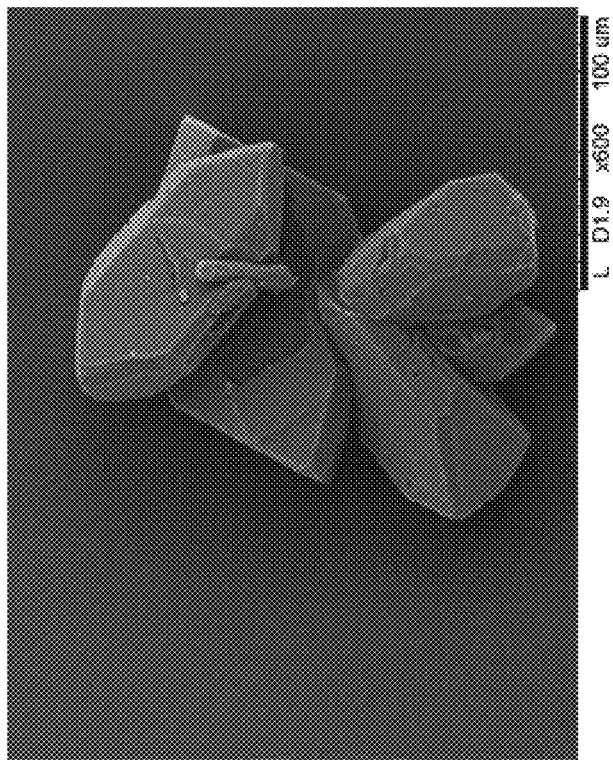
FIG. 1A, FIG. 1B, FIG. 1C and FIG. 1D present SEM images of crystalline (S)-(4,5-dihydro-7H-thieno[2,3-c]pyran-7-yl)-N-methylmethanamine hydrochloride; polymorph Form A (FIG. 1A and FIG. 1B) and polymorph Form B (FIG. 1C and FIG. 1D).

All published documents cited herein are hereby incorporated herein by reference in their entirety.

Reference in the specification to "one embodiment," "an embodiment," "one aspect," or "an aspect" means that a particular, feature, structure or characteristic described in connection with the embodiment or aspect is included in at least one embodiment or aspect of the teachings. As used herein, the singular forms "a", "an" and "the" are intended to include the plural forms as well, unless the context clearly indicates otherwise.

Unless otherwise specified, the word "includes" (or any variation thereon, e.g., "include", "including", etc.) is intended to be open-ended. For example, "A includes 1, 2 and 3" means that A includes but is not limited to 1, 2 and 3.

As used herein, the term "subject," to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. In some embodiments, the term "subject" refers to patient, such as a human patient.

As used herein, the terms "treatment," "treat," and "treating" refer to reversing, alleviating, delaying the onset of, or inhibiting the progress of a disease or disorder, or one or more symptoms thereof, including but not limited to therapeutic benefit. In various embodiments, treatment may be administered after one or more symptoms have developed. In other embodiments, treatment may be administered in the absence of symptoms. For example, treatment may be administered to a subject prior to the onset of symptoms (e.g., in light of a history of symptoms and/or in light of genetic or other susceptibility factors). Treatment may also be continued after symptoms have resolved, for example to prevent or delay their recurrence.

Therapeutic benefit includes eradication and/or amelioration of the underlying disorder being treated; it also includes the eradication and/or amelioration of one or more of the symptoms associated with the underlying disorder such that an improvement is observed in the subject, notwithstanding that the subject may still be afflicted with the underlying disorder. In some embodiments, "treatment" or "treating" includes one or more of the following: (a) inhibiting the disorder (for example, decreasing one or more symptoms resulting from the disorder, and/or diminishing the extent of the disorder); (b) slowing or arresting the development of one or more symptoms associated with the disorder (for example, stabilizing the disorder and/or delaying the worsening or progression of the disorder); and/or (c) relieving the disorder (for example, causing the regression of clinical symptoms, ameliorating the disorder, delaying the progression of the disorder, and/or increasing quality of life.)

As used herein, the term "therapeutically effective amount" or "effective amount" refers to an amount that is effective to elicit the desired biological or medical response, including the amount of a compound that, when administered to a subject for treating a disorder, is sufficient to effect such treatment of the disorder. The effective amount will vary depending on the compound, the disorder, and its severity, and the age, weight, etc. of the subject to be treated. The effective amount may be in one or more doses (for example, a single dose or multiple doses may be required to achieve the desired treatment endpoint). An effective amount may be considered to be given in an effective amount if, in conjunction with one or more other agents, a desirable or beneficial result may be or is achieved. Suitable doses of any co-administered compounds may optionally be lowered due to the combined action, additive or synergistic, of the compound.

As used herein, "delaying" development of a disorder mean to defer, hinder, slow, stabilize, and/or postpone development of the disorder. Delay can be of varying lengths of time, depending on the history of the disease and/or the individual being treated.

As used herein, "prevention" or "preventing" refers to a regimen that protects against the onset of the disorder such that the clinical symptoms of the disorder do not develop. Accordingly, "prevention" relates to administration of a therapy, including administration of a compound disclosed herein, to a subject before signs of the diseases are detectable in the subject (for example, administration of a compound disclosed herein to a subject in the absence of a detectable syndrome of the disorder). The subject may be an individual at risk or developing the disorder.

As used herein, an "at risk" individual is an individual who is at risk of developing a disorder to be treated. This may be shown, for example, by one or more risk factors, which are measurable parameters that correlate with development of a disorder and are known in the art.

Compositions of the present inventions may be administered orally, parenterally, by inhalation, topically, rectally, nasally, buccally, sublingually, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of the present inventions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, such as, for example, as a solution in 1,3-butanediol. Acceptable vehicles and solvents that may be employed, include, but are not limited to, water, Ringer's solution and isotonic sodium chloride solution. In addition, sterile, fixed oils are conventionally employed as a solvent or suspending medium. Pharmaceutically acceptable compositions of this invention may be orally administered in any orally acceptable dosage form including capsules, tablets, aqueous suspensions or solutions.

Polymorphism is the ability of an element or compound to crystallize into distinct crystalline phases. Although the term polymorph implies more than one morphology, the term is still used in the art, and herein, to refer to a crystalline structure of a compound as a polymorph even when only one crystalline phase is currently known. Thus, polymorphs are distinct solids sharing the same molecular formula as other polymorphs and the amorphous (non-crystalline) phase, however since the properties of any solid depend on its structure, polymorphs often exhibit physical properties distinct from each other and the amorphous phase, such as different solubility profiles, different melting points, different dissolution profiles, different thermal stability, different photostability, different hygroscopic properties, different shelf life, different suspension properties and different physiological absorption rates. Inclusion of a solvent in the crystalline solid leads to solvates, and in the case of water as a solvent, hydrates, often leads to a distinct crystalline form with one or more physical properties that are distinctly different from the non-solvated and non-hydrated (e.g., anhydrous) crystalline form.

As used herein, the term "polymorph" refers to different crystal structures achieved by a particular chemical entity. As used herein, the term "solvate" refers to a crystal form where a stoichiometric or non-stoichiometric amount of solvent, or mixture of solvents, is incorporated into the crystal structure. Similarly, the term "hydrate" refers to a crystal form where a stoichiometric or non-stoichiometric amount of water is incorporated into the crystal structure.

As used herein the term "span," when referring to a PSD is evaluated as follows: Span=[(D90−D10)/D50], for D values of a PSD distribution based on volume.

As used herein, the term "prominent peak," in the context of an XRPD, means a peak with a greater than about 15% relative intensity. As used herein, the term "insignificant peak," in the context of an XRPD, means a peak with a less than about 2% relative intensity.

As used herein the term "polymorph purity" refers to the weight % that is the specified polymorph form. For example, when a crystalline (S)-TPMA HCl of Form A is characterized as having greater than 95% polymorph purity, that means that greater than 95% by weight of the substance is crystalline (S)-TPMA HCl of Form A and less than 5% by weight of any other polymorph (e.g., Form B) or amorphous form of (S)-TPMA HCl.

As used herein the terms "chiral purity" and "enantiomeric purity" are used interchangeably and refers to the weight % that is the specified enantiomer. For example, when a (S)-TPMA containing substance (such as a compound or crystal) is characterized as having greater than 90% chiral purity, that means that greater than 95% by weight of the TPMA in the substance is the (S)-TPMA enantiomer and less than 5% by weight is in any other enantiomeric form of TPMA.

As used herein the term "chemical purity" refers to the weight % that is the specified chemical entity, including specified enantiomeric or polymorph form. For example, when a crystalline (S)-TPMA HCl of Form A is characterized as having greater than 95% chemical purity, that means that greater than 95% by weight of the substance is (S)-

TPMA HCl of Form A and less than 5% by weight of any other compound including other enantiomers and polymorphs.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Although pharmaceutically acceptable counter ions will be preferred for preparing pharmaceutical formulations, other anions are quite acceptable as synthetic intermediates. Thus X may be pharmaceutically undesirable anions, such as iodide, oxalate, trifluoromethanesulfonate and the like, when such salts are chemical intermediates.

As used herein, the term "pharmaceutically acceptable excipient" includes, without limitation, any binder, filler, adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, anti-caking agent, flavor, desiccants, plasticizers, disintegrants, lubricant, polymer matrix system, and polishing agents, that have been approved by the United States Food and Drug Administration as being acceptable for use in humans or domestic animals.

It is to be understood that in various embodiments, the pharmaceutical compositions of the present inventions comprise one or more pharmaceutically acceptable excipients, including, but not limited to, one or more binders, bulking agents, buffers, stabilizing agents, surfactants, wetting agents, lubricating agents, diluents, disintegrants, viscosity enhancing or reducing agents, emulsifiers, suspending agents, preservatives, antioxidants, opacifying agents, glidants, processing aids, colorants, sweeteners, taste-masking agents, perfuming agents, flavoring agents, polishing agents, polymer matrix systems, plasticizers and other known additives to provide an elegant presentation of the drug or aid in the manufacturing of a medicament or pharmaceutical product comprising a composition of the present inventions. Examples of carriers and excipients well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005.

In various embodiments, non-limiting examples of excipients include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), hydroxypropyl cellulose, titanium dioxide, talc, calcium carbonate (e.g., granules or powder), microcrystalline cellulose, powdered cellulose, dextrates, kaolin, silicic acid, sorbitol, starch, pre-gelatinized starch, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, a syloid silica gel (AEROSIL200 (fumed silica, manufactured by Evonik), a coagulated aerosol of synthetic silica (marketed by Evonik Degussa), CAB-O-SIL (a pyrogenic silicon dioxide product sold by Cabot Co. of Boston, Mass.), colorants and mixtures thereof.

In various embodiments, the compositions are formulated with one or more pharmaceutically acceptable excipients in accordance with known and established practice. In various embodiments, the compositions described herein are referred to as formulation or medicament. Thus, in various embodiments the composition are formulated as, for example, a liquid, powder, elixir, injectable solution, or suspension. Formulations for oral use are preferred and may be provided, for instance, as tablets, caplets, or capsules, wherein the pharmacologically active ingredients are mixed with an inert solid diluent. In various embodiments, the compositions described herein are formulated as a tablet. In various embodiments, the oral dosage form is a solid oral dosage form. In various embodiments, the solid oral dosage form comprises a tablet, and in various embodiments the solid oral dosage form comprises a capsule. Tablets may also include granulating and disintegrating agents, and may be coated or uncoated. Formulations for topical use may be provided, for example as topical solutions, lotions, creams, ointments, gels, foams, patches, powders, solids, sponges, tapes, vapors, pastes or tinctures.

Accordingly, in various aspects and embodiments provided herein are methods for preparing a particular salt of a specific enantiomer in a crystalline polymorph form that lends itself to pharmaceutical dosage forms. In addition, in various aspects and embodiments provided are formulations for salt polymorph for a unique dosage form that exhibits advantageous properties as a medicament.

Provided herein is compound (S)-(−)-(4,5-dihydro-7H-thieno[2,3-c]pyran-7-yl)-N-methylmethanamine, having the following structure:

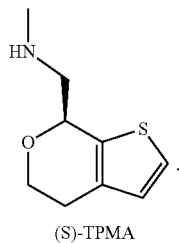

(S)-TPMA (S)-(−)-(4,5-dihydro-7H-thieno[2,3-c]pyran-7-yl)-N-methylmethanamine is named or identified using other commonly recognized nomenclature systems. For example, the compound may be named or identified with common names, systematic names, or non-systematic names. The nomenclature systems that are commonly recognized in the art of chemistry include, but are not limited to, Chemical Abstract Service (CAS) and International Union of Pure and Applied Chemistry (IUPAC). The IUPAC name provided by ChemDraw Professional 15.0 has been used herein for Compound 1.

(S)-(−)-(4,5-dihydro-7H-thieno[2,3-c]pyran-7-yl)-N-methylmethanamine referred to herein for the sake of brevity as (S)-TPMA. In some embodiments, (S)-TPMA may be prepared as a pharmaceutically acceptable salt. Non-limiting examples of pharmaceutically acceptable salts include hydrochlorides, malates, tartrates, citrates, phosphates, sulfates, pyrosulfates, bisulfates, sulfites, bisulfites, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, tosylates, xylenesulfonates, naphthalene-1-sulfonates, naphthalene-2-sulfonates, phenylacetates, phenylpropionates, phenylbutyrates, lactates, gamma-hydroxybutyrates, glycolates, and mandelates. Lists of other suitable pharmaceutically acceptable salts are found in Remington: The Science and Practice of Pharmacy, 21st Edition, Lippincott Williams and Wilkins, Philadelphia, Pa., 2006.

In some embodiments, provided herein is (S)-(4,5-dihydro-7H-thieno[2,3-c]pyran-7-yl)-N-methylmethanamine hydrochloride, (S)-(4,5-dihydro-7H-thieno[2,3-c]pyran-7-yl)-N-methylmethanamine besylate, (S)-(4,5-dihydro-7H-thieno[2,3-c]pyran-7-yl)-N-methylmethanamine R-mandelate, (S)-(4,5-dihydro-7H-thieno[2,3-c]pyran-7-yl)-N-methylmethanamine L-tartrate, (S)-(4,5-dihydro-7H-thieno[2,3-c]pyran-7-yl)-N-methylmethanamine D-tartrate, (S)-(4,5-dihydro-7H-thieno[2,3-c]pyran-7-yl)-N-methylmethanamine mesylate, and (S)-(4,5-dihydro-7H-thieno[2,3-c]pyran-7-yl)-N-methylmethanamine L-malate.

The present inventors have found that the (S)-(−)-(4,5-dihydro-7H-thieno[2,3-c]pyran-7-yl)-N-methylmethanamine hydrochloride anhydrate, henceforth referred to as (S)-(4,5-dihydro-7H-thieno[2,3-c]pyran-7-yl)-N-methylmethanamine hydrochloride, also referred to herein for the sake of brevity as (S)-TPMA HCl,

(S)-TPMA HCl has desirable solubility under physiologic conditions, is chemically stable and a crystalline solid physically well-suited to formulation.

The present inventors have also found that (S)-TPMA HCl exists in two polymorphic forms, polymorph Form A and polymorph Form B. In addition, Form A was found to be thermodynamically stable, not substantially converting to other polymorphs or amorphous form. Formation of Form B was found to be kinetically favored over Form A. Form B was, however, found to be less thermodynamically stable than Form A; Form B being transformed to Form A when Form B is held as a slurry and slightly heated.

Crystal forms of (S)-TPMA and (S)-TPMA HCl and crystalline forms of other salts, hydrates and solvates, including those of the present inventions, may be characterized and differentiated using a number of conventional analytical techniques, including but not limited to X-ray powder diffraction (XRPD) patterns, nuclear magnetic resonance (NMR) spectra, Raman spectra, Infrared (IR) absorption spectra, dynamic vapor sorption (DVS), Differential Scanning calorimetry (DSC), and melting point. Chemical purity may be characterized using a number of conventional analytical techniques, including but not limited to high performance liquid chromatography (HPLC) and gas chromatography (GC). Chiral purity (also known as enantiomeric purity) may be characterized using a number of conventional analytical techniques, including but not limited to high performance liquid chromatography (HPLC).

In various embodiments, the crystal forms of (S)-TPMA HCl are characterized by X-ray powder diffraction (XRPD). XRPD is a technique of characterizing a powdered sample of a material by measuring the diffraction of X-rays by the material. The result of an XRPD experiment is a diffraction pattern. Each crystalline solid produces a distinctive diffraction pattern containing sharp peaks as a function of the scattering angle 2θ (2-theta). Both the positions (corresponding to lattice spacing) and the relative intensity of the peaks in a diffraction pattern are indicative of a particular phase and material. This provides a "fingerprint" for comparison to other materials. In contrast to a crystalline pattern comprising a series of sharp peaks, amorphous materials (liquids, glasses etc.) produce a broad background signal in a diffraction pattern.

It is to be understood that the apparatus employed, humidity, temperature, orientation of the powder crystals, and other parameters involved in obtaining an XRPD pattern may cause some variability in the appearance, intensities, and positions of the lines in the diffraction pattern. An XRPD pattern that is "substantially in accord with" that of a FIG. provided herein (e.g., FIG. 2A) is an XRPD pattern that would be considered by one skilled in the art to represent a compound possessing the same crystal form as the compound that provided the XRPD pattern of that FIG. That is, the XRPD pattern may be identical to that of the FIG., or more likely it may be somewhat different. Such an XRPD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns.

Figure 2A:
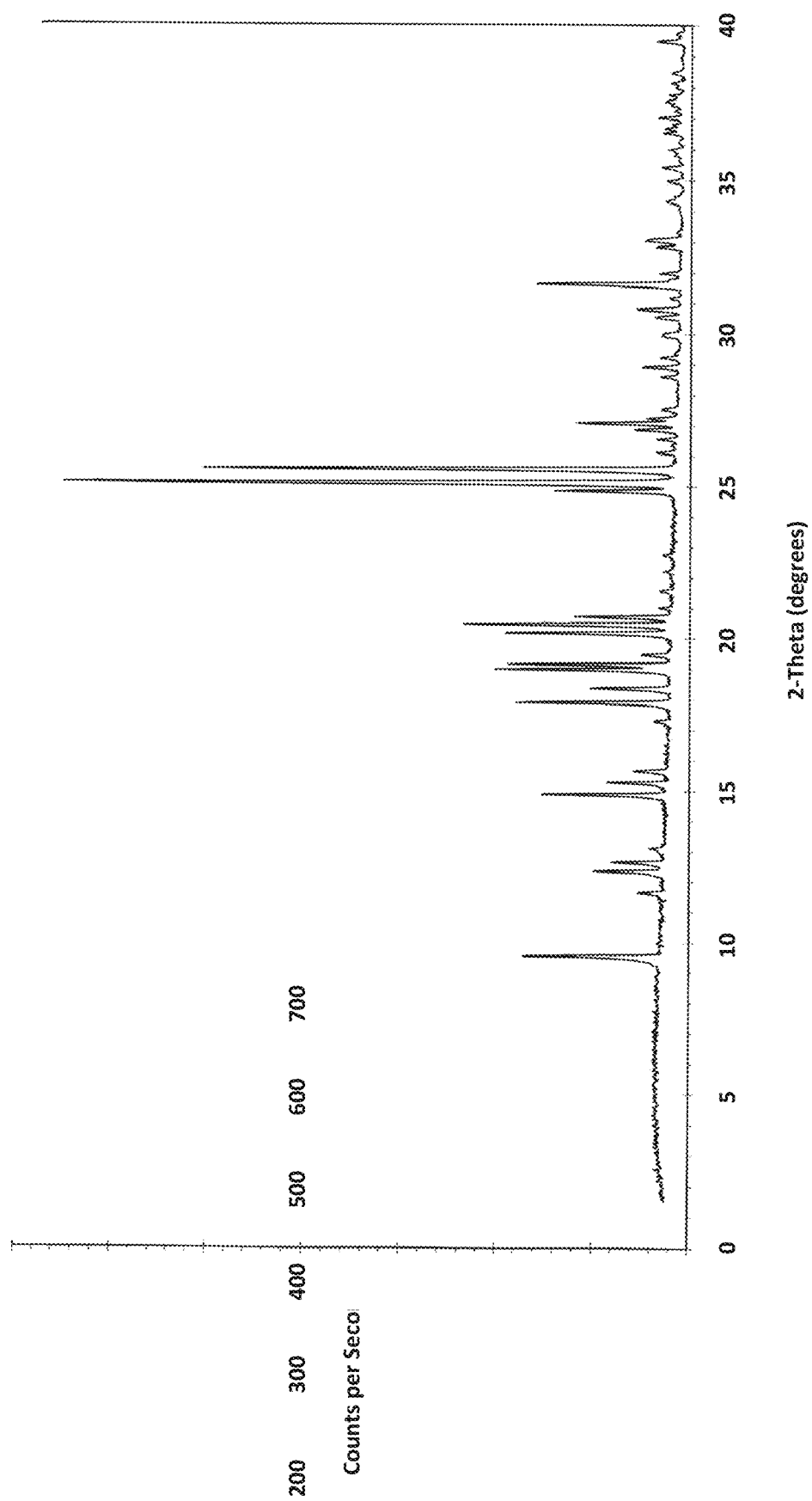
FIG. 2A and FIG. 2B present XRPD patterns for (S)-(4,5-dihydro-7H-thieno[2,3-c]pyran-7-yl)-N-methylmethanamine hydrochloride of Form A.
Figure 2B:
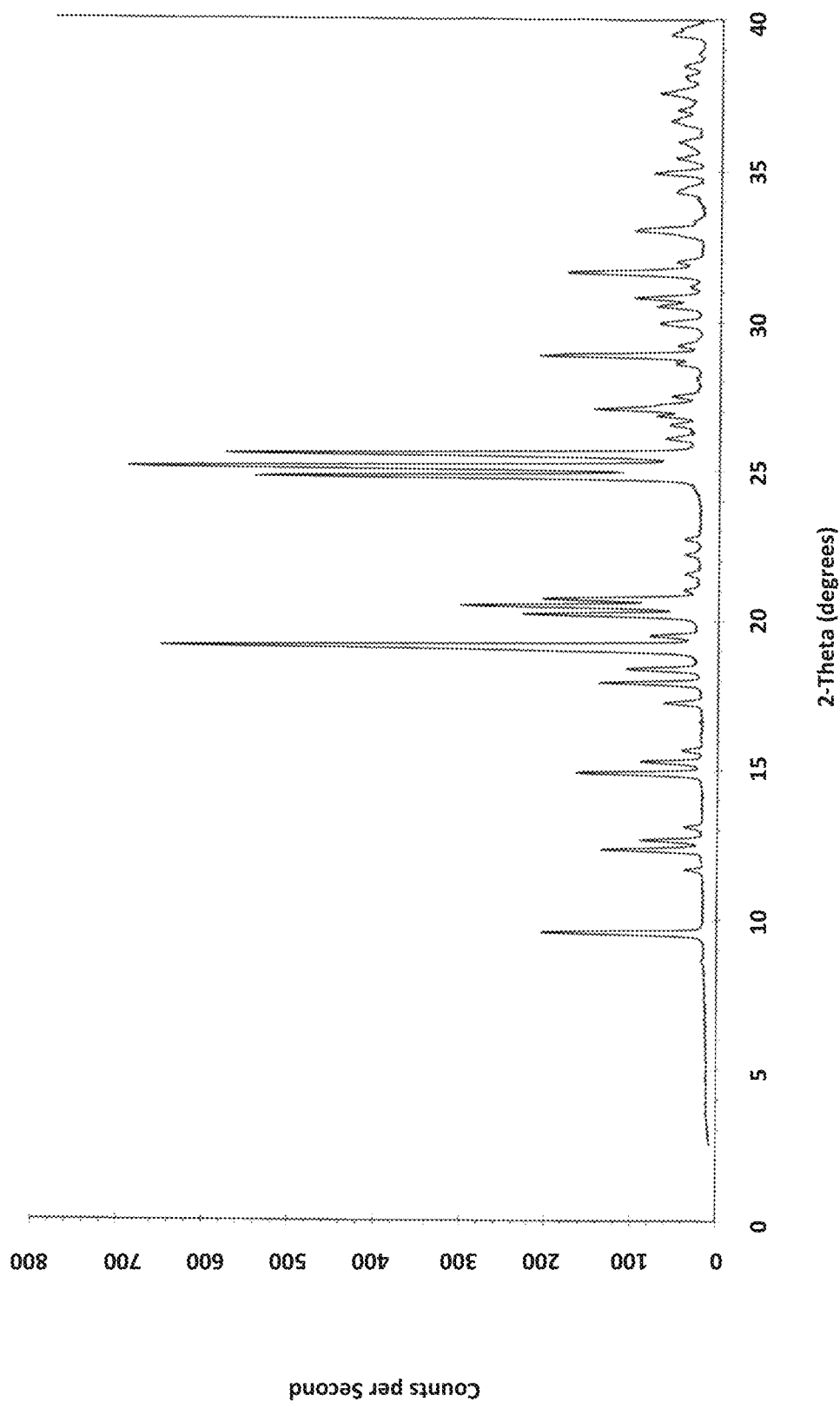

For example, one skilled in the art could use HPLC to determine the enantiomeric identity of an (4,5-dihydro-7H-thieno[2,3-c]pyran-7-yl)-N-methylmethanamine hydrochloride (TPMA HCl) sample and if, for example, the sample is identified as (S)-TPMA HCl, one skilled in the art can overlay an XRPD pattern of the sample with FIG. 2A and/or FIG. 2B, and using expertise and knowledge in the art, readily determine whether the XRPD pattern of the sample is substantially in accordance with the XRPD pattern of crystalline (S)-TPMA HCl of Form A presented in FIG. 2A or (S)-TPMA HCl of Form B presented in FIG. 2B, or neither. If, for example, HPLC identifies the sample as being (S)-TPMA HCl and the sample XRPD pattern is substantially in accord with FIG. 2A, the sample can be readily and accurately identified as (S)-TPMA HCl of Form A.

In various embodiments, the crystal forms of (S)-TPMA HCl are characterized by Raman Spectroscopy and THz Raman Spectroscopy. The positions and the relative intensity of the peaks are indicative of the vibrational, and other low frequency modes, of a compound and can provides a "fingerprint" for comparison to other compounds. THz Raman spectroscopy provides further "fingerprint" information by extending the range into the terahertz frequency region of both Stokes and anti-Stokes signals, and THz Raman spectroscopy in general providing greater structural information, such as distinguishing between polymorphs, than Raman spectroscopy.

In various embodiments, the crystal forms of (S)-TPMA HCl are characterized by melting point. Melting points were determined by conventional methods such as capillary tube and may exhibit a range over which complete melting occurs, or in the case of a single number, a melt point of that temperature ±1° C.

In various embodiments, the crystal forms of (S)-TPMA HCl are characterized by differential scanning calorimetry (DSC). DSC is a thermoanalytical technique in which the difference in the amount of heat required to increase the temperature of a sample and a reference is measured as a function of temperature. Both the sample and reference are maintained at substantially the same temperature throughout the experiment. The result of a DSC experiment is a curve of heat flow versus temperature, called a DSC thermogram.

In various embodiments, the hygroscopicity of crystal forms of (S)-TPMA HCl are characterized by dynamic vapor sorption (DVS). DVS is a gravimetric technique that measures how much of a solvent is adsorbed by a sample by varying the vapor concentration surrounding the sample (e.g., relative humidity) and measuring the change in mass. In the present application, DVS is used to generate water sorption isotherms, which represent the equilibrium amount of vapor sorbed as a function of steady state relative vapor pressure at a constant temperature.

As used herein, the term "substantially non-hygroscopic" refers to a compound exhibiting less than a 1% maximum mass change in water sorption isotherms, at 25° C. scanned over 0 to 90% relative humidity, as measured by dynamic vapor sorption (DVS).

In various aspects and embodiments, the present inventions relate to new crystalline forms of (S)-TPMA HCl, Form A and Form B. Form A has been found to be a distinct polymorph from Form B, having a distinctly different structure and XRPD pattern, as well as different THz Raman spectra.

Figure 1A:
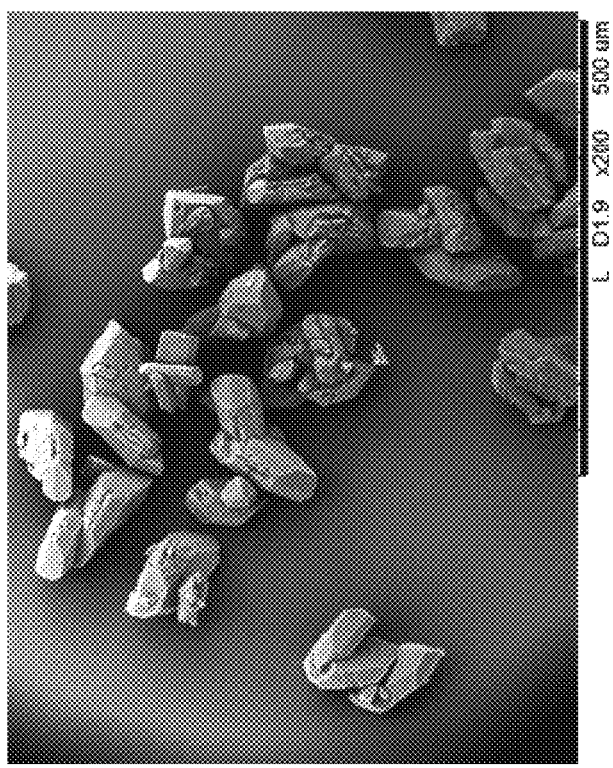
Figure 1D:
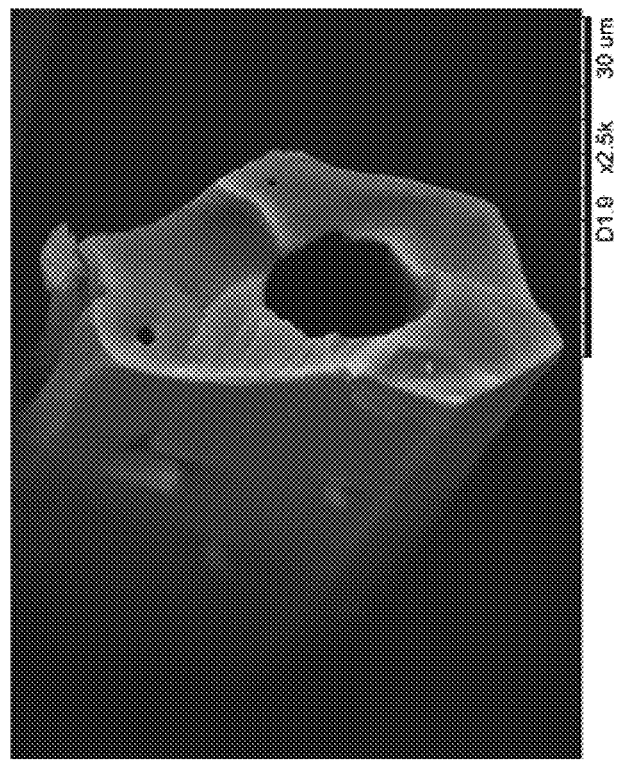
Figure 1C:
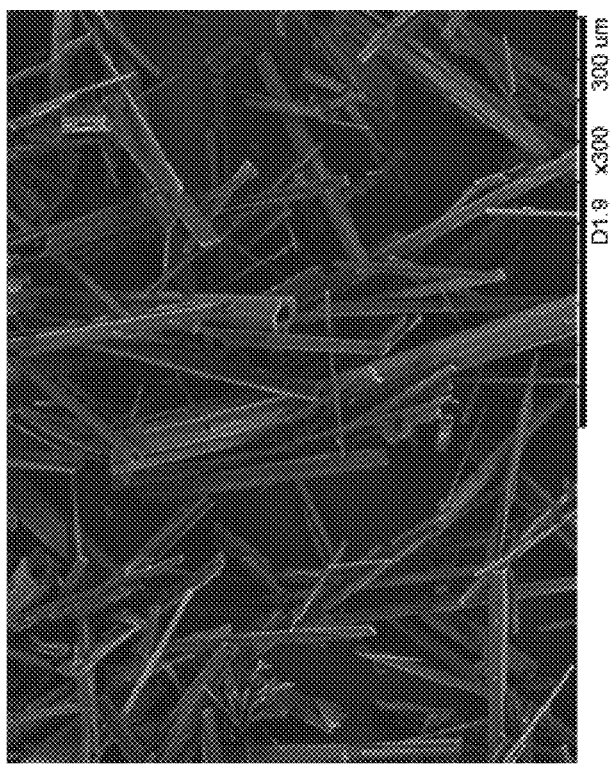

FIGS. 1A and 1B present SEM images of (S)-TPMA HCl Form A crystals and FIGS. 1C and 1D SEM images of (S)-TPMA HCl Form B crystals. Form A was observed to form plate crystals and was determined by XRPD to have a monoclinic crystal system, while the Form B was observed to form hollow needle crystals and was determined by XRPD to have an orthorhombic crystal system. As isolated from conventional synthesis or salt conversion, (S)-TPMA hydrochloride typically appears as a mixture of Forms A and B.

Form B was determined to be less thermodynamically stable than Form A, and can be converted by solid state conversion to Form A. The solid state conversion of the polymorph Form B needles to polymorph Form A blocks can be monitored by X-ray diffraction, and it was discovered unexpectedly that the visible morphology retains the needle shape while the crystal lattice changes to that of Form A.

The XRPD pattern of FIG. 2A was obtained in transmission mode with a Stoe Stadi P (G.52.SYS.S072) with a Mythen1K detector, using Cu Kα radiation; with measurements in transmission mode; 40 kV and 40 mA tube power; a curved Ge monochromator detector; 0.02° 2θ step size, with a 12 s step time, and a 1.5-50.5° 2θ scanning range. The detector mode was set to: step scan with 1° 2θ detector step and sample preparation was a 10 to 20 mg sample placed between two acetate foils and clamped in a Stoe transmission sample holder. Samples were rotated during the measurement.

Figure 2C:
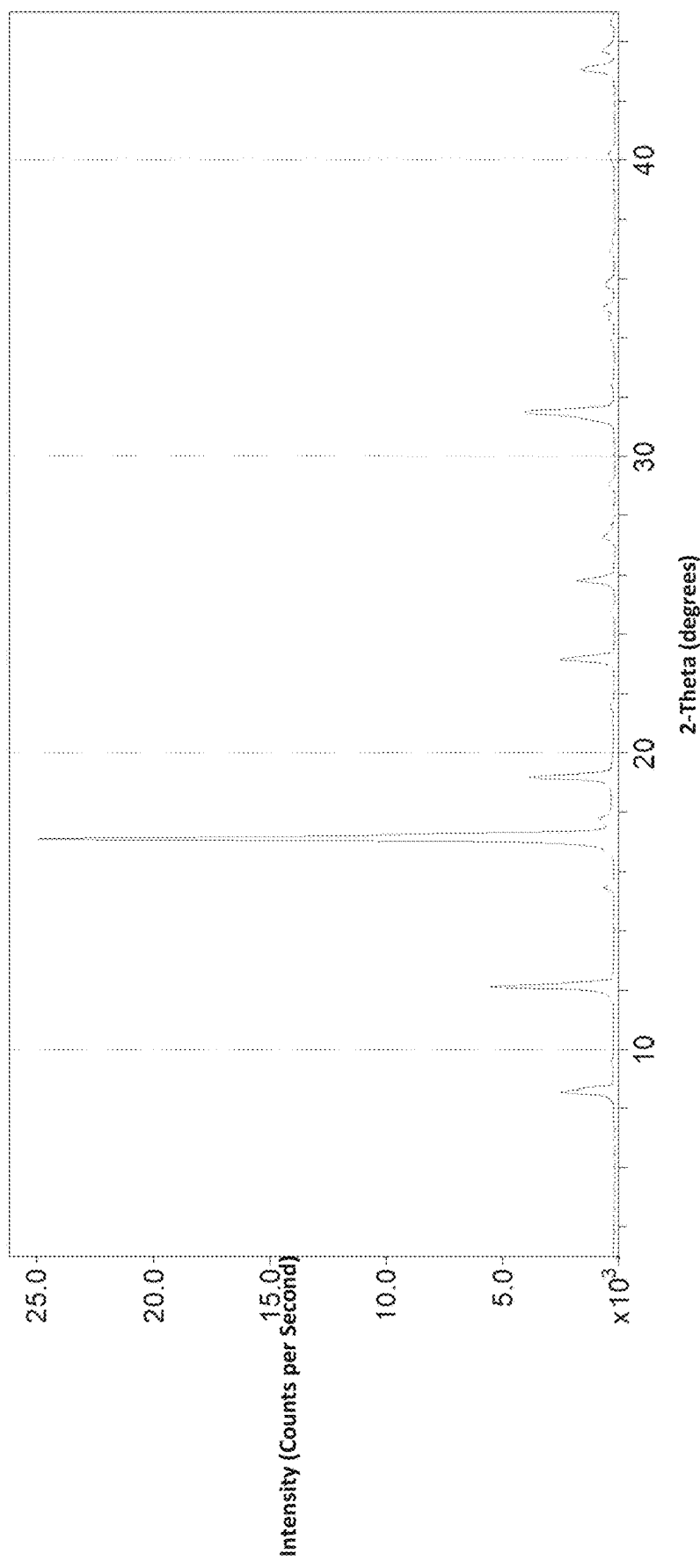
FIG. 2C presents an XRPD pattern for (S)-(4,5-dihydro-7H-thieno[2,3-c]pyran-7-yl)-N-methylmethanamine hydrochloride of Form B.

The XRPD patterns of FIGS. 2B and 2C were obtained with a Bruker 08 Advance, Cu Kα radiation (λ=1.54180 Å), with measurements in reflection mode; 40 kV/40 mA tube power; LynxEye detector, 0.02° step size in 2θ, using 37 s per step, and a 2.5°-50° 2θ scanning range. The sample was prepared on silicon single crystal sample holders with 1.0 mm depth and was covered with Kapton foil. The sample was rotated during the measurement.

Further details of the crystal data and crystallographic data collection parameters are summarized in Table 1, and a listing of the peaks of the XRPD of FIG. 2A are listed in Table 2A, the peaks of the XRPD of FIG. 2B are listed in Table 2B, and the peaks of the XRPD of FIG. 2C are listed in Table 2C.

TABLE 1

(S)-TPMA hydrochloride Form A and Form B Single Crystal Data and Collection Parameters

| | Form A, blocks | Form B, needles |
|---|---|---|
| Empirical formula | $C_9H_{14}NOSCl$ | $C_9H_{14}NOSCl$ |
| Molecular formula | $[C_9H_{14}NOS]^+[Cl]^-$ | $[C_9H_{14}NOS]^+[Cl]^-$ |
| Formula weight | 219.72 | 219.72 |
| Temperature | 100(2) K | 100(2) K |
| Wavelength | 1.54184 Å | 1.54184 Å |
| Crystal system | Monoclinic | Orthorhombic |
| Space group | P21 (#4) | P212121 (#19) |
| Unit cell dimensions | a = 9.1719(2) Å; α = 90°. b = 11.2183(3) Å; β = 92.146(2)°. c = 10.2092(2) Å; γ = 90°. | a = 5.10405(5) Å; α = 90°. b = 10.2114(1) Å; β = 90°. c = 20.5496(2) Å; γ = 90°. |
| Volume | 1049.72(4) Å^3 | 1071.035(18) Å^3 |
| Z | 4 | 4 |
| Density (calculated) | 1.390 Mg/m$^3$ | 1.363 Mg/m$^3$ |
| Absorption coefficient | 4.765 mm$^{-1}$ | 4.670 mm$^{-1}$ |
| F(000) | 464 | 464 |
| Crystal size | 0.0823 × 0.0529 × 0.0396 mm$^3$ | 0.3254 × 0.0539 × 0.0366 mm$^3$ |
| Theta range for data collection | 4.33 to 76.58°. | 4.30 to 76.77°. |
| Index ranges | −11 <= h <= 10, −13 <= k <= 14, −12 <= l <= 12 | −6 <= h <= 6, −12 <= k <= 12, −25 <= l <= 25 |
| Reflections collected | 11895 | 22468 |
| Independent reflections | 4211 [R(int) = 0.0362] | 2261 [R(int) = 0.0532] |
| Completeness to θ = 76.58° | 99.50% | 100.00% |
| Absorption correction | Analytical | Analytical |
| Max. and min. transmission | 0.860 and 0.776 | 0.864 and 0.435 |
| Refinement method | Full-matrix least-squares on F2 | Full-matrix least-squares on F2 |
| Data/restraints/parameters | 4211/1/237 | 2261/3/136 |
| Goodness-of-fit on F2 | 1.041 | 1.085 |
| Final R indices [I > 2σ (I)] | R1 = 0.0264, wR2 = 0.0587 | R1 = 0.0270, wR2 = 0.0665 |
| R indices (all data) | R1 = 0.0289, wR2 = 0.0601 | R1 = 0.0291, wR2 = 0.0680 |
| Absolute structure parameter | −0.001(10) | −0.032(18) |
| Largest diff. peak and hole | 0.260 and −0.188 e.Å$^{-3}$ | 0.329 and −0.573 e.Å$^{-3}$ |

In some embodiments, provided herein is crystalline (S)-(4,5-dihydro-7H-thieno[2,3-c]pyran-7-yl)-N-methylmethanamine hydrochloride characterized by monoclinic space group P21. In some embodiments, the crystalline (S)-(4,5-dihydro-7H-thieno[2,3-c]pyran-7-yl)-N-methylmethanamine hydrochloride has unit cell dimensions: a is about 9.2 Å, b is about 11.2 Å, c is about 10.2 Å, α is about 90°, β is about 92°, and γ is about 90°.

In some embodiments, provided herein is crystalline (S)-(4,5-dihydro-7H-thieno[2,3-c]pyran-7-yl)-N-methylmethanamine hydrochloride characterized by orthorhombic space group P212121. In some embodiments, the crystalline (S)-(4,5-dihydro-7H-thieno[2,3-c]pyran-7-yl)-N-methylmethanamine hydrochloride has unit cell dimensions: a is about 5.1 Å, b is about 10.2 Å, c is about 20.5 Å, α is about 90°, β is about 90°, and γ is about 90°.

TABLE 2A (S)-TPMA hydrochloride Form A XRPD (FIG. 2A) Peak List

| 2-Theta | Relative Height |
|---|---|
| 9.55 | 22.61 |
| 11.63 | 3.1 |
| 12.35 | 11.47 |
| 12.65 | 8.6 |
| 14.89 | 20.7 |
| 15.27 | 9.77 |
| 15.67 | 5.44 |
| 17.91 | 24.67 |
| 18.38 | 12.71 |
| 19.00 | 28.32 |
| 19.16 | 25.92 |
| 19.49 | 4.49 |
| 20.19 | 27.17 |
| 20.48 | 33.87 |
| 20.72 | 15.32 |
| 24.84 | 19.16 |
| 25.11 | 100 |
| 25.57 | 76.5 |
| 26.11 | 3.05 |
| 26.56 | 2.56 |
| 26.86 | 6.74 |
| 27.07 | 16.04 |
| 27.24 | 4.78 |
| 27.52 | 2.28 |
| 28.60 | 2.32 |
| 28.91 | 5.9 |
| 29.22 | 2.58 |
| 29.98 | 2.52 |
| 30.55 | 3.87 |
| 30.81 | 6.64 |
| 31.63 | 23.29 |
| 32.00 | 2.86 |
| 32.84 | 4.04 |
| 33.05 | 5.83 |
| 34.37 | 1.81 |
| 34.98 | 2.25 |
| 35.41 | 2.97 |

TABLE 2A-continued (S)-TPMA hydrochloride Form A XRPD (FIG. 2A) Peak List

| 2-Theta | Relative Height |
| --- | --- |
| 36.61 | 1.82 |
| 37.02 | 3.83 |
| 37.59 | 1.99 |
| 38.46 | 1.71 |
| 39.47 | 4.25 |

TABLE 2B (S)-TPMA hydrochloride Form A XRPD (FIG. 2B) Peak List

| 2-Theta | Relative Height |
| --- | --- |
| 9.59 | 27.73 |
| 11.70 | 3.44 |
| 12.35 | 17.88 |
| 12.69 | 11.1 |
| 13.12 | 3.52 |
| 14.93 | 22.25 |
| 15.31 | 11.24 |
| 15.71 | 4.04 |
| 17.28 | 7.28 |
| 17.95 | 18.38 |
| 18.41 | 14.03 |
| 19.16 | 91.74 |
| 19.53 | 9.85 |
| 20.23 | 31.95 |
| 20.51 | 42.51 |
| 20.76 | 27.67 |
| 21.60 | 3.41 |
| 22.25 | 3.33 |
| 22.77 | 3.87 |
| 24.82 | 77.41 |
| 25.14 | 100 |
| 25.59 | 82 |
| 26.13 | 7.25 |
| 26.58 | 6.46 |
| 27.10 | 19.49 |
| 27.55 | 6.3 |
| 28.87 | 27.5 |
| 29.24 | 5.41 |
| 29.99 | 8.48 |
| 30.55 | 8.74 |
| 30.83 | 12.69 |
| 31.63 | 24.78 |
| 32.02 | 5.46 |
| 33.03 | 12.75 |
| 34.31 | 5.42 |
| 34.93 | 9.12 |
| 35.45 | 5.72 |
| 35.99 | 4.93 |
| 36.68 | 6.56 |
| 37.58 | 8.48 |
| 38.49 | 4.42 |
| 39.47 | 6.41 |

TABLE 2C (S)-TPMA hydrochloride Form B XRPD (FIG. 2C) Peak List

| 2-Theta | Relative Height |
| --- | --- |
| 8.54 | 9.1 |
| 8.89 | 0.3 |
| 11.76 | 0.8 |
| 12.12 | 21.6 |
| 12.45 | 0.2 |
| 15.46 | 1.8 |
| 17.12 | 100 |
| 17.48 | 1.7 |
| 17.82 | 2.6 |
| 18.32 | 0.5 |

TABLE 2C-continued (S)-TPMA hydrochloride Form B XRPD (FIG. 2C) Peak List

| 2-Theta | Relative Height |
| --- | --- |
| 19.18 | 14.2 |
| 21.56 | 0.5 |
| 23.16 | 9.5 |
| 24.80 | 0.9 |
| 25.80 | 6.6 |
| 26.20 | 0.2 |
| 27.26 | 2.1 |
| 27.62 | 0.6 |
| 29.06 | 1.2 |
| 31.50 | 15.4 |
| 31.81 | 0.4 |
| 32.42 | 0.5 |
| 33.87 | 0.6 |
| 34.68 | 1 |
| 35.00 | 1.9 |
| 35.76 | 1.6 |
| 36.94 | 0.9 |
| 37.24 | 0.4 |
| 39.28 | 0.1 |
| 40.00 | 0.7 |
| 40.20 | 1.1 |
| 43.08 | 5.8 |
| 43.74 | 2 |
| 44.60 | 0.6 |

Raman and THz Raman Spectra

The Raman and THz Raman spectroscopic analysis was performed using a Kaiser Raman RXN-Hybrid-785 system with laser wavelength 785 nm, with a spectral coverage of +100 $cm^{-1}$ to +1875 $cm^{-1}$ for the Raman spectra and a spectral coverage of −200 $cm^{-1}$ to +200 $cm^{-1}$ for the Tz Raman spectra; spectral resolution was 4 $cm^{-1}$. The Raman spectra of FIGS. 4A, 4B and 4C were collected with the regular immerse Raman probe, and the THz Raman spectra of FIGS. 4D and 4E were collected with the THz-Raman® Probe.

Figure 4A:
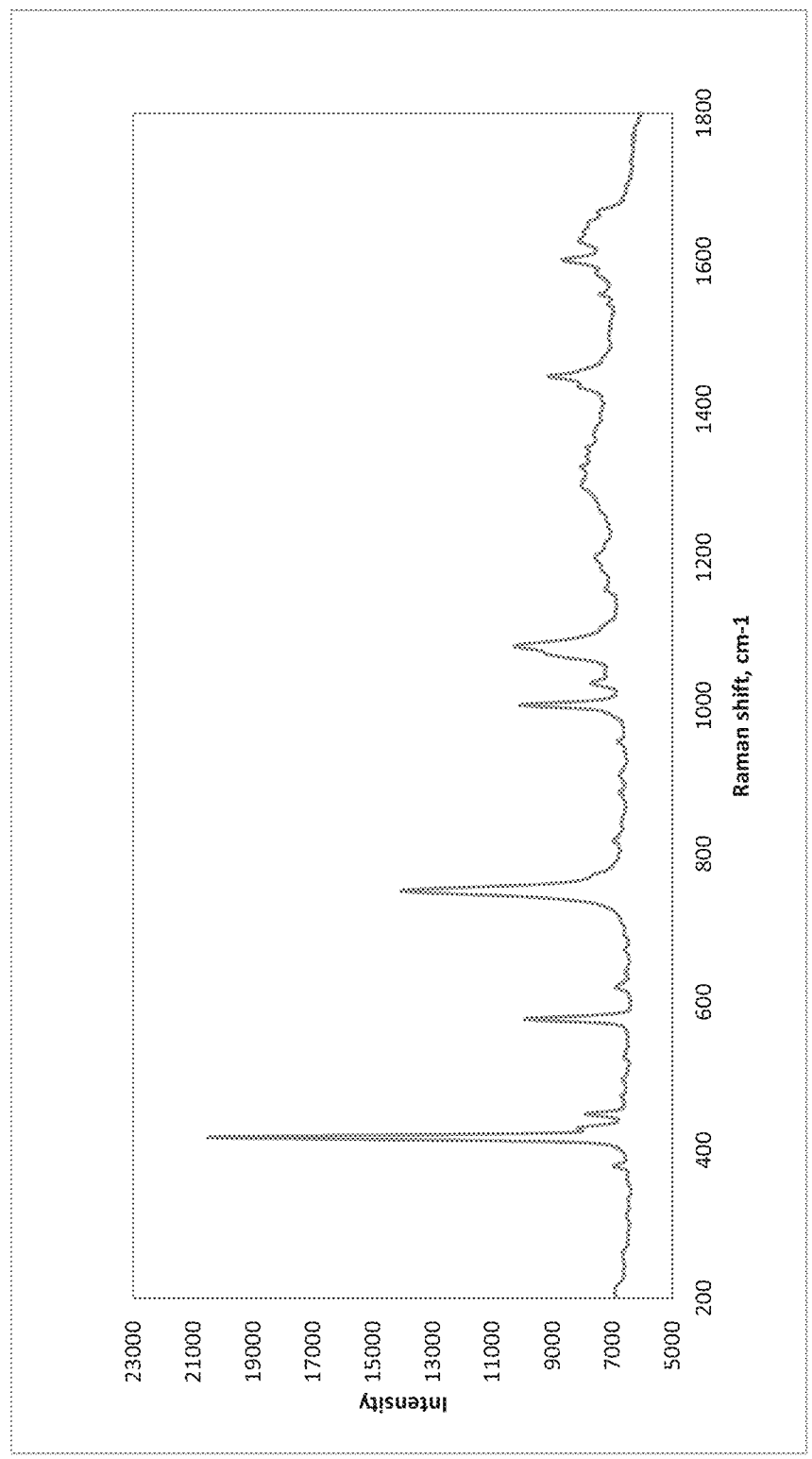
FIG. 4A, FIG. 4B, FIG. 4C, FIG. 4D, and FIG. 4E present various types of Raman spectra of for (S)-(4,5-dihydro-7H-thieno[2,3-c]pyran-7-yl)-N-methylmethanamine hydrochloride of polymorph Form A and polymorph Form B; where
Figure 4B:
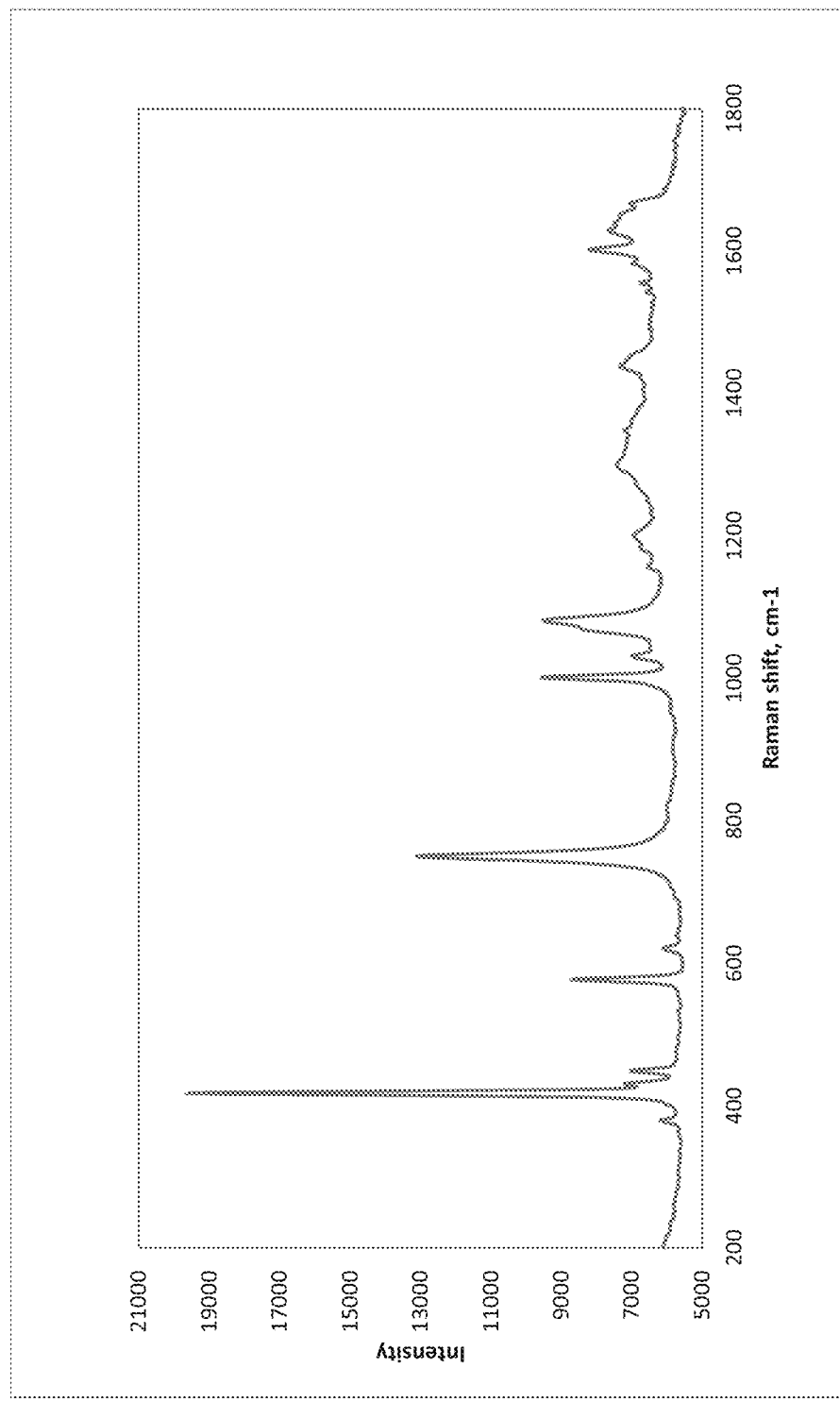
Figure 4C:
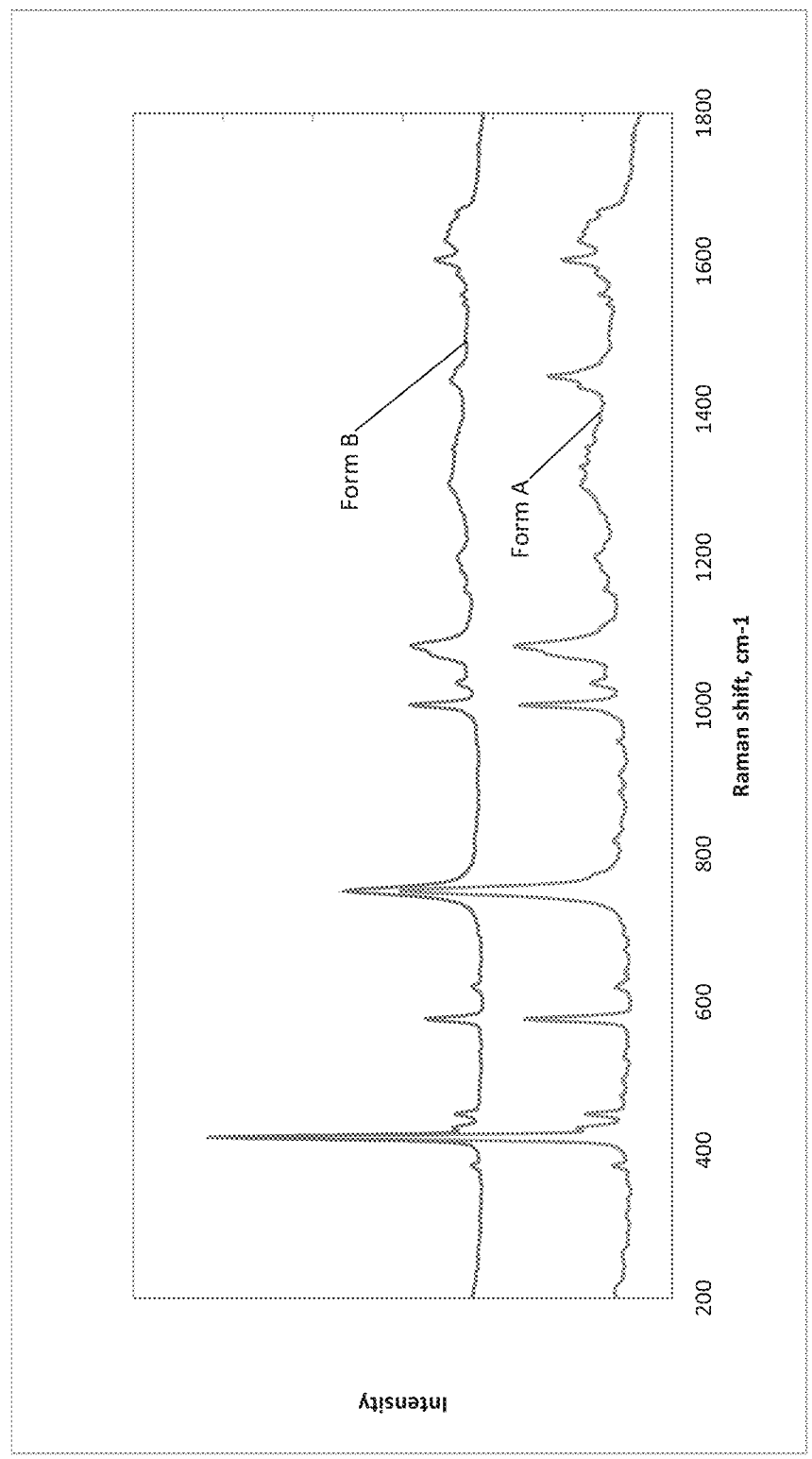

Referring to FIGS. 4A and 4C, the Form A crystals of (S)-TPMA HCl were used as a powder and the spectra taken in a dark chamber. Referring to FIGS. 4B and 4C, the Form B crystals of (S)-TPMA HCl were freshly generated by dissolving Form A crystals in isopropanol and then rotary evaporating off the solvent, then the Form B crystals were used as a powder and the spectra taken in a dark chamber. A listing of various peaks in the spectra of FIG. 4A are listed in Table 3A, and various peaks in the spectra of FIG. 4B are listed in Table 3B.

Figure 4D:
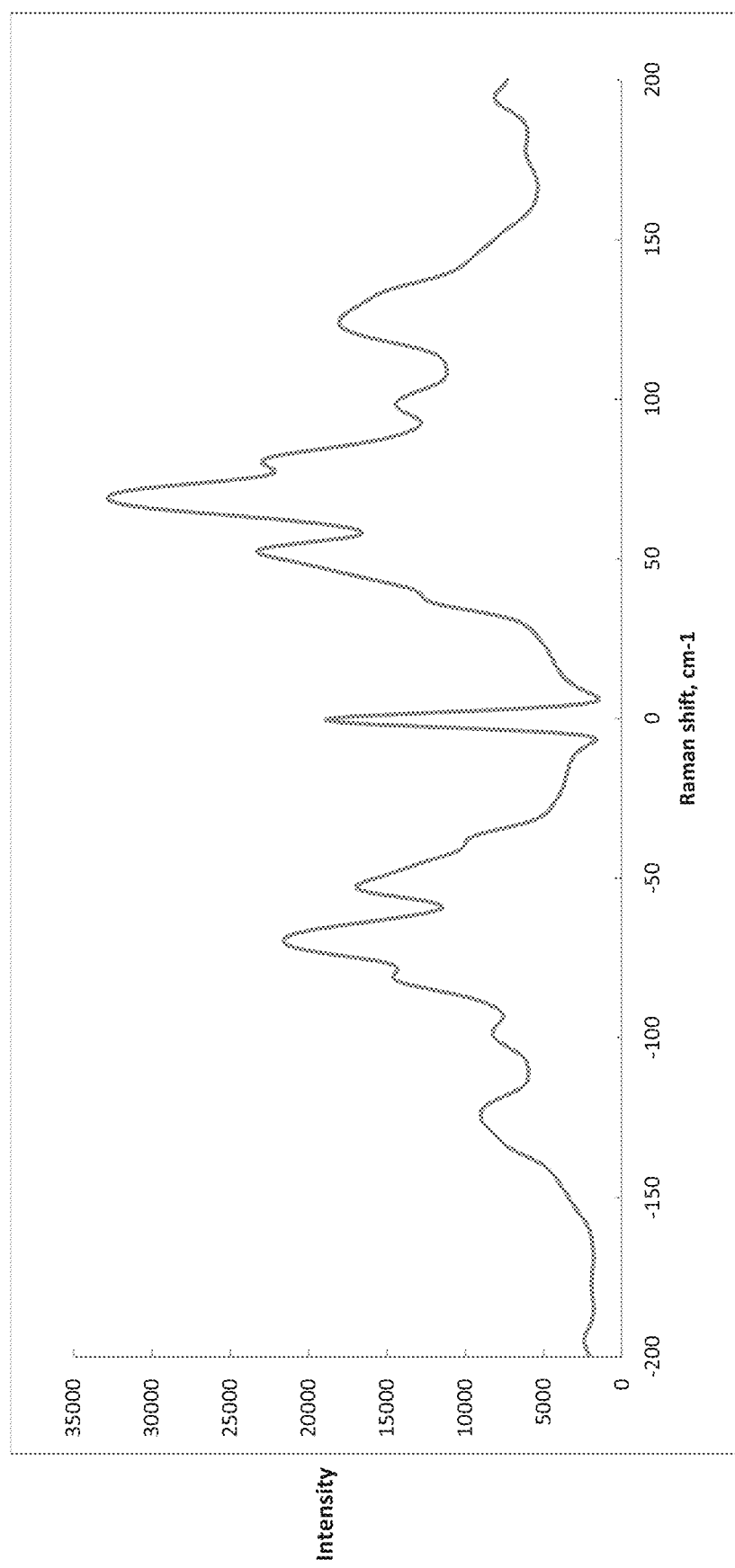
Figure 4E:
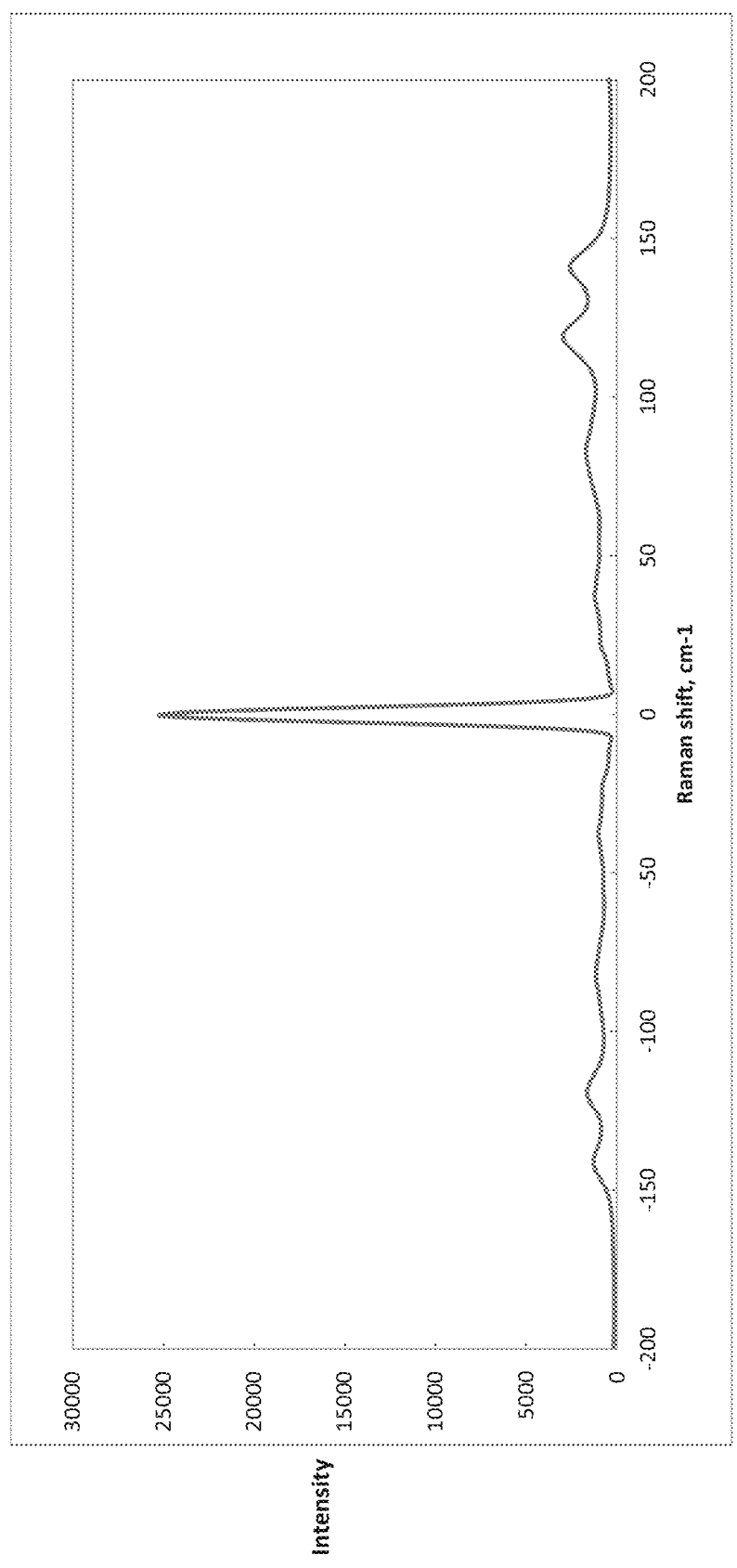

Referring to FIG. 4D, the Form A crystals of (S)-TPMA HCl were suspended in isopropanol at room temperature and the THz-Raman® Probe used to take the spectra in the suspension. Referring to FIG. 4E, the Form B crystals of (S)-TPMA HCl were generated by the reverse dumping addition of freebase (S)-TPMA to the HCl solution, and THz-Raman® Probe immediately used to take the spectra in suspension.

Both the Raman spectra and THz Raman spectra were obtained using: (a) cosmic ray filtering' and (b) baseline correction and smoothing to obtain interpretable data when necessary; and for the THz Raman spectra background subtraction of a well filled with IPA collected with the same conditions.

TABLE 3A (S)-TPMA hydrochloride Form A Raman
Spectra (FIG. 4A) Peak List

| Raman shift, cm$^{-1}$ | Relative Peak Height |
|---|---|
| 378.9 | 31.53 |
| 417.6 | 100.00 |
| 430.2 | 36.77 |
| 448.8 | 35.97 |
| 576.9 | 44.40 |
| 620.7 | 31.18 |
| 750.0 | 66.84 |
| 1001.1 | 48.84 |
| 1030.8 | 35.65 |
| 1080.9 | 48.59 |
| 1439.1 | 37.41 |
| 1602.3 | 41.81 |

TABLE 3B (S)-TPMA hydrochloride Form B Raman Spectra (FIG. 4B) Peak List

| Raman shift, cm$^{-1}$ | Relative Peak Height |
|---|---|
| 378.9 | 33.95 |
| 417.6 | 100.00 |
| 429.6 | 39.79 |
| 448.8 | 38.43 |
| 577.2 | 48.47 |
| 620.4 | 33.63 |
| 750.3 | 68.58 |
| 1001.1 | 49.14 |
| 1030.8 | 37.64 |
| 1080.6 | 50.10 |
| 1445.1 | 44.63 |

Referring to FIGS. 4D and 4E, the THz Raman spectra of the two polymorphs is distinctly different. For example, in various embodiments, the THZ Raman spectra of the Raman peak of Form B at 1162 cm$^{-1}$ and the THZ Raman spectra of the Raman peak of Form A at 1089 cm$^{-1}$ can be used to distinguish these polymorphs.

Crystalline (S)-TPMA HCl of Forms A and B exhibit different properties and different "fingerprints". Various measurements presented herein on these polymorphs are summarized in Table 4.

TABLE 4

Figure 3A:
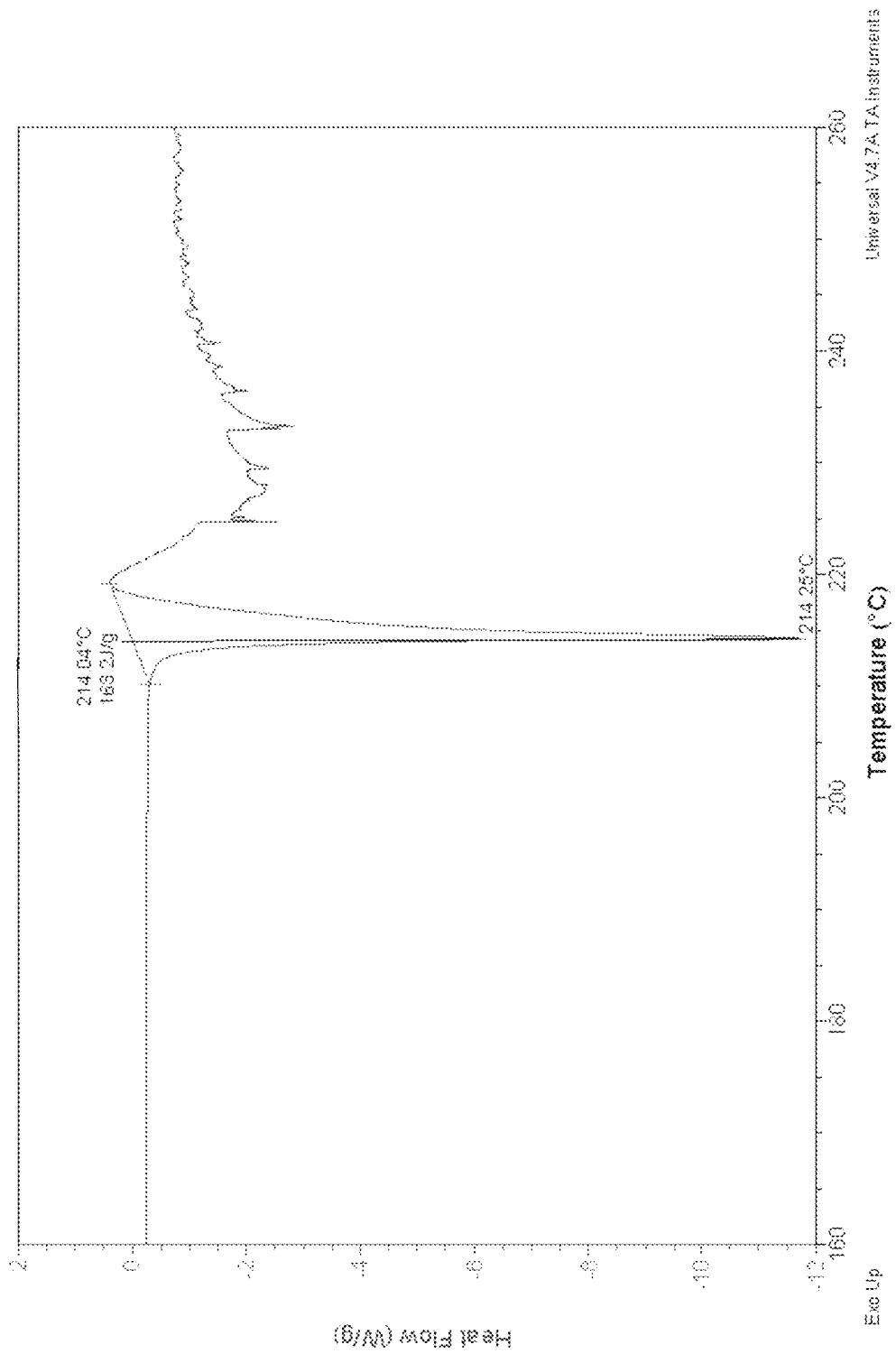
FIG. 3A is a DSC thermogram for (S)-(4,5-dihydro-7H-thieno[2,3-c]pyran-7-yl)-N-methylmethanamine hydrochloride, of polymorph Form A.
Figure 3B:
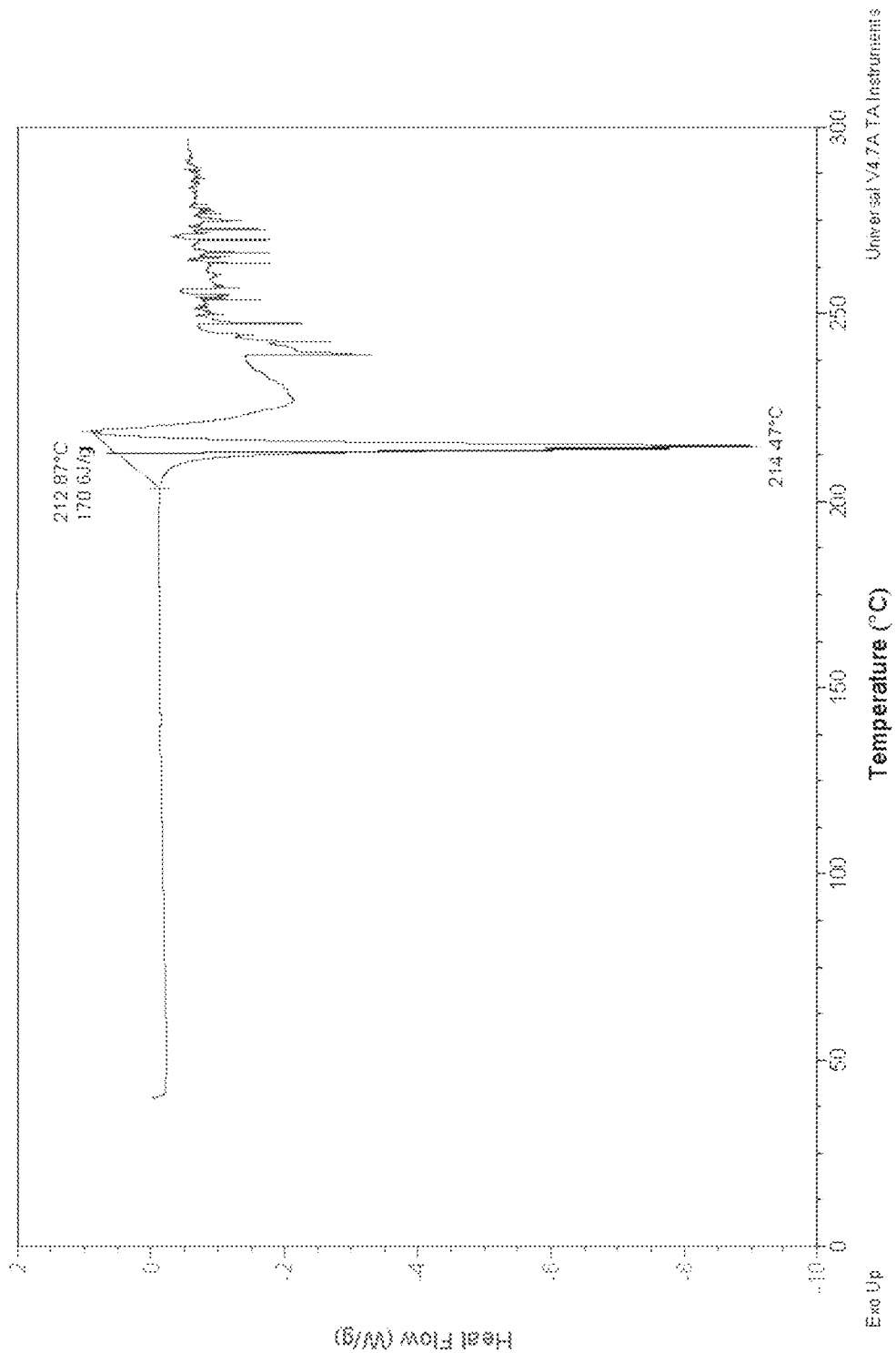
FIG. 3B and FIG. 3C are DSC thermograms for (S)-(4,5-dihydro-7H-thieno[2,3-c]pyran-7-yl)-N-methylmethanamine hydrochloride, of polymorph Form B.
Figure 3C:
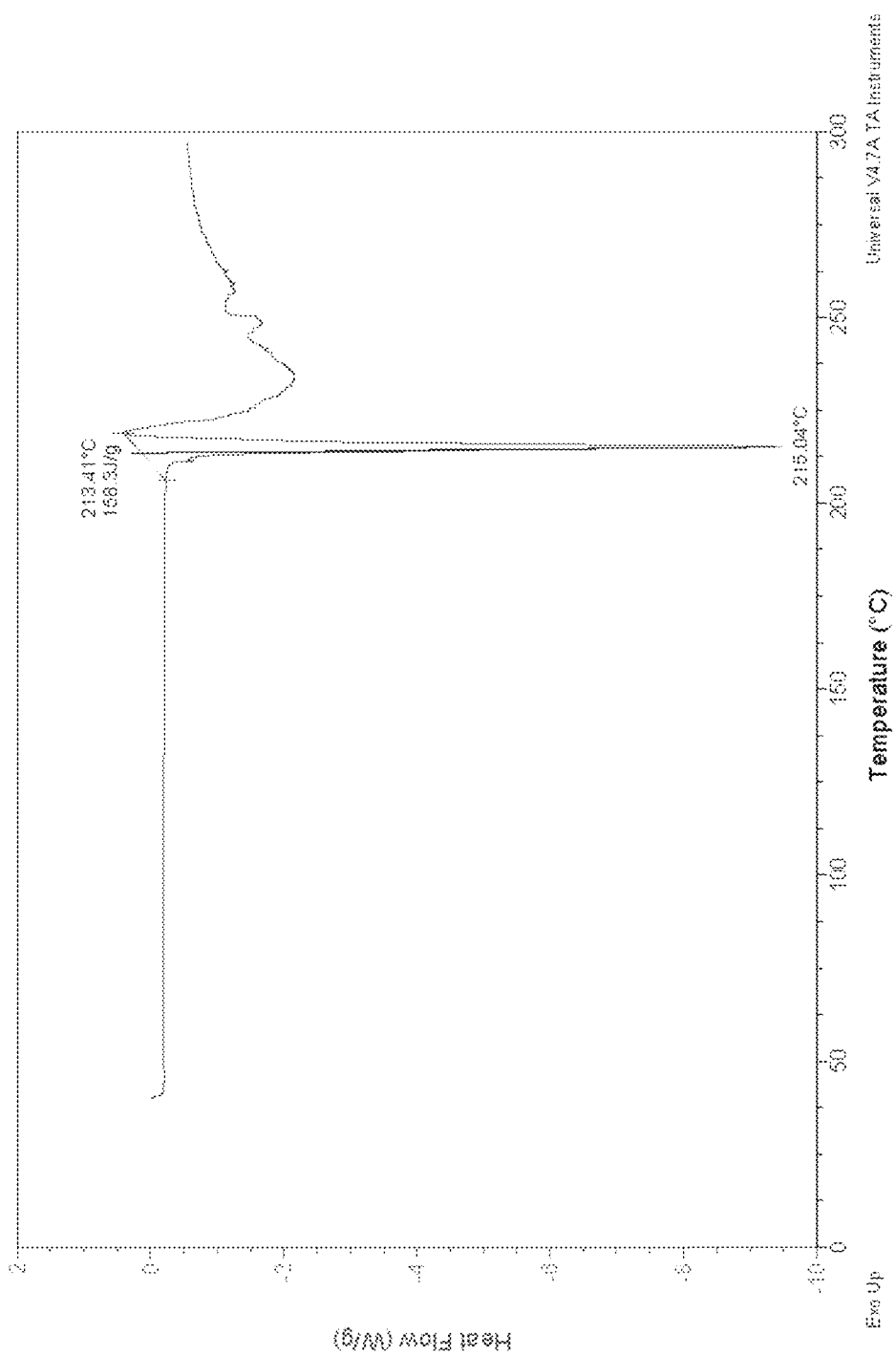

|  | Form A | Form B |
|---|---|---|
| SEM Image | FIG. 1A, FIG. 1B | FIG. 1C, FIG. 1D |
| XRPD Pattern | FIG. 2A, FIG. 2B | FIG. 2C |
| DSC Thermograph | FIG. 3A | FIGS. 3B-3C |
| Raman | FIG. 4A | FIG. 4B |
| THz Raman | FIG. 4D | FIG. 4E |

In various embodiments, the present inventions provide a crystalline form of (S)-TPMA HCl characterized by an XRPD pattern comprising peaks, in terms of 2-theta, at 9.6±0.2°, 14.9±0.2°, 20.5±0.2°, and 25.1±0.2°, and a DSC thermogram having a peak at 214±2° C.

In various embodiments, the present inventions provide a crystalline form of (S)-TPMA HCl characterized by an XRPD pattern comprising peaks, in terms of 2-theta, at 9.6±0.2°, 14.9±0.2°, 20.5±0.2°, and 25.1±0.2°, and a differential scanning calorimetry thermogram substantially in accord with FIG. 3A.

In various embodiments, the present inventions provide a crystalline form of (S)-TPMA HCl characterized by an XRPD pattern comprising peaks, in terms of 2-theta, at 9.6±0.2°, 14.9±0.2°, 20.5±0.2°, and 25.1±0.2°, and a Raman spectra substantially in accord with FIG. 4A and/or a THz Raman spectra substantially in accord with FIG. 4D.

In various embodiments, the present inventions provide a crystalline form of (S)-TPMA HCl characterized by an XRPD pattern comprising peaks, in terms of 2-theta, at 8.6±0.2°, 17.2±0.2°, and 25.9±0.2°, and a DSC thermogram having a peak at 215±2° C.

In various embodiments, the present inventions provide a crystalline form of (S)-TPMA HCl characterized by an XRPD pattern comprising peaks, in terms of 2-theta, at 8.6±0.2°, 17.2±0.2°, and 25.9±0.2°, and a differential scanning calorimetry thermogram substantially in accord with FIG. 3B or FIG. 3C.

In various embodiments, the present inventions provide a crystalline form of (S)-TPMA HCl characterized by an XRPD pattern comprising peaks, in terms of 2-theta, at 8.6±0.2°, 17.2±0.2°, and 25.9±0.2°, and a Raman spectra substantially in accord with FIG. 4B and/or a THz Raman spectra substantially in accord with FIG. 4E.

In various embodiments, the present inventions provide a crystalline form of (S)-TPMA HCl that is the substantially non-hygroscopic. In various embodiments, the present inventions provide a crystalline (S)-TPMA HCl of Form A that has a maximum mass change of less than about 1%, less than about 0.5%, less than about 0.3%, less than about 0.2%, or less than about 0.1% in water sorption isotherms as measured by dynamic vapor sorption (DVS), at 25° C. scanned over 0 to 90% relative humidity.

Figure 5:
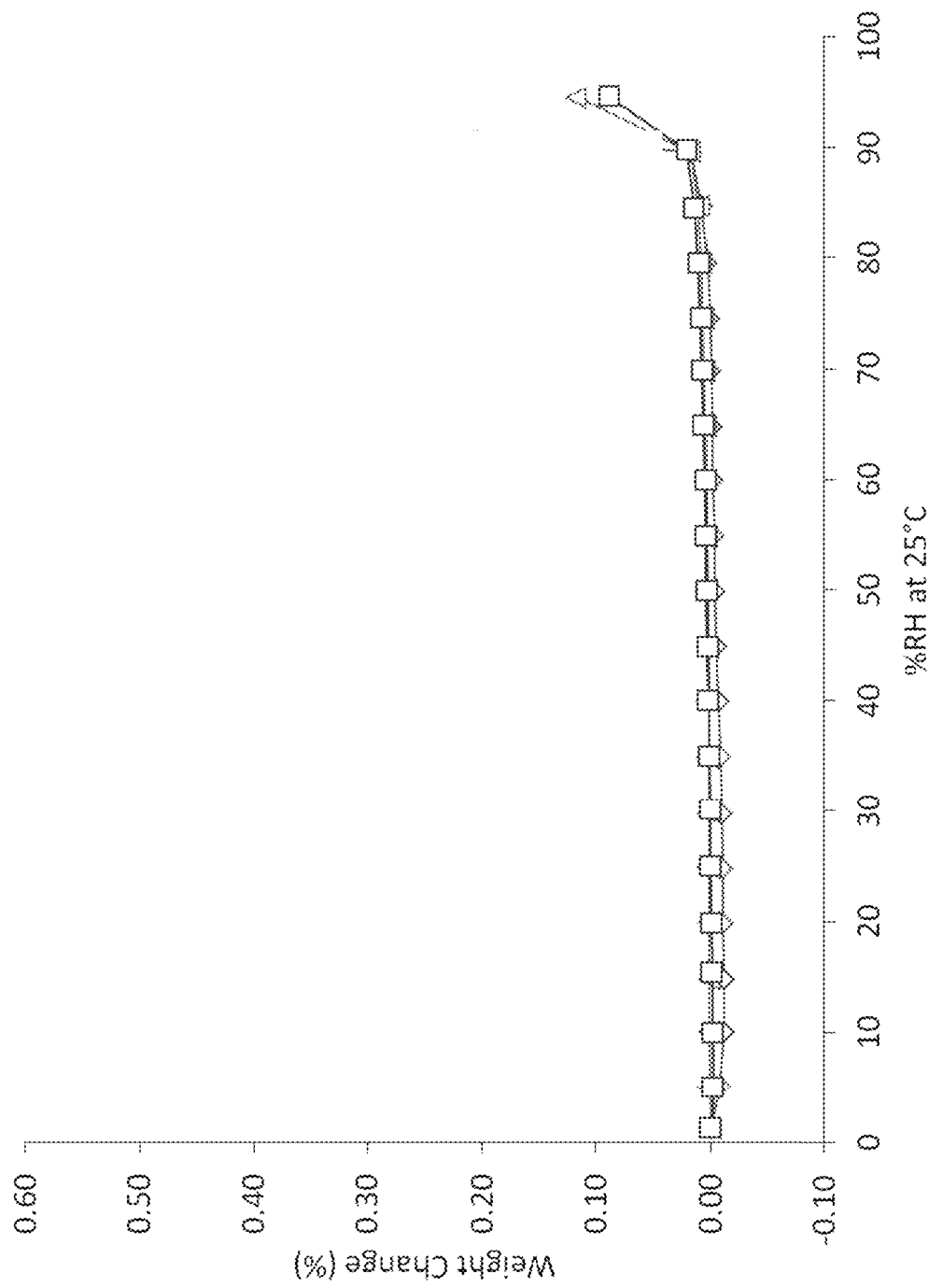
FIG. 5 is a DVS water sorption isotherm for (S)-(4,5-dihydro-7H-thieno[2,3-c]pyran-7-yl)-N-methylmethanamine hydrochloride, of polymorph Form A.

FIG. 5 and Table 5 present DVS water sorption isotherms for crystalline (S)-TPMA HCl of Form A. The water sorption isotherms were generated using a VTI SGA-100 dynamic vapor sorption analyzer. Samples were dried pre-analysis at 25° C. with equilibrium criteria of 0.0000 wt % changes in 5 minutes or a maximum of 180 minutes. Isotherm equilibrium criteria were the lesser of 0.01 wt % change in 5 minutes or 180 minutes at each relative humidity (RH) step. Temperature was fixed at 25° C. and the relative humidity steps (5% to 95% to 5%) were in 5% increments. Initial sample size ranged from 41 to 47 mg.

FIG. 5 presents DVS water sorption for two different lots of crystalline (S)-TPMA HCl of Form A, and Table 5 lists the data plotted in FIG. 5. As can be seen, crystalline (S)-TPMA HCl Form A is substantially non-hygroscopic, exhibiting a maximum mass change of only 0.2% at 95% relative humidity (RH), and less than a 0.1% mass change at 90% RH and below.

TABLE 5

(S)-TPMA HCl Form A DVS Water Sorption Isotherms of FIG. 5

| Relative Humidity (%) | Lot 1 (square symbols) | | Lot 2 (upright triangle symbols) | |
|---|---|---|---|---|
| | Change Mass (%) | Elapse Time (min) | Change Mass (%) | Elapse Time (min) |
| 1 | 0.000 | 155.6 | 0.000 | 41.6 |
| 5 | -0.002 | 329.5 | 0.001 | 52.2 |
| 10 | -0.002 | 416.5 | 0.001 | 61.2 |
| 15 | -0.001 | 425.0 | 0.001 | 69.7 |
| 20 | -0.001 | 434.5 | 0.001 | 81.7 |
| 25 | 0.000 | 454.0 | 0.001 | 93.7 |
| 30 | 0.001 | 466.0 | 0.001 | 105.2 |
| 35 | 0.001 | 479.5 | 0.002 | 118.2 |
| 40 | 0.002 | 491.0 | 0.002 | 129.7 |
| 45 | 0.003 | 500.6 | 0.003 | 139.2 |
| 50 | 0.003 | 511.6 | 0.003 | 150.2 |

TABLE 5-continued (S)-TPMA HCl Form A DVS Water Sorption Isotherms of FIG. 5

| Relative Humidity (%) | Lot 1 (square symbols) | | Lot 2 (upright triangle symbols) | |
|---|---|---|---|---|
| | Change Mass (%) | Elapse Time (min) | Change Mass (%) | Elapse Time (min) |
| 55 | 0.004 | 520.6 | 0.003 | 159.2 |
| 60 | 0.005 | 531.6 | 0.004 | 170.2 |
| 65 | 0.006 | 542.6 | 0.005 | 181.2 |
| 70 | 0.007 | 553.6 | 0.005 | 192.2 |
| 75 | 0.008 | 562.6 | 0.006 | 201.2 |
| 80 | 0.010 | 571.6 | 0.008 | 210.2 |
| 85 | 0.014 | 580.6 | 0.011 | 219.2 |
| 90 | 0.021 | 589.6 | 0.017 | 228.2 |
| 95 | 0.088 | 616.0 | 0.117 | 260.2 |

In various embodiments, the present inventions provide a crystalline form of (S)-TPMA HCl characterized by an XRPD pattern comprising peaks, in terms of 2-theta, at 9.6±0.2°, 14.9±0.2°, 20.5±0.2°, and 25.1±0.2°; in various embodiments, further characterized by peaks at 20.2±0.2° and 20.8±0.2°; and in various embodiments, further characterized by two or more prominent peaks in its XRPD pattern selected from those at 17.9±0.2°, 24.8±0.2° and 27.1±0.2°, in terms of 2-theta. In various embodiments, the present inventions provide a crystalline form of (S)-TPMA HCl characterized by an XRPD pattern substantially in accord with FIG. 2B.

In various embodiments, the present inventions provide a crystalline form of (S)-TPMA HCl of Form A characterized by the following properties, an XRPD pattern comprising peaks, in terms of 2-theta, at 9.6±0.2°, 14.9±0.2°, 20.5±0.2°, and 25.1±0.2°, a melting point of 214±2° C., a chiral purity of greater than about 99%, a chemical purity greater than about 99%, a residual solvent content of less than about 8000 ppm, and is substantially non-hygroscopic.

In various embodiments, the present inventions provide a crystalline form of (S)-TPMA HCl characterized by the following properties, an XRPD pattern comprising peaks, in terms of 2-theta, at 9.6±0.2°, 14.9±0.2°, 20.5±0.2°, and 25.1±0.2° and one or more of the following:
  (a) the powder x-ray diffraction pattern further comprising peaks, in terms of 2-theta, at 20.2±0.2° and 20.8±0.2°;
  (b) the powder x-ray diffraction pattern further comprising a prominent peak, in terms of 2-theta, at two or more of 17.9±0.2°, 24.8±0.2° and 27.1±0.2°;
  (c) a melting point of 214±2° C.;
  (d) a differential scanning calorimetry thermogram comprising a peak at 214±2° C.;
  (e) a differential scanning calorimetry thermogram substantially in accord with FIG. 3A;
  (f) a Raman spectra substantially in accord with FIG. 4A, a THz Raman spectra substantially in accord with FIG. 4D, or both;
  (g) a chiral purity of greater than about: (i) 90%, (ii) 95%, (iii) 97%, (iv) 99%, (v) 99.5%, (vi) 99.7%, or (vii) 99.9%;
  (h) a chemical purity of greater than about: (i) 80%, (ii) 90%, (iii) 95%, (iv) 97%, (v) 99%, (vi) 99.5%, (vii) 99.7%, or (viii) 99.9%;
  (i) residual solvents present in an amount less than about: (i) 8000 ppm, (ii) 6000 ppm, (iii) 4000 ppm, (iv) 2000 ppm, (v) 1000 ppm, (vi) 800 ppm, or 500 ppm;
  (j) as measured by dynamic vapor sorption (DVS), at 25° C. scanned over 0 to 95% relative humidity, a maximum mass change in water sorption isotherms of less than about (i) 2%, (ii) 1%, (iii) 0.5%, (iv) 0.4%, (v) 0.3%, (vi) 0.2%, or (vii) 0.1%; and
  (k) as measured by dynamic vapor sorption (DVS), at 25° C. scanned over 0 to 90% relative humidity, a maximum mass change in water sorption isotherms of less than about (i) 1%, (ii) 0.5%, (iii) 0.4%, (iv) 0.3%, (v) 0.2%, or (vi) 0.1%; and preferably less than about 0.2%.

In various embodiments, the present inventions provide a crystalline form of (S)-TPMA HCl characterized by an XRPD pattern comprising peaks, in terms of 2-theta, at 8.6±0.2°, 17.2±0.2°, and 25.9±0.2°; and in various embodiments, further characterized by peaks in its XRPD pattern selected at, 23.2±0.2°, and 31.5±0.2°, in terms of 2-theta. In various embodiments, the present inventions provide a crystalline form of (S)-TPMA HCl characterized by an XRPD pattern substantially in accord with FIG. 2C.

In various embodiments, the present inventions provide a crystalline form of (S)-TPMA HCl of Form B characterized by the following properties, an XRPD pattern comprising peaks, in terms of 2-theta, at 8.6±0.2°, 17.2±0.2°, and 25.9±0.2°, and a melting point of 215±2° C.

In various embodiments, the present inventions provide a crystalline form of (S)-TPMA HCl characterized by the following properties, an XRPD pattern comprising peaks, in terms of 2-theta, at 8.6±0.2°, 17.2±0.2°, and 25.9±0.2° and one or more of the following:
  (a) the powder x-ray diffraction pattern further comprising peaks, in terms of 2-theta, at 23.2±0.2°, and 31.5±0.2°;
  (b) a melting point of 215±2° C.;
  (c) a differential scanning calorimetry thermogram comprising a peak at 215±2° C.;
  (d) a differential scanning calorimetry thermogram substantially in accord with FIG. 3B or 3C;
  (e) a Raman spectra substantially in accord with FIG. 4B, a THz Raman spectra substantially in accord with FIG. 4E, or both;
  (f) a chiral purity of greater than about: (i) 90%, (ii) 95%, (iii) 97%, (iv) 99%, (v) 99.5%, (vi) 99.7%, or (vii) 99.9%;
  (g) a chemical purity of greater than about: (i) 80%, (ii) 90%, (iii) 95%, (iv) 97%, (v) 99%, (vi) 99.5%, (vii) 99.7%, or (viii) 99.9%; and
  (h) residual solvents present in an amount less than about: (i) 8000 ppm, (ii) 6000 ppm, (iii) 4000 ppm, (iv) 2000 ppm, (v) 1000 ppm, (vi) 800 ppm, or 500 ppm; and In some embodiments, provided herein is compound selected from:
(S)-(4,5-dihydro-7H-thieno[2,3-c]pyran-7-yl)-N-methylmethanamine besylate,
(S)-(4,5-dihydro-7H-thieno[2,3-c]pyran-7-yl)-N-methylmethanamine R-mandelate,
(S)-(4,5-dihydro-7H-thieno[2,3-c]pyran-7-yl)-N-methylmethanamine L-tartrate,
(S)-(4,5-dihydro-7H-thieno[2,3-c]pyran-7-yl)-N-methylmethanamine D-tartrate,
(S)-(4,5-dihydro-7H-thieno[2,3-c]pyran-7-yl)-N-methylmethanamine mesylate, and
(S)-(4,5-dihydro-7H-thieno[2,3-c]pyran-7-yl)-N-methylmethanamine L-malate.

(S)-(4,5-dihydro-7H-thieno[2,3-c]pyran-7-yl)-N-methylmethanamine besylate

Provided herein is (S)-(4,5-dihydro-7H-thieno[2,3-c]pyran-7-yl)-N-methylmethanamine besylate, which is also referred to as (S)-TPMA besylate. In some embodiments, (S)-TPMA besylate is crystalline.

In some embodiments, the crystalline form of (S)-TPMA besylate is characterized by a powder x-ray diffraction pattern comprising peaks, in terms of 2-theta, at 6.1±0.2°, 12.3±0.2°, and 16.7±0.2°. In some embodiments, the crystalline (S)-TPMA besylate is characterized by a powder x-ray diffraction pattern comprising peaks, in terms of 2-theta, at 6.1±0.2°. In some embodiments, the crystalline (S)-TPMA besylate is characterized by a powder x-ray diffraction pattern comprising peaks, in terms of 2-theta, at 12.3±0.2°. In some embodiments, the crystalline (S)-TPMA besylate is characterized by a powder x-ray diffraction pattern comprising peaks, in terms of 2-theta, at 16.7±0.2°. In some embodiments, the crystalline (S)-TPMA besylate is further characterized by the powder x-ray diffraction pattern further comprising a peak, in terms of 2-theta, at 19.0±0.2° and 24.7±0.2°. In some embodiments, the crystalline (S)-TPMA besylate is further characterized by the powder x-ray diffraction pattern further comprising a peak, in terms of 2-theta, at two or more of 21.9±0.2°, 22.4±0.2° and 22.8±0.2°.

Figure 25:
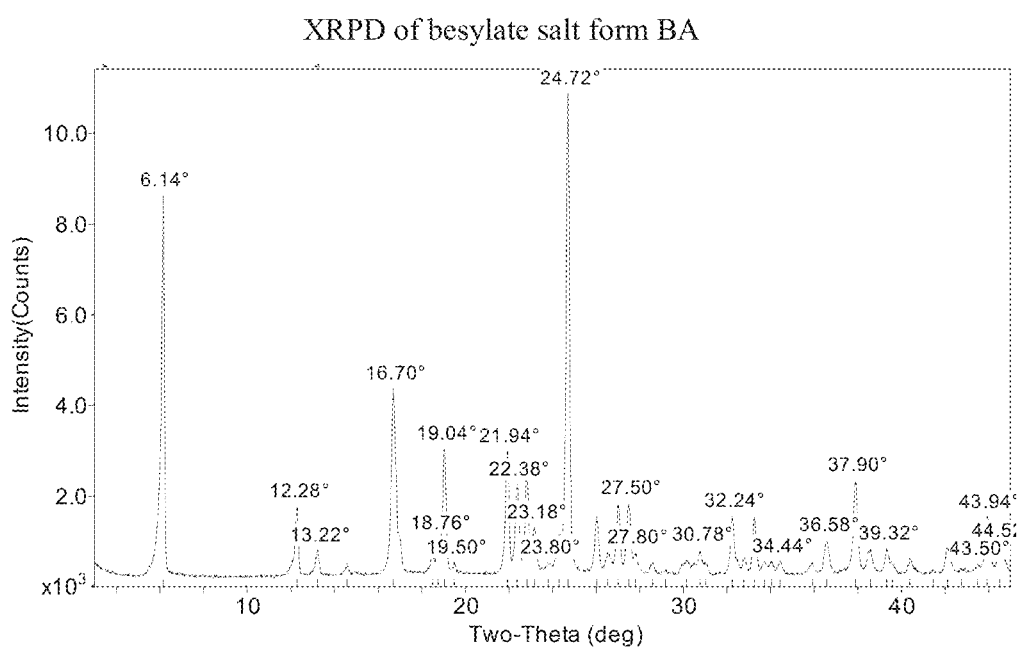
FIG. 25 presents an XRPD pattern for (S)-(4,5-dihydro-7H-thieno[2,3-c]pyran-7-yl)-N-methylmethanamine besylate Form BA.

In some embodiments, the crystalline (S)-TPMA besylate is characterized by a powder x-ray diffraction pattern substantially in accord with FIG. 25.

In some embodiments, the crystalline (S)-TPMA besylate has a differential scanning calorimetry thermogram comprising a peak at 142±2° C. In some embodiments, the crystalline (S)-TPMA besylate has a differential scanning calorimetry thermogram substantially in accord with FIG. 26.

In some embodiments, the crystalline form of (S)-TPMA besylate is characterized by a powder x-ray diffraction pattern comprising peaks, in terms of 2-theta, at 6.1±0.2°, 12.3±0.2°, and 16.7±0.2°, and a powder x-ray diffraction pattern substantially in accord with FIG. 25. In some embodiments, the crystalline form of (S)-TPMA besylate is characterized by a powder x-ray diffraction pattern comprising peaks, in terms of 2-theta, at 6.1±0.2°, 12.3±0.2°, and 16.7±0.2°, and has a differential scanning calorimetry thermogram comprising a peak at 142±2° C. In some embodiments, the crystalline form of (S)-TPMA besylate is characterized by a powder x-ray diffraction pattern comprising peaks, in terms of 2-theta, at 6.1±0.2°, 12.3±0.2°, and 16.7±0.2°, and has a differential scanning calorimetry thermogram substantially in accord with FIG. 26.

In some embodiments, the crystalline (S)-TPMA besylate is characterized by monoclinic space group P21. In some embodiments, the crystalline (S)-TPMA besylate has unit cell dimensions: a is about 7.7 Å, b is about 7.5 Å, c is about 14.8 Å, α is about 90°, β is about 103°, and γ is about 90°.

In some embodiments, the substance comprising (S)-TPMA besylate where the chiral purity of the substance is greater than about 90% (S)-TPMA besylate. In some embodiments, the substance comprising (S)-TPMA besylate where the chiral purity of the substance is greater than about 95% (S)-TPMA besylate. In some embodiments, the substance comprising (S)-TPMA besylate where the chiral purity of the substance is greater than about 97.5% (S)-TPMA besylate. In some embodiments, the substance comprising (S)-TPMA besylate where the chiral purity of the substance is greater than about 99% (S)-TPMA besylate.

In some embodiments, the substance comprising (S)-TPMA besylate where the chemical purity of the substance is greater than about 90% (S)-TPMA besylate. In some embodiments, the substance comprising (S)-TPMA besylate where the chemical purity of the substance is greater than about 95% (S)-TPMA besylate. In some embodiments, the substance comprising (S)-TPMA besylate where the chemical purity of the substance is greater than about 97.5% (S)-TPMA besylate. In some embodiments, the substance comprising (S)-TPMA besylate where the chemical purity of the substance is greater than about 99% (S)-TPMA besylate.

(S)-(4,5-dihydro-7H-thieno[2,3-c]pyran-7-yl)-N-methylmethanamine R-mandelate Provided herein is (S)-(4,5-dihydro-7H-thieno[2,3-c]pyran-7-yl)-N-methylmethanamine R-mandelate, which is also referred to as (S)-TPMA R-mandelate. In some embodiments, (S)-TPMA R-mandelate is crystalline.

In some embodiments, the crystalline form of (S)-TPMA R-mandelate is characterized by a powder x-ray diffraction pattern comprising peaks, in terms of 2-theta, at 9.4±0.2°, 14.3±0.2°, and 16.3±0.2°. In some embodiments, the crystalline (S)-TPMA R-mandelate is characterized by a powder x-ray diffraction pattern comprising peaks, in terms of 2-theta, at 9.4±0.2°. In some embodiments, the crystalline (S)-TPMA R-mandelate is characterized by a powder x-ray diffraction pattern comprising peaks, in terms of 2-theta, at 14.3±0.2°. In some embodiments, the crystalline (S)-TPMA R-mandelate is characterized by a powder x-ray diffraction pattern comprising peaks, in terms of 2-theta, at 16.3±0.2°. In some embodiments, the crystalline (S)-TPMA R-mandelate is further characterized by the powder x-ray diffraction pattern further comprising a peak, in terms of 2-theta, at 4.7±0.2° and 19.6±0.2°. In some embodiments, the crystalline (S)-TPMA R-mandelate is further characterized by the powder x-ray diffraction pattern further comprising a peak, in terms of 2-theta, at two or more of 21.8±0.2°, 23.7±0.2° and 25.0±0.2°.

Figure 11:
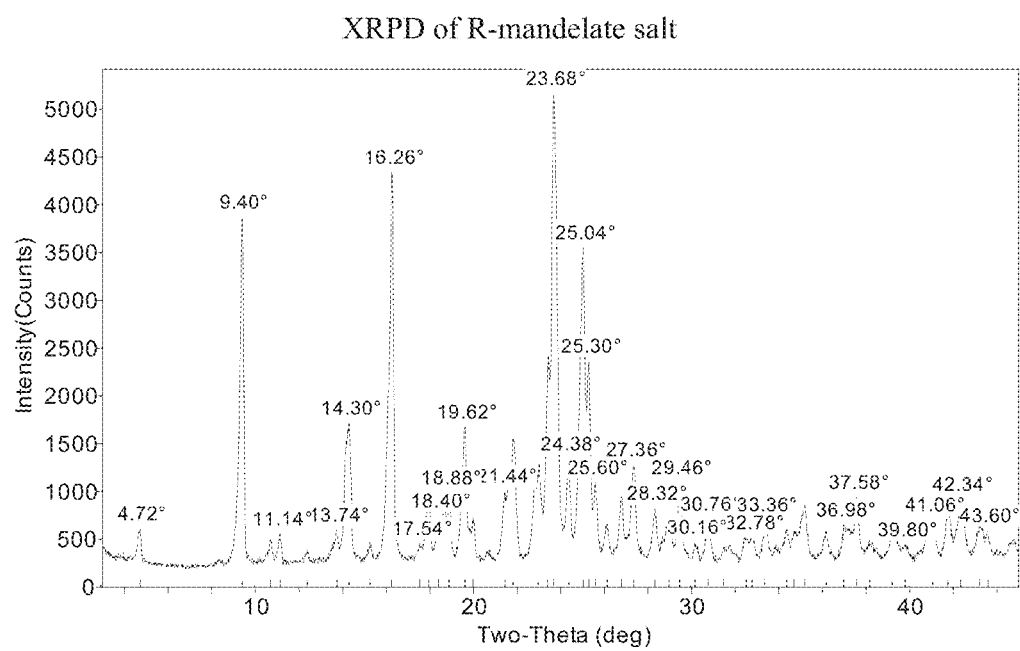
FIG. 11 presents an XRPD pattern for (S)-(4,5-dihydro-7H-thieno[2,3-c]pyran-7-yl)-N-methylmethanamine R-mandelate.

In some embodiments, the crystalline (S)-TPMA R-mandelate is characterized by a powder x-ray diffraction pattern substantially in accord with FIG. 11.

In some embodiments, the crystalline (S)-TPMA R-mandelate has a differential scanning calorimetry thermogram comprising a peak at 129±2° C. In some embodiments, the crystalline (S)-TPMA R-mandelate has a differential scanning calorimetry thermogram substantially in accord with FIG. 12.

In some embodiments, the crystalline form of (S)-TPMA R-mandelate is characterized by a powder x-ray diffraction pattern comprising peaks, in terms of 2-theta, at 9.4±0.2°, 14.3±0.2°, and 16.3±0.2°, and a powder x-ray diffraction pattern substantially in accord with FIG. 11. In some embodiments, the crystalline form of (S)-TPMA R-mandelate is characterized by a powder x-ray diffraction pattern comprising peaks, in terms of 2-theta, at 9.4±0.2°, 14.3±0.2°, and 16.3±0.2°, and has a differential scanning calorimetry thermogram comprising a peak at 129±2° C. In some embodiments, the crystalline form of (S)-TPMA R-mandelate is characterized by a powder x-ray diffraction pattern comprising peaks, in terms of 2-theta, at 9.4±0.2°, 14.3±0.2°, and 16.3±0.2°, and has a differential scanning calorimetry thermogram substantially in accord with FIG. 12.

In some embodiments, the substance comprising (S)-TPMA R-mandelate where the chiral purity of the substance is greater than about 90% (S)-TPMA R-mandelate. In some embodiments, the substance comprising (S)-TPMA R-mandelate where the chiral purity of the substance is greater than about 95% (S)-TPMA R-mandelate. In some embodiments, the substance comprising (S)-TPMA R-mandelate where the chiral purity of the substance is greater than about 97.5%

(S)-TPMA R-mandelate. In some embodiments, the substance comprising (S)-TPMA R-mandelate where the chiral purity of the substance is greater than about 99% (S)-TPMA R-mandelate.

In some embodiments, the substance comprising (S)-TPMA R-mandelate where the chemical purity of the substance is greater than about 90% (S)-TPMA R-mandelate. In some embodiments, the substance comprising (S)-TPMA R-mandelate where the chemical purity of the substance is greater than about 95% (S)-TPMA R-mandelate. In some embodiments, the substance comprising (S)-TPMA R-mandelate where the chemical purity of the substance is greater than about 97.5% (S)-TPMA R-mandelate. In some embodiments, the substance comprising (S)-TPMA R-mandelate where the chemical purity of the substance is greater than about 99% (S)-TPMA R-mandelate.

(S)-(4,5-dihydro-7H-thieno[2,3-c]pyran-7-yl)-N-methylmethanamine L-tartrate

Provided herein is (S)-(4,5-dihydro-7H-thieno[2,3-c]pyran-7-yl)-N-methylmethanamine L-tartrate, which is also referred to as (S)-TPMA L-tartrate. In some embodiments, (S)-TPMA L-tartrate is crystalline.

In some embodiments, the crystalline form of (S)-TPMA L-tartrate is characterized by a powder x-ray diffraction pattern comprising peaks, in terms of 2-theta, at 6.3±0.2°, 12.7±0.2°, and 19.1±0.2°. In some embodiments, the crystalline (S)-TPMA L-tartrate is characterized by a powder x-ray diffraction pattern comprising peaks, in terms of 2-theta, at 6.3±0.2°. In some embodiments, the crystalline (S)-TPMA L-tartrate is characterized by a powder x-ray diffraction pattern comprising peaks, in terms of 2-theta, at 12.7±0.2°. In some embodiments, the crystalline (S)-TPMA L-tartrate is characterized by a powder x-ray diffraction pattern comprising peaks, in terms of 2-theta, at 19.1±0.2°. In some embodiments, the crystalline (S)-TPMA L-tartrate is further characterized by the powder x-ray diffraction pattern further comprising a peak, in terms of 2-theta, at 12.9±0.2°, 16.0±0.2°, 17.1±0.2°, and 17.4±0.2°. In some embodiments, the crystalline (S)-TPMA L-tartrate is further characterized by the powder x-ray diffraction pattern further comprising a peak, in terms of 2-theta, at two or more of 18.1±0.2°, 22.9±0.2°, 25.8±0.2°, and 26.3±0.2°.

Figure 14:
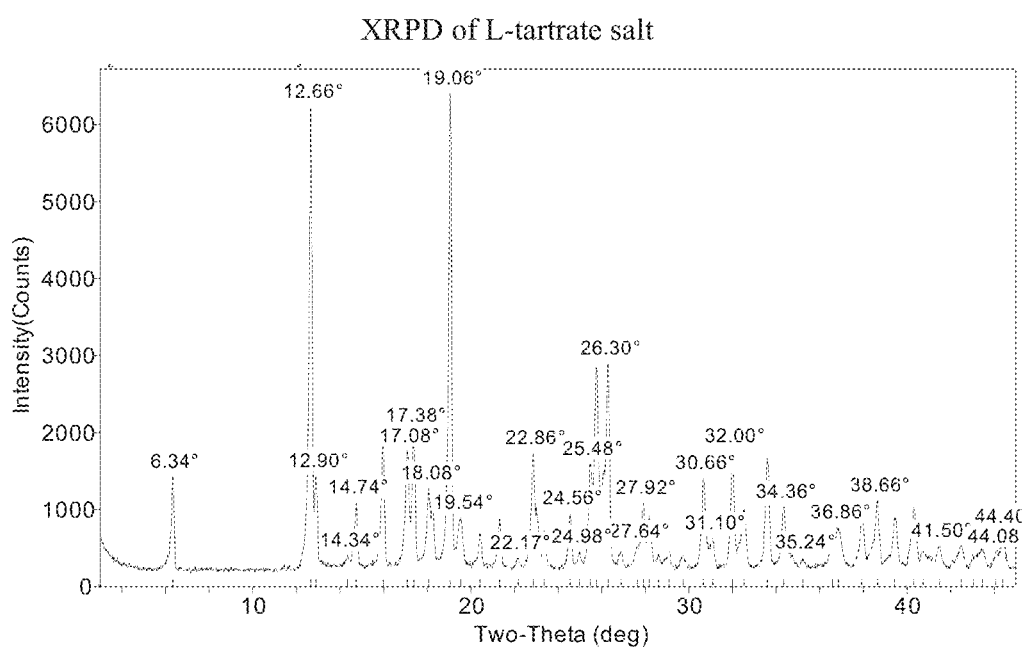
FIG. 14 presents an XRPD pattern for (S)-(4,5-dihydro-7H-thieno[2,3-c]pyran-7-yl)-N-methylmethanamine L-tartrate.

In some embodiments, the crystalline (S)-TPMA L-tartrate is characterized by a powder x-ray diffraction pattern substantially in accord with FIG. 14. In some embodiments, the crystalline (S)-TPMA L-tartrate has a differential scanning calorimetry thermogram comprising a peak at 152±2° C.

Figure 15:
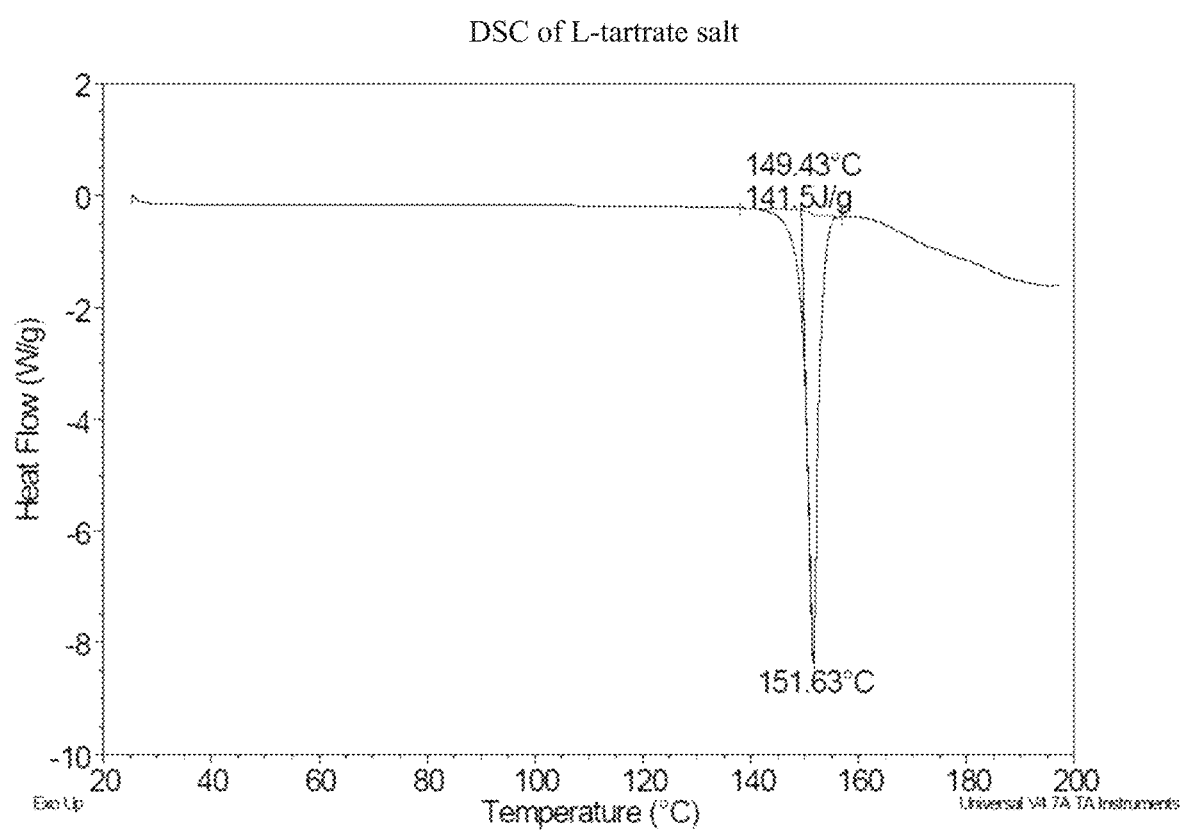
FIG. 15 is a DSC thermogram for (S)-(4,5-dihydro-7H-thieno[2,3-c]pyran-7-yl)-N-methylmethanamine L-tartrate.

In some embodiments, the crystalline (S)-TPMA L-tartrate has a differential scanning calorimetry thermogram substantially in accord with FIG. 15.

In some embodiments, the crystalline form of (S)-TPMA L-tartrate is characterized by a powder x-ray diffraction pattern comprising peaks, in terms of 2-theta, at 6.3±0.2°, 12.7±0.2°, and 19.1±0.2°, and a powder x-ray diffraction pattern substantially in accord with FIG. 14. In some embodiments, the crystalline form of (S)-TPMA L-tartrate is characterized by a powder x-ray diffraction pattern comprising peaks, in terms of 2-theta, at 6.3±0.2°, 12.7±0.2°, and 19.1±0.2°, and has a differential scanning calorimetry thermogram comprising a peak at 152±2° C. In some embodiments, the crystalline form of (S)-TPMA L-tartrate is characterized by a powder x-ray diffraction pattern comprising peaks, in terms of 2-theta, at 6.3±0.2°, 12.7±0.2°, and 19.1±0.2°, and has a differential scanning calorimetry thermogram substantially in accord with FIG. 15.

In some embodiments, the substance comprising (S)-TPMA L-tartrate where the chiral purity of the substance is greater than about 90% (S)-TPMA L-tartrate. In some embodiments, the substance comprising (S)-TPMA L-tartrate where the chiral purity of the substance is greater than about 95% (S)-TPMA L-tartrate. In some embodiments, the substance comprising (S)-TPMA L-tartrate where the chiral purity of the substance is greater than about 97.5% (S)-TPMA L-tartrate. In some embodiments, the substance comprising (S)-TPMA L-tartrate where the chiral purity of the substance is greater than about 99% (S)-TPMA L-tartrate.

In some embodiments, the substance comprising (S)-TPMA L-tartrate where the chemical purity of the substance is greater than about 90% (S)-TPMA L-tartrate. In some embodiments, the substance comprising (S)-TPMA L-tartrate where the chemical purity of the substance is greater than about 95% (S)-TPMA L-tartrate. In some embodiments, the substance comprising (S)-TPMA L-tartrate where the chemical purity of the substance is greater than about 97.5% (S)-TPMA L-tartrate. In some embodiments, the substance comprising (S)-TPMA L-tartrate where the chemical purity of the substance is greater than about 99% (S)-TPMA L-tartrate.

(S)-(4,5-dihydro-7H-thieno[2,3-c]pyran-7-yl)-N-methylmethanamine D-tartrate

Provided herein is (S)-(4,5-dihydro-7H-thieno[2,3-c]pyran-7-yl)-N-methylmethanamine D-tartrate, which is also referred to as (S)-TPMA D-tartrate. In some embodiments, (S)-TPMA D-tartrate is crystalline. In some embodiments, the crystalline form of (S)-TPMA D-tartrate is referred to as Form DA, Form DB, or Form DC.

In some embodiments, the crystalline Form DA of (S)-TPMA D-tartrate is characterized by a powder x-ray diffraction pattern comprising peaks, in terms of 2-theta, at 7.0±0.2°, 15.0±0.2°, and 17.6±0.2°. In some embodiments, the crystalline Form DA of (S)-TPMA D-tartrate is characterized by a powder x-ray diffraction pattern comprising peaks, in terms of 2-theta, at 7.0±0.2°. In some embodiments, the crystalline Form DA of (S)-TPMA D-tartrate is characterized by a powder x-ray diffraction pattern comprising peaks, in terms of 2-theta, at 15.0±0.2°. In some embodiments, the crystalline Form DA of (S)-TPMA D-tartrate is characterized by a powder x-ray diffraction pattern comprising peaks, in terms of 2-theta, at 17.6±0.2°. In some embodiments, the crystalline Form DA of (S)-TPMA D-tartrate is further characterized by the powder x-ray diffraction pattern further comprising a peak, in terms of 2-theta, at 12.9±0.2°, 19.5±0.2°, and 20.8±0.2°. In some embodiments, the crystalline Form DA of (S)-TPMA D-tartrate is further characterized by the powder x-ray diffraction pattern further comprising a peak, in terms of 2-theta, at two or more of 21.8±0.2°, 22.0±0.2°, 26.0±0.2°, and 27.8±0.2°.

Figure 17:
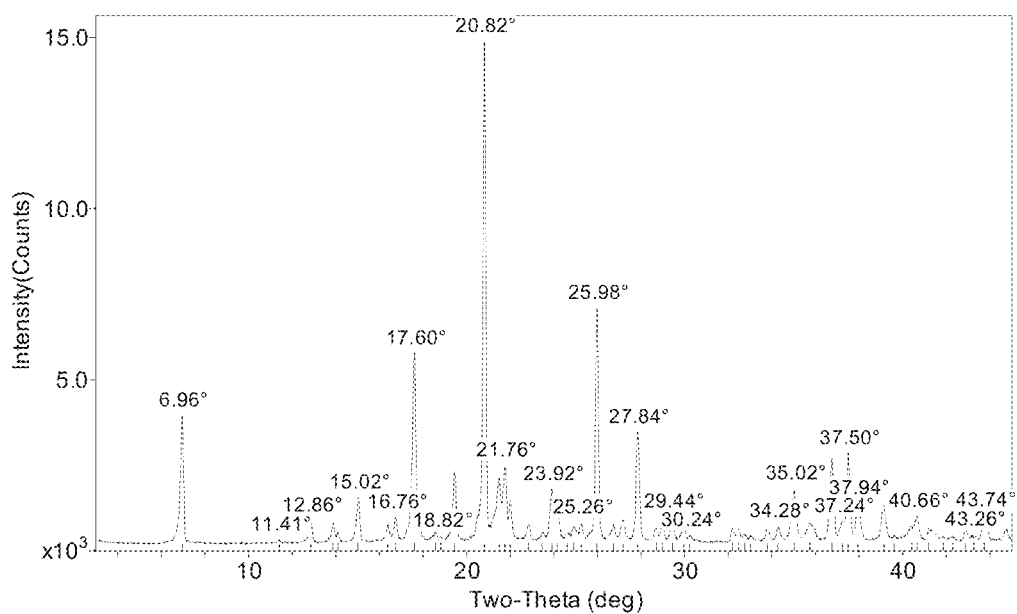
FIG. 17 presents an XRPD pattern for (S)-(4,5-dihydro-7H-thieno[2,3-c]pyran-7-yl)-N-methylmethanamine D-tartrate Form DA.

In some embodiments, the crystalline Form DA of (S)-TPMA D-tartrate is characterized by a powder x-ray diffraction pattern substantially in accord with FIG. 17.

In some embodiments, the crystalline Form DA of (S)-TPMA D-tartrate has a differential scanning calorimetry thermogram comprising a peak at 169±2° C. In some embodiments, the crystalline Form DA of (S)-TPMA D-tartrate has a differential scanning calorimetry thermogram substantially in accord with FIG. 20.

In some embodiments, the crystalline Form DA of (S)-TPMA D-tartrate is characterized by a powder x-ray diffraction pattern comprising peaks, in terms of 2-theta, at 7.0±0.2°, 15.0±0.2°, and 17.6±0.2°, and a powder x-ray diffraction pattern substantially in accord with FIG. 17. In some embodiments, the crystalline Form DA of (S)-TPMA D-tartrate is characterized by a powder x-ray diffraction pattern comprising peaks, in terms of 2-theta, at 7.0±0.2°, 15.0±0.2°, and 17.6±0.2°, and has a differential scanning calorimetry thermogram comprising a peak at 169±2° C. In some embodiments, the crystalline Form DA of (S)-TPMA D-tartrate is characterized by a powder x-ray diffraction pattern comprising peaks, in terms of 2-theta, at 7.0±0.2°, 15.0±0.2°, and 17.6±0.2°, and has a differential scanning calorimetry thermogram substantially in accord with FIG. 20.

In some embodiments, the crystalline Form DB of (S)-TPMA D-tartrate is characterized by a powder x-ray diffraction pattern comprising peaks, in terms of 2-theta, at 11.6±0.2°, 17.5±0.2°, and 20.7±0.2°. In some embodiments, the crystalline Form DB of (S)-TPMA D-tartrate is characterized by a powder x-ray diffraction pattern comprising peaks, in terms of 2-theta, at 11.6±0.2°. In some embodiments, the crystalline Form DB of (S)-TPMA D-tartrate is characterized by a powder x-ray diffraction pattern comprising peaks, in terms of 2-theta, at 17.5±0.2°. In some embodiments, the crystalline Form DB of (S)-TPMA D-tartrate is characterized by a powder x-ray diffraction pattern comprising peaks, in terms of 2-theta, at 20.7±0.2°. In some embodiments, the crystalline Form DB of (S)-TPMA D-tartrate is further characterized by the powder x-ray diffraction pattern further comprising a peak, in terms of 2-theta, at 23.4±0.2°, 29.2±0.2°, and 35.8±0.2°. In some embodiments, the crystalline Form DB of (S)-TPMA D-tartrate is further characterized by the powder x-ray diffraction pattern further comprising a peak, in terms of 2-theta, at two or more of 26.9±0.2°, 33.4±0.2°, 35.3±0.2°, and 36.7±0.2°.

Figure 18:
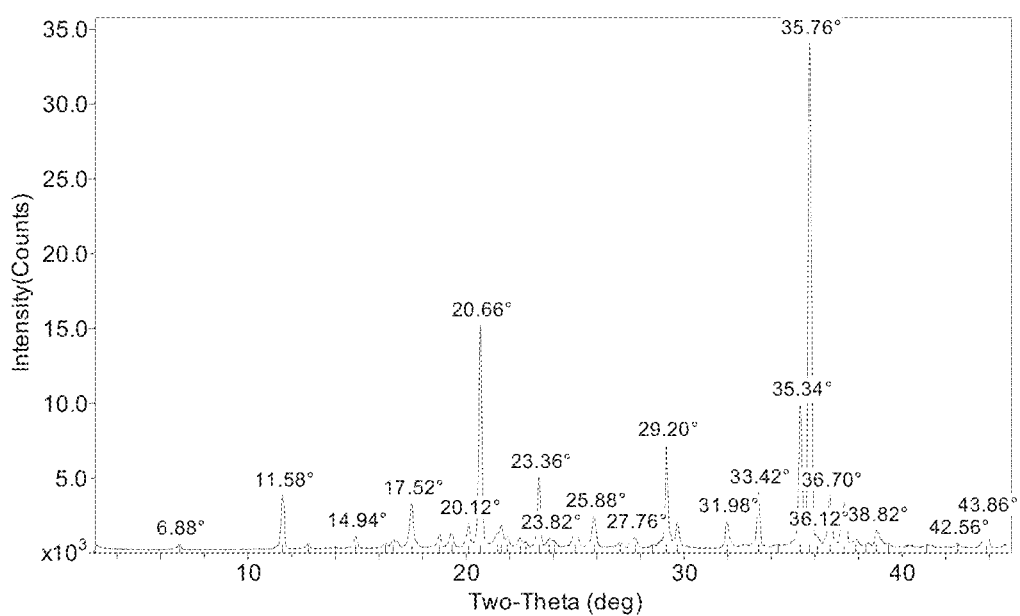
FIG. 18 presents an XRPD pattern for (S)-(4,5-dihydro-7H-thieno[2,3-c]pyran-7-yl)-N-methylmethanamine D-tartrate Form DB.

In some embodiments, the crystalline Form DB of (S)-TPMA D-tartrate is characterized by a powder x-ray diffraction pattern substantially in accord with FIG. 18.

In some embodiments, the crystalline Form DB of (S)-TPMA D-tartrate has a differential scanning calorimetry thermogram comprising a peak at 111±2° C. In some embodiments, the crystalline Form DB of (S)-TPMA D-tartrate has a differential scanning calorimetry thermogram substantially in accord with FIG. 21.

In some embodiments, the crystalline Form DB of (S)-TPMA D-tartrate is characterized by a powder x-ray diffraction pattern comprising peaks, in terms of 2-theta, at 11.6±0.2°, 17.5±0.2°, and 20.7±0.2°, and a powder x-ray diffraction pattern substantially in accord with FIG. 18. In some embodiments, the crystalline Form DB of (S)-TPMA D-tartrate is characterized by a powder x-ray diffraction pattern comprising peaks, in terms of 2-theta, at 11.6±0.2°, 17.5±0.2°, and 20.7±0.2°, and has a differential scanning calorimetry thermogram comprising a peak at 111±2° C. In some embodiments, the crystalline Form DB of (S)-TPMA D-tartrate is characterized by a powder x-ray diffraction pattern comprising peaks, in terms of 2-theta, at 11.6±0.2°, 17.5±0.2°, and 20.7±0.2°, and has a differential scanning calorimetry thermogram substantially in accord with FIG. 21.

In some embodiments, the crystalline Form DC of (S)-TPMA D-tartrate is characterized by a powder x-ray diffraction pattern comprising peaks, in terms of 2-theta, at 10.8±0.2°, 15.8±0.2°, and 17.5±0.2°. In some embodiments, the crystalline Form DC of (S)-TPMA D-tartrate is characterized by a powder x-ray diffraction pattern comprising peaks, in terms of 2-theta, at 10.8±0.2°. In some embodiments, the crystalline Form DC of (S)-TPMA D-tartrate is characterized by a powder x-ray diffraction pattern comprising peaks, in terms of 2-theta, at 15.8±0.2°. In some embodiments, the crystalline Form DC of (S)-TPMA D-tartrate is characterized by a powder x-ray diffraction pattern comprising peaks, in terms of 2-theta, at 17.5±0.2°. In some embodiments, the crystalline Form DC of (S)-TPMA D-tartrate is further characterized by the powder x-ray diffraction pattern further comprising a peak, in terms of 2-theta, at 20.7±0.2° and 23.6±0.2°. In some embodiments, the crystalline Form DC of (S)-TPMA D-tartrate is further characterized by the powder x-ray diffraction pattern further comprising a peak, in terms of 2-theta, at two or more of 19.4±0.2°, 21.7±0.2°, and 26.8±0.2°.

Figure 19:
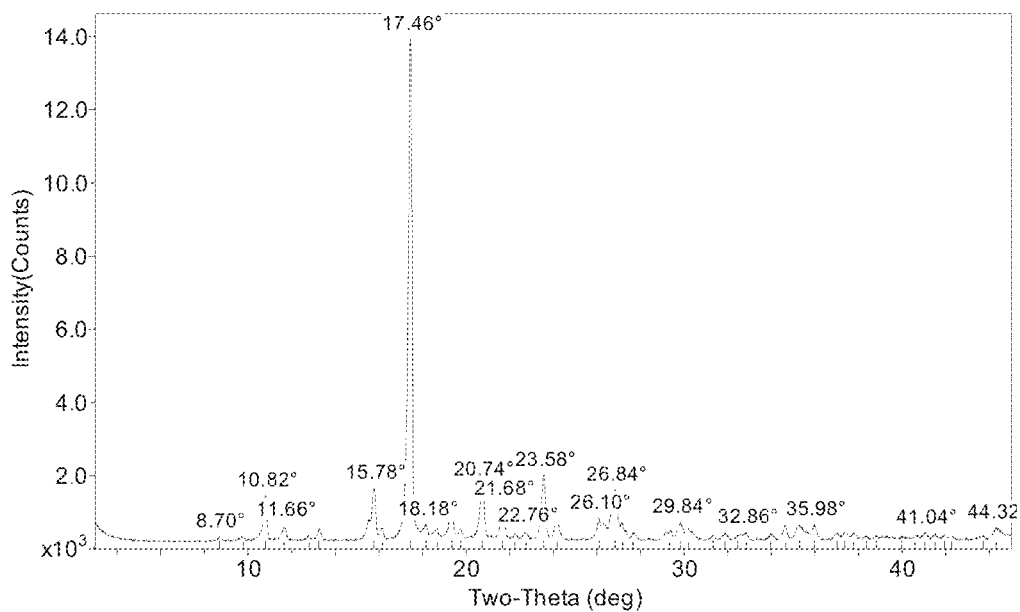
FIG. 19 presents an XRPD pattern for (S)-(4,5-dihydro-7H-thieno[2,3-c]pyran-7-yl)-N-methylmethanamine D-tartrate Form DC.

In some embodiments, the crystalline Form DC of (S)-TPMA D-tartrate is characterized by a powder x-ray diffraction pattern substantially in accord with FIG. 19.

In some embodiments, the crystalline Form DC of (S)-TPMA D-tartrate has a differential scanning calorimetry thermogram comprising a peak at 185±2° C. In some embodiments, the crystalline Form DC of (S)-TPMA D-tartrate has a differential scanning calorimetry thermogram substantially in accord with FIG. 22.

In some embodiments, the crystalline Form DC of (S)-TPMA D-tartrate is characterized by a powder x-ray diffraction pattern comprising peaks, in terms of 2-theta, at 10.8±0.2°, 15.8±0.2°, and 17.5±0.2°, and a powder x-ray diffraction pattern substantially in accord with FIG. 19. In some embodiments, the crystalline Form DC of (S)-TPMA D-tartrate is characterized by a powder x-ray diffraction pattern comprising peaks, in terms of 2-theta, at 10.8±0.2°, 15.8±0.2°, and 17.5±0.2°, and has a differential scanning calorimetry thermogram comprising a peak at 185±2° C. In some embodiments, the crystalline Form DC of (S)-TPMA D-tartrate is characterized by a powder x-ray diffraction pattern comprising peaks, in terms of 2-theta, at 10.8±0.2°, 15.8±0.2°, and 17.5±0.2°, and has a differential scanning calorimetry thermogram substantially in accord with FIG. 22.

In some embodiments, the substance comprising (S)-TPMA D-tartrate where the chiral purity of the substance is greater than about 90% (S)-TPMA D-tartrate. In some embodiments, the substance comprising (S)-TPMA D-tartrate where the chiral purity of the substance is greater than about 95% (S)-TPMA D-tartrate. In some embodiments, the substance comprising (S)-TPMA D-tartrate where the chiral purity of the substance is greater than about 97.5% (S)-TPMA D-tartrate. In some embodiments, the substance comprising (S)-TPMA D-tartrate where the chiral purity of the substance is greater than about 99% (S)-TPMA D-tartrate.

In some embodiments, the substance comprising (S)-TPMA D-tartrate where the chemical purity of the substance is greater than about 90% (S)-TPMA D-tartrate. In some embodiments, the substance comprising (S)-TPMA D-tartrate where the chemical purity of the substance is greater than about 95% (S)-TPMA D-tartrate. In some embodiments, the substance comprising (S)-TPMA D-tartrate where the chemical purity of the substance is greater than about 97.5% (S)-TPMA D-tartrate. In some embodiments, the substance comprising (S)-TPMA D-tartrate where the chemical purity of the substance is greater than about 99% (S)-TPMA D-tartrate.

(S)-(4,5-dihydro-7H-thieno[2,3-c]pyran-7-yl)-N-methylmethanamine mesylate

Provided herein is (S)-(4,5-dihydro-7H-thieno[2,3-c]pyran-7-yl)-N-methylmethanamine mesylate, which is also referred to as (S)-TPMA mesylate. In some embodiments, the crystalline form of (S)-TPMA mesylate is characterized by DVS of substantially in accord with FIG. 24.

In some embodiments, the substance comprising (S)-TPMA mesylate where the chiral purity of the substance is greater than about 90% (S)-TPMA mesylate. In some embodiments, the substance comprising (S)-TPMA mesylate where the chiral purity of the substance is greater than about 95% (S)-TPMA mesylate. In some embodiments, the substance comprising (S)-TPMA mesylate where the chiral purity of the substance is greater than about 97.5% (S)-TPMA mesylate. In some embodiments, the substance comprising (S)-TPMA mesylate where the chiral purity of the substance is greater than about 99% (S)-TPMA mesylate.

In some embodiments, the substance comprising (S)-TPMA mesylate where the chemical purity of the substance is greater than about 90% (S)-TPMA mesylate. In some embodiments, the substance comprising (S)-TPMA mesylate where the chemical purity of the substance is greater than about 95% (S)-TPMA mesylate. In some embodiments, the substance comprising (S)-TPMA mesylate where the chemical purity of the substance is greater than about 97.5% (S)-TPMA mesylate. In some embodiments, the substance comprising (S)-TPMA mesylate where the chemical purity of the substance is greater than about 99% (S)-TPMA mesylate.

(S)-(4,5-dihydro-7H-thieno[2,3-c]pyran-7-yl)-N-methylmethanamine L-malate

Provided herein is (S)-(4,5-dihydro-7H-thieno[2,3-c]pyran-7-yl)-N-methylmethanamine L-malate, which is also referred to as (S)-TPMA L-malate.

In some embodiments, the substance comprising (S)-TPMA L-malate where the chiral purity of the substance is greater than about 90% (S)-TPMA L-malate. In some embodiments, the substance comprising (S)-TPMA L-malate where the chiral purity of the substance is greater than about 95% (S)-TPMA L-malate. In some embodiments, the substance comprising (S)-TPMA L-malate where the chiral purity of the substance is greater than about 97.5% (S)-TPMA L-malate. In some embodiments, the substance comprising (S)-TPMA L-malate where the chiral purity of the substance is greater than about 99% (S)-TPMA L-malate.

In some embodiments, the substance comprising (S)-TPMA L-malate where the chemical purity of the substance is greater than about 90% (S)-TPMA L-malate. In some embodiments, the substance comprising (S)-TPMA L-malate where the chemical purity of the substance is greater than about 95% (S)-TPMA L-malate. In some embodiments, the substance comprising (S)-TPMA L-malate where the chemical purity of the substance is greater than about 97.5% (S)-TPMA L-malate. In some embodiments, the substance comprising (S)-TPMA L-malate where the chemical purity of the substance is greater than about 99% (S)-TPMA L-malate.

(S)-(4,5-dihydro-7H-thieno[2,3-c]pyran-7-yl)-N-methylmethanamine Free Base

Provided herein is (S)-(4,5-dihydro-7H-thieno[2,3-c]pyran-7-yl)-N-methylmethanamine free base, which is also referred to as (S)-TPMA, or (S)-TPMA free base. In some embodiments, (S)-TPMA free base is crystalline.

In some embodiments, the crystalline form of (S)-TPMA free base is characterized by a powder x-ray diffraction pattern comprising peaks, in terms of 2-theta, at 13.6±0.2°, 16.4±0.2°, 20.0±0.2°, and 20.4±0.2°. In some embodiments, the crystalline (S)-TPMA free base is characterized by a powder x-ray diffraction pattern comprising peaks, in terms of 2-theta, at 13.6±0.2°. In some embodiments, the crystalline (S)-TPMA free base is characterized by a powder x-ray diffraction pattern comprising peaks, in terms of 2-theta, at 16.4±0.2°. In some embodiments, the crystalline (S)-TPMA free base is characterized by a powder x-ray diffraction pattern comprising peaks, in terms of 2-theta, at 20.0±0.2°. In some embodiments, the crystalline (S)-TPMA free base is characterized by a powder x-ray diffraction pattern comprising peaks, in terms of 2-theta, at 20.4±0.2°. In some embodiments, the crystalline (S)-TPMA free base is further characterized by the powder x-ray diffraction pattern further comprising a peak, in terms of 2-theta, at 22.4±0.2°, 23.2±0.2°, and 27.3±0.2°.

Figure 32:
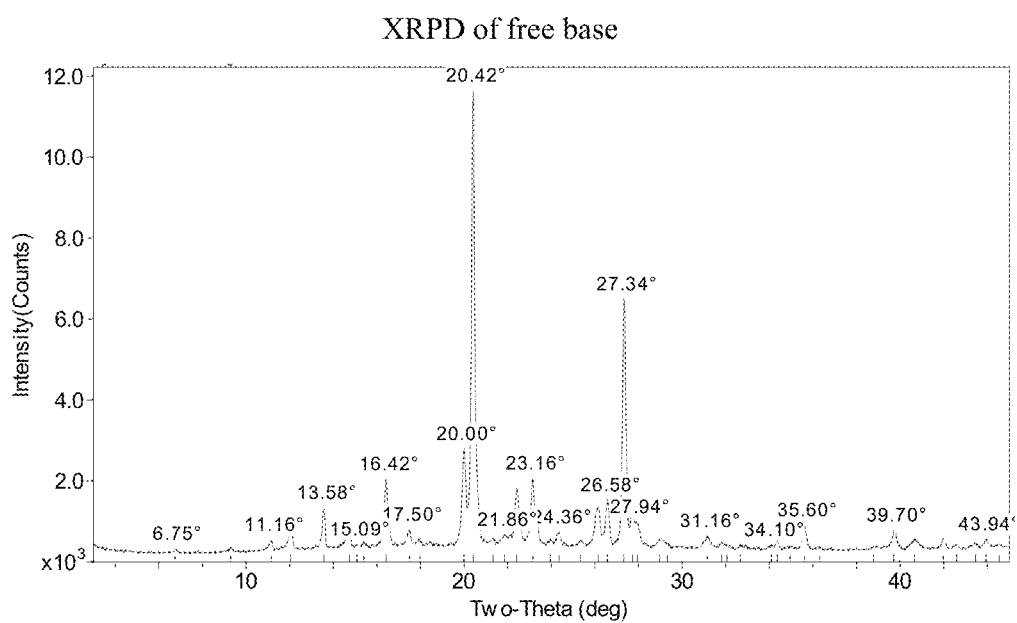
FIG. 32 presents an XRPD pattern for (S)-(4,5-dihydro-7H-thieno[2,3-c]pyran-7-yl)-N-methylmethanamine free base.

In some embodiments, the crystalline (S)-TPMA free base is characterized by a powder x-ray diffraction pattern substantially in accord with FIG. 32.

In some embodiments, the crystalline (S)-TPMA free base is characterized by a powder x-ray diffraction pattern comprising peaks, in terms of 2-theta, at 13.6±0.2°, 16.4±0.2°, 20.0±0.2°, and 20.4±0.2°, and a powder x-ray diffraction pattern substantially in accord with FIG. 32.

In various aspects, provided are methods for preparing (S)-(4,5-dihydro-7H-thieno[2,3-c]pyran-7-yl)-N-methylmethanamine hydrochloride as crystalline Form A. In various embodiments, methods of making (S)-TPMA HCl of Form A begin with (S)-(4,5-dihydro-7H-thieno[2,3-c]pyran-7-yl)-N-methylmethanamine, various other embodiments begin with substantially racemic (4,5-dihydro-7H-thieno[2,3-c]pyran-7-yl)-N-methylmethanamine.

In various aspects, provided are methods for preparing (S)-(4,5-dihydro-7H-thieno[2,3-c]pyran-7-yl)-N-methylmethanamine hydrochloride as crystalline Form A with various particle size distributions.

Example 1A-1C provides and illustrates various embodiments of methods of making (S)-TPMA HCl of Form A. Example 2 provides and illustrates various embodiments of methods of making various particle size distributions of (S)-TPMA HCl of Form A.

A synthesis of racemic (4,5-dihydro-7H-thieno[2,3-c]pyran-7-yl)-N-methylmethanamine HCl

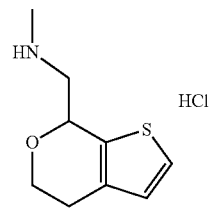

is disclosed in U.S. Pat. No. 8,710,245. In the '245 patent, the racemate is resolved into the single (R) and (S) enantiomers:

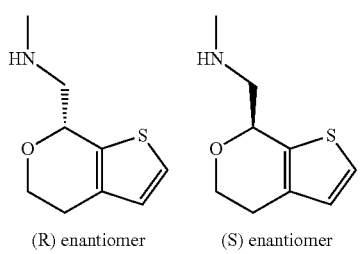

(R) enantiomer    (S) enantiomer by column chromatography. The free base of (S)-(4,5-dihydro-7H-thieno[2,3-c]pyran-7-yl)-N-methylmethanamine is a yellow oil that degrades over time when exposed to air.

In various embodiments of the methods of the present inventions, the balance between polymorphs A and B is driven to substantially pure polymorph Form A by the controlled addition of a solution of between about 5% to about 10% HCl in isopropanol into a solution of (S)-TPMA free base in isopropanol at a temperature between 20° C. and 60° C., preferably about 40° C. In various embodiments, the controlled addition is preferably carried out as a logarithmic-like addition where the HCl solution is added slowly at first and the rate is steadily increased. The HCl addition rate, in various embodiments, 10% of the HCl solution is added over a first time period of between about 10 minutes and about 90 minutes, 30% of the HCl solution is added over a second time period of between about 10 minutes and about 90 minutes, and the remainder of the HCl solution is added over a third time period of between about 10 minutes and about 90 minutes.

In various embodiments, the slow addition of acid solution (e.g., slower supersaturation rate) with a logarithmic-like addition profile (examples include, but are not limited to, the Mullin-Nyvlt type addition profile, see, e.g., J. W. Mullin and J. Nývlt, *Chem Eng Sci.* 1971; 26:3, 369-377), higher operation temperature, lower concentration of starting freebase solution, and higher water content of the crystallization mixture, favor the generation of large crystals of (S)-TPMA HCl of Form A; whereas lower operation temperature, higher concentration of starting freebase solution, and lower water content of the crystallization mixture, favor the generation of smaller crystals of (S)-TPMA HCl of Form A. It is to be understood, that mean, average and/or median particle size is generally not the sole determinant of a desirable PSD, rather, the width of a PSD is often of importance.

The present inventors have also discovered methods of modulating the particle size distribution of crystalline (S)-TPMA hydrochloride and in particular of crystalline (S)-TPMA hydrochloride of Form A, into a desired range, for example, a PSD favorable for compressing tablets and/or providing good solution kinetics. In various embodiments, it has been discovered that the particle size distribution of the (S)-TPMA hydrochloride can be modulated by: (i) the addition rate of HCl during the formation of (S)-TPMA HCl (e.g. Step 4b in Scheme 4), (ii). the concentration of (S)-TPMA freebase in the solution prior to HCl addition (e.g. Compound F concentration in Scheme 4 between Steps 4a and 4b); (ii) the temperature of the solution during HCl addition; (iv) the water content of the crystallization mixture; and (v) the reaction process.

Referring to FIGS. 7A, 7B, 8A, 8B, 8C, and 9A, presented are various PSD data for (S)-TPMA HCl of Form A, obtained under various conditions as further discussed in Example 2. The PSD data of FIGS. 7A, 7B, 8A, 8B and 8C was obtained by a laser diffraction particle sizing technique using a Malvern Mastersizer 2000 analyzer instrument and the PSD data of FIG. 9A by a laser diffraction particle sizing technique using a Horiba LA-920 instrument, and all data is presented as volume % as a function of particle size.

It has been discovered that, the PSD of crystals of (S)-TPMA HCl of Form A can in various embodiments be affected by the supersaturation generation rate (e.g. controlled by the dosing profile of the HCl solution Step 4b of Scheme 4), operation temperature, water content, and reaction process (e.g. mixing, sonication, etc.). For example, in various embodiments, it has been discovered that sonication during addition of HCl to form (S)-TPMA HCl (e.g. Step 4b in Scheme 4) can dramatically decrease the final (S)-TPMA HCl crystal size (e.g. D50=20 to 30 μm) of Form A by promoting the nucleation over the course of addition of HCl.

In various embodiments, of the reactive-crystallization of (S)-TPMA HCl, the supersaturation generation rate can be directly controlled by the HCl solution addition rate; faster dosing (HCl addition) favoring the formation of smaller crystals and slower dosing favoring the formation of larger crystals. However, faster addition results in wider PSD distributions.

In various embodiments, operational temperature can be used to affect the kinetic behavior for nucleation and crystal growth, as well as solubility. It has been discovered that higher temperature increases mean crystal size and width of the PSD.

In various embodiments, starting (S)-(−)-TPMA freebase concentration prior to reactive recrystallization can be used to affect the kinetic behavior for nucleation and crystal growth. It has been discovered that higher starting (S)-(−)-TPMA freebase concentration decreased both the median particle size and the width of the PSD.

While the solvent in the experiments described in Example 1A, and above, was isopropanol, the temperature/solubility, in various embodiments, alkyl alcohols of 4 carbons or less, including but not limited to, n-propanol, isopropanol, and n-butanol can be used.

In various embodiments, the (S)-TPMA free base is dissolved in a solvent system comprising from 90% to 100% isopropanol.

In various embodiments, the solvent system is 90% to 99% isopropanol and the remainder is water. In various embodiments the solvent system is 93% to 97% isopropanol and the remainder is water.

In various embodiments, the solvent system is >99% isopropanol. The presence of water, in various embodiments, of up to about 5% leads to crystals of (S)-TPMA HCl polymorph Form A that are more cubic than hexagonal in morphology. In various embodiments, the methods of the present inventions provide for (S)-TPMA HCl crystals of Form A with increased cubic morphology. In various embodiments of the composition, medicaments and formulations of the present inventions, (S)-TPMA HCl crystals of Form A with increased cubic morphology are preferred as being more flowable than the hexagonal morphology, and as possessing advantages in formation of certain solid oral dosage forms, e.g., in certain tableting operations.

In Example 1A, the hydrogen chloride in isopropanol was prepared at 6% by weight, but could be employed in other concentrations; for example, in various embodiments from about 4% to about 10%. In various embodiments, the HCl in an alkyl alcohol of 4 carbons or less, e.g. isopropanol, can be added in ratios from 1.0 to 1 up to 1.2 to 1 stoichiometry based on the amine in (S)-TPMA.

The concentration of (S)-TPMA free base in the alkyl alcohol of 4 carbons or less, e.g. isopropanol, was observed to be operable over a wide range. In various embodiments, the concentration of (S)-TPMA free base solution is between about 5.0% to 25.0% by weight %, and preferably between about 10% and about 15%. In various embodiments, the concentration of (S)-TPMA free base solution is about 10.0%, about 11.0%, about 13.0%, or in some, about 15.0% by weight %.

With references to the teachings herein the skilled artisan would understand that very dilute solutions of (S)-TPMA free base are likely to produce lower yields because of the finite solubility of (S)-TPMA hydrochloride in alkyl alcohols of 4 carbons or less, e.g. isopropanol.

In some embodiments, the particle size distribution of crystals of (S)-TPMA HCl of Form A can be controlled by the balance among the reactant addition rate, local and global supersaturation, mass transfer and crystal surface area. It was discovered that the slow addition of acid solution, for example, with a Mullin-Nyvlt-like addition profile, higher operation temperature, lower concentration of starting freebase solution, presence of water in the solvent system, seeding favors the formation of the larger polymorph Form A (S)-TPMA HCl crystals, and sonication during supersaturation favors the formation of the smaller polymorph Form A (S)-TPMA HCl crystals.

In various embodiments, provided are compounds comprising Form A crystals of (S)-TPMA HCl having a particle size distribution (when measured by laser diffraction, for example, as set forth in Example 2) with a median (D50) between about 15 µm to about 30 µm, a D10 greater than about 10 µm and a D90 less than about 40 µm; and preferably with a D50 between about 20 µm to about 30 µm.

In various embodiments, provided are compounds comprising Form A crystals of (S)-TPMA HCl having a particle size distribution (when measured by laser diffraction, for example, as set forth in Example 2) with a median (D50) between about 15 µm to about 30 µm, (and preferably between about 20 µm to about 30 µm), and a span less than about 1.75, less than about 1.5, less than about 1, or less than about 0.8.

In various embodiments, provided are compounds comprising Form A crystals of (S)-TPMA HCl having a particle size distribution (when measured by laser diffraction, for example, as set forth in Example 2) with a median (D50) between about 100 µm to about 135 µm (and preferably a D50 between about 100 µm to about 110 µm), a D10 greater than about 60 µm and a D90 less than about 165 µm; and preferably with a D10 greater than about 70 µm and a D90 less than about 150 µm.

In various embodiments, provided are compounds comprising Form A crystals of (S)-TPMA HCl having a particle size distribution (when measured by laser diffraction, for example, as set forth in Example 2) with a median (D50) between about 100 µm to about 135 µm (and preferably a D50 between about 100 µm to about 110 µm), and a span less than about 1.75, less than about 1.5, less than about 1, or less than about 0.8.

In various embodiments, provided are compounds comprising Form A crystals of (S)-TPMA HCl having a particle size distribution (when measured by laser diffraction, for example, as set forth in Example 2) with a median (D50) between about 135 µm to about 180 µm (and preferably a D50 between about 160 µm to about 170 µm), a D10 greater than about 100 µm and a D90 less than about 250 µm; and preferably with a D10 greater than about 110 µm and a D90 less than about 230 µm.

In various embodiments, provided are compounds comprising Form A crystals of (S)-TPMA HCl having a particle size distribution (when measured by laser diffraction, for example, as set forth in Example 2) with a median (D50) between about 135 µm to about 180 µm (and preferably a D50 between about 160 µm to about 170 µm), and a span less than about 1.75, less than about 1.5, less than about 1, or less than about 0.8.

In various embodiments, provided are compounds comprising Form A crystals of (S)-TPMA HCl having a particle size distribution (when measured by laser diffraction, for example, as set forth in Example 2) with a median (D50) between about 180 µm to about 230 µm (and preferably a D50 between about 190 µm to about 220 µm), a D10 greater than about 110 µm and a D90 less than about 350 µm; and preferably with a D10 greater than about 120 µm and a D90 less than about 340 µm.

In some embodiments, D10 is greater than about 50 µm. In some embodiments, D10 is greater than about 75 µm. In some embodiments, D10 is greater than about 80 µm. In some embodiments, D10 is greater than about 90 µm. In some embodiments, D10 is greater than about 100 µm. In some embodiments, D10 is greater than about 110 µm. In some embodiments, D10 is greater than about 120 µm. In some embodiments, D10 is greater than about 130 µm. In some embodiments, D10 is greater than about 150 µm. In some embodiments, D90 is greater than about 200 µm. In some embodiments, D90 is greater than about 250 µm. In some embodiments, D90 is greater than about 300 µm. In some embodiments, D90 is greater than about 350 µm. In some embodiments, D90 is greater than about 400 µm. In some embodiments, the median (D50) is in the range in any of the embodiments provided herein, e.g., between about 50 µm to about 400 µm, between about 100 µm to about 300 µm, between about 120 µm to about 300 µm, etc.

In various embodiments, provided are compounds comprising Form A crystals of (S)-TPMA HCl having a particle size distribution (when measured by laser diffraction, for example, as set forth in Example 2) with a median (D50) between about 180 µm to about 230 µm (and preferably a D50 between about 190 µm to about 220 µm), and a span less than about 1.75, less than about 1.5, less than about 1, or less than about 0.8.

In various embodiments, the methods of the present inventions provide for Form A crystals of (S)-TPMA HCl having a PSD (when measured by laser diffraction, for example, as set forth in Example 2) with a median (D50) between about 15 µm to about 30 µm, a D10 greater than about 10 µm and a D90 less than about 40 µm; and preferably with a D50 between about 20 µm to about 30 µm, a D10 greater than about 10 µm and a D90 less than about 40 µm; where the methods comprise sonication during a step of supersaturation of a freebase solution of (S)-TPMA to form (S)-TPMA HCl.

In various embodiments, the methods of the present inventions provide for Form A crystals of (S)-TPMA HCl having a PSD (when measured by laser diffraction, for example, as set forth in Example 2) with a median (D50), in various embodiments, between about 100 µm to about 230 µm, between about 100 µm to about 135 µm, between about 135 µm to about 180 µm, or between about 180 µm to about 230 µm; and having a span less than about 1.75, less than about 1.5, less than about 1, or less than about 0.8; where the methods comprise using a logarithmic-like addition of HCl during the reactive-recrystallization of (S)-TPMA to form (S)-TPMA HCl. In various embodiments, the logarithmic-like addition comprises addition of between about 10% to about 15% of an HCl solution over a first time period, addition of about 30% to about 40% of the HCl solution over a second time period after the first time period, and addition of the remainder (between about 45% to about 60%) of the HCl solution over a third time period after the second time period. In various embodiments, the first, second and third time periods are independently in the range between about 10 minutes to about 90 minutes. In various embodiments, the first, second and third time periods are substantially equal within ±10% of each other.

In various aspects, provided are methods for preparing (S)-(4,5-dihydro-7H-thieno[2,3-c]pyran-7-yl)-N-methylmethanamine hydrochloride as crystalline Form A. In various embodiments, the method comprises:
 (a) dissolving (S)-(4,5-dihydro-7H-thieno[2,3-c]pyran-7-yl)-N-methylmethanamine free base in a solvent system comprising an alkyl alcohol of 4 carbons or less;
 (b) adding excess HCl in an alkyl alcohol of 4 carbons or less; and
 (c) isolating crystalline (S)-(4,5-dihydro-7H-thieno[2,3-c]pyran-7-yl)-N-methylmethanamine hydrochloride. In various embodiments, the alkyl alcohol is one or more of n-propanol, isopropanol, and n-butanol, and in various embodiments, the alkyl alcohol is preferably isopropanol.

In various embodiments of methods for preparing (S)-(4,5-dihydro-7H-thieno[2,3-c]pyran-7-yl)-N-methylmethanamine hydrochloride as Form A, the method comprises:
 (a) combining racemic-(4,5-dihydro-7H-thieno[2,3-c]pyran-7-yl)-N-methylmethanamine with a stoichiometric excess of (R)-mandelic acid in a solvent;
 (b) isolating (S)-(4,5-dihydro-7H-thieno[2,3-c]pyran-7-yl)-N-methylmethanamine R-mandelate salt;
 (c) freeing (S)-(4,5-dihydro-7H-thieno[2,3-c]pyran-7-yl)-N-methylmethanamine from the (R)-mandelate salt;
 (d) dissolving the (S)-(4,5-dihydro-7H-thieno[2,3-c]pyran-7-yl)-N-methylmethanamine in a solvent system comprising an alkyl alcohol of 4 carbons or less;
 (e) adding HCl in an alkyl alcohol of 4 carbons or less; and
 (f) isolating crystalline (S)-(4,5-dihydro-7H-thieno[2,3-c]pyran-7-yl)-N-methylmethanamine hydrochloride. In various embodiments, the alkyl alcohol is one or more of n-propanol, isopropanol, and n-butanol, and in various embodiments, the alkyl alcohol is preferably isopropanol.

A synthesis of (S)-TPMA hydrochloride is disclosed in U.S. Pat. No. 8,710,245. The synthesis procedure reported in the '245 patent is used to produce small quantities of the compound. This procedure requires chromatographic separations, which is typically not suitable for large scale manufacture. For instance, normal phase or chiral phase chromatographic separations are not practical for the large scale manufacture. Resolution procedures are developed to replace chiral chromatographic separations. Resolution procedures are robust, practical, easy to scale up and are routinely used in production of chiral of compounds at various scales. In the large scale preparation of (S)-TPMA hydrochloride, a R-mandelic acid mediated resolution of (S)-TPMA free base to replace chiral chromatographic separation of N-Boc-TPMA was developed.

The procedure in the '245 patent is performed on 1 g scale. The work up of reaction involved neutralization of the product (S)-TPMA triflate salt with potassium carbonate and the resulting free base was treated with methanolic HCl to produce (S)-TPMA HCl salt that was isolated after addition of anti-solvent MTBE. The process described herein provided (S)-TPMA triflate with high purity. Typically, (S)-TPMA triflate is obtained with 76-80% yield with >99.2% purity. The process described herein is shorter as there is no need to make free base and further convert it to (S)-TPMA HCl salt. 2-methyl THF is suitable solvent for this step. MTBE is used as an anti-solvent for the crystallization step. 2-methyl THF is a green solvent that is highly desirable than the Class II solvent 1,4-dioxane used in the process in the '245 patent.

In some embodiments, provided herein is a method of preparing (4,5-dihydro-7H-thieno[2,3-c]pyran-7-yl)-N-methylmethanamine, wherein the method comprises
 (a) reacting 2-(thiophen-3-yl)ethan-1-ol with N-methylaminoacetaldehyde dimethylacetal and triflic acid to provide (4,5-dihydro-7H-thieno[2,3-c]pyran-7-yl)-N-methylmethanamine triflate; and
 (b) reacting (4,5-dihydro-7H-thieno[2,3-c]pyran-7-yl)-N-methylmethanamine triflate with a base to provide (4,5-dihydro-7H-thieno[2,3-c]pyran-7-yl)-N-methylmethanamine.

In some embodiments, provide herein is a method of preparing (S)-(4,5-dihydro-7H-thieno[2,3-c]pyran-7-yl)-N-methylmethanamine, wherein the method comprises:
 (a) reacting 2-(thiophen-3-yl)ethan-1-ol with N-methylaminoacetaldehyde dimethylacetal and triflic acid to provide (4,5-dihydro-7H-thieno[2,3-c]pyran-7-yl)-N-methylmethanamine triflate;
 (b) reacting (4,5-dihydro-7H-thieno[2,3-c]pyran-7-yl)-N-methylmethanamine triflate with a base to provide (4,5-dihydro-7H-thieno[2,3-c]pyran-7-yl)-N-methylmethanamine;
 (c) reacting (4,5-dihydro-7H-thieno[2,3-c]pyran-7-yl)-N-methylmethanamine with (R)-mandelic acid to provide (S)-(4,5-dihydro-7H-thieno[2,3-c]pyran-7-yl)-N-methylmethanamine (R)-mandelate; and
 (d) reacting (S)-(4,5-dihydro-7H-thieno[2,3-c]pyran-7-yl)-N-methylmethanamine (R)-mandelate with a base to provide (S)-(4,5-dihydro-7H-thieno[2,3-c]pyran-7-yl)-N-methylmethanamine.

In some embodiments, provided herein is a method of preparing salts of (S)-(4,5-dihydro-7H-thieno[2,3-c]pyran-7-yl)-N-methylmethanamine, wherein the method comprises reacting (S)-(4,5-dihydro-7H-thieno[2,3-c]pyran-7-yl)-N-methylmethanamine with an acid. For example, reacting (S)-(4,5-dihydro-7H-thieno[2,3-c]pyran-7-yl)-N-methylmethanamine with HCl would generate the corresponding HCl salt.

In some embodiments, provided herein is a method of preparing (4,5-dihydro-7H-thieno[2,3-c]pyran-7-yl)-N-methylmethanamine triflate. In some embodiments, the method comprises reacting 2-(thiophen-3-yl)ethan-1-ol with N-methylaminoacetaldehyde dimethylacetal and triflic acid to provide (4,5-dihydro-7H-thieno[2,3-c]pyran-7-yl)-N-methylmethanamine triflate. In some embodiments, the reacting can be carried out in the presence of a solvent. The solvent can be an ether such as 2-methyl tetrahydrofuran. In some embodiments, the reacting of 2-(thiophen-3-yl)ethan-1-ol with N-methylaminoacetaldehyde dimethylacetal and triflic acid is carried out at temperature of about 50° C. to 100° C. In some embodiments, the temperature is about 75° C. to 85° C., e.g., 80° C. In some embodiments, the method comprises reacting 2-(thiophen-3-yl)ethan-1-ol with sulfuric acid, N-methylaminoacetaldehyde dimethylacetal and triflic acid.

In some embodiments, provided herein is a method of preparing (4,5-dihydro-7H-thieno[2,3-c]pyran-7-yl)-N-methylmethanamine. In some embodiments, the method comprises reacting (4,5-dihydro-7H-thieno[2,3-c]pyran-7-yl)-N-methylmethanamine triflate with a base to provide (4,5-dihydro-7H-thieno[2,3-c]pyran-7-yl)-N-methylmethanamine. In some embodiments, the base is an alkali metal base such as KOH. In some embodiments, the reacting is carried out in the presence of a solvent. The solvent can be an ether such as methyl t-butyl ether.

In some embodiments, provided herein is a method of preparing (S)-(4,5-dihydro-7H-thieno[2,3-c]pyran-7-yl)-N-methylmethanamine (R)-mandelate. In some embodiments, the method comprises reacting (4,5-dihydro-7H-thieno[2,3-c]pyran-7-yl)-N-methylmethanamine with (R)-mandelic acid to provide (S)-(4,5-dihydro-7H-thieno[2,3-c]pyran-7-yl)-N-methylmethanamine (R)-mandelate. In some embodiments, the reacting is carried out in polar aprotic solvent such as acetonitrile and acetone, or a mixture thereof.

In some embodiments, provided herein is a method of preparing (S)-(4,5-dihydro-7H-thieno[2,3-c]pyran-7-yl)-N-methylmethanamine. In some embodiments, the method comprises reacting (S)-(4,5-dihydro-7H-thieno[2,3-c]pyran-7-yl)-N-methylmethanamine (R)-mandelate with a base to provide (S)-(4,5-dihydro-7H-thieno[2,3-c]pyran-7-yl)-N-methylmethanamine. In some embodiments, the base is an alkali metal base such as KOH. In some embodiments, the reacting is carried out in a solvent. The solvent can be an ether or water, or a mixture thereof. In some embodiments, the ether is methyl t-butyl ether.

Example 1A: Preparation of (S)-(4,5-dihydro-7H-thieno[2,3-c]pyran-7-yl)-N-methylmethanamine HCl of Crystalline Form A Scheme 1: Preparation of (4,5-dihydro-7H-thieno[2,3-c]pyran-7-yl)-N-methylmethanamine triflate

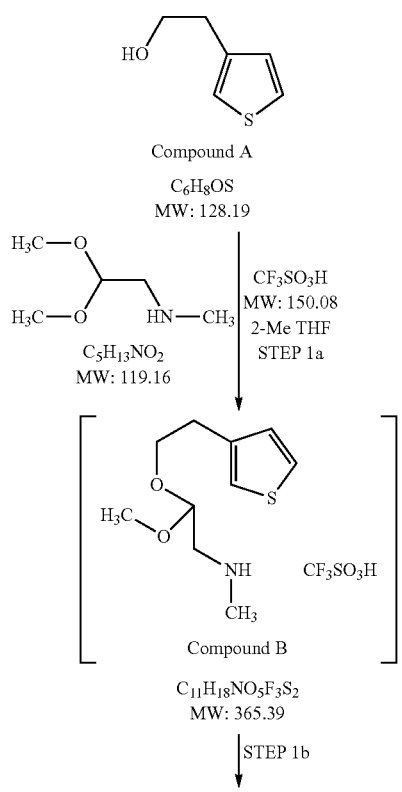

Compound A
$C_6H_8OS$
MW: 128.19

$CF_3SO_3H$
MW: 150.08
2-Me THF
STEP 1a

Compound B
$C_{11}H_{18}NO_5F_3S_2$
MW: 365.39

STEP 1b

-continued

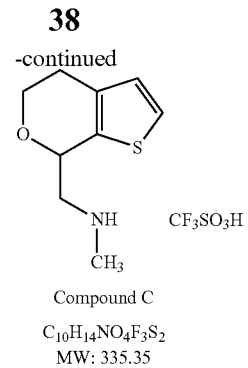

Compound C
$C_{10}H_{14}NO_4F_3S_2$
MW: 335.35

77 g of 3-thiopheneethanol (Compound A) was added to a solution of 69 g of N-methylaminoacetadehyde dimethyl acetal in 595 ml (508 g) of 2-methyl tetrahydrofuran (2Me THF). After stirring for 5 minutes 99 g (58.2 ml) trifluoromethanesulfonic acid was added. It is important to note that trifluoromethanesulfonic acid is a very hazardous substance. The reaction was heated to reflux for 1 hour (80±2° C.). The reaction was then distilled at atmospheric pressure to remove the byproduct methanol and to reduce the reaction volume to a targeted volume of 460 ml over 4-8 hours. The reaction was judged complete when 1.0% or less (HPLC Peak Area % of peaks of interest, Compounds A, B and C) of compound 1B remained by a sample HPLC analysis.

If the amount of Compound B was greater than or equal to 1%, an appropriate amount of 2-methyl THF was added and distillation continued to the target volume. If the target volume was reached before the completion of reaction (about 4 hours), 300 ml 2-methyl THF was added to the reaction for continuation of the distillation. After reaction completion, the reaction was cooled to about 40-50° C. and concentrated to a target volume of 325 ml under vacuum distillation. 218 g (325 ml) of Toluene was then added over about 15 minutes and the reaction slurry formed was then stirred for 1 hour at 50±2° C., and then cooled to 20±2° C. linearly over 1 hour 45 minutes while being stirred. The slurry was filtered and the product cake was washed with a 2-methyl THF and toluene mixture (1:1 volume/volume). The wet-cake was dried under vacuum at 40±5° C. to constant weight to yield racemic TPMA triflate (Compound C) as an off-white solid and a yield of about 79% was obtained.

Scheme 2: Preparation of (S)-(-)-(4,5-dihydro-7H-thieno[2,3-c]pyran-7-yl)-N-methylmethanamine (R) mandelate

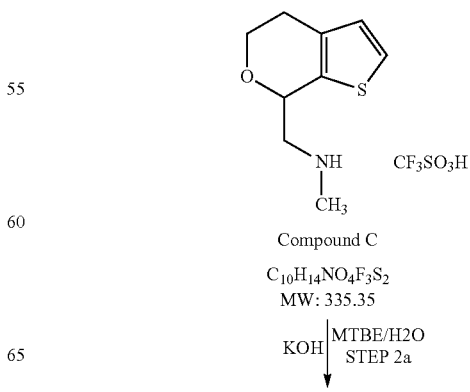

Compound C
$C_{10}H_{14}NO_4F_3S_2$
MW: 335.35

KOH | MTBE/H2O
STEP 2a

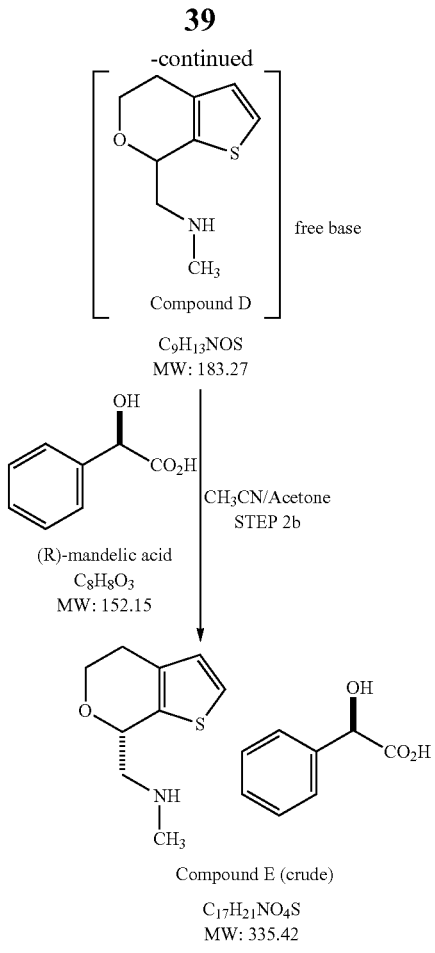

Compound D
C9H13NOS
MW: 183.27

(R)-mandelic acid
C8H8O3
MW: 152.15

CH3CN/Acetone
STEP 2b

Compound E (crude)
C17H21NO4S
MW: 335.42

In various embodiments, di-p-toluoyl-D-tartaric acid (D-TTA) was used as the resolving agent to produce a (S)-TPMA-D-DTTA salt and the present inventors discovered that use of D-DTTA provided for a kinetic based resolution. However, Scheme 2 of the present example provides for use of (R)-mandelic acid and the present inventors discovered that diasteromeric crystallization with (R)-mandelic acid is a thermodynamic based separation.

To a suspension of 555.3 g of TPMA triflate (Compound 1C) in 1668 ml methyl tert-butyl ether (MTBE) was added 1076 g of 1.77 N aqueous KOH. After stirring for 10 minutes the pH was checked and if less than 13, small portions of 1.77 N KOH were added until the pH was 13 or greater. The aqueous and organic layers were allowed to settle and separate and separately collected. The MTBE (upper) organic phase layer was held for further processing. The aqueous (bottom) phase layer was extracted twice with MTBE (first with 835 ml and second with 150 ml), the organic (MBTE) layer being collected each time. The MTBE layers (organic layers) were combined, and washed with 20% aqueous NaCl solution (492.9 g) stirred and the phases allowed to settle for 10 minutes. The aqueous layer was removed and the remaining MTBE organic layer was distilled at atmospheric pressure to reduce the reaction volume to a targeted level of 1.9 L. After completion, the process stream was cooled to about 45° C. and concentrated to a target volume of 890 ml under vacuum distillation while maintaining the temperature at 35-45° C. The water content after vacuum distillation was found to be about 0.37% by weight. A filtration was then performed to remove insoluble materials using a wash of 204 ml MTBE, and the process stream (filtrate) was transferred to a clean reactor. 2512 mL of acetonitrile was added and a solvent switch was performed via vacuum distillation at 35-45° C. to the targeted volume of 800 ml, and the reactor washed with 150 ml of acetonitrile and added to the process stream. Acetonitrile was then added, if needed, to the acetonitrile solution of TPMA free base (Compound D) to achieve about a 33 weight % of Compound D.

A solution of 250.3 g of (R)-mandelic acid in 1828 ml of acetone was warmed to 48±2° C. The acetone solvent can be replaced with acetonitrile. The TPMA free base solution in acetonitrile (917.7 g solution of 302.1 g of Compound D in acetonitrile) was then added at a rate maintaining the reaction temperature below 51° C. After stirring at 48±2° C. for about 10 minutes the process stream was cooled to 45±2° C. and charged with 1.5 g of (S)-TPMA (R)-mandelate seed crystals. The process stream was stirred at 45±2° C. for about 30 minutes and cooled linearly to 21±2° C. over 90 minutes. After holding at 45±2° C. for about 30 minutes the process stream was cooled linearly to 10±2° C. over 45 minutes. The reaction slurry was then stirred for 60 minutes at 10±2° C., filtered and the product cake was washed with acetone/CH3CN mixture (2.3:1 weight/weight). The wet-cake was dried under vacuum at 40±2° C. to a constant weight to yield crude (S)-TPMA (R)-mandelate (Compound E) as a white crystalline solid, and a yield of about 41% was obtained.

Scheme 3: Recyrstallization of (S)-(4,5-dihydro-7H-thieno[2,3-c]pyran-7-yl)-N-methylmethanamine (R) mandelate

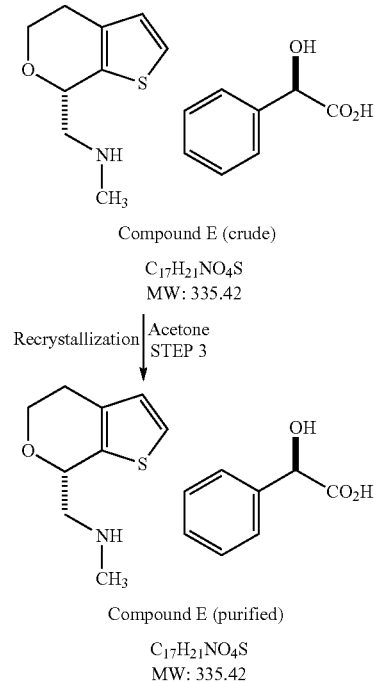

Compound E (crude)
C17H21NO4S
MW: 335.42

Recrystallization Acetone
STEP 3

Compound E (purified)
C17H21NO4S
MW: 335.42

Scheme 3 presents a process for the recrystallization of (S)-(4,5-dihydro-7H-thieno[2,3-c]pyran-7-yl)-N-methyl-methanamine (R) mandelate, ((S)-TPMA (R)-mandelate). It is to be understood that various other recrystallization solvents can be used. Scheme 3 of the present example provides for use of acetone and the present inventors have discovered that acetone can provide a combination of sufficiently high yield and effective rejection of key impurities. In various embodiments, the amount of acetone was selected based on solubility of (S)-TPMA (R)-mandelate in acetone at reflux temperature, preferably the minimum amount of acetone required for dissolution of crude (S)-TPMA (R)-mandelate at reflux was used. In various embodiments, the solvent is acetonitrile instead of acetone, where (S)-TPMA (R)-mandelate is dissolved at about 52±2° C. In various embodiments, Scheme 3 is a seed-induced crystallization and is conducted with linear cooling from 47±2° C. to 21±2° C. over 90 minutes followed by a hold for 30 minutes at 21±2° C., followed by linear cooling to 10±2° C. over 45 minutes and a hold at 10±2° C. preferably for a minimum of 1 hour.

A slurry of crude (S)-TPMA (R)-mandelate (Compound E) from Scheme 2 (200.1 g) in 4205 ml of acetone was warmed to about 56° C. (boiling point of acetone) and stirred until a clear solution was obtained. After cooling the solution to 47±2° C. over approximately 20 minutes (S)-TPMA (R)-mandelate seed crystals were added. The process stream was stirred at 47±2° C. for about 30 minutes and cooled linearly to 21±2° C. over 90 minutes. After holding at 21±2° C. for about 30 minutes the slurry was cooled linearly to 10±2° C. over 45 minutes and then stirred for 1 hour at 10±2° C., filtered, and the product cake was washed with acetone (twice with 401 ml each time). The wet-cake was dried under vacuum at about 40±2° C. to a constant weight to yield (S)-TPMA (R)-mandelate (purified Compound E) as a white crystalline solid, and a yield of about 77% was obtained.

Scheme 4: Formation of (S)-(-)-(4,5-dihydro-7H-thieno[2,3-c]pyran-7-yl)-N-methylmethanamine hydrochloride of Crystalline Form A

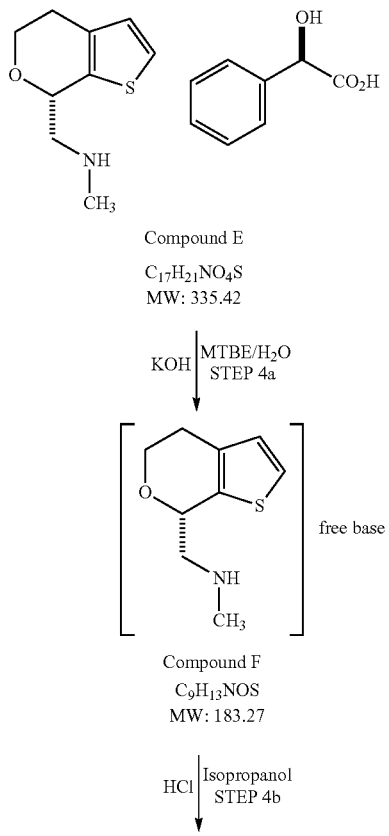

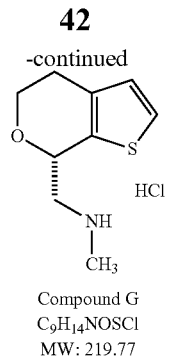

Compound G
C9H14NOSCl
MW: 219.77

Scheme 4 of the present example provides a reactive crystallization of (S)-(−)-(4,5-dihydro-7H-thieno[2,3-c]pyran-7-yl)-N-methylmethanamine HCl, ((S)-TPMA HCl), as crystalline Form A. The present inventors have discovered that as (S)-TPMA HCl crystallizes it displays two distinct morphologies (polymorphs), the first a block like crystal (Form A) and the second a needle like crystal (Form B). Based on single crystal x-ray diffraction studies, described herein, Form A has a monoclinic crystal system while Form B has an orthorhombic crystal system. The present inventors have discovered that Form A is the stable form under the reaction conditions of the present example and have discovered how to avoid formation of Form B. In various embodiments, (S)-TPMA (R)-mandelate is first converted to the free base and HCl added to form a slurry.

To a suspension of (S)-(4,5-dihydro-7H-thieno[2,3-c]pyran-7-yl)-N-methylmethanamine (R)-mandelate salt (Compound E) from Scheme 3 (100 g) in 305 ml of MTBE, 172.5 ml of a 10% KOH aqueous solution was added. After stirring for 10 minutes at 20±2° C. the aqueous and organic layers were separated. The organic MTBE (upper) layer was saved for further processing. If the pH of the aqueous layer was less than 13, small portions of the 10% KOH solution were added to raise the pH to 13. The aqueous (bottom) layer was back extracted twice with MTBE (first with 208 ml MTBE, second with 155 ml MTBE), the organic layer being saved for further processing each time. The saved organic layers were combined, and the combined organic layer was subjected to azeotropic distillation to remove water and distilled at atmospheric pressure to a target volume of 140 ml. The process stream was then filtered, to remove insoluble material (e.g. salt precipitated due to removal of water), and the filtrate transferred to a clean reactor. 775 ml of Isopropanol was added (resulting in a total process stream volume of about 1030 ml) and a solvent switch was performed via vacuum distillation at less than 45° C. to provide a 16-19% solution of (S)-(4,5-dihydro-7H-thieno[2,3-c]pyran-7-yl)-N-methylmethanamine in isopropanol.

In various embodiments, the amount of isopropanol added was selected so to adjust the freebase (Compound F) weight % concentration to 16-19%. The reaction mixture was cooled to 20±2° C., polish filtered, the filter washed with 78 ml isopropanol, and the filtrate transferred to a clean reactor. 201.6 g of a 6% HCl (w/w) solution in isopropanol was then added into the reactor over 45 minutes at about 20±2° C. It is to be understood that in various embodiments, the target amount of HCl is about 10% excess relative to the freebase (Compound F) molar equivalence. The HCl was added as follows, the first 10% was added over 15 mins., the next 30% was added over 15 mins, and the remainder was then added over 15 mins. A retreat curve impeller at 160 rpm to 270 rpm in a 5 L scale reactor was used, with a process stream volume of about 740 ml, and produced reasonable-sized particles and particle distributions with no obvious agglomeration observed. The slurry formed was warmed up to 40±2° C. linearly over 20 minutes and held at 40±2° C. for about 30 minutes. It was then cooled linearly to 20±2° C. over 20 minutes. After stirring at 20±2° C. for about 30 minutes the slurry was filtered and the product cake was washed with isopropanol (first with 86 ml, second with 92 ml). The cake was dried under vacuum at 40±2° C. to a constant weight to yield (S)-(−)-TPMA hydrochloride (Compound G) as a white crystalline solid, and a yield of about 84% was obtained.

In Step 4b of Scheme 4, slow addition, that results in low supersaturation generation rate, favors the formation of desired block (S)-(−)-TPMA HCl crystals (Form A) while decreasing the generation the undesired needles (Form B). Higher temperature also favored the formation of the block like Form A crystals over Form B.

Figure 10:
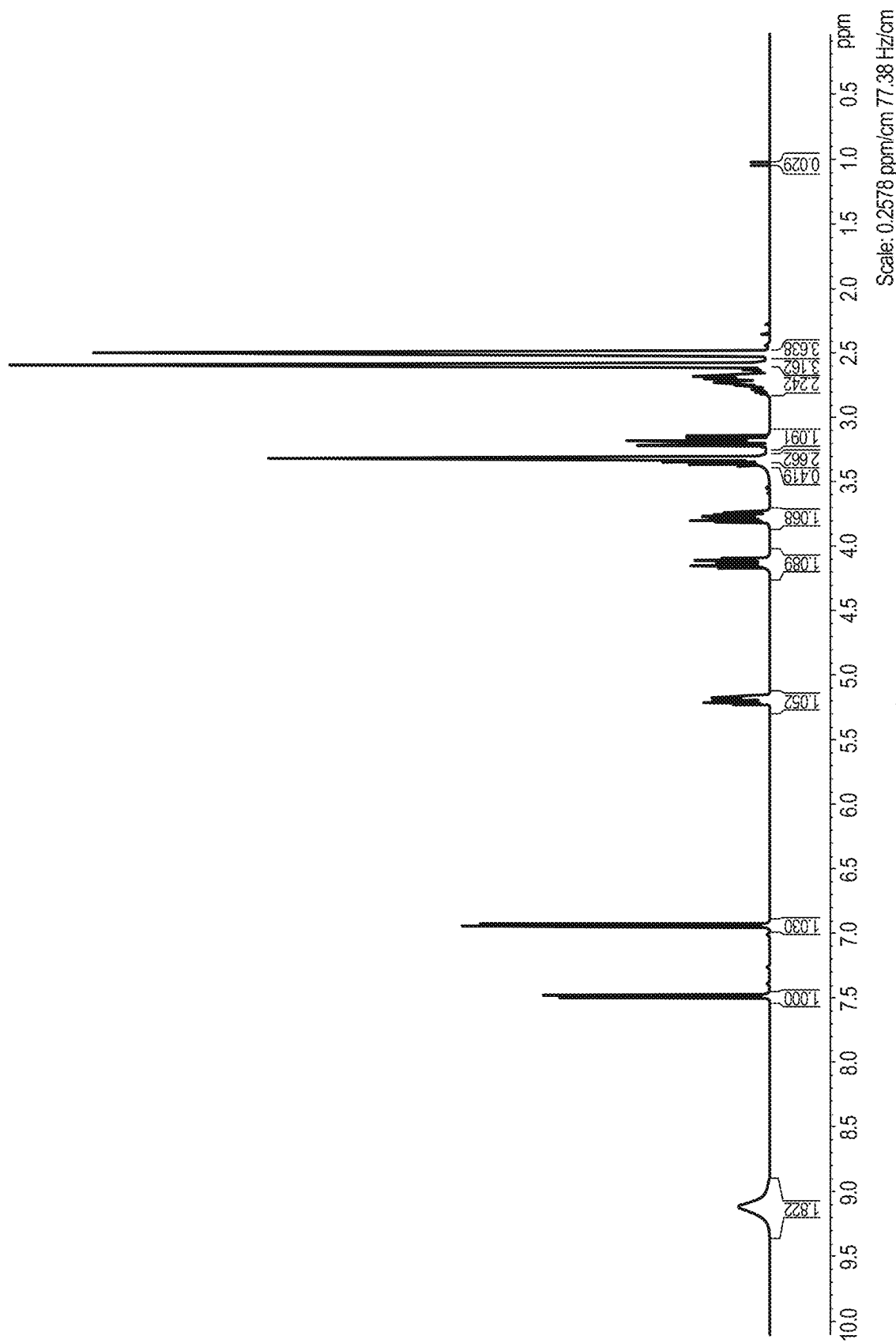
FIG. 10 is a $^1$H NMR spectrum of (S)-(4,5-dihydro-7H-thieno[2,3-c]pyran-7-yl)-N-methylmethanamine hydrochloride, of polymorph Form A.

An $^1$H NMR spectrum of the (S)-(−)-(4,5-dihydro-7H-thieno[2,3-c]pyran-7-yl)-N-methylmethanamine hydrochloride (Compound G) obtained in Example 1A is illustrated in FIG. 10, having the following characteristics: $^1$H NMR (300 MHz, DMSO-$d_6$); δ (ppm): 2.53 (s, 3H, —$CH_3$); 2.5-2.8 (m, H, —$CH_2$—); 3.15-3.37 (2dd, 2H, $CH_2$—NH); 3.77 and 4.13 (2ddd, 2H, $CH_2$—O); 5.19 (dd, 1H, O—CH—C=); 6.95 (d, J=5 Hz, 1H, HC=); 7.49 (dd, J=5 Hz, 1H, HC=); 9.12 (br, 2H, $NH_2^+$).

Example 1B: Alternative Preparation of (4,5-dihydro-7H-thieno[2,3-c]pyran-7-yl)-N-methylmethanamine triflate 2-(Thiophene-3-yl)ethanol (40 g, 0.31 mole) was placed in a 1 L reactor equipped with a mechanical stirrer, $N_2$ inlet and thermocouple. N-methylaminoacetaldehyde dimethylacetal (38.8 g, 0.28 mole) and 600 mL of 2-methyltetrahydrofuran were added. The resulting solution was cooled to about 5° C. Sulfuric acid (111.3 g, 1.13 mole) was added slowly while maintaining the reaction temperature below 20° C. The reaction was warmed to 35° C. and stirred for 4 hours. The HPLC examination of the reaction indicated about 31% formation of the product (4,5-dihydro-7H-thieno[2,3-c]pyran-7-yl)-N-methylmethanamine (TPMA). The reaction was cooled to room temperature and solvent was removed under vacuum. The resulting residue diluted with 300 mL of methyl tertbutylether (MTBE). The mixture was cooled to about 10° C. and 500 mL 25 wt % aq. NaOH was added while maintaining the reaction temperature below 30° C. The mixture was stirred for 20 minutes the layers were separated. The aqueous layer was extracted with twice (150 mL and 100 mL) with MTBE. The combined organic layer was then concentrated via removal of solvent by distillation. The concentrated organic layer was then cooled to 0° C. and 20 g (0.13 mol) of triflic acid was then added slowly while maintaining the reaction temperature below 10° C. The resulting slurry was stirred at 0° C. for 30 minutes. The slurry was filtered, and wet cake was washed with MTBE (2×20 mL), dried in vacuo to give TPMA-triflate salt as white solid (13.0 g, 13.75% yield with 97% purity).

$^1$H NMR (400 MHz, DMSO-$d_6$) δ ppm 2.62 (s, 3H) 2.64-2.76 (m, 2H) 3.22 (dd, J=12.91, 9.78 Hz, 1H) 3.40 (dd, J=12.91, 2.74 Hz, 1H) 3.79 (ddd, J=11.54, 8.80, 4.30 Hz, 1H) 4.00-4.20 (m, 1H) 5.09 (dd, J=9.59, 1.76 Hz, 1H) 6.95 (d, J=5.09 Hz, 1H) 7.50 (d, J=5.02 Hz, 1H) 8.59 (br s, 2H)

$^{13}$C NMR (101 MHz, DMSO-$d_6$) δ ppm 25.53, 33.02, 52.19, 62.73, 70.23, 124.62, 127.54, 131.01, 134.87.

Example 1C. Alternative Preparation of (S)-(4,5-dihydro-7H-thieno[2,3-c]pyran-7-yl)-N-methylmethanamine (R) Mandelate Salt To a slurry of 1.0 g (3.0 mmole) of TPMA-triflate in 3 mL MTBE 10% KOH (0.217 g in 2 mL water, 3.8 mmole) was added and stirred for 15 min. Organic layer was separated and aq. layer was extracted with MTBE (2×3 mL). Combined organic layer was washed with 1×2 mL of 20 wt % aqueous NaCl. Organic layer was dried over sodium sulfate, filtered and evaporated to dryness to give (S)-(4,5-dihydro-7H-thieno[2,3-c]pyran-7-yl)-N-methylmethanamine free base as colorless oil (0.473 g, 86.2%). This was dissolved into 2.4 mL acetonitrile and added to a solution of 0.392 g (2.5 mmole) of R-mandelic acid in 2.4 mL of acetonitrile. The resulting solution was heated to 38° C. and seeded with 15 mg of (S)-(4,5-dihydro-7H-thieno[2,3-c]pyran-7-yl)-N-methylmethanamine (R) mandelate salt crystals, stirred for 30 min at 38° C. and cooled to RT and then to 10° C. The slurry was stirred at 10° C. for 30 minutes and filtered. Wet cake was washed with cold (10° C.) acetonitrile, 2×1 mL, dried to afford crude (S)-TPMA (R)-mandelate salt as white solid (0.292 g, 33.75% yield, 96% purity, 9.3:91.7 ratio of R:S isomers)

$^1$H NMR (400 MHz, DMSO-$d_6$) δ ppm 2.49 (s, 3H), 2.57-2.79 (m, 2H) 3.00-3.17 (m, 2H) 3.69 (ddd, J=11.64, 8.90, 4.50 Hz, 1H) 4.08 (ddd, J=11.35, 5.48, 3.52 Hz, 1H) 4.66 (s, 1H) 4.89-5.07 (m, 1H) 6.91 (d, J=4.70 Hz, 1H) 7.13-7.32 (m, 3H) 7.36-7.44 (m, 3H)

$^{13}$C NMR (101 MHz, DMSO-$d_6$) δ ppm 25.63, 33.72, 53.42, 62.70, 71.26, 73.20, 124.23, 126.36, 126.42, 127.29, 127.52, 132.48, 134.24, 142.85, 174.78.

Example 2: Particle Size Distribution Control of (S)-(4,5-dihydro-7H-thieno[2,3-c]pyran-7-yl)-N-methylmethanamine HCl Form A Crystals A series of experiments was conducted on various aspects of the reactive-recrystallization (e.g. Scheme 4 in Example 1A) to develop methods and provide various particle size distribution of (S)-(−)-TPMA HCl Form A crystals. Reaction conditions were substantially similar to those set for in Example 1A with respect to Scheme 4 except as modified as described in this Example 2.

The PSD data of this Example 2 was obtained using laser diffraction particle sizing of the sample dispersed in a solvent. The data of FIGS. 7A, 7B, 8A, 8B and 8C was obtained using a Malvern Mastersizer 2000 analyzer, and the data of FIG. 9A was obtained using a Horiba LA-920 laser diffraction particle size analyzer. All particle sizes and D(4,3), D10, D50, D90, etc. values are in micrometers (μm), and all distributions are for volume % as a function of particle size.

The (S)-TPMA HCl sample was dispersed in a solution of Span®-85 (sorbitan trioleate) and hexanes. In this Example, the dispersant solution was 2 g of Span®-85 in 1 liter of hexanes, to make a 0.2% (w/v) Span®-85 in hexanes solution. All samples were gently sieved through a #30 mesh screen prior to addition to the dispersant solution.

The suspension solution for analysis was prepared by addition of approximately 5 mL of the 0.2% Span®-85 in hexanes dispersant solution to 1.5 to 3 grams of the sieved (S)-TPMA HCl sample, and the solution gently swirled until all of the solids were wetted. Then 35 mL of the 0.2% Span®-85 in hexanes dispersant solution was added and the solution mixed for at least 1 minute prior to measurement with an impeller set to 500 rpm to make the suspension solution. The actual amount of (S)-TPMA HCl sample, to which the dispersant solution is added, was determined experimentally and adjusted such that 2 to 3 mL of the resultant suspension solution will result in a laser obscuration between 10% and 20% as measured by the instrument used.

Prior to measurement, the instrument was aligned and background measured, and 2-3 mL of the suspension solution transferred to the sample cell of the instrument for measurement.

The data of FIGS. 7A, 7B, 8A, 8B and 8C was obtained using a Malvern Mastersizer 2000 analyzer, and Table 6 provides further details on the instrument settings of the Malvern Mastersizer 2000 analyzer used in this Example. Corresponding and similar setting were used on the Horiba LA-920 laser diffraction particle size analyzer used to acquire the data of FIG. 9A, specifically, PSD data generated on the Horiba LA-920 used 3% lecithin in Isopar G.

TABLE 6

Malvern Mastersizer 2000 Analyzer Instrument Settings

| Parameter | Setting |
| --- | --- |
| Stirrer/Pump Speed | 1750 rpm |
| Ultrasound | 0 |
| Sample Refractive Index | 1.5 (red and blue light) |
| Sample Absorption | 0 (red and blue light) |
| Dispersant name | 0.2% Span 85 in hexanes |
| Dispersant Refractive Index | 1.38 |
| Model | General Purpose-normal sensitivity |
| Sample measurement time | 30 seconds |
| Sample measurement snaps | 30000 |
| Background measurement time | 30 seconds |
| Background measurement snaps | 30000 |
| Number of measurement cycles | 1 |

Modulation by Supersaturation Generation Rate

Figure 6A:
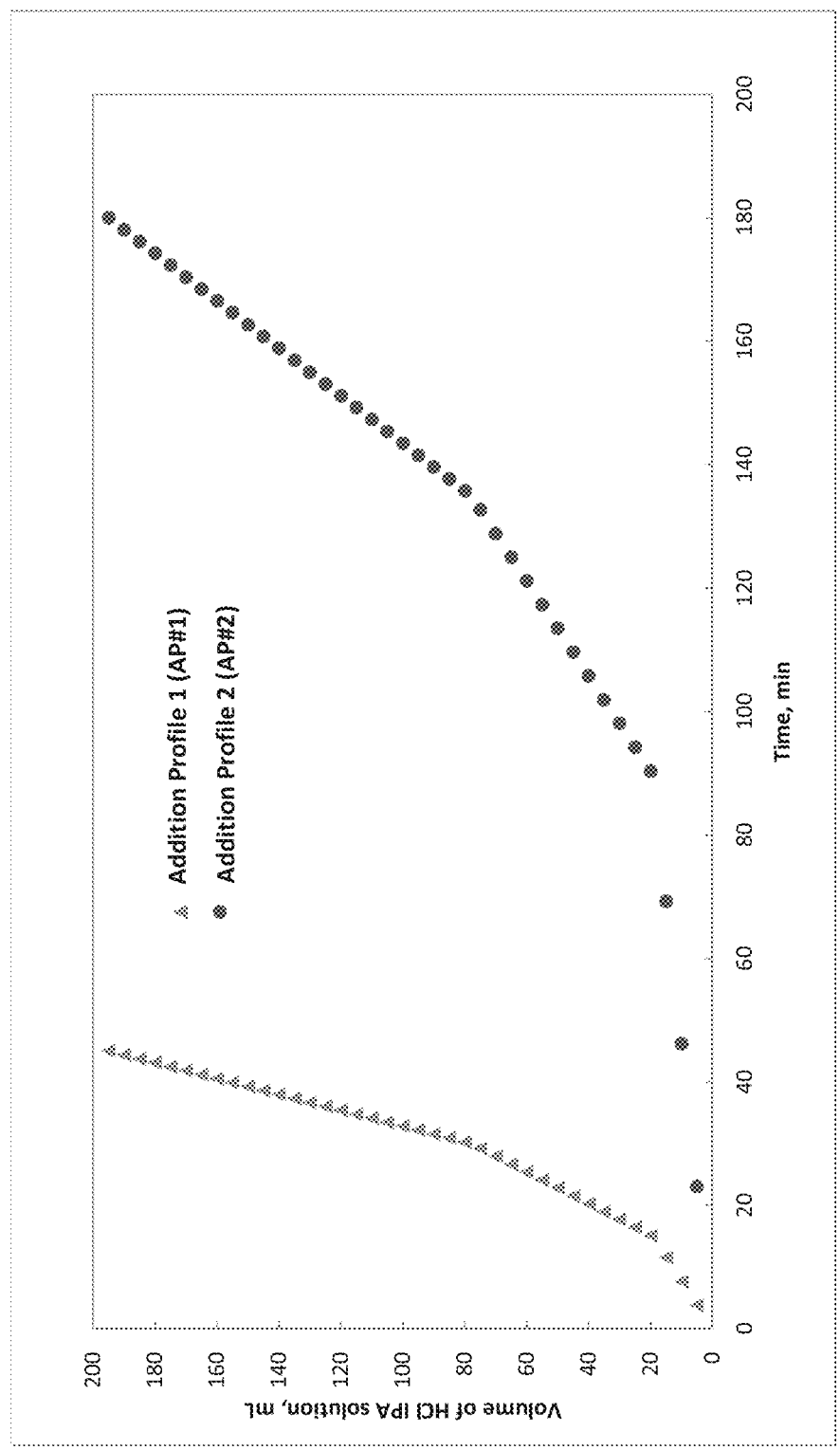
FIG. 6A and FIG. 6B present various HCl dosing profiles data of Example 2 for (S)-(4,5-dihydro-7H-thieno[2,3-c]pyran-7-yl)-N-methylmethanamine hydrochloride, of polymorph Form A.
Figure 6B:
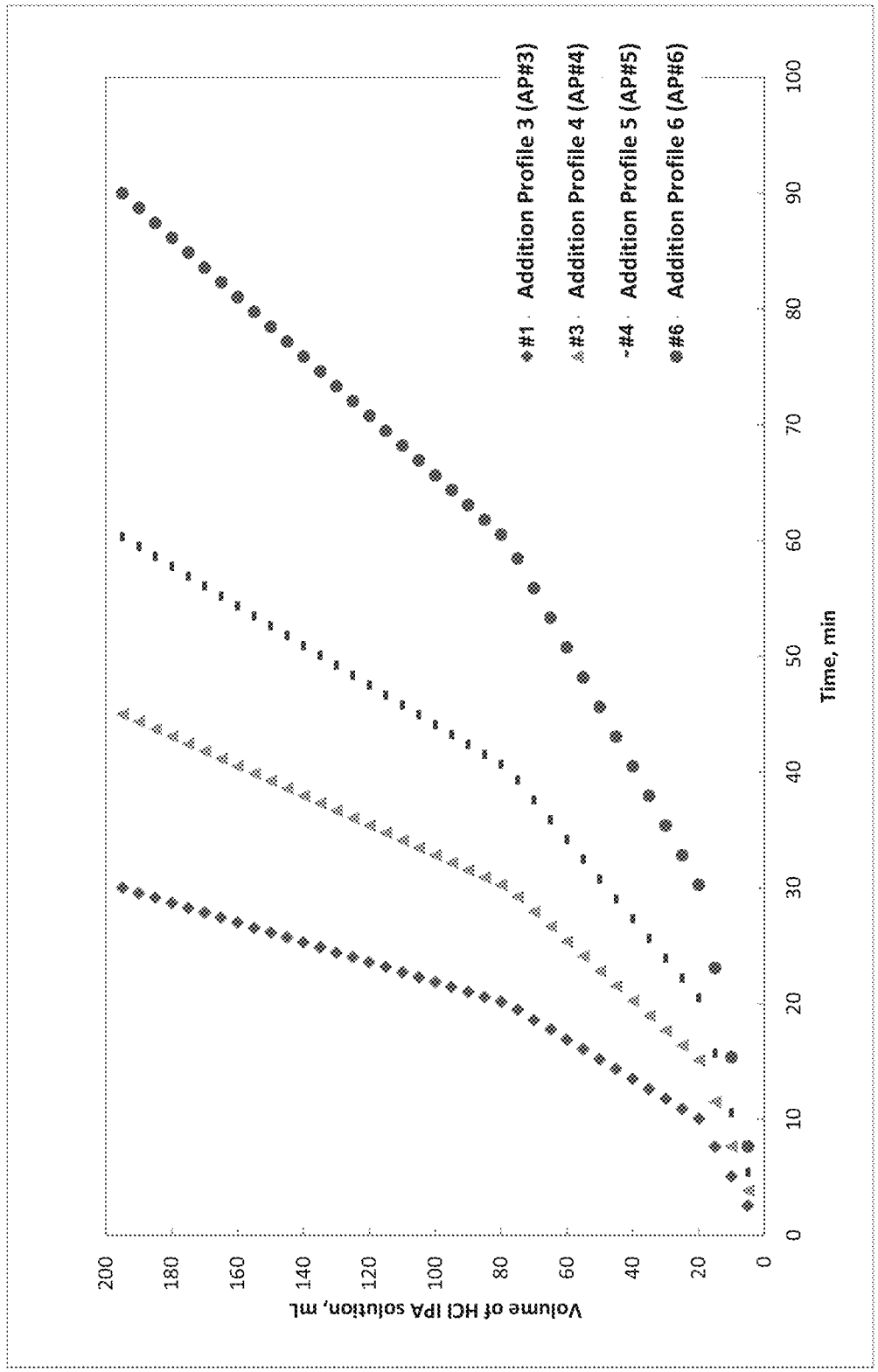
Figure 7A:
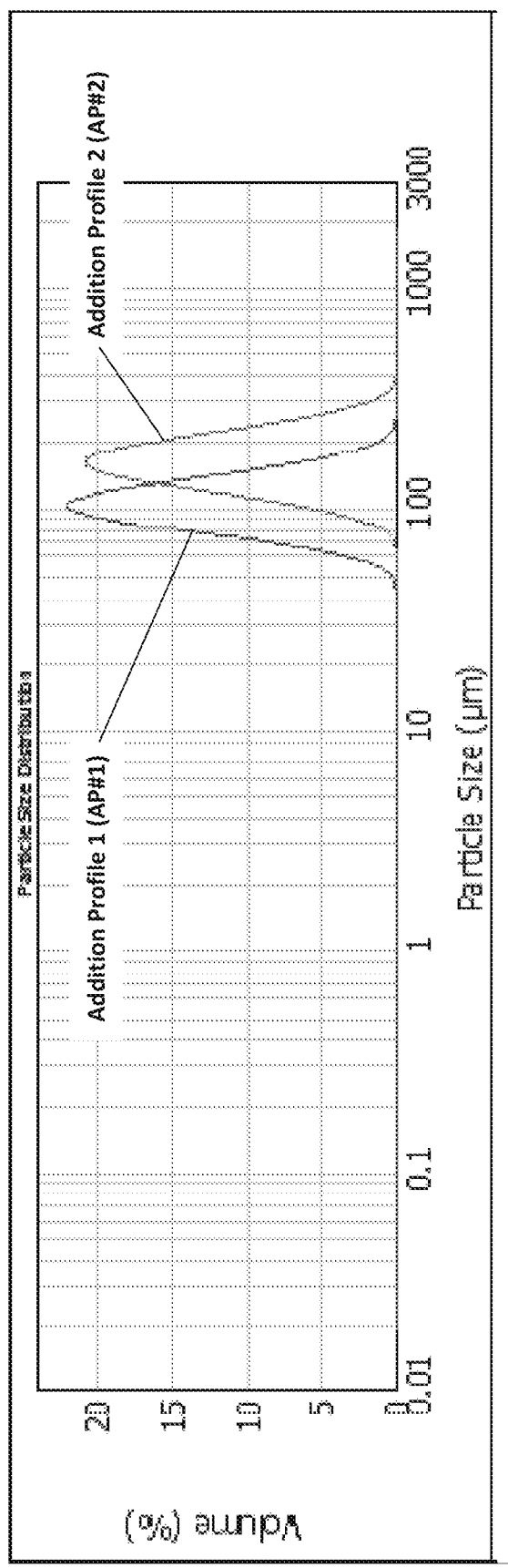
FIG. 7A and FIG. 7B present various PSD (particle size distribution) data of Example 2 for (S)-(4,5-dihydro-7H-thieno[2,3-c]pyran-7-yl)-N-methylmethanamine hydrochloride, of polymorph Form A.
Figure 7B:
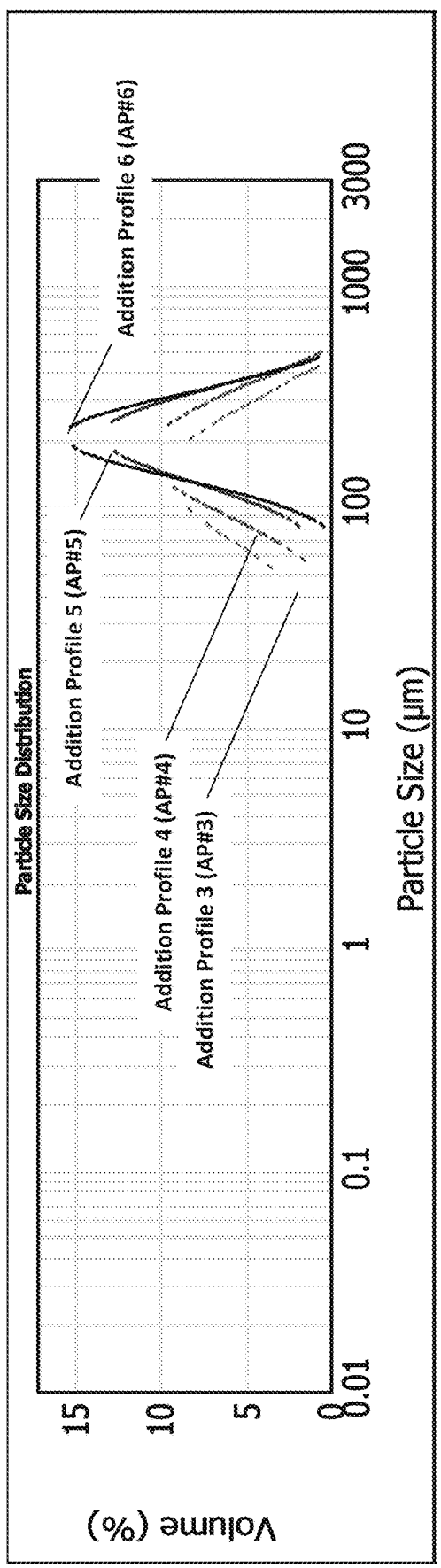

The (S)-(−)-TPMA freebase containing solution (e.g. solution of Compound F in Scheme 4) was reactively-recrystallized as a crystalline form of the (S)-(−)-TPMA HCl salt by addition of an HCl in isopropanol (IPA) to form a super saturated (S)-(−)-TPMA HCl from which crystallization occurred. FIGS. 6A and 6B present various 6% HCl in IPA addition profiles, which are also summarized in Table 7. Measured resultant PSD for the addition profiles of FIGS. 6A and 6B are presented respectively in FIGS. 7A and 7B. Table 8 provides various PSD parameters of the PSD data presented in FIGS. 7A and 7B.

It was discovered that a logarithmic-like addition of the reagent (HCl in IPA) responsible for supersaturation favored formation of Form A crystals and that a slower addition rate resulted in a larger median particle size and a lower span to the PSD.

TABLE 7

HCL IPA Solution Dosing Profiles

| Profile | HCl IPA solution addition |
| --- | --- |
| Addition Profile 1 (AP#1) | (i) first 10% added over approximately 15 minutes (ii) next 30% added over approximately 15 minutes (iii) remainder added over approximately 15 minutes |
| Addition Profile 2 (AP#2) | (i) first 10% added over approximately 90 minutes (ii) next 30% added over approximately 45 minutes (iii) remainder added over approximately 45 minutes |
| Addition Profile 3 (AP#3) | (i) first 10% added over approximately 10 minutes (ii) next 30% added over approximately 10 minutes (iii) remainder added over approximately 10 minutes |

TABLE 7-continued

HCL IPA Solution Dosing Profiles

| Profile | HCl IPA solution addition |
| --- | --- |
| Addition Profile 4 (AP#4) | (i) first 10% added over approximately 15 minutes (ii) next 30% added over approximately 15 minutes (iii) remainder added over approximately 15 minutes |
| Addition Profile 5 (AP#5) | (i) first 10% added over approximately 20 minutes (ii) next 30% added over approximately 20 minutes (iii) remainder added over approximately 20 minutes |
| Addition Profile 6 (AP#6) | (i) first 10% added over approximately 30 minutes (ii) next 30% added over approximately 30 minutes (iii) remainder added over approximately 30 minutes |

TABLE 8

Particle Size Distribution Parameters for Dosing Profiles

| Profile | D(4, 3) (µm) | D10 (µm) | D50 (µm) | D90 (µm) |
| --- | --- | --- | --- | --- |
| Addition Profile 1 | 109.50 | 74.66 | 105.41 | 149.78 |
| Addition Profile 2 | 170.79 | 114.16 | 164.31 | 236.27 |
| Addition Profile 3 | 149.43 | 55.23 | 131.21 | 273.25 |
| Addition Profile 4 | 185.80 | 79.73 | 167.51 | 323.92 |
| Addition Profile 5 | 209.45 | 103.82 | 199.11 | 335.44 |
| Addition Profile 6 | 222.06 | 129.01 | 209.38 | 334.41 |

Modulation by Temperature

The (S)-(−)-TPMA freebase containing solution (e.g. solution of Compound F in Scheme 4) was reactively-recrystallized as a crystalline form of the (S)-(−)-TPMA HCl salt by addition of an HCl in isopropanol (IPA) at two different temperatures, 25° C. and 40° C. Table 9 provides various PSD parameters of the measured PSD data at these two temperatures.

It was discovered that increasing temperature increased the median and mean particle size of the Form A crystals of (S)-(−)-TPMA HCl but increased temperature also increased the span of the PSD.

TABLE 9

Particle Size Distribution Parameters for Various Temperatures

| Temperature | D(4, 3) (µm) | D10 (µm) | D50 (µm) | D90 (µm) |
| --- | --- | --- | --- | --- |
| 40° C. | 180 | 86 | 164 | 302 |
| 25° C. | 109 | 65 | 102 | 167 |

Modulation by Freebase Concentration

Figure 8A:
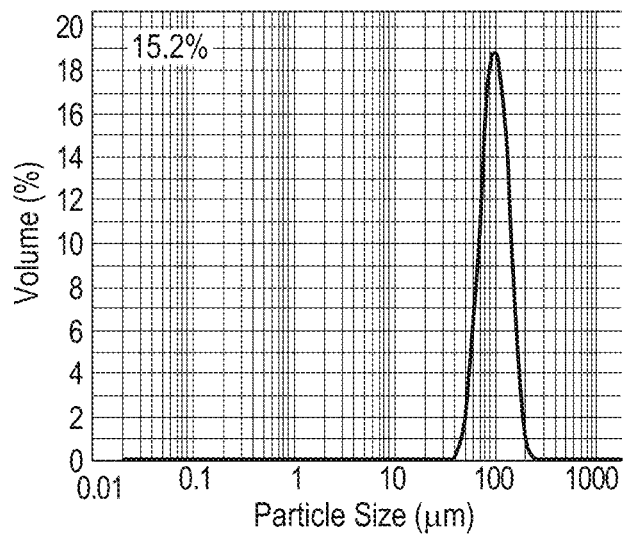
FIG. 8A, FIG. 8B, and FIG. 8C present various PSD (particle size distribution) data of Example 2 for (S)-(4,5-dihydro-7H-thieno[2,3-c]pyran-7-yl)-N-methylmethanamine hydrochloride, of polymorph Form A.
Figure 8B:
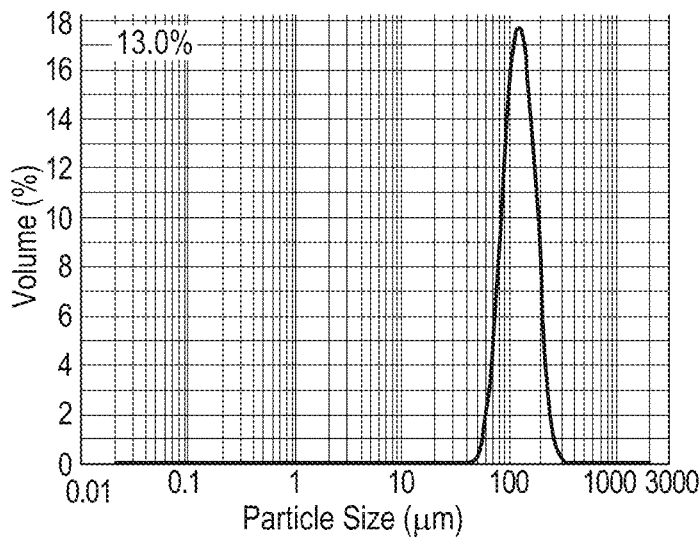
Figure 8C:
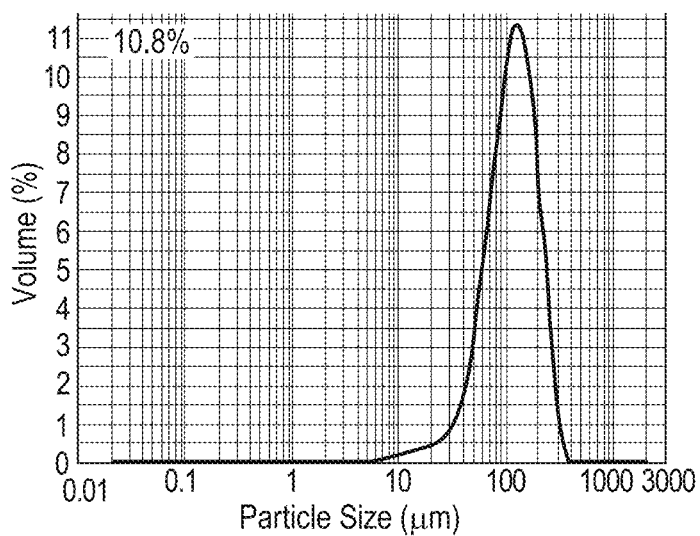

The (S)-(−)-TPMA freebase containing solution (e.g. solution of Compound F in Scheme 4) was reactively-recrystallized as a crystalline form of the (S)-(−)-TPMA HCl salt by addition of an HCl in isopropanol (IPA) from three different starting concentrations of (S)-(−)-TPMA freebase, 10.8%, 13.0% and 15.2%. Table 10 provides various PSD parameters of the measured PSD data presented in FIGS. 8A-8C; where FIG. 8A presents PSD data for a 15.2% (S)-(−)-TPMA freebase concentration, FIG. 8B presents PSD data for a 13.0% (S)-(−)-TPMA freebase concentration, and FIG. 8C presents PSD data for a 10.8% (S)-(−)-TPMA freebase concentration.

It was discovered that increasing starting (S)-(−)-TPMA freebase concentration decreased both the median particle size and the PSD span and that decreasing the starting (S)-(−)-TPMA freebase concentration increased the both the median particle size and the PSD span.

TABLE 10

Particle Size Distribution Parameters for Various Freebase Concentrations

| Freebase Concentration (weight %) | D(4, 3) (μm) | D10 (μm) | D50 (μm) | D90 (μm) |
|---|---|---|---|---|
| 15.2% | 104 | 66 | 99 | 148 |
| 13.0% | 109 | 65 | 102 | 167 |
| 10.8% | 134 | 55 | 124 | 228 |

Modulation by Water Content

The (S)-(−)-TPMA freebase containing solution (e.g. solution of Compound F in Scheme 4) was reactively-recrystallized as a crystalline form of the (S)-(−)-TPMA HCl salt by addition of an HCl in isopropanol (IPA) from solutions of (S)-(−)-TPMA freebase with different water content (i.e. pre-nucleation water content), ranging from 2%-5.5%. Table 11 provides various PSD parameters of the measured PSD data for the indicated water content.

It was discovered that increased water content generally resulted in increased median particle size but decreased PSD span.

TABLE 11

Particle Size Distribution Parameters for Various Water Contents

| Water Content (before nucleation) | D(4, 3) (μm) | D10 (μm) | D50 (μm) | D90 (μm) |
|---|---|---|---|---|
| 2% | 189.0 | 120.8 | 179.6 | 268.7 |
| 2.5% | 154.4 | 77.5 | 140.4 | 249.3 |
| 3% | 160.6 | 97.2 | 148.4 | 236.7 |
| 3.5% | 158.4 | 100.3 | 150.0 | 225.5 |
| 4% | 201.1 | 116.8 | 192.3 | 294.6 |
| 5% | 216.8 | 115.1 | 204.9 | 332.6 |
| 5% | 191.9 | 105.9 | 173.9 | 297.9 |
| 5.5% | 220.7 | 141.4 | 211.3 | 309.0 |

Modulation by Reaction Process

The reactive-recrystallization was carried out by two different process, (i) Process 1 employing a Plug Flow Reactor (PFR) process with ultrasound applied to the reaction mixture during nucleation (e.g. during Step 4b of Scheme 4); and (ii) Process 2 a multi-stage mixed suspension and mixed product removal (MSMPR) process.

The chemistry, e.g., chemicals, concentrations, and stoichiometry, used in the reactive-recrystallization under Process 1 and Process 2, were substantially similar to that of Example 1A where Process 1 and Process 2 starting with the (S)-(−)-TPMA free base solution (Compound F) of Scheme 4 in Example 1A of various concentrations.

Reactive-recrystallization under Process 1 was conducted as follows. The (S)-(−)-TPMA free base solution and the HCl/IPA solution were pumped, using peristaltic pumps, as separate feed streams into a tubing crystallizer through a Tee mixer, at a controlled temperature (e.g., 40° C.) and residence time, to perform Step 4b of Scheme 4. The crystallization occurred as the process stream flowed through the tubing after contact at the Tee. A $N_2$ injection system was integrated into both feed streams to enable periodic introduction of gas. The output solution, post mixer Tee, was passed through a tubular coil (⅛" PFA tubing) of predetermined length depending on the desired residence time. For a residence time of about 2.5 minutes a coil length of 3.5 m was used, and for a residence time of about 5 minutes a coil length of 7 m was used. The temperature control for the coil was achieved using a water bath in which the Tee, approximately 10 cm of each of the input stream tubes, and the coil were immersed, and sonication was achieved by sonication of the water bath during process flow.

Reactive-recrystallization under Process 2 was conducted as follows. The multi-sage MSMPR process employed three stages with process streams continually pumping starting materials into a first reaction vessel (first stage crystallizer), continually pumping products out of the first reaction vessel into a second reaction vessel (second stage crystallizer), continually pumping products out of the second reaction vessel into a third reaction vessel (third stage crystallizer) and continually pumping products out of the third reaction vessel to a product receiving vessel. The operation volume and reaction conditions were kept steady state during the process and each reaction vessel was stirred.

A starting (S)-(−)-TPMA free base isopropanol solution and 13% of the HCl isopropanol solution were pumped into the first stage with set flow rates to control the residence time and the ratio of (S)-(−)-TPMA free base to HCl for each stage. The suspension from the first stage crystallizer was transferred to the second stage crystallizer and 37% of the HCl isopropanol solution was pumped to the second stage crystallizer. The suspension from the second stage crystallizer was transferred to the third stage crystallizer and the reminder (50%) of the HCl isopropanol solution was pumped to the third stage crystallizer. Pumping was performed with peristaltic pumps. The various flow and other conditions for each stage are summarized in Table 12.

TABLE 12

MSMPR Stage Conditions and Parameters

| STAGE 1 | |
|---|---|
| Average volume (mL) | 65.00 |
| Tau 1 (min) | 10.00 |
| Overall flow rate in Stage 1 (mL/min) | 6.50 |
| Slug volume (mL) | 10.00 |
| Slug interval (min) | 1.54 |
| Feed flow rate (mL/Min) | 6.12 |
| HCL in IPA flow rate (mL/min) | 0.38 |
| Operating temperature (° C.) | 40 |
| Agitation rate, reaction vessel stirring, (rpm) | 300 |
| STAGE 1 | |
| Average volume (mL) | 75.8 |
| Tau 1 (min) | 10.00 |
| Overall flow rate in Stage 1 (mL/min) | 7.58 |
| Slug volume (mL) | 11.66 |
| Slug interval (min) | 1.54 |
| HCL in IPA flow rate (mL/min) | 1.08 |
| Operating temperature (° C.) | 40 |
| Agitation rate, reaction vessel stirring, (rpm) | 300 |
| STAGE 1 | |
| Average volume (mL) | 90.3 |
| Tau 1 (min) | 10.00 |
| Overall flow rate in Stage 1 (mL/min) | 9.03 |
| Slug volume (mL) | 13.89 |
| Slug interval (min) | 1.54 |
| HCL in IPA flow rate (mL/min) | 1.45 |
| Operating temperature (° C.) | 40 |
| Agitation rate, reaction vessel stirring, (rpm) | 300 |

Table 13 provides various PSD parameters of the measured PSD data presented in FIG. 9A; and FIGS. 9B and 9C present SEM images of (S)-(−)-TPMA HCl of crystalline Form A obtained, respectively, by Process 2 and Process 1.

It was discovered that sonication during the step of supersaturation provided a PSD with a small median particle size and an acceptable PSD span. On addition, it was discovered that sonication during the step of supersaturation favors primary nucleation of the block-like crystal form (Form A) of (S)-(−)-TPMA HCl, and facilitates avoiding the needle form (Form B).

TABLE 13

Particle Size Distribution Parameters for Various Reaction Processes

| Reaction Process | D(4, 3) (μm) | D10 (μm) | D50 (μm) | D90 (μm) |
|---|---|---|---|---|
| Process 1 (PRF with ultra-sonication) | 21.9 | 11.4 | 20.3 | 34.8 |
| Process 2 (multi-stage MSMPR) | 210.6 | 77.0 | 190.2 | 377.1 |

In various embodiments, crystalline forms of the present inventions have several advantageous physical properties. For example, (S)-(4,5-dihydro-7H-thieno[2,3-c]pyran-7-yl)-N-methylmethanamine hydrochloride polymorph Form A crystalline form is substantially non-hygroscopic, in various embodiments exhibiting less than about a 0.2%, and preferably less than about 0.1%, maximum mass change in water sorption isotherms, at 25° C. scanned over 0 to 90% relative humidity, as measured by dynamic vapor sorption (DVS) (see, for example, FIG. 5).

It is to be understood that various embodiments of the present inventions provide crystalline (S)-(4,5-dihydro-7H-thieno[2,3-c]pyran-7-yl)-N-methylmethanamine hydrochloride of polymorph Form A, in high chiral purity and high chemical purity.

In various embodiments the present inventions provide substantially enantiomerically pure crystalline forms of (S)-(4,5-dihydro-7H-thieno[2,3-c]pyran-7-yl)-N-methylmethanamine hydrochloride of polymorph Form A. For example, in various embodiments, the present inventions provide crystalline forms of (4,5-dihydro-7H-thieno[2,3-c]pyran-7-yl)-N-methylmethanamine hydrochloride that contain greater than about 90% (S)-(4,5-dihydro-7H-thieno[2,3-c]pyran-7-yl)-N-methylmethanamine hydrochloride and less than about 10% of (R)-(4,5-dihydro-7H-thieno[2,3-c]pyran-7-yl)-N-methylmethanamine hydrochloride, greater than about 95% (S)-(4,5-dihydro-7H-thieno[2,3-c]pyran-7-yl)-N-methylmethanamine hydrochloride and less than about 5% of (R)-(4,5-dihydro-7H-thieno[2,3-c]pyran-7-yl)-N-methylmethanamine hydrochloride, greater than about 97% (S)-(4,5-dihydro-7H-thieno[2,3-c]pyran-7-yl)-N-methylmethanamine hydrochloride and less than about 3% of (R)-(4,5-dihydro-7H-thieno[2,3-c]pyran-7-yl)-N-methylmethanamine hydrochloride, greater than about 99% (S)-(4,5-dihydro-7H-thieno[2,3-c]pyran-7-yl)-N-methylmethanamine hydrochloride and less than about 1% of (R)-(4,5-dihydro-7H-thieno[2,3-c]pyran-7-yl)-N-methylmethanamine hydrochloride, greater than about 99.5% (S)-(4,5-dihydro-7H-thieno[2,3-c]pyran-7-yl)-N-methylmethanamine hydrochloride and less than about 0.5% of (R)-(4,5-dihydro-7H-thieno[2,3-c]pyran-7-yl)-N-methylmethanamine hydrochloride, greater than about 99.7% (S)-(4,5-dihydro-7H-thieno[2,3-c]pyran-7-yl)-N-methylmethanamine hydrochloride and less than about 0.3% of (R)-(4,5-dihydro-7H-thieno[2,3-c]pyran-7-yl)-N-methylmethanamine hydrochloride, or greater than about 99.9% (S)-(4,5-dihydro-7H-thieno[2,3-c]pyran-7-yl)-N-methylmethanamine hydrochloride and less than about 0.1% of (R)-(4,5-dihydro-7H-thieno[2,3-c]pyran-7-yl)-N-methylmethanamine hydrochloride.

In various embodiments the present inventions provide substantially chemically pure crystalline forms of (S)-(4,5-dihydro-7H-thieno[2,3-c]pyran-7-yl)-N-methylmethanamine hydrochloride of polymorph Form A. For example, in various embodiments, the present inventions provide crystalline (S)-(4,5-dihydro-7H-thieno[2,3-c]pyran-7-yl)-N-methylmethanamine hydrochloride of polymorph Form A that has a greater than about 80% chemical purity, greater than about 90% chemical purity, greater than about 95% chemical purity, greater than about 97% chemical purity, greater than about 99% chemical purity, greater than about 99.5% chemical purity, greater than about 99.7% chemical purity, or greater than about 99.9% chemical purity. In various embodiments, provided is crystalline (S)-(4,5-dihydro-7H-thieno[2,3-c]pyran-7-yl)-N-methylmethanamine hydrochloride of polymorph Form A that has less than about 8000 ppm residual solvents, less than about 6000 ppm residual solvents, less than about 4000 ppm residual solvents, less than about 2000 ppm residual solvents, less than about 1000 ppm residual solvents, less than about 800 ppm residual solvents, or less than about 500 ppm residual solvents.

In various aspects, the present inventions provide formulations and compositions comprising (S)-TPMA HCl, and/or crystalline forms thereof, and one or more pharmaceutically acceptable excipient, carrier, adjuvant, or vehicle.

In various embodiments, the compositions are formulated with one or more pharmaceutically acceptable excipients in accordance with known and established practice. Thus, in various embodiments the composition are formulated as, for example, a liquid, powder, elixir, injectable solution, or suspension. Formulations for oral use are preferred and may be provided, for instance, as tablets, caplets, or capsules, wherein the pharmacologically active ingredients are mixed with an inert solid diluent. Tablets may also include granulating and disintegrating agents, and may be coated or uncoated. Formulations for topical use may be provided, for example as topical solutions, lotions, creams, ointments, gels, foams, patches, powders, solids, sponges, tapes, vapors, pastes or tinctures.

In various embodiments, provided herein are compositions comprising (S)-TPMA, or a pharmaceutically acceptable salt thereof, and one or more pharmaceutically acceptable excipient, carrier, adjuvant, or vehicle, where the amount of (S)-TPMA is between about 10 mg and about 120 mg on a free base basis. In some embodiments, the amount of (S)-TPMA is between about 30 mg and about 100 mg on a free base basis. In some embodiments, the amount of (S)-TPMA is about 30 mg, about 40 mg, about 50 mg, about 60 mg, about 70 mg, about 75 mg, about 80 mg, about 90 mg, or about 100 mg, on a free base basis. In some embodiments, the amount of (S)-TPMA is about 30 mg on a free base basis. In some embodiments, the amount of (S)-TPMA is about 50 mg on a free base basis. In some embodiments, the amount of (S)-TPMA is about 75 mg on a free base basis. In some embodiments, the amount of (S)-TPMA is about 100 mg on a free base basis.

In various embodiments, the present inventions comprise compositions comprising (S)-TPMA HCl and one or more pharmaceutically acceptable excipient, carrier, adjuvant, or vehicle, where the amount of (S)-TPMA HCl is between about 30 mg and about 120 mg, and in various embodiments preferably between about 30 mg and about 90 mg.

In various embodiments, provided herein are compositions comprising (S)-TPMA HCl, and one or more pharmaceutically acceptable excipient, carrier, adjuvant, or vehicle, where the amount of (S)-TPMA HCl is between about 10 mg and about 120 mg on a free base basis. In some embodiments, the amount of (S)-TPMA HCl is between about 30 mg and about 100 mg on a free base basis. In some embodiments, the amount of (S)-TPMA HCl is about 30 mg, about 40 mg, about 50 mg, about 60 mg, about 70 mg, about 75 mg, about 80 mg, about 90 mg, or about 100 mg, on a free base basis. In some embodiments, the amount of (S)-TPMA HCl is about 30 mg on a free base basis. In some embodiments, the amount of (S)-TPMA HCl is about 50 mg on a free base basis. In some embodiments, the amount of (S)-TPMA HCl is about 75 mg on a free base basis. In some embodiments, the amount of (S)-TPMA HCl is about 100 mg on a free base basis In various embodiments, compositions comprising (S)-TPMA HCl formulated as a solid oral dosage form. It is to be understood that the total amount of a composition comprising (S)-TPMA HCl need not be provided in a single dosage unit forms, e.g. a single tablet, capsule, etc. In various embodiments, it is preferred that the compositions be provided in dosage unit forms such that, for example, the administration of two of the dosage unit forms will result in administration of the desired amount of (S)-TPMA HCl.

Pharmaceutical compositions containing the active ingredient ((S)-TPMA HCl and crystalline forms thereof) may be in any form suitable for the intended method of administration. For example, tablets, troches, lozenges, aqueous or oil suspensions, dispersible powders or granules, emulsions, hard or soft capsules, syrups or elixirs are suitable forms for oral administration. Compositions intended for oral use can contain one or more excipients, for example, sweetening agents, flavoring agents, coloring agents and preserving agents, in order to provide a palatable preparation.

In various embodiments, a composition of the inventions is formulated for oral administration to a subject; and in various preferred embodiments the compositions are provided in a solid oral dosage form. In various embodiments, the solid oral dosage form comprises a tablet.

In various embodiments, tablets containing the active ingredient in admixture with non-toxic pharmaceutically acceptable excipients, which are suitable for manufacture of tablets, are provided. These excipients may be, for example, inert diluents, such as microcrystalline cellulose, mannitol, calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; disintegrating agents such as crospovidone, croscarmellose sodium or sodium starch glycolate, and lubricating agents, such as magnesium stearate, stearic acid or talc. Tablets may be uncoated or may be coated by known techniques.

The preparation of tablets almost universally requires the presence of excipients in the formulations to facilitate handling, enhance the physical appearance, improve stability and aid in the delivery of the drug to the bloodstream after administration. These supposedly inert ingredients, as well as the production methods employed, often influence the absorption or bioavailability of the drug substances. Therefore, care must be taken in the selection and evaluation of additives and preparation methods to ensure that the drug-delivery goals and therapeutic efficacy of the active ingredient will not be diminished. A drug substance's solubility and other physicochemical characteristics influence its physiological availability from a solid dosage form. Important physicochemical characteristics include its particle size, whether it is amorphous or crystalline, whether it is solvated or nonsolvated and its polymorphic form. Even when otherwise clinically effective formulations are obtained, variations among dosage units of a given batch, as well as batch-to-batch differences, can result in pharmacologically unacceptable outcomes.

In various embodiments, provided are formulations comprising (S)-TPMA, or a pharmaceutically acceptable salt thereof, in the range of between about 2 to about 80% w/w, on a free base basis. In various embodiments, provided are formulations comprising (S)-TPMA, or a pharmaceutically acceptable salt thereof, in the range of between about 5 to about 75% w/w, on a free base basis. In various embodiments, provided are formulations comprising (S)-TPMA, or a pharmaceutically acceptable salt thereof, in the range of between about 40 to about 80% w/w, on a free base basis. In various embodiments, provided are formulations comprising (S)-TPMA, or a pharmaceutically acceptable salt thereof, in the range of between about 50 to about 80% w/w, on a free base basis. In various embodiments, provided are formulations comprising (S)-TPMA, or a pharmaceutically acceptable salt thereof, in the range of between about 60 to about 80% w/w, on a free base basis. In some embodiments, the amount is about 70% w/w.

In various embodiments, provided are formulations comprising (S)-TPMA, or a pharmaceutically acceptable salt thereof, in the amount of about 40, about 45, about 50, about 55, about 60, about 65, about 70, about 75, or about 80% w/w, on a free base basis. In various embodiments, provided are formulations comprising (S)-TPMA, or a pharmaceutically acceptable salt thereof, in the amount of about 10% w/w on a free base basis. In various embodiments, provided are formulations comprising (S)-TPMA, or a pharmaceutically acceptable salt thereof, in the amount of about 20% w/w on a free base basis. In various embodiments, provided are formulations comprising (S)-TPMA, or a pharmaceutically acceptable salt thereof, in the amount of about 40% w/w on a free base basis. In various embodiments, provided are formulations comprising (S)-TPMA, or a pharmaceutically acceptable salt thereof, in the amount of about 50% w/w on a free base basis. In various embodiments, provided are formulations comprising (S)-TPMA, or a pharmaceutically acceptable salt thereof, in the amount of about 60% w/w on a free base basis. In various embodiments, provided are formulations comprising (S)-TPMA, or a pharmaceutically acceptable salt thereof, in the amount of about 70% w/w on a free base basis.

In various embodiments, provided are tablet formulations comprising (S)-TPMA hydrochloride in the range of between about 2.4% w/w to about 60% w/w, and in various preferred embodiments in the range of between about 10% w/w to about 40% w/w.

In various embodiments, provided are formulations comprising (S)-TPMA HCl in the range of between about 2 to about 80% w/w, on a free base basis. In various embodiments, provided are formulations comprising (S)-TPMA HCl in the range of between about 5 to about 75% w/w, on a free base basis. In various embodiments, provided are formulations comprising (S)-TPMA HCl in the range of between about 5 to about 50% w/w, on a free base basis. In various embodiments, provided are formulations comprising (S)-TPMA HCl in the range of between about 5 to about 40% w/w, on a free base basis. In various embodiments, provided are formulations comprising (S)-TPMA HCl in the range of between about 10 to about 40% w/w, on a free base basis. In various embodiments, provided are formulations comprising (S)-TPMA HCl in the range of between about 10 to about 40% w/w, on a free base basis.

In various embodiments, provided are formulations comprising (S)-TPMA HCl in the amount of about 10% w/w on a free base basis. In various embodiments, provided are formulations comprising (S)-TPMA HCl in the amount of about 20% w/w on a free base basis. In various embodiments, provided are formulations comprising (S)-TPMA HCl in the amount of about 25% w/w on a free base basis. In various embodiments, provided are formulations comprising (S)-TPMA HCl in the amount of about 30% w/w on a free base basis. In various embodiments, provided are formulations comprising (S)-TPMA HCl in the amount of about 35% w/w on a free base basis.

In some embodiments, the formulation is a tablet. In some embodiments, the formulation further comprises a filler. In some embodiments, the formulation further comprises a disintegrant. In some embodiments, the formulation further comprises a lubricant. In some embodiments, the formulation further comprises a coating.

In various embodiments, tablets provided herein comprise a core comprising: (i) (S)-TPMA, or a pharmaceutically acceptable salt thereof, in the range of between about 10 to about 40% w/w, on a free base basis; (ii) filler; (iii) disintegrant; (iv) lubricant; and optionally (v) glidant. In some embodiments, tablet comprises a coating comprising: (i) a matrix as a polymer coating system; and optionally one or more of: (ii) opacifier and colorant, (iii) polishing agent, and (iv) and other colorants to provide various tablet colors for, e.g., market need.

In some embodiments, a pharmaceutically acceptable salt of (S)-TPMA is (S)-TPMA HCl. In some embodiments, (S)-TPMA HCl is Form A or Form B. In some embodiments, provided herein is a formulation comprising (S)-(4,5-dihydro-7H-thieno[2,3-c]pyran-7-yl)-N-methylmethanamine, or a pharmaceutically acceptable salt thereof, in the range of between about 2 to about 80% w/w, on a free base basis, wherein, the (S)-(4,5-dihydro-7H-thieno[2,3-c]pyran-7-yl)-N-methylmethanamine hydrochloride is Form A or Form B.

In some embodiments, the filler is microcrystalline cellulose, mannitol, or a combination thereof. In some embodiments, the disintegrant is sodium starch glycolate. In some embodiments, the lubricant is magnesium stearate. In some embodiments, the glidant is colloidal silicon dioxide. In some embodiments, the polymer coating system is (hydroxypropyl) methyl cellulose (HPMC)/hydroxypropylcellulose (HPC). In some embodiments, the opacifier and colorant is titanium dioxide. In some embodiments, the polishing agent is carnauba wax.

In various embodiments, tablets of the present inventions comprise: (a) a core comprising: (i) (S)-TPMA hydrochloride in the range of between about 2.4% w/w to about 60% w/w, and in various preferred embodiments in the range of between about 10% w/w to about 40% w/w; (ii) microcrystalline cellulose and mannitol as filler; (iii) sodium starch glycolate as disintegrant; (iv) magnesium stearate as lubricant; and optionally (v) colloidal silicon dioxide (if needed) as glidant; and (b) a coating comprising: (i) a (hydroxypropyl) methyl cellulose (HPMC)/hydroxypropylcellulose (HPC) matrix as a polymer coating system; and optionally one or more of: (ii) titanium dioxide as opacifier and colorant, (iii) carnauba wax as polishing agent, and (iv) and other colorants to provide various tablet colors for, e.g., market need. In various preferred embodiments, the concentration of each ingredient is selected based on powder flowability, tabletability and tablet stability after storage at accelerated and long-term conditions.

In some formulations, micro-cracking in tablets was observed. This was addressed by changing the compression process, e.g., changing the compression location within the die. The ejection force can be decreased by eliminating colloidal silicon dioxide (Cabosil) from the formulation and increasing microcrystalline cellulose (MCC):mannitol ratio. In some embodiments, the formulation does not include colloidal silicon dioxide and the MCC:mannitol ratio is approximately 5:1. It has been shown that binary mixtures (1:1) of API with Opadry 03F110000 (green), Opadry 03F180011 (white), Opadry II 85F18422 (white), copovidone, crospovidone, and sodium stearyl fumarate, are stable when stored in closed glass vials for 6 or 9 months at 40° C./75% RH. Based on binary excipient compatibility data, these excipients can potentially be used for tablet formulations. Binary mixture of API (1:1) with colloidal silicon dioxide are not stable even after 2 weeks at 40° C./75% RH.

In some embodiments, the formulation does not include colloidal silicon dioxide (e.g., (S)-TPMA hydrochloride granule, microcrystalline cellulose, mannitol, sodium starch glycolate, and magnesium stearate). In some embodiments, the formulation does not include mannitol (e.g., (S)-TPMA hydrochloride granule, microcrystalline cellulose, sodium starch glycolate, colloidal silicon dioxide and magnesium stearate). In some embodiments, the formulation does not include mannitol and colloidal silicon dioxide (e.g., (S)-TPMA hydrochloride granule, microcrystalline cellulose, sodium starch glycolate, and magnesium stearate).

In some embodiments, the (S)-TPMA hydrochloride is Form A or Form B. In some embodiments, the (S)-TPMA hydrochloride is Form A. In some embodiments, the (S)-TPMA hydrochloride is Form B.

In various aspects, provided are methods of manufacture for a solid oral dosage form comprising (S)-TPMA. In various embodiments, provided are methods for formation of a tablet by, for example, direct compression or dry granulation.

Example 3: Tablet Formulations and Manufacture (S)-TPMA hydrochloride tablets were manufactured by using a dry process. Direct compression was used for 25 mg tablets, and dry granulation followed by compression was used for dose strengths of 50, 75 and 100 mg. In some embodiments, the API is milled prior to blending with excipients. The composition of the 25 mg strength tablets is summarized in Table 14, and the compositions of the 50, 75 and 100 mg strength tablets are summarized in Table 15A, Table 15B, Table 15C, and Table 15D; including the core tablet and the coating applied to the core. It is to be understood that although yellow is listed as the color for the coated tablet in these tables, the tablet color may be changed based, e.g., on market need, with the polymer coating system remaining unchanged. For the dosage strength of 25 mg based on the amount of free base, i.e. (S)-TPMA, in the compound (S)-TPMA hydrochloride, microcrystalline cellulose, mannitol, and sodium starch glycolate were sieved individually through a #30 mesh screen and charged into a low shear blender. The mixture was blended for up to 500 revolutions. In some examples, the mixture was blended for up to 300 revolutions. Magnesium stearate was sieved though a #60 mesh screen, charged into the blender and the mixture blended for an additional 75 revolutions. The blend was then compressed into tablets with a target tablet weight of 300 mg. The tablets were then coated with Opadry 20A120006 Yellow, Opadry 20A18407 White or Opadry 20A110008 Green (hydroxypropylmethyl cellulose/hydroxypropyl cellulose), and carnauba wax was applied onto the tablets after drying.

For the dose strengths (based on the amount of free base) greater than 25 mg, intra-granular blend included (S)-TPMA hydrochloride, microcrystalline cellulose, and sodium starch glycolate were sieved individually through a #30 mesh screen and charged into a low shear blender. The mixture was blended for up to 500 revolutions. In some examples, the mixture was blended for up to 300 revolutions. In some examples, the mixture was blended for up to 250 revolutions, Magnesium stearate was sieved though a #60 mesh screen, charged into the blender and the mixture blended for additional 75 revolutions. The intra-granular blend was then dry granulated into ribbons, and milled into granules.

After dry granulation, depending on the target tablet strength, different amount of granules were used and blended with the extra-granular excipients before compression. The final blend included (S)-TPMA hydrochloride granule, microcrystalline cellulose, mannitol, sodium starch glycolate, colloidal silicon dioxide (for 75 and 100 mg only) and magnesium stearate. In some examples, the final blend does not include colloidal silicon dioxide (e.g., (S)-TPMA hydrochloride granule, microcrystalline cellulose, mannitol, sodium starch glycolate, and magnesium stearate). In some embodiments, the final blend does not include mannitol (e.g., (S)-TPMA hydrochloride granule, microcrystalline cellulose, sodium starch glycolate, colloidal silicon dioxide and magnesium stearate). In some examples, the final blend does not include mannitol and colloidal silicon dioxide (e.g., (S)-TPMA hydrochloride granule, microcrystalline cellulose, sodium starch glycolate, and magnesium stearate). The strengths of 25 mg, 50 mg, 75 mg, and 100 mg of (S)-TPMA hydrochloride on a free base basis can be prepared from the final blend with or without colloidal silicon dioxide, or from the final blend with or without mannitol. Microcrystalline cellulose, mannitol, sodium starch glycolate and colloidal silicon dioxide were sieved individually or co-sieved with microcrystalline cellulose (for colloidal silicon dioxide only) through a #30 mesh screen and charged into a low shear blender with (S)-TPMA hydrochloride granule for blending. The mixture was blended for 250 revolutions. Extra-granular magnesium stearate was sieved through a #60 mesh screen and charged into the blender. The mixture was then blended for 75 revolutions and then compressed into tablets with target tablet weight of 300 mg. The tablets were then coated with Opadry 20A120006 Yellow, Opadry 20A18407 White or Opadry 20A110008 Green (hydroxypropylmethyl cellulose/hydroxypropyl cellulose), and carnauba wax was applied onto the tablets after drying.

For the dose strengths (based on the amount of free base) greater than 25 mg, intra-granular blend included (S)-TPMA hydrochloride, microcrystalline cellulose, and sodium starch glycolate were sieved individually through a #30 mesh screen and charged into a low shear blender. In some examples, (S)-TPMA hydrochloride was milled prior to granulation. The mixture was blended for 300 revolutions. Magnesium stearate was sieved though a #60 mesh screen, charged into the blender and the mixture blended for additional 75 revolutions. The intra-granular blend was then dry granulated into ribbons, and milled into granules. After dry granulation, the granules and the extra-granular excipients were blended before compression. The final blend included (S)-TPMA hydrochloride granule, microcrystalline cellulose, sodium starch glycolate and magnesium stearate. The 50 mg and 75 mg also contained mannitol as extra-granular excipient. Microcrystalline cellulose, mannitol, sodium starch glycolate were sieved through a #30 mesh screen and charged into a low shear blender with (S)-TPMA hydrochloride granule for blending. The mixture was blended for 300 revolutions. Extra-granular magnesium stearate was sieved through a #60 mesh screen and charged into the blender. The mixture was then blended for 75 revolutions and then compressed into tablets with target tablet weight of 300 mg. The tablets were then coated with Opadry 20A120006 Yellow, Opadry 20A18407 White or Opadry 20A110008 Green (hydroxypropylmethyl cellulose/hydroxypropyl cellulose), and carnauba wax was applied onto the tablets after drying.

For all four dose strengths of 25 mg, 50 mg, 75 mg, and 100 mg a common blend can be used and made into tablets at 75 mg, 150 mg, 225 mg, and 300 mg weight respectively. For example, intra-granular blend included (S)-TPMA hydrochloride, microcrystalline cellulose, and sodium starch glycolate sieved individually through a #30 mesh screen and charged into a low shear blender. The mixture was blended for 300 revolutions. Magnesium stearate was sieved though a #60 mesh screen, charged into the blender and the mixture blended for additional 75 revolutions. The intra-granular blend was then dry granulated into ribbons and milled into granules. After dry granulation, the granules and the extra-granular excipients were blended before compression. The final blend included (S)-TPMA hydrochloride granule, microcrystalline cellulose, sodium starch glycolate and magnesium stearate. Microcrystalline cellulose and sodium starch glycolate were sieved through a #30 mesh screen and charged into a low shear blender with (S)-TPMA hydrochloride granule for blending. The mixture was blended for 300 revolutions. Extra-granular magnesium stearate was sieved through a #60 mesh screen and charged into the blender. The mixture was then blended for 75 revolutions. The blend can be compressed into tablets of 75 mg, 150 mg, 225 mg, and 300 mg for 25 mg, 50 mg, 75 mg, and 100 mg tablet strengths, respectively. In other words, different strengths of (S)-TPMA hydrochloride can be prepared from a single blend having the same components by taking the corresponding amounts of the blend and compressing them into tablets. See e.g., Table 15C and Table 15D.

TABLE 14

Example Compositions of (S)-TPMA hydrochloride Tablets, Dose Strength 25 mg

| Ingredient | Function | Composition mg/tablet (% w/w) |
|---|---|---|
| Core Tablet | | |
| (S)-TPMA hydrochloride | API | 30.00 (10.00) |
| Microcrystalline Cellulose | Filler | 173.0 (57.67) |
| Mannitol | Filler | 86.50 (28.83) |
| Sodium Starch Glycolate | Disintegrant | 9.000 (3.00) |
| Magnesium Stearate | Lubricant | 1.500 (0.50) |
| Total | | 300.0 (100.0) |
| Coating | | |
| Core Tablet | Core Tablet | 300.0 (96.7) |
| Opadry 20A120006 Yellow, Opadry 20A18407 White, or Opadry 20A110008 Green (HPMC/HPC) | Polymer Coating System | 10.30 (3.32) |
| Carnauba wax | Polishing agent | 0.012 (0.00387) |
| Total | | 310.3 (100.0) |

TABLE 15A

Example Compositions of (S)-TPMA hydrochloride Tablets, Dose Strengths 50, 75 and 100 mg

| Dose Strength (mg) | | 50 | 75 | 100 |
|---|---|---|---|---|
| Ingredient | Function | Composition | | |
| Core Tablet, Intra-Granular (% w/w) | | | | |
| (S)-TPMA hydrochloride | API | 70.00 | | |
| Microcrystalline Cellulose | Filler | 27.80 | | |
| Sodium Starch Glycolate | Disintegrant | 2.00 | | |
| Magnesium Stearate | Lubricant | 0.20 | | |
| Total | | 100 | | |
| Core Tablet mg/tablet (% w/w) | | | | |
| (S)-TPMA hydrochloride Granules | API | 85.71 (28.57) | 128.6 (42.86) | 171.4 (57.14) |
| Microcrystalline Cellulose | Filler | 137.9 (45.97) | 108.8 (36.27) | 90.24 (30.08) |
| Mannitol | Filler | 68.93 (22.98) | 54.39 (18.13) | 30.08 (10.03) |
| Sodium Starch Glycolate | Disintegrant | 6.000 (2.00) | 6.000 (2.00) | 6.000 (2.00) |
| Colloidal silicon dioxide | Glidant | n/a | 0.7500 (0.25) | 0.7500 (0.25) |
| Magnesium Stearate | Lubricant | 1.500 (0.500) | 1.500 (0.500) | 1.500 (0.500) |
| Total | | 300.0 (100) | 300.0 (100) | 300.0 (100) |
| Coating | | | | |
| Core Tablet | Core Tablet | 300.0 (96.7) | 300.0 (96.7) | 300.0 (96.7) |
| Opadry 20A120006 Yellow, Opadry 20A18407 White, or Opadry 20A110008 Green (HPMC/HPC) | Polymer Coating System | 10.30 (3.32) | 10.30 (3.32) | 10.30 (3.32) |
| Carnauba wax | Polishing agent | 0.012 (0.00387) | 0.012 (0.00387) | 0.012 (0.00387) |
| Total | | 310.3 (100) | 310.3 (100) | 310.3 (100) |

Note,
a similar batch was made with colloidal silicon dioxide (cabosil) for 50 mg strength as in Table 15A. Also batches of 75 and 100 mg strengths were made without cabosil as in Table 15A.

TABLE 15B

Additional Example Compositions of (S)-TPMA hydrochloride Tablets, Dose Strengths 50, 75 and 100 mg

| Dose Strength (mg) | | 50 | 75 | 100 |
|---|---|---|---|---|
| Ingredient | Function | Composition | | |
| Core Tablet, Intra-Granular (% w/w) | | | | |
| (S)-TPMA hydrochloride | API | 70.00 | | |
| Microcrystalline Cellulose | Filler | 27.80 | | |
| Sodium Starch Glycolate | Disintegrant | 2.00 | | |
| Magnesium Stearate | Lubricant | 0.2 | | |
| Total | | 100 | | |
| Core Tablet mg/tablet (% w/w) | | | | |
| (S)-TPMA hydrochloride Granules | API | 85.71 (28.57) | 128.6 (42.86) | 171.4 (57.14) |
| Microcrystalline Cellulose | Filler | 155.1 (51.70) | 137.4 (45.81) | 121.1 (40.36) |
| Mannitol | Filler | 51.70 (17.23) | 26.50 (8.83) | n/a |
| Sodium Starch Glycolate | Disintegrant | 6.000 (2.00) | 6.000 (2.00) | 6.000 (2.00) |
| Magnesium Stearate | Lubricant | 1.500 (0.50) | 1.500 (0.50) | 1.500 (0.50) |
| Total | | 300.0 (100) | 300.0 (100) | 300.0 (100) |
| Coating | | | | |
| Core Tablet | Core Tablet | 300.0 (96.7) | 300.0 (96.7) | 300.0 (96.7) |
| Opadry 20A120006 Yellow, Opadry 20A18407 White, or Opadry 20A110008 Green (HPMC/HPC) | Polymer Coating System | 10.30 (3.32) | 10.30 (3.32) | 10.30 (3.32) |
| Carnauba wax | Polishing agent | 0.012 (0.00387) | 0.012 (0.00387) | 0.012 (0.00387) |
| Total | | 310.3 (100) | 310.3 (100) | 310.3 (100) |

TABLE 15C

Common blend formulation

| Ingredient | Function | % w/w |
|---|---|---|
| Common Blend, Intra Granular | | |
| (S)-TPMA hydrochloride | API | 70.00 |
| Microcrystalline Cellulose | Filler | 27.80 |
| Sodium Starch Glycolate | Disintegrant | 2.00 |
| Magnesium Stearate | Lubricant | 0.20 |
| Total | | 100 |
| Common Blend for Compression | | |
| (S)-TPMA hydrochloride Granules | API | 57.14 |
| Microcrystalline Cellulose | Filler | 40.36 |
| Sodium Starch Glycolate | Disintegrant | 2.00 |
| Magnesium Stearate | Lubricant | 0.50 |
| Total | | 100 |

TABLE 15D

Tablet formulation composition using common blend for compression formulation

| Dose Strength (mg) | | 25 mg | 50 mg | 75 mg | 100 mg |
|---|---|---|---|---|---|
| Ingredient | Function | | % w/w | | |
| (S)-TPMA hydrochloride | API | | 40.00 | | |
| Microcrystalline Cellulose | Filler | | 56.24 | | |
| Sodium Starch Glycolate | Disintegrant | | 3.14 | | |
| Magnesium Stearate | Lubricant | | 0.62 | | |
| | Total (%) | | 100 | | |
| | Total (mg/tablet) | 75.0 | 150.0 | 225.0 | 300.0 |
| | Coating, mg (% w/w) | | | | |
| Core Tablet | Core Tablet | 75.0 (96.7) | 150.0 (96.7) | 225.0 (96.7) | 300.0 (96.7) |
| Opadry 20A120006 Yellow, Opadry 20A18407 White, or Opadry 20A110008 Green (HPMC/HPC) | Polymer Coating System | 2.58 (3.32) | 5.15 (3.32) | 7.73 (3.32) | 10.30 (3.32) |
| Carnauba wax | Polishing agent | 0.003 (0.00387) | 0.006 (0.00387) | 0.009 (0.00387) | 0.012 (0.00387) |
| | Total | 77.6 (100) | 155.2 (100) | 232.7 (100) | 310.3 (100) |

The actual amount of polymer coating system is an estimate in Table 15D. The actual quantities may change when tablets of lower weights are made and coated. Similarly, the actual amount of polishing agent is an estimate. The actual quantities may change when tablets of lower weights are made and coated and waxed/polished.

XRPD analyses for Examples 4-8 and 12 were performed using a Rigaku MiniFlex II Desktop X-Ray diffractometer using Cu radiation. The tube voltage and amperage were set to 30 kV and 15 mA, respectively. The scattering slit was fixed at 1.25° and the receiving slit was fixed at 0.3 mm. Diffracted radiation was detected by a NaI scintillation detector. A θ-2θ continuous scan at 1.0°/min with a step size of 0.02-0.05° from 3 to 45° 2θ was used. Data were collected and analyzed using Jade 8.5.4. Each sample was prepared for analysis by placing it in a low background, round, 0.1 mm indent sample holder.

The DSC analyses for Examples 4-8 were performed using TA Instruments Q100 differential scanning calorimeter. Each sample was analyzed in an aluminum pan with crimped lid. Each sample was heated under a 50 mL/min nitrogen purge at a heating rate of 10° C./min, from a starting temperature of 25° C. up to a final temperature of 200-300° C. Sample size ranged from 1.6 to 8.0 mg.

Water content by coulometric titration analyses for Examples 4-8 were performed using an EM Scientific Aquastar C3000 titrator to determine water content. Sample size ranged from 18 mg to 134 mg.

DVS moisture sorption isotherms for Examples 4-8 were generated using the VTI SGA-100 Symmetric Vapor Sorption Analyzer. Analysis included pre-analysis drying at 25° C. with equilibrium criteria of 0.0000 wt % change in 5 minutes or a maximum of 180 minutes. Equilibrium criteria were the lesser of 0.01 wt % change in 5 minutes or 180 minutes at each RH step. Temperature was fixed at 25° C. and the relative humidity steps (25% to 95% to 25%) were in 5% increments. Analysis was repeated for each sample in consecutive analyses (sample was not removed from analyzer). Sample sizes ranged from 14 mg to 73 mg.

Example 4: (S)-TPMA R-Mandelate

The crystalline form of (S)-TPMA R-mandelate was analyzed using XRPD, DSC, coulometric titration, and DVS. FIG. 11 shows the XRPD and Table 4 provides a list of the peaks.

TABLE 4

(S)-TPMA R-Mandelate XRPD (FIG. 12) Peak List

| 2-Theta (degree) | Relative height (%) |
|---|---|
| 4.7 | 6.9 |
| 9.4 | 74.8 |
| 10.7 | 4.9 |
| 11.1 | 6.1 |
| 12.4 | 2.5 |
| 13.7 | 5.9 |
| 14.3 | 29.2 |
| 15.3 | 3.7 |
| 16.3 | 83.7 |
| 17.5 | 2.4 |
| 18.0 | 10.9 |
| 18.4 | 8.3 |
| 18.9 | 12.8 |
| 19.6 | 27.8 |
| 20.0 | 8.3 |
| 21.4 | 14.3 |
| 21.8 | 25.7 |
| 23.0 | 17.9 |
| 23.4 | 40.9 |
| 23.7 | 100 |
| 24.4 | 20.8 |
| 25.0 | 63.2 |
| 25.3 | 39.3 |
| 25.6 | 13.4 |
| 26.1 | 5.8 |
| 26.8 | 12.2 |
| 27.4 | 19.4 |
| 28.3 | 8.9 |
| 29.0 | 8.7 |
| 29.5 | 15 |
| 30.2 | 3.1 |
| 30.8 | 8.6 |
| 31.5 | 2.8 |
| 32.5 | 4.3 |
| 32.8 | 3.8 |
| 33.4 | 7.3 |

TABLE 4-continued (S)-TPMA R-Mandelate XRPD (FIG. 12) Peak List

| 2-Theta (degree) | Relative height (%) |
|---|---|
| 34.4 | 3.6 |
| 34.7 | 5.5 |
| 35.2 | 10.6 |
| 36.2 | 5.7 |
| 37.0 | 6.6 |
| 37.6 | 12.7 |
| 38.2 | 2.7 |
| 39.2 | 7.5 |
| 39.8 | 2.7 |
| 41.1 | 7.4 |
| 41.8 | 9.5 |
| 42.3 | 11.5 |
| 43.2 | 6.1 |
| 43.6 | 5 |

Figure 12:
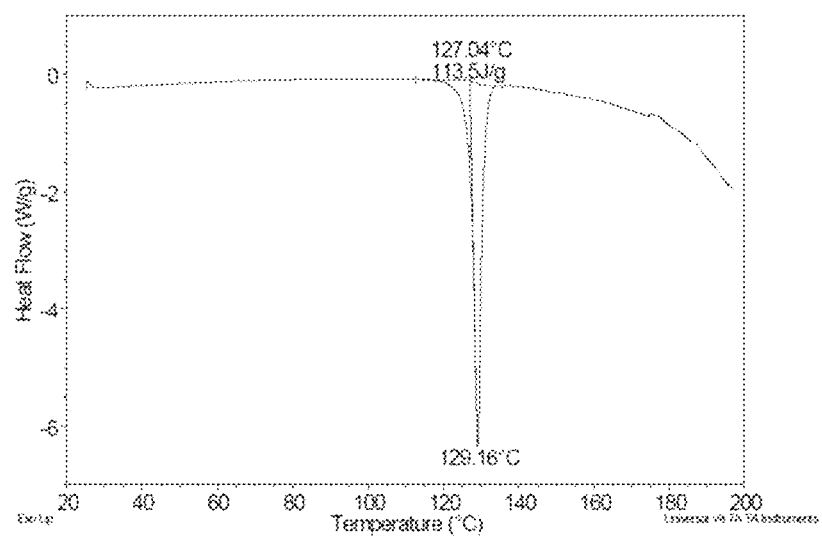
FIG. 12 is a DSC thermogram for (S)-(4,5-dihydro-7H-thieno[2,3-c]pyran-7-yl)-N-methylmethanamine R-mandelate.
Figure 13:
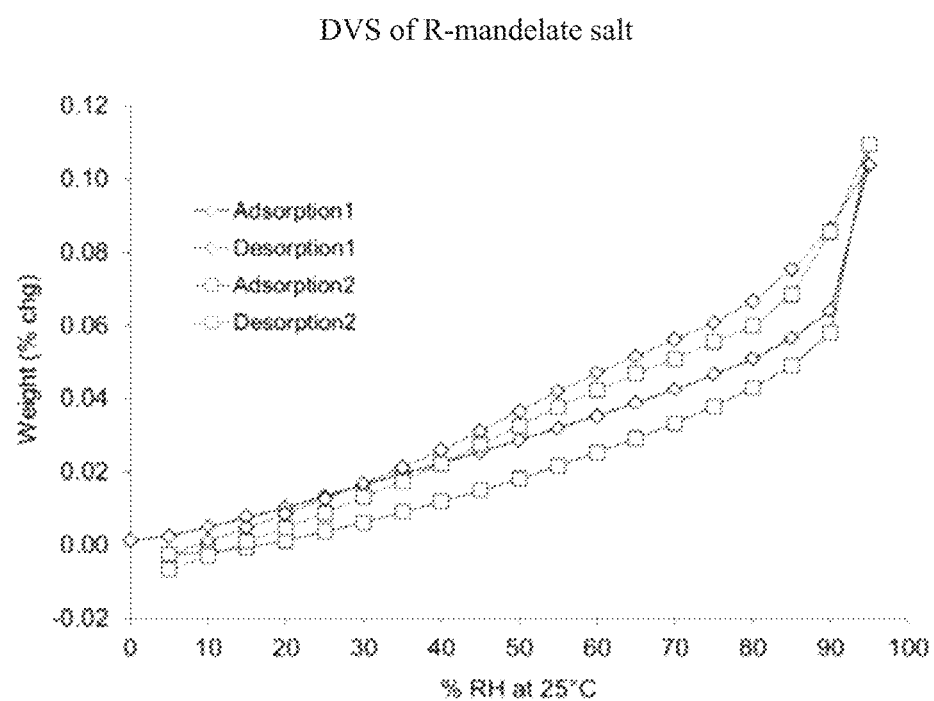
FIG. 13 is a DVS isotherm for (S)-(4,5-dihydro-7H-thieno[2,3-c]pyran-7-yl)-N-methylmethanamine R-mandelate.

The DSC as shown in FIG. 12 displays an onset temperature of 127° C. with an endotherm peak at 129° C. The amount of water content as determined by coulometric titration was 0.03% water. The TGA is shown in FIG. 13.

Example 5: (S)-TPMA L-Tartrate

The crystalline form of (S)-TPMA L-tartrate was analyzed using XRPD, DSC, coulometric titration, and DVS. FIG. 14 shows the XRPD and Table 5 provides a list of the peaks.

TABLE 5

(S)-TPMA L-tartrate XRPD (FIG. 14) Peak List

| 2-Theta (degree) | Relative height (%) |
|---|---|
| 6.3 | 20.1 |
| 12.7 | 99.0 |
| 12.9 | 19.6 |
| 14.3 | 2.4 |
| 14.7 | 13.7 |
| 16.0 | 26.5 |
| 17.1 | 23.8 |
| 17.4 | 27.9 |
| 18.1 | 14.9 |
| 19.1 | 100.0 |
| 19.5 | 9.6 |
| 20.4 | 6.8 |
| 21.3 | 10.2 |
| 22.2 | 1.8 |
| 22.9 | 24.7 |
| 23.4 | 7.9 |
| 24.6 | 11.0 |
| 25.0 | 2.4 |
| 25.5 | 20.6 |
| 25.8 | 41.9 |
| 26.3 | 43.6 |
| 26.9 | 3.0 |
| 27.6 | 3.9 |
| 27.9 | 13.1 |
| 28.2 | 10.4 |
| 28.6 | 1.9 |
| 29.1 | 2.8 |
| 29.7 | 2.7 |
| 30.7 | 19.1 |
| 31.1 | 6.0 |
| 32.0 | 24.7 |
| 32.5 | 12.4 |
| 33.6 | 22.7 |
| 34.4 | 12.4 |
| 35.2 | 2.0 |
| 36.6 | 5.0 |
| 36.9 | 8.1 |
| 37.9 | 10.4 |
| 38.7 | 12.7 |

TABLE 5-continued (S)-TPMA L-tartrate XRPD (FIG. 14) Peak List

| 2-Theta (degree) | Relative height (%) |
|---|---|
| 39.4 | 10.2 |
| 40.3 | 12.0 |
| 40.7 | 3.3 |
| 41.5 | 3.7 |
| 42.5 | 4.5 |
| 43.0 | 2.5 |
| 43.5 | 4.4 |
| 44.1 | 3.0 |
| 44.4 | 7.6 |

Figure 16:
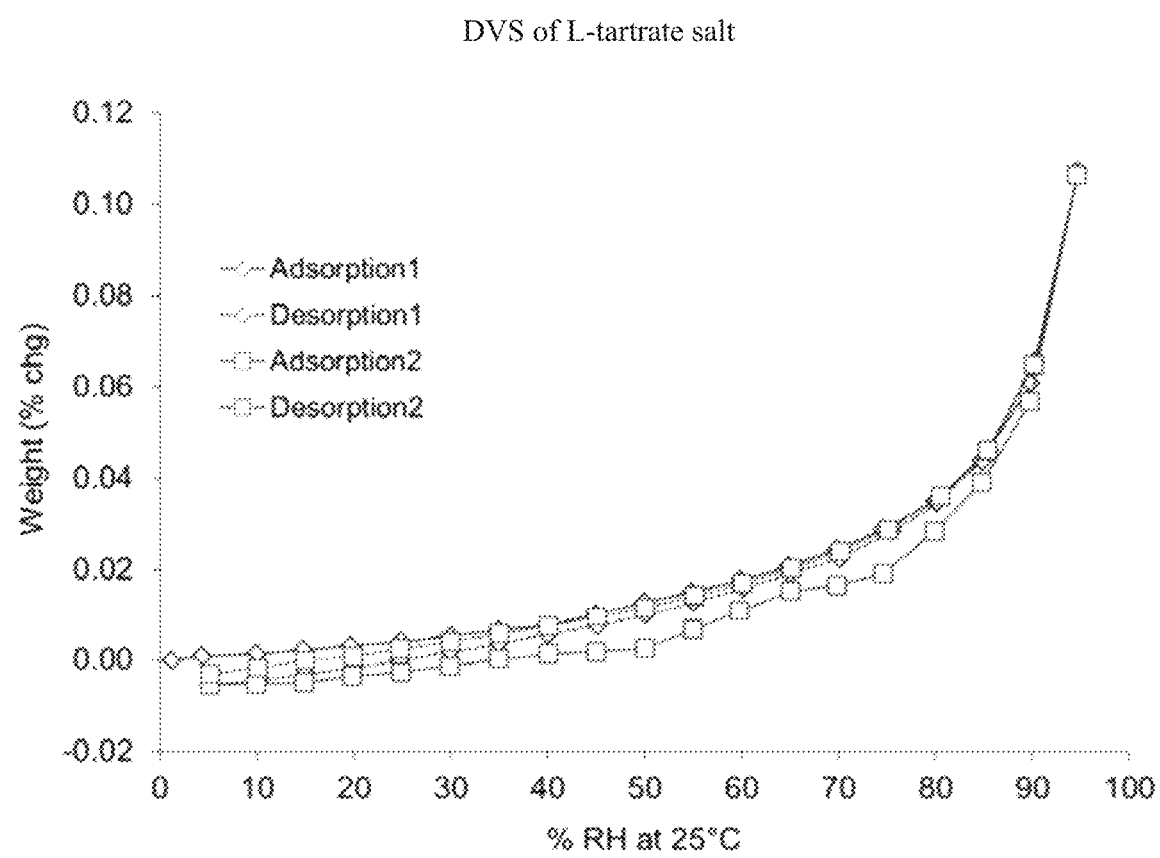
FIG. 16 is a DVS isotherm for (S)-(4,5-dihydro-7H-thieno[2,3-c]pyran-7-yl)-N-methylmethanamine L-tartrate.

The DSC as shown in FIG. 15 displays an onset temperature of 149° C. with an endotherm peak at 152° C. The amount of water content as determined by coulometric titration was 0.07% water. The DVS is shown in FIG. 16.

Example 6: (S)-TPMA D-Tartrate

The crystalline form of (S)-TPMA D-tartrate was analyzed using XRPD, DSC, coulometric titration, and DVS. Three crystalline forms were observed: Form DA, Form DB, and form DC. FIG. 17 shows the XRPD of Form DA; Table 6A provides a list of the peaks. FIG. 18 shows the XRPD of Form DB; Table 6B provides a list of the peaks. FIG. 19 shows the XRPD of Form DC; Table 6C provides a list of the peaks. XRPD patterns of Form DA, DB, and DC may not represent unique pure polymorphic forms and can be a mixture of forms.

TABLE 6A (S)-TPMA D-tartrate XRPD (FIG. 17) Peak List

| 2-Theta (degree) | Relative height (%) |
|---|---|
| 7.0 | 25.5 |
| 11.4 | 0.7 |
| 12.9 | 4.3 |
| 13.9 | 3.7 |
| 14.1 | 1.9 |
| 15.0 | 8.8 |
| 16.4 | 3.0 |
| 16.8 | 4.5 |
| 17.6 | 37.3 |
| 18.6 | 1.4 |
| 18.8 | 0.7 |
| 19.5 | 13.7 |
| 20.8 | 100.0 |
| 21.5 | 12.6 |
| 21.8 | 14.6 |
| 22.0 | 7.6 |
| 22.8 | 3.0 |
| 23.5 | 1.4 |
| 23.9 | 9.8 |
| 24.2 | 7.3 |
| 24.6 | 0.9 |
| 24.9 | 2.1 |
| 25.3 | 2.9 |
| 26.0 | 46.2 |
| 26.7 | 2.8 |
| 27.2 | 3.7 |
| 27.8 | 21.5 |
| 28.7 | 2.2 |
| 29.0 | 3.2 |
| 29.4 | 4.7 |
| 30.0 | 3.5 |
| 30.2 | 1.0 |
| 32.2 | 2.5 |
| 32.5 | 2.4 |
| 32.8 | 1.4 |
| 33.0 | 1.1 |

TABLE 6A-continued (S)-TPMA D-tartrate XRPD (FIG. 17) Peak List

| 2-Theta (degree) | Relative height (%) |
|---|---|
| 33.8 | 2.2 |
| 34.3 | 2.6 |
| 35.0 | 9.9 |
| 35.7 | 3.0 |
| 36.8 | 15.5 |
| 37.2 | 3.6 |
| 37.5 | 17.0 |
| 37.9 | 6.8 |
| 39.1 | 6.6 |
| 39.6 | 0.6 |
| 40.4 | 2.5 |
| 40.7 | 4.5 |
| 41.2 | 2.1 |
| 41.9 | 0.8 |
| 42.3 | 0.8 |
| 42.9 | 2.0 |
| 43.3 | 1.1 |
| 43.7 | 4.8 |

TABLE 6B (S)-TPMA D-tartrate XRPD (FIG. 18) Peak List

| 2-Theta (degree) | Relative height (%) |
|---|---|
| 6.9 | 1.3 |
| 11.6 | 10.7 |
| 12.8 | 1.1 |
| 14.0 | 0.3 |
| 14.9 | 2.4 |
| 16.3 | 1.2 |
| 16.7 | 1.6 |
| 17.5 | 8.8 |
| 18.8 | 2.5 |
| 19.4 | 3.0 |
| 20.1 | 4.7 |
| 20.7 | 44.3 |
| 21.5 | 2.8 |
| 21.6 | 4.3 |
| 21.9 | 2.0 |
| 22.5 | 1.6 |
| 22.8 | 0.8 |
| 23.4 | 13.9 |
| 23.8 | 1.7 |
| 24.1 | 1.1 |
| 25.0 | 5.6 |
| 25.9 | 6.2 |
| 27.1 | 1.0 |
| 27.8 | 2.0 |
| 28.6 | 0.8 |
| 29.2 | 20.4 |
| 29.7 | 5.3 |
| 32.0 | 5.2 |
| 33.4 | 10.8 |
| 34.3 | 0.4 |
| 35.3 | 27.8 |
| 35.8 | 100.0 |
| 36.1 | 1.6 |
| 36.7 | 9.5 |
| 37.4 | 8.3 |
| 37.9 | 1.3 |
| 38.4 | 0.6 |
| 38.8 | 3.2 |
| 39.4 | 0.6 |
| 41.1 | 0.6 |
| 42.6 | 0.9 |
| 43.9 | 5.4 |

TABLE 6C (S)-TPMA D-tartrate XRPD (FIG. 19) Peak List

| 2-Theta (degree) | Relative height (%) |
|---|---|
| 8.7 | 0.9 |
| 9.8 | 0.8 |
| 10.8 | 8.8 |
| 11.7 | 3.0 |
| 12.8 | 1.0 |
| 13.3 | 2.3 |
| 15.8 | 10.3 |
| 16.2 | 2.1 |
| 17.5 | 100.0 |
| 18.2 | 2.9 |
| 18.7 | 2.1 |
| 19.4 | 5.8 |
| 19.8 | 1.8 |
| 20.7 | 10.4 |
| 21.7 | 6.7 |
| 22.2 | 0.9 |
| 22.8 | 1.5 |
| 23.6 | 12.7 |
| 24.2 | 4.1 |
| 26.1 | 4.4 |
| 26.8 | 10.0 |
| 27.2 | 3.2 |
| 27.7 | 1.6 |
| 29.3 | 1.8 |
| 29.8 | 3.7 |
| 30.2 | 2.5 |
| 31.3 | 1.0 |
| 31.9 | 1.4 |
| 32.5 | 0.9 |
| 32.9 | 1.6 |
| 34.0 | 1.2 |
| 34.7 | 2.6 |
| 35.3 | 2.8 |
| 36.0 | 2.9 |
| 37.0 | 1.2 |
| 37.4 | 1.5 |
| 37.8 | 1.2 |
| 38.4 | 0.5 |
| 38.8 | 0.7 |
| 40.0 | 0.4 |
| 40.6 | 0.6 |
| 41.0 | 1.1 |
| 41.5 | 0.9 |
| 42.0 | 0.8 |
| 42.3 | 0.8 |
| 43.7 | 0.7 |
| 44.3 | 2.3 |

Figure 20:
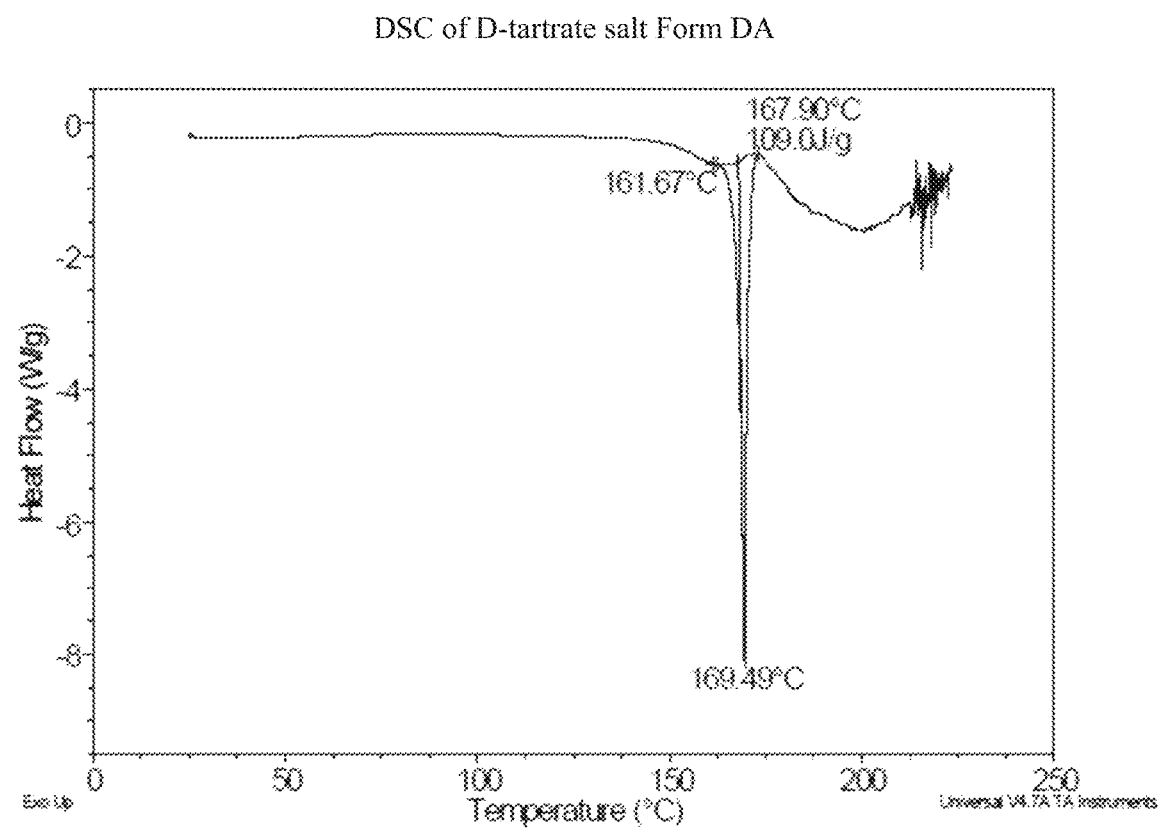
FIG. 20 is a DSC thermogram for (S)-(4,5-dihydro-7H-thieno[2,3-c]pyran-7-yl)-N-methylmethanamine D-tartrate Form DA.
Figure 21:
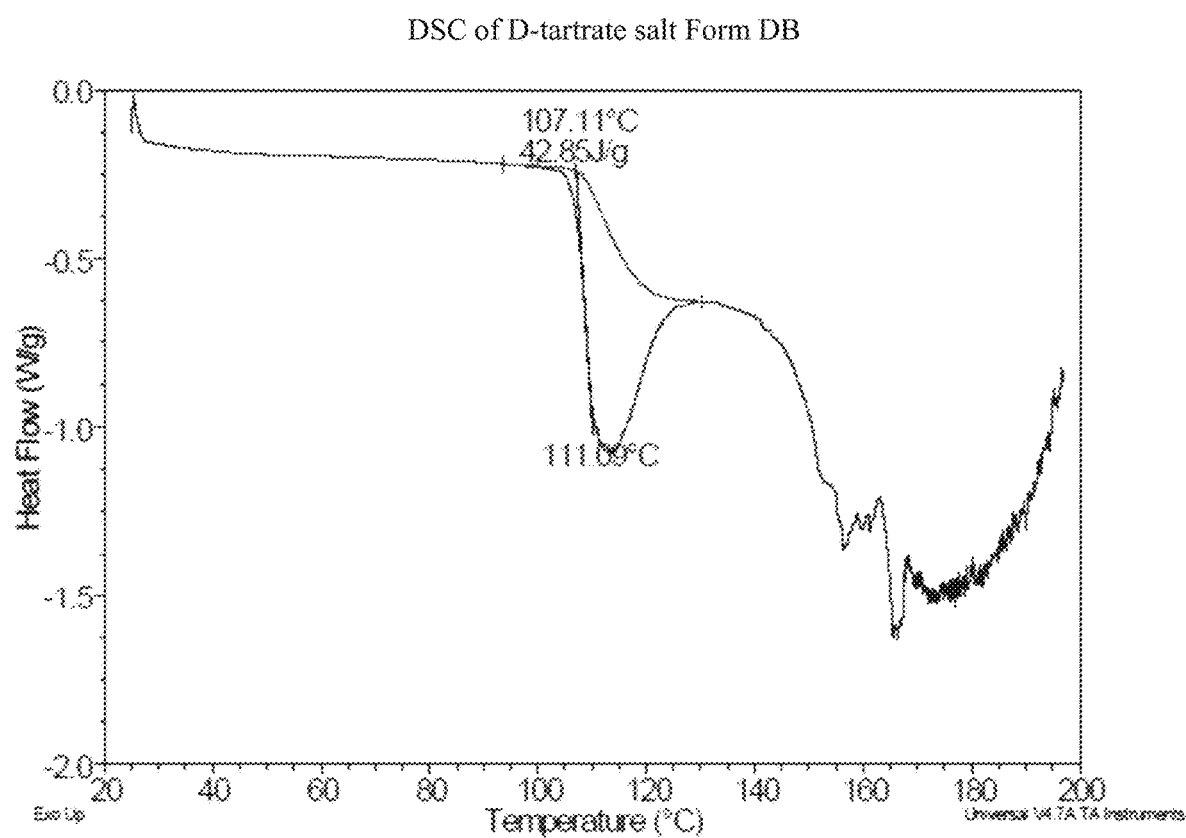
FIG. 21 is a DSC thermogram for (S)-(4,5-dihydro-7H-thieno[2,3-c]pyran-7-yl)-N-methylmethanamine D-tartrate Form DB.
Figure 22:
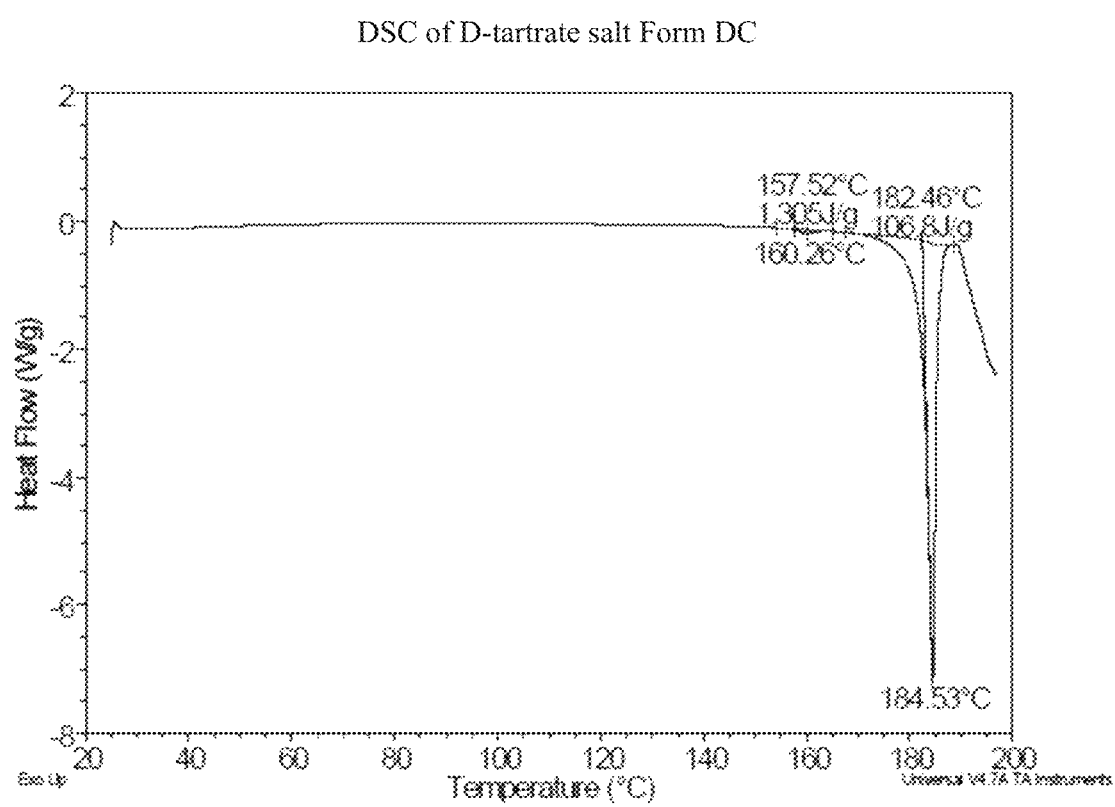
FIG. 22 is a DSC thermogram for (S)-(4,5-dihydro-7H-thieno[2,3-c]pyran-7-yl)-N-methylmethanamine D-tartrate Form DC.

The DSC of Form DA as shown in FIG. 20 displays an onset temperature of 168° C. with an endotherm peak at 170° C. The DSC of Form DB as shown in FIG. 21 displays an onset temperature of 107° C. with an endotherm peak at 111° C. The DSC of Form DC as shown in FIG. 22 displays an onset temperature of 158° C. with an endotherm peak at 160° C., and an onset temperature of 183° C. and an endotherm peak at 185° C.

Figure 23:
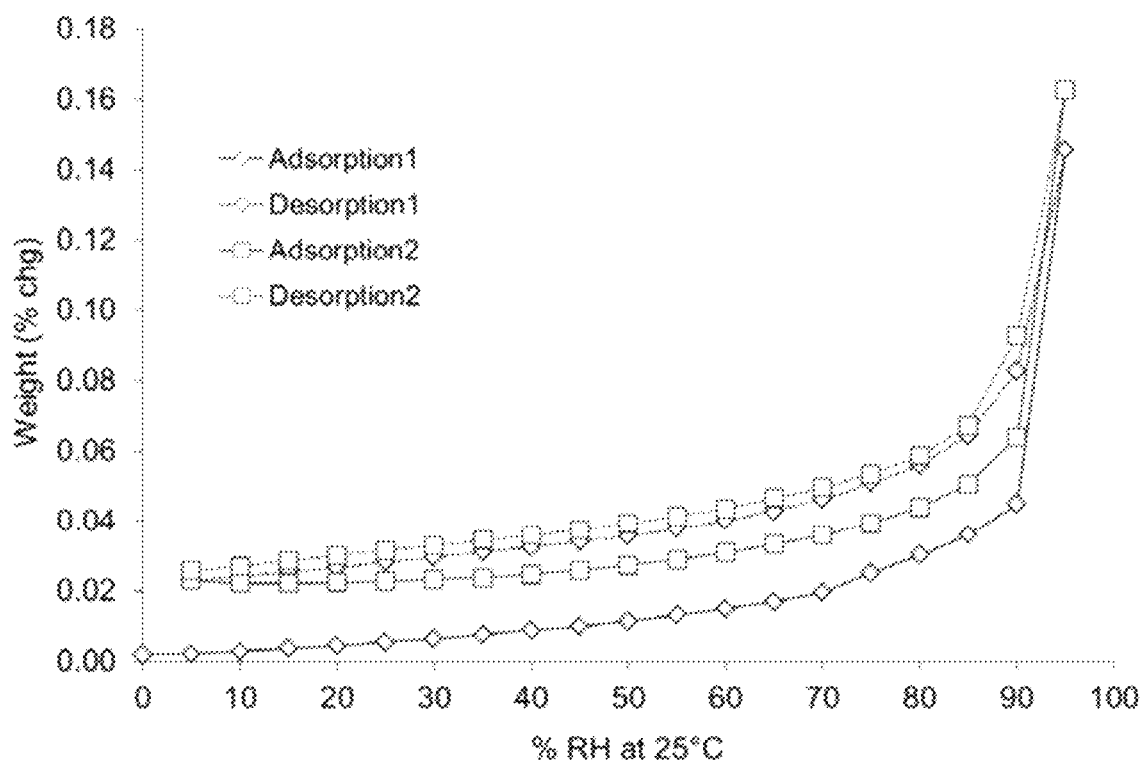
FIG. 23 is a DVS isotherm for (S)-(4,5-dihydro-7H-thieno[2,3-c]pyran-7-yl)-N-methylmethanamine D-tartrate DA.

The amount of water content as determined by coulometric titration was 0.12% for Form DA, 0.09% for Form DB, and 0.06% for Form DC. The DVS for Form DA is shown in FIG. 23.

Example 7: (S)-TPMA Mesylate and (S)-TPMA L-Malate

Figure 24:
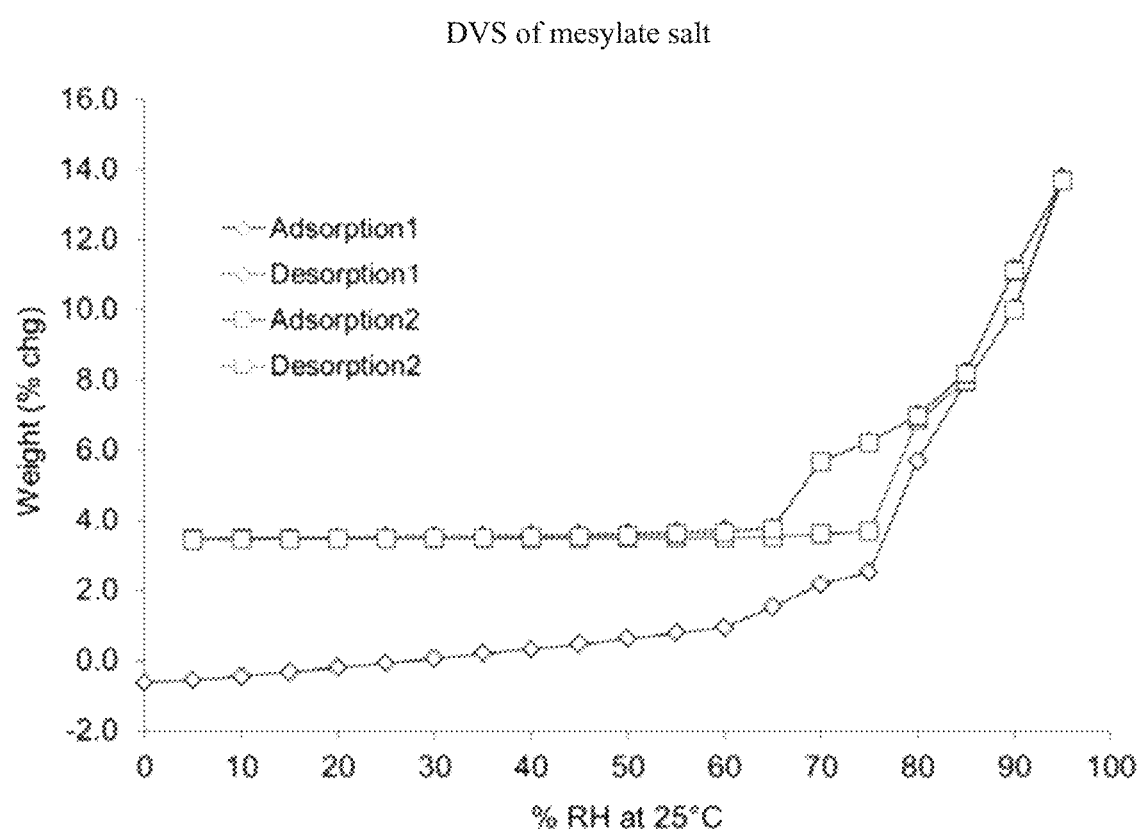
FIG. 24 is a DVS isotherm for (S)-(4,5-dihydro-7H-thieno[2,3-c]pyran-7-yl)-N-methylmethanamine mesylate.

The mesylate salt was observed in a polymorph study and was analyzed using DVS. FIG. 24 shows the DVS.

The L-maleate salt was observed in a polymorph study and was analyzed using DVS. FIG. 25 shows the DVS.

Example 8: (S)-TPMA Besylate

The crystalline form of (S)-TPMA besylate was analyzed using XRPD, DSC, coulometric titration, and DVS. Form BA was observed. FIG. 25 shows the XRPD and Table 8 provides a list of the peaks of Form BA.

TABLE 8

(S)-TPMA besylate Form BA XRPD (FIG. 25) Peak List

| 2-Theta (degree) | Relative height (%) |
|---|---|
| 6.1 | 79.3 |
| 12.3 | 14.3 |
| 13.2 | 5.0 |
| 14.6 | 2.3 |
| 16.7 | 38.4 |

TABLE 8-continued (S)-TPMA besylate Form BA XRPD (FIG. 25) Peak List

| 2-Theta (degree) | Relative height (%) |
|---|---|
| 18.5 | 3.6 |
| 18.8 | 7.1 |
| 19.0 | 25.9 |
| 19.5 | 2.2 |
| 21.9 | 25.4 |
| 22.4 | 18.5 |
| 22.8 | 22.4 |
| 23.2 | 9.6 |
| 23.8 | 2.2 |
| 24.3 | 8.0 |
| 24.7 | 100.0 |
| 26.0 | 10.6 |
| 26.5 | 3.7 |
| 27.0 | 13.9 |
| 27.5 | 14.6 |
| 27.8 | 4.3 |
| 28.6 | 2.2 |
| 29.2 | 0.8 |
| 30.1 | 2.5 |
| 30.8 | 5.0 |
| 31.0 | 2.7 |
| 32.2 | 11.6 |
| 32.8 | 2.6 |
| 33.3 | 10.8 |
| 33.7 | 2.0 |
| 34.1 | 2.7 |
| 34.4 | 2.8 |
| 35.9 | 2.1 |
| 36.6 | 6.8 |
| 37.9 | 19.0 |
| 38.6 | 4.3 |
| 39.3 | 4.9 |
| 39.6 | 1.7 |
| 40.4 | 3.1 |
| 41.5 | 0.8 |
| 42.1 | 5.2 |
| 42.8 | 0.7 |
| 43.5 | 1.7 |
| 43.9 | 11.2 |
| 44.5 | 5.1 |

Figure 26:
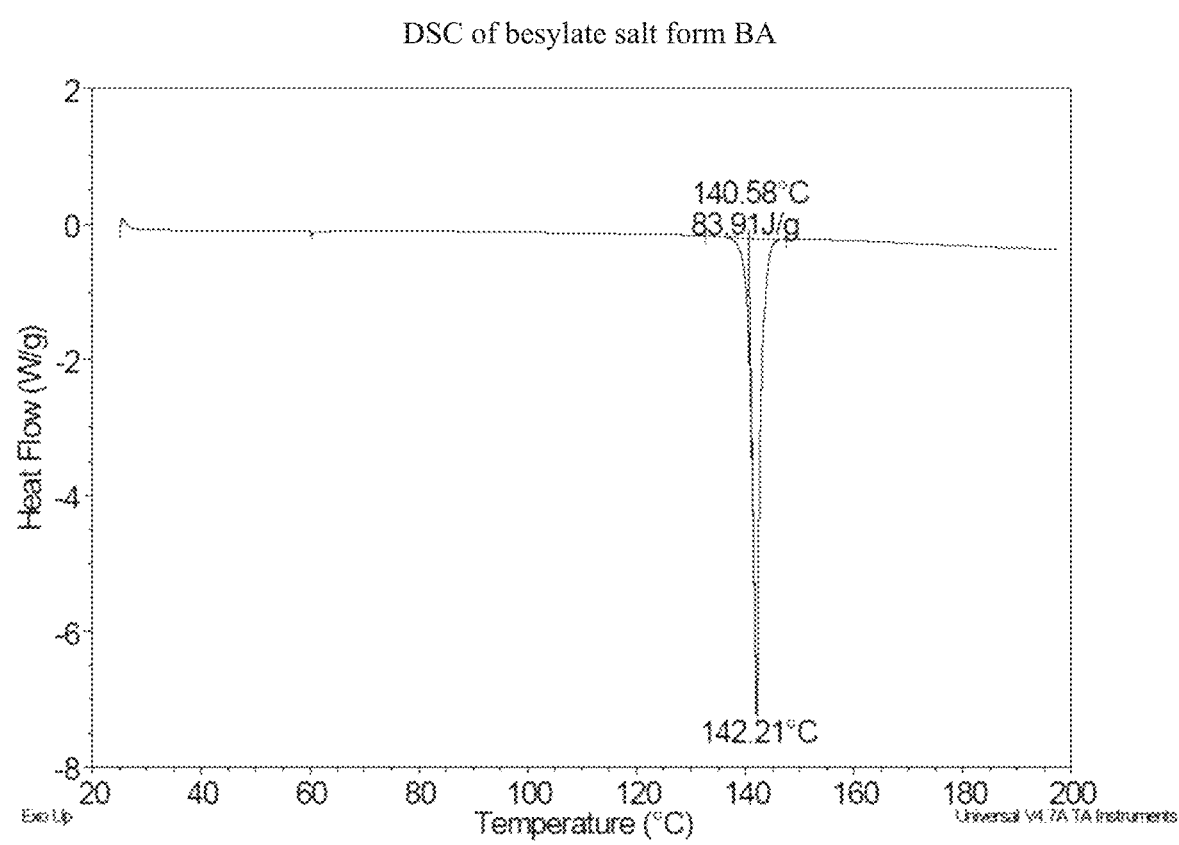
FIG. 26 is a DSC thermogram for (S)-(4,5-dihydro-7H-thieno[2,3-c]pyran-7-yl)-N-methylmethanamine besylate Form BA.
Figure 27:
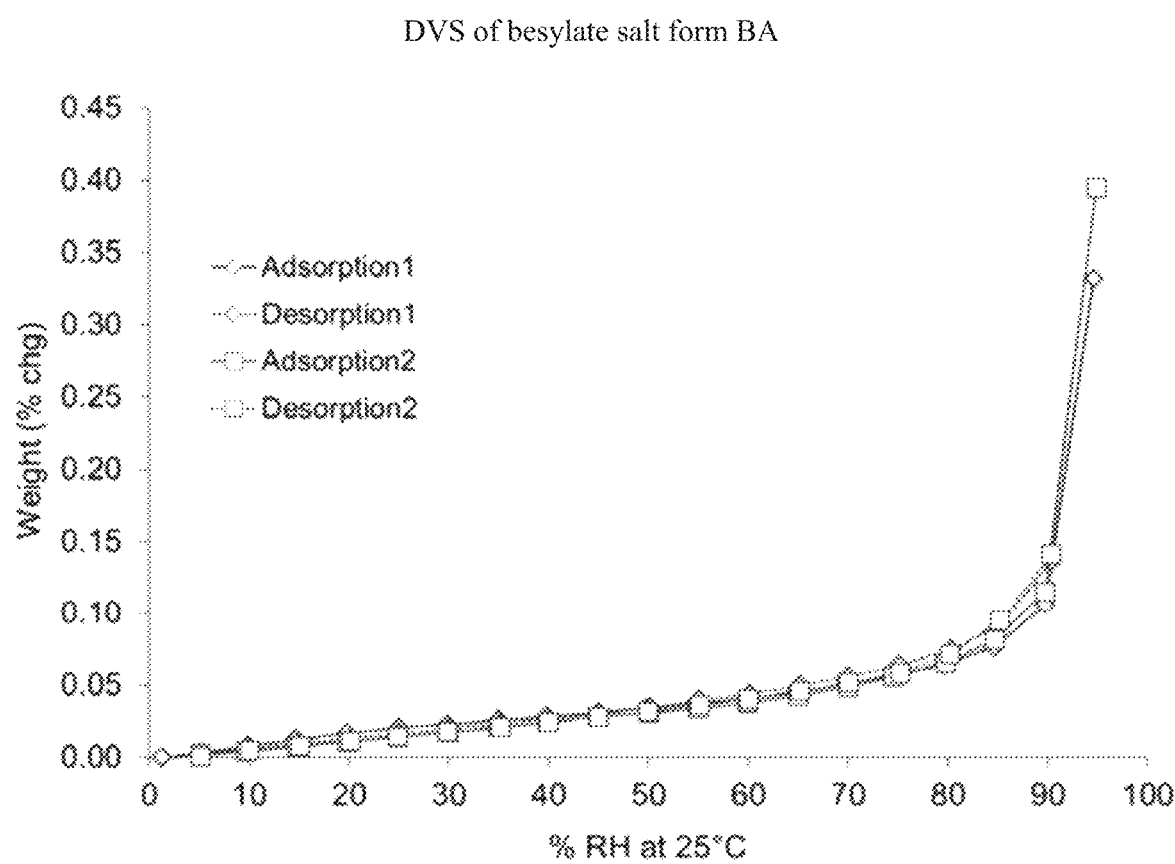
FIG. 27 is a DVS isotherm for (S)-(4,5-dihydro-7H-thieno[2,3-c]pyran-7-yl)-N-methylmethanamine besylate Form BA.

The DSC as shown in FIG. 26 displays an onset temperature of 141° C. with an endotherm peak at 142° C. The amount of water content as determined by coulometric titration was 0.03% water. The DVS is shown in FIG. 27.

Example 9: Study of Solid State Stability

Solid samples (~25 mg each) of (S)-TPMA HCl and (S)-TPMA besylate were placed in 4 mL clear glass borosilicate vials with screw caps. Samples were stored at 40° C./75% RH and analyzed by AR&D after 27 days storage.

Results show no change in parent peak area or impurity area percent in either HCL or besylate salts. Refer to results in Table 9.

TABLE 9

Solid State Stability Results for HCl and Besylate Salts

| | Time Point (days) | Peak Area | Wt. (mg) | RF (counts/mg) | Unknown Impurities (%) | Impurity 1 (%) | Total Impurities (%) |
|---|---|---|---|---|---|---|---|
| HCl | 0 | 16,969,358 | 25.42 | 667,559 | 0 | 1.20 | 1.20 |
| | 27 | 17,199,832 | 25.79 | 666,919 | 0 | 1.21 | 1.21 |
| Besylate | 0 | 10,901,819 | 25.15 | 433,472 | 0 | 0.64 | 0.64 |
| | 27 | 11,126,833 | 25.61 | 434,472 | 0 | 0.64 | 0.64 |

Both HCl and besylate salts are stable in the solid state after 27 days at 40° C./75% RH. Impurity 1 is:

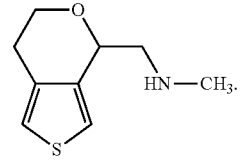 [SMILES: CNCC1OCCc2cscc21]

Example 10: Study of Solubility in Aqueous Systems

Buffer preparation for simulated gastric fluid (pH 1.2, ~0.1N HCl, 0.03M NaCl), simulated intestinal fluid (pH 6.7, 0.05M KH2PO4, ~0.02N NaOH), and acetate buffer (pH 4.6, 0.02M sodium acetate, 0.03M acetic acid) were in accordance with USP27 [Ref 3]. Enzymes were not added to the simulated gastric or intestinal fluids. Approximately 200 mg of selected salts were weighed into clear glass HPLC vials. One milliliter of de-ionized water was added to each vial. In each case, a clear solution resulted and pH of final solution measured. Results (Table 11a) were reported as "greater than" the concentration of the solution.

Additional solubility experiments were performed on (S)-TPMA HCl salt. Approximately 250 mg of (S)-TPMA HCl salt were weighed into clear glass HPLC vials. Approximately 900 μL of each test solvent were added to each vial. In each case, a clear yellow solution resulted and the pH of the final solution was measured.

Results (Table 10a) were reported as "greater than" the concentration of the solution. Refer to solubility results in Table 10a and Table 10b.

TABLE 10a

Apparent Solubility Values for (S)-TPMA Salts in De-Ionized Water

| Salt | Solubility (mgA/mL)[a] | Final solution PH | USP Descriptor |
|---|---|---|---|
| HCl | >167 | 5.3 | Freely Soluble |
| L-Tartrate | >110 | 3.3 | Freely Soluble |
| Besylate | >109 | 4.7 | Freely Soluble |
| R-Mandelate | >107 | 6.2 | Freely Soluble |

[a] = solubility expressed in terms of free base.

TABLE 10b

Apparent Solubility Values for (S)-TPMA HCl in Aqueous Buffer Systems

| Solvent | Final Solution pH | Solubility (mgA/mL)[a] | USP Descriptor |
|---|---|---|---|
| Simulated Gastric Fluid (SGF) | 1.28 | >200 | Freely Soluble |
| 0.05M Acetate Buffer | 4.60 | >200 | Freely Soluble |
| Deionized H$_2$O | 6.20 | >200 | Freely Soluble |
| Simulated Intestinal Fluid (SIF) | 7.70 | >200 | Freely Soluble |

[a] = solubility is expressed in terms of free base.
Enzymes were not added to the stimulated gastric or intestinal fluids.

The selected salt has good solubility (i.e. >1 mgA/mL) at physiological pHs and conditions such as SGF (pH 1.2), SIF (pH 6.8), and acetate buffer (pH 4.5). All salts tested (HCl, L-tartrate, besylate, and R-mandelate) are freely soluble in de-ionized water. HCl salt is freely soluble in aqueous buffers ranging from pH 1.3 to 7.7.

Example 11: Polymorph Study of (S)-TPMA Besylate

A polymorph study was conducted on (S)-TPMA besylate. The starting material used in the study was designated Form BA, with characterization discussed below.

(S)-TPMA was treated as being light sensitive, with exposure to light minimized throughout the experiments. These abbreviations are used in this study: ACN—Acetonitrile, B/E—Birefringence/Extinction, CC—Crash Cool, DCM—Dichloromethane, DSC—Differential Scanning calorimetry, EtOAc—Ethyl Acetate, EtOH—Ethanol, FE—Fast Evaporation, H2O—Water, IPA—Isopropanol, IS—Insufficient Sample, MEK—Methyl Ethyl Ketone, MeOH—Methanol, mg—Milligram, mL—Milliliter, PO—Preferred Orientation, Rotovap—Rotary Evaporation, RT—Room/ambient temperature, S/AS—Solvent/Anti-Solvent, SC—Slow Cool, SE—Slow Evaporation, Tg—Glass Transition Temperature, THF—Tetrahydrofuran, UM—Undefined Morphology, v/v—Volume by Volume, vac—Vacuum, VD—Vapor Diffusion, VT—Variable Temperature, and XRPD—X-Ray Powder Diffraction.

Approximate Solubility Determination: Aliquots of the test solvent were added to a weighed sample of (S)-TPMA besylate with sonication at each addition. Dissolution was determined by visual inspection. If the sample dissolved upon addition of the first aliquot, the solubility is reported as "greater than or equal to". If the sample did not dissolve, the solubility is reported as "less than". Actual solubilities may be higher than reported due to slow rates of dissolution and to addition of over-sized aliquots.

Fast Evaporation: A solution of (S)-TPMA besylate was prepared and filtered. The sample was left open under ambient conditions for evaporation.

Slow Evaporation: A solution of (S)-TPMA besylate was prepared and filtered. The vial containing the sample was covered with foil containing pinholes. The covered sample was left under ambient conditions for evaporation.

Slurries: A solution of (S)-TPMA besylate containing excess solids was prepared and agitated at a given temperature for a given time.

Slow Cool: A saturated solution of (S)-TPMA besylate was prepared in an elevated temperature oil bath. The sample was filtered with a warm filter into a warm vial and then returned to the oil bath. The heat was turned off, and the sample was allowed to slowly cool to ambient temperature. When precipitation was not observed at ambient temperature, the sample was placed in a refrigerator. After the refrigerator, samples were moved to a freezer.

Crash Cool: A saturated solution of (S)-TPMA besylate was prepared in an elevated temperature oil bath. The sample was filtered with a warm filter into a vial and then plunged into a dry ice/acetone bath. If precipitation did not occur, the sample was placed in a freezer.

Solvent/Anti-Solvent Crash Precipitation: A solution of (S)-TPMA besylate was prepared, filtered, and combined with an anti-solvent. If precipitation was not observed, the sample was placed in a freezer. If precipitation was not achieved in the freezer, samples were evaporated either partially or to dryness.

Grinding Experiments: A sample of (S)-TPMA besylate was placed in an agate canister with an agate ball. In the case of solvent drop grinding experiments, a small amount (10 μL) of solvent was added. The sample was capped, parafilmed and ground on a Retsch mixer mill model MM200 for 20 minutes at 30 Hertz.

Vapor Diffusion: A solution of (S)-TPMA besylate was prepared and filtered into a vial. The vial was placed, uncapped, into a larger vial containing anti-solvent. The larger vial was capped, and the sample was allowed to equilibrate.

Rotary Evaporation: A solution of (S)-TPMA besylate was prepared and filtered. The sample was placed on a rotary evaporated at ambient temperature and evaporated to dryness.

Lyophilization: An aqueous solution of (S)-TPMA besylate was prepared, filtered, and frozen using a dry ice/acetone bath. The sample was placed on an FTS-Systems Flexi-Dry lyophilizer.

Heating Experiments: A sample of (S)-TPMA besylate was placed in a vial, capped, and placed in an oil bath at a given temperature.

Instrumental Techniques

XRPD: Most XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the Si 111 peak position. A specimen of the sample was sandwiched between 3 μm thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report including the divergence slit (DS) before the mirror and the incident-beam antiscatter slit (SS).

One XRPD pattern was collected with a PANalytical X'Pert PRO MPD diffractometer using an incident beam of Cu Kα radiation produced using a long, fine-focus source and a nickel filter. The diffractometer was configured using the symmetric Bragg-Brentano. Prior to the analysis, a silicon specimen (NIST SRM 640d) was analyzed to verify the Si 111 peak position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. The diffraction pattern was collected using a scanning position-sensitive detector (X'Celerator) located 240 mm from the sample and Data Collector software v. 2.2b. The data-acquisition parameters for the pattern are displayed above the image in the Data section of this report including the divergence slit (DS) and the incident-beam SS.

VT-XRPD (non-cGMP): VT-XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Data were collected and analyzed using Data Collector software v. 2.2b. Prior to the analysis, a silicon specimen (NIST SRM 640d) was analyzed to verify the observed position of the Si 111 peak is consistent with the NIST-certified position. A specimen of the sample was packed in a nickel-coated copper well. Antiscatter slits (SS) were used to minimize the background generated by air scattering. Soller slits for the incident and diffracted beams were used to minimize broadening from axial divergence. Diffraction patterns were collected using a scanning position-sensitive detector (X'Celerator) located 240 mm from the sample. The data acquisition parameters for each pattern are displayed above the image in the Data section of this report including the divergence slit (DS) and the incident-beam SS.

An Anton Paar TTK 450 stage was used to collect in-situ XRPD patterns as a function of temperature. The sample was heated with a resistance heater located directly under the sample holder, and the temperature was monitored with a platinum-100 resistance sensor located in the specimen holder. The heater was powered and controlled by an Anton Paar TCU 100 interfaced with Data Collector.

Standard DSC: Standard DSC was performed using a TA Instruments Q2000 differential scanning calorimeter. Temperature calibration was performed using NIST traceable indium metal. The sample was placed into an aluminum DSC pan, covered with a lid, the lid was crimped, and the weight was accurately recorded. (This pan configuration is designated with a "T0C" in the comments of the thermogram in the Data section.) A weighed aluminum pan configured as the sample pan was placed on the reference side of the cell. The sample was heated from −30° C. to 250° C., at 10° C./min. (abbreviated as "−30-250-10" in the method field in the thermogram).

Cycling Hyper-DSC: Hyper cycling-DSC was performed using a Perkin Elmer diamond power compensated differential scanning calorimeter. Temperature calibration was performed using NIST traceable indium metal. The sample was placed into an aluminum DSC pan, and the weight was accurately recorded. The pan was covered with a lid, which was crimped. A weighed, crimped aluminum pan was placed on the reference side of the cell. The sample cell was equilibrated at −50° C. and heated under a helium purge at a rate of 100° C./min. to 145° C., where it was held for five minutes. The sample was then cooled at approximately 500° C./min. to −50° C. The sample was then heated to 50° C. at 100° C./min. and again cooled at approximately 500° C./min. to −50° C. Finally, the sample was heated at 100° C./min. to a final temperature of 150° C. It is noted that the instrument was not calibrated for the 500° C./min. cooling, and these cooling steps are considered to be "uncontrolled" cooling.

Hotstage Microscopy: Hot stage microscopy was performed using a Linkam hot stage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20×0.40 N.A. long working distance objective with crossed polarizers and a first order red compensator. Images were captured using SPOT software (v. 4.5.9).

Optical Microscopy: Optical microscopy observations were made using a Wolfe stereomicroscope with polarizers and a 2× or 4× objective.

Indexing (non-cGMP): The XRPD pattern of (S)-TPMA besylate Form BA was indexed using proprietary SSCI software.

Indexing and structure refinement are computational studies which are performed under the "Procedures for SSCI Non-cGMP Activities."

Results

Approximate solubilities of (S)-TPMA besylate in different solvents show that it has high solubility in methanol and water, as well as in aqueous mixtures.

TABLE 11a

Approximate Solubilities of (S)-TPMA Besylate

| Solvent | Approximate Solubility[a] |
|---|---|
| Acetone | 5 mg/mL |
| 9:1 (v/v) Acetone: $H_2O$ | ≥92 mg/mL |
| ACN | 26 mg/mL |
| DCM | 51 mg/mL |
| EtOAc | <2 mg/mL [b] |
| EtOH | 28 mg/mL |
| IPA | 8 mg/mL |
| 9:1 (v/v) IPA: $H_2O$ | ≥96 mg/mL |
| MEK | 1 mg/mL |
| MeOH | ≥116 mg/mL |
| THF | <1 mg/mL [b] |
| 9:1 (v/v) THF: $H_2O$ | ≥88 mg/mL |
| Toluene | <1 mg/mL [b] |
| $H_2O$ | ≥108 mg/mL |

[a]: Solubility rounded to nearest mg/mL. Dissolution was determined by visual inspection, and the actual solubility may be higher than reported due to slow rates of dissolution or to addition of over-sized aliquots. If dissolution was not observed, the solubility is reported as "less than". If dissolution was observed upon addition of the first aliquot, the solubility is reported as "greater than or equal to".
[b]: Following the experiment at RT, the sample was set on a hot plate at ~68° C. Most solids dissolved at the solids dissolved at the elevated temperature. The elevated temperature observation is considered non-cGMP, because the hot plate and thermometer identification information were not documented.

Over 60 the (S)-TPMA beyslate polymorph crystallization experiments were conducted during the screen. Types of experiments included evaporation and cooling at different rates, slurries, grinding with and without solvent, antisolvent crash precipitation, rotary evaporation, vapor diffusion, lyophilization, and a heating experiment. Isolated solids were analyzed using XRPD. The XRPD patterns were compared to each other and to the starting material.

Overall, material consistent with Form BA was obtained in the majority of the experiments conducted. Selected samples of Form BA showed signs of preferred orientation, consistent with the observed plate-like morphology. Material B was produced in a single experiment. Exhibiting severe preferred orientation, Material B displayed an XRPD pattern similar to that of Form BA with additional peaks. DSC and repeat XRPD data collected on the material appeared to be consistent with Form BA, suggesting conversion. Attempts to reproduce Material B resulted in Form BA. X-ray amorphous (S)-TPMA was not produced during the polymorph experiments.

Form BA

Hotstage microscopy data are presented in Table 11b. Based on the combined characterization data, (S)-TPMA Form BA is a crystalline, stable, anhydrous, non-hygroscopic material with a melt at 142 to 143° C.

TABLE 11b

Hotstage Microscopy Analysis

| Temperature | Observation/Comments |
|---|---|
| 24.9° C. | Heating at 5° C./min |
| 90.0° C. | No apparent change |
| 135.0° C. | No apparent change |
| 140.8° C. | Melting |
| 142.0° C. | Melting |
| 142.2° C. | Complete melt; start cooling. Melt was sharp. No noticeable discoloration of the melt was observed |
| 62.1° C. | Crystallization on cooling noted between ~60-70° C. |
| 50.0° C. | Reheating 10° C./min to ~130° C., then 5° C./min. |
| 142.2° C. | Final melt~melting point |
| — | Sample recrystallized on cooling |

Figure 28:
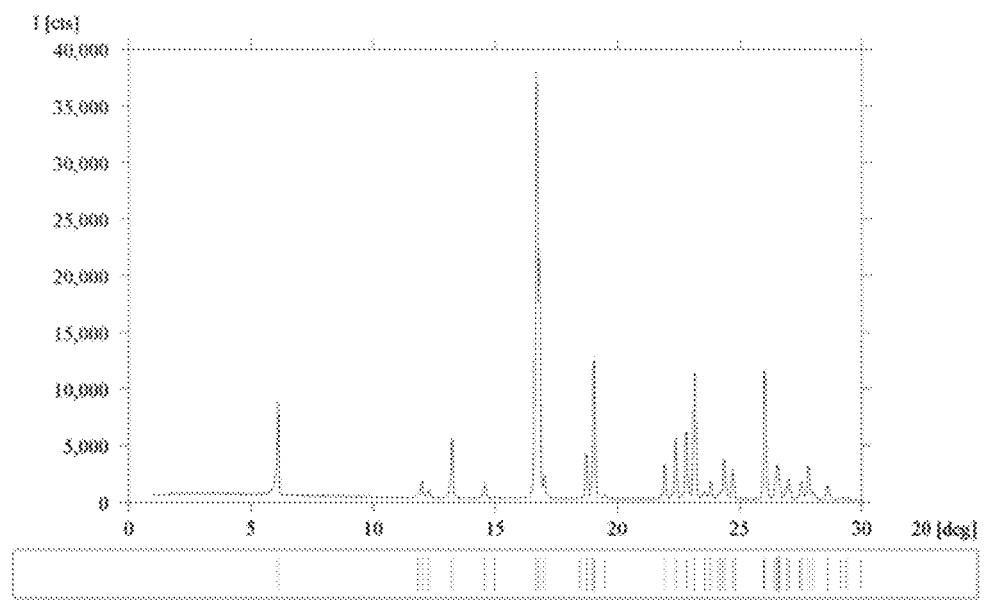
FIG. 28 is an XRPD of (S)-(4,5-dihydro-7H-thieno[2,3-c]pyran-7-yl)-N-methylmethanamine besylate Form BA showing the indexing results.

(S)-TPMA Form BA XRPD pattern was successfully indexed, suggesting that the sample is composed primarily of a single crystalline phase. See FIG. 28 Agreement between the allowed peak positions, marked with red bars in the figure, and the observed peaks indicates a consistent unit cell determination. Space groups consistent with the assigned extinction symbol, unit cell parameters, and derived quantities are tabulated below the figure. To confirm the tentative indexing solution, the molecular packing motifs within the crystallographic unit cells must be determined. No attempts at molecular packing were performed.

DSC data for (S)-TPMA Form BA revealed a single endothermic transition at 142-143° C., attributable to a melt based on hotstage microscopy analysis. The hotstage microscopy experiment did not show evidence of decomposition at the melt, and crystallization was observed upon cooling. Reheating of the sample revealed a melt at the same temperature as the first melt, consistent with the sample crystallizing to the same form. A VT-XRPD experiment indicated melt of Form BA crystallized to Form A upon cooling. Specifically, at room temperature, Form BA is observed, at 145° C. (ramp rate from room temperature is 35° C./min) shows a halo indicative of melt, and −60 to −90° C. shows Form BA with some disorder.

Material B

Material B was obtained once from an acetone slow cool experiment from 45° C. The XRPD pattern for the material exhibited severe preferred orientation effects and showed few peaks. While some of the peaks appeared to be consistent with Form BA, additional peaks were observed that are likely not associated with Form BA. The observed additional peaks do not appear to arise from either (S)-TPMA free base or from benzenesulfonic acid.

The Material B sample was analyzed using DSC. The resulting thermogram was not distinguishable from that of Form BA. Subsequent, repeat XRPD analysis of the sample revealed conversion to Form BA. Additional experiments were attempted targeting Material B. Selected samples were analyzed wet under the assumption the material may be an unstable solvate. The experiments, however, resulted in Form BA, based on XRPD data. Alternatively, Material B may represent a mixture of primarily Form A with a low-level contaminant.

Amorphous Material

Amorphous (S)-TPMA besyalte has a glass transition temperature at approximately 20° C., and tends to crystallize to Form A.

In summary, a polymorph study of (S)-TPMA was conducted to estimate the number and types of solid forms. Overall, one crystalline form, designated as Form BA, was observed during the majority of the screen experiments. Characterization data indicated (S)-TPMA besylate Form A is a crystalline, stable, anhydrous, non-hygroscopic material with a melt in the range of 142 to 143° C. One experiment resulted in Material B, suggesting the existence of another possible form. Attempts to reproduce the material resulted in Form BA. Finally, amorphous (S)-TPMA besylate appears to be unstable, exhibits a glass transition temperature at approximately 20° C., and tends to crystallize to Form A.

Example 12. Crystalline Form of (S)-TPMA Free Base

The crystalline form of (S)-TPMA free base was analyzed using XRPD, DSC, coulometric titration, and DVS. FIG. 32 shows the XRPD and Table 12a provides a list of the peaks of Form BA.

TABLE 12a (S)-TPMA free base XRPD (FIG. 32) Peak List

| 2-Theta (degree) | Relative height (%) |
|---|---|
| 6.8 | 0.9 |
| 9.3 | 1.0 |
| 11.2 | 1.9 |
| 12.1 | 6.0 |
| 13.6 | 8.8 |
| 14.8 | 5.3 |
| 15.1 | 0.5 |
| 15.4 | 1.1 |
| 16.4 | 14.7 |
| 17.5 | 3.4 |
| 18.0 | 1.5 |
| 20.0 | 20.9 |
| 20.4 | 100.0 |
| 21.3 | 0.9 |
| 21.9 | 1.5 |
| 22.4 | 11.6 |
| 23.2 | 13.9 |
| 24.0 | 1.2 |
| 24.4 | 2.7 |
| 25.3 | 1.2 |
| 26.2 | 8.6 |
| 26.6 | 9.7 |
| 27.3 | 54.0 |
| 27.7 | 8.5 |
| 27.9 | 5.1 |
| 29.0 | 1.9 |
| 29.3 | 0.9 |
| 31.2 | 2.6 |
| 31.8 | 1.1 |
| 32.1 | 0.7 |
| 32.7 | 1.0 |
| 34.1 | 1.0 |

TABLE 12a-continued (S)-TPMA free base XRPD (FIG. 32) Peak List

| 2-Theta (degree) | Relative height (%) |
|---|---|
| 34.4 | 1.9 |
| 35.0 | 0.7 |
| 35.6 | 5.4 |
| 36.3 | 0.6 |
| 38.8 | 0.6 |
| 39.7 | 3.9 |
| 40.7 | 2.1 |
| 42.0 | 2.2 |
| 42.6 | 0.8 |
| 43.5 | 1.3 |
| 43.9 | 1.8 |
| 44.6 | 0.7 |

Example 13. PSD and Agglomeration Control in Scale-Up of Reactive-Crystallization The agglomeration and Particle Size Distribution (PSD) of (S)-(4,5-dihydro-7H-thieno[2,3-c]pyran-7-yl)-N-methyl-methanamine HCl Form A Crystals have been investigated and successfully implemented during scale-up to industrial scale manufacturing.

The results indicated that the mixing control and flow dynamics are affect agglomeration and PSD control. The mesomixing time, when the incoming HCl solution stream mixes with the bulk freebase solution, plays a role in terms of the agglomeration and PSD control. Therefore, it is necessary to understand the flow pattern and the mixing behavior of the reactors with Computational Fluid Dynamics (CFD) calculation through simulation tools.

In order to address the agglomeration and PSD, certain process parameters were identified, including the dosing types (subsurface addition, or overhead addition), dosing tubing discharge location in subsurface addition (well defined mixing zone, or dead zone), diameter of the dosing tubing (which affects the meso-mixing time), dosing profiles of the HCl stream (dosing rate).

A series of studies were conducted on various aspects of the reactive-recrystallization (e.g. Scheme 4 in Example 1A) to develop methods and provide various particle size distribution of (S)-(−)-TPMA HCl Form A crystals. Reaction conditions were substantially similar to those set for in Example 1A with respect to Scheme 4 except as modified as described in the studies below.

Study 1.

Figure 29:
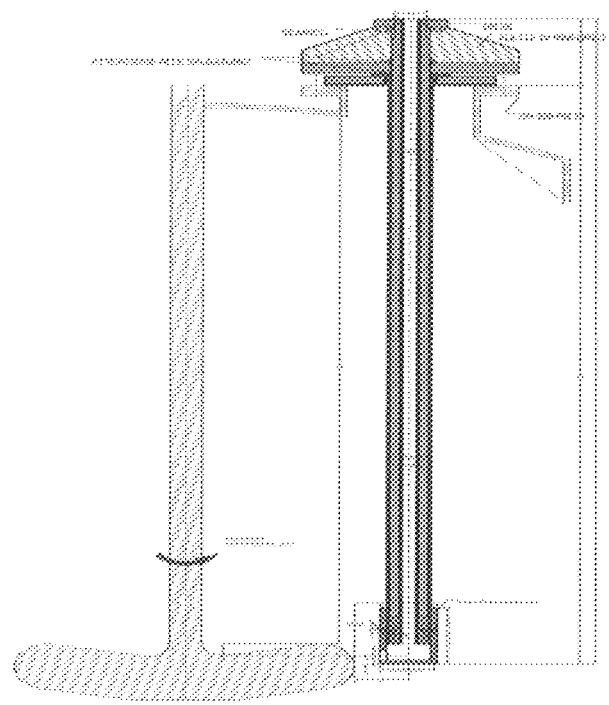
FIG. 29 is schematic diagram showing the controlled sub-surface addition of the acid stream at the region of a high mixing zone near the impeller tip.

Elimination of agglomeration in the final crystallization of (S)-(−)-TPMA HCl was demonstrated through use of controlled sub-surface addition of the acid stream at the region of a high mixing zone near the impeller tip. FIG. 29 illustrates the impact of such controlled addition of two different addition points: when adding the acid stream into the center of the free base solution the resulting morphology is that of an agglomerate form. When adding the acid stream below surface and near the impeller tip (FIG. 29), the resulting morphology is that of an agglomerate free and larger size crystalline product.

Study 2.

For any crystallization process, the balance between nucleation, crystal growth and agglomeration determine the size distribution, and the supersaturation generation rate could be the driving force for the crystallization and the decisive parameter to balance the nucleation and crystal growth, etc.

Figure 30:
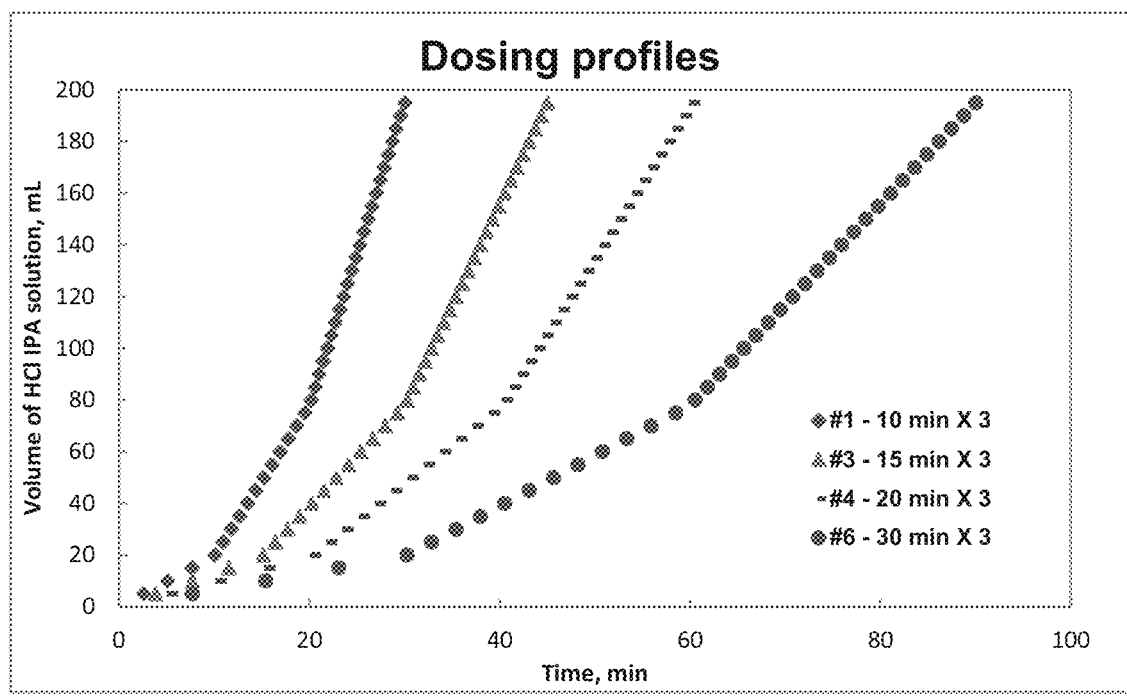
FIG. 30 is a dosing profile of HCl IPA solution (mL) over time (minute).
Figure 31:
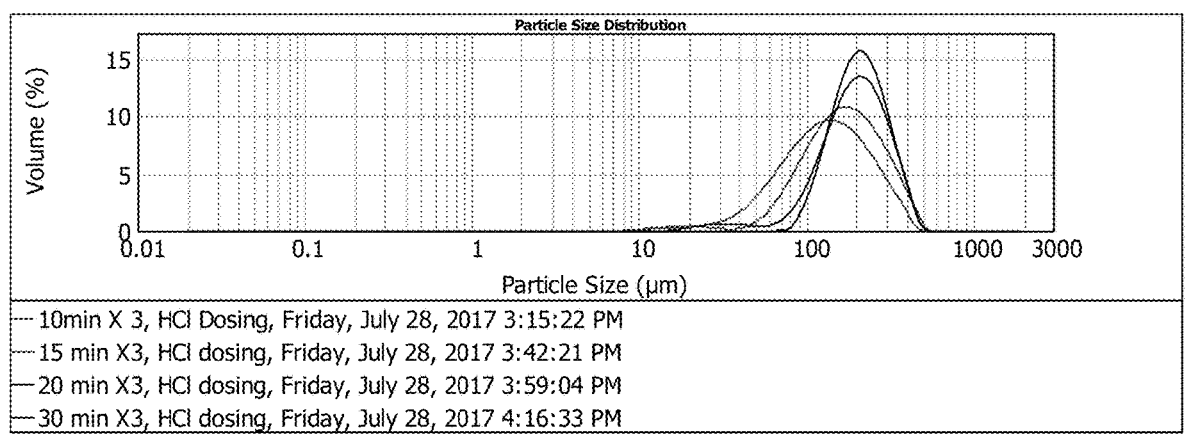
FIG. 31 is a graph of the particle side distribution for the dosing profiles, volume (%) over particle size (um).

In the current reactive-crystallization of (S)-TPMA HCl, the supersaturation generation rate can be directly controlled by the HCl solution addition rate. A series of experiments have been executed with different HCl addition profiles effect on particle size distribution. The results summarized in Table 13A and Table 13B and FIG. 30 and FIG. 31 indicate that faster dosing favors the formation of the smaller crystals and slower dosing favors the formation of bigger crystals.

TABLE 13A

HCl IPA Solution Dosing Profiles

| Profile | HCl IPA solution addition |
|---|---|
| 10 min × 3, HCl dosing | (i) first 10% added over approximately 10 minutes<br>(ii) next 30% added over approximately 10 minutes<br>(iii) remainder added over approximately 10 minutes |
| 15 min × 3, HCl dosing | (i) first 10% added over approximately 15 minutes<br>(ii) next 30% added over approximately 15 minutes<br>(iii) remainder added over approximately 15 minutes |
| 20 min × 3, HCl dosing | (i) first 10% added over approximately 20 minutes<br>(ii) next 30% added over approximately 20 minutes<br>(iii) remainder added over approximately 20 minutes |
| 30 min × 3, HCl dosing | (i) first 10% added over approximately 30 minutes<br>(ii) next 30% added over approximately 30 minutes<br>(iii) remainder added over approximately 30 minutes |

TABLE 13B

Particle Size Distribution Parameters for Dosing Profiles

| Sample Name | D (4,3) | d (0.1) | d (0.5) | d (0.9) | Span |
|---|---|---|---|---|---|
| 10 min × 3, HCl Dosing | 149.43 | 55.23 | 131.21 | 273.25 | 1.662 |
| 15 min × 3, HCl dosing | 185.80 | 79.73 | 167.51 | 323.92 | 1.458 |
| 20 min × 3, HCl dosing | 209.45 | 103.82 | 199.11 | 335.44 | 1.163 |
| 30 min × 3, HCl dosing | 222.06 | 129.01 | 209.38 | 334.41 | 0.981 |

Note:
1 mm ID dosing tubing, operating temperature: 20° C.

Study 3.

The PSD control strategy has been implemented and demonstrated effectively during the process scale-up to manufacturing plant (100 Kg input). Using a sub-surface addition and maintaining a mesomixing time constant during scale-up a simple acid addition profile change from Profile A to profile B results to a mean size decrease from ~175 μm to a size of ~100 μm (D50).

| Dosing Profiles | D10 | D50 | D90 | D(4, 3) | Span | Quantity, Kg |
|---|---|---|---|---|---|---|
| Dosing Profile A | 67.6 | 176.2 | 359.8 | 196.9 | 1.66 | 61.32 |
| Dosing Profile B | 46.1 | 108.0 | 239.4 | 128.0 | 1.79 | 69.90 | dosing Profile A: The first 10%: add over approximately 90 minutes; the next 30%: add over approximately 45 minutes; the remainder: add over approximately 45 minutes;
Dosing Profile B: The first 10%: add over approximately 15 minutes; the next 30%: add over approximately 15 minutes; the remainder: add over approximately 18 minutes.

The Diagnostic and Statistical Manual of Mental Disorders, Fifth Ed., hereinafter, the "DSM-5"), published by the American Psychiatric Association in 2013, and is incorporated herein by reference, provides a standard diagnostic system upon which persons of skill rely for diagnosis of various diseases and disorders.

The term "mood disorder" as used herein includes depression, major depression, major depressive disorder, mild depression, severe depression without psychosis, severe depression with psychosis, melancholia (formerly endogenous depression), atypical depression, dysthymic disorder, manic depression, bipolar disorder, bipolar depression, bipolar I disorder, bipolar II disorder, bipolar III disorder, cyclothymic disorder, and chronic hypomania.

Psychiatric disorders are pathological conditions of the brain characterized by identifiable symptoms that result in abnormalities in cognition, emotion or mood, or the highest integrative aspects of behavior. These disorders may vary in severity of symptoms, duration, and functional impairment. Psychiatric disorders afflict millions of people worldwide resulting in tremendous human suffering and economic burden due to lost productivity. Mood disorders are a type of psychiatric disorder often defined as a group of heterogeneous, typically recurrent illnesses including unipolar (depressive) and bipolar (manic-depressive) disorders characterized by pervasive mood disturbances, psychomotor dysfunction, and vegetative symptoms. Suicide, the most serious complication in patients with mood disorders, is the cause of death in 15 to 25% of untreated patients with mood disorders; unrecognized or inadequately treated depression contributes to 50 to 70% of all completed suicides.

In various embodiments, the neurological disorder is: depression (e.g., major depressive disorder or dysthymia); bipolar disorder, seasonal affective disorder; cognitive deficit; fibromyalgia; pain (e.g., neuropathic pain); sleep related disorder (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; post-traumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic disorder; dysthymic disorder; cyclothymic disorder; obesity; and substance abuse or dependency (e.g., cocaine addiction, nicotine addiction). In another embodiment, the compounds provided herein are useful to treat, prevent, and/or manage two or more conditions/disorders, which are co-morbid, such as psychosis and depression.

Neurological disorders may also include cerebral function disorders, including without limitation, senile dementia, Alzheimer's type dementia, cognition, memory loss, amnesia/amnestic syndrome, epilepsy, disturbances of consciousness, coma, lowering of attention, speech disorder, Lennox syndrome, autism, and hyperkinetic syndrome.

In various aspects, the disease or disorder which the medicaments and methods of the present inventions treat comprises one of more of a mood disorder, bipolar disorder (BPD), bipolar depression, sleep disorders, REM behavior disorder, psychosis disorders, Alzheimer's disease with agitation and/or psychosis, Parkinson's disease psychosis, schizophrenia, attenuated psychosis syndrome, prodromal schizophrenia, and schizoaffective disorder.

In various embodiments, the neurological or psychiatric disease or disorder is one or more of a mood disorder, bipolar disorder (BPD), bipolar depression, sleep disorders, REM behavior disorder, psychosis disorders, Alzheimer's disease with agitation and/or psychosis, Parkinson's disease psychosis, schizophrenia, attenuated psychosis syndrome, prodromal schizophrenia, and schizoaffective disorder.

In various embodiments, the neurological or psychiatric disease or disorder is selected from a psychosis, including schizophrenia (paranoid, disorganized, catatonic or undifferentiated), schizophreniform disorder, schizoaffective disorder, delusional disorder, brief psychotic disorder, shared psychotic disorder, psychoaffective disorder, aggression, delirium, Parkinson's psychosis, excitative psychosis, psychotic disorder due to a general medical condition and substance-induced or drug-induced (e.g., phencyclidine, ketamine and other dissociative anesthetics, amphetamine and other psychostimulants and cocaine) psychosis disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both positive, negative, and cognitive symptoms of schizophrenia and other psychoses; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, *cannabis*, cocaine, hallucinogens, inhalants, nicotine, opioids, phencyclidine, sedatives, hypnotics or anxiolytics); and Alzheimer's disease with agitation and/or psychosis.

In some embodiments, provided herein is a method of treating schizophrenia comprising administering to the subject a formulation (e.g., tablet) as described herein, in the amount of about 25 mg to about 100 mg per day of (S)-TPMA, or pharmaceutically acceptable salt thereof, on a free base basis. In some embodiments, the amount is about 25 mg, about 30 mg, about 40 mg, about 50 mg, about 60 mg, about 70 mg, about 75 mg, about 80 mg, about 90 mg, or about 100 mg per day of (S)-TPMA, or pharmaceutically acceptable salt thereof, on a free base basis.

In various embodiments, the neurological or psychiatric disease or disorder is selected from a depressive disorders including, but not limited to, unipolar depression, seasonal depression and post-partum depression, atypical depression, catatonic depression, elderly depression, endogenous depression, melancholic depression, perinatal depression, situational depression, chronic depression, bipolar depression, major depressive disorder (MDD), major depressive disorder with mixed features (MDD-MF), treatment resistant depression (TRD), and dysthymia, and are associated with depressed mood (sadness), poor concentration, insomnia, fatigue, appetite disturbances, excessive guilt and thoughts of suicide, premenstrual syndrome (PMS) and premenstrual dysphoric disorder (PDD), mood disorders due to a general medical condition, and substance-induced mood disorders.

In various embodiments, the neurological or psychiatric disease or disorder is selected from a bipolar disorders including, but not limited to, bipolar depression, bipolar I disorder, bipolar II disorder, cyclothymic disorder, substance/medication-induced bipolar and related disorders, bipolar and related disorder due to another medical condition, other specified bipolar and related disorder, and unspecified bipolar and related disorders.

In various embodiments, the neurological or psychiatric disease or disorder is selected from an eating disorder including, but not limited to, eating disorders such as obesity, bulimia nervosa, pica and compulsive eating disorders.

In various embodiments, the neurological or psychiatric disease or disorder is selected from a sleep disorder including, but not limited to, insomnia, disturbed sleep, jet lag, hypersomnia, cataplexy, sleep apnea, obstructive sleep apnea, REM sleep behavior disorder, Restless Leg Syndrome, periodic limb movement disorder, circadian rhythm sleep disorders, delayed sleep phase disorder, sleepwalking, night terrors, bed wetting, rapid eye movement sleep behavior disorder, shift work sleep disorder, excessive daytime sleepiness, non-24-hour sleep-wake disorder, sleep paralysis and narcolepsy.

In various embodiments, the neurological or psychiatric disease or disorder is a bipolar disorder. Bipolar disorders (including both bipolar I and bipolar II) are serious psychiatric disorders that have a prevalence of approximately 2% of the population, and affect both genders alike. It is a relapsing-remitting condition characterized by cycling between elevated (i.e., manic) and depressed moods, which distinguishes it from other disorders such as major depressive disorder and schizophrenia. Bipolar I is defined by the occurrence of a full manic episode, although most individuals experience significant depression. Symptoms of mania include elevated or irritable mood, hyperactivity, grandiosity, decreased need for sleep, racing thoughts and in some cases, psychosis. The depressive episodes are characterized by anhedonia, sad mood, hopelessness, poor self-esteem, diminished concentration and lethargy. Bipolar II is defined as the occurrence of a major depressive episode and hypomanic (less severe mania) episode although patients spend considerable more time in the depressive state. Other related conditions include cyclothymic disorder.

In bipolar I disorder, full-fledged manic and major depressive episodes alternate. Bipolar I disorder commonly begins with depression and is characterized by at least one manic or excited period during its course. The depressive phase can be an immediate prelude or aftermath of mania, or depression and mania can be separated by months or years.

In bipolar II disorder, depressive episodes alternate with hypomanias (relatively mild, nonpsychotic periods of usually <1 week). During the hypomanic period, mood brightens, the need for sleep decreases, and psychomotor activity accelerates beyond the patient's usual level. Often, the switch is induced by circadian factors (e.g., going to bed depressed and waking early in the morning in a hypomanic state). Hypersomnia and overeating are characteristic and may recur seasonally (e.g., in autumn or winter); insomnia and poor appetite occur during the depressive phase. For some persons, hypomanic periods are adaptive because they are associated with high energy, confidence, and supernormal social functioning. Many patients who experience pleasant elevation of mood, usually at the end of a depression, do not report it unless specifically questioned.

Patients with major depressive episodes and a family history of bipolar disorders (unofficially called bipolar III) often exhibit subtle hypomanic tendencies; their temperament is termed hyperthymic (i.e., driven, ambitious, and achievement-oriented).

In cyclothymic disorder, less severe hypomanic and mini-depressive periods follow an irregular course, with each period lasting a few days. Cyclothymic disorder is commonly a precursor of bipolar II disorder. But it can also occur as extreme moodiness without being complicated by major mood disorders. In such cases, brief cycles of retarded depression accompanied by low self-confidence and increased sleep alternate with elation or increased enthusiasm and shortened sleep. In another form, low-grade depressive features predominate; the bipolar tendency is shown primarily by how easily elation or irritability is induced by antidepressants. In chronic hypomania, a form rarely seen clinically, elated periods predominate, with habitual reduction of sleep to <6 hours. Persons with this form are constantly overcheerful, self-assured, overenergetic, full of plans, improvident, overinvolved, and meddlesome; they rush off with restless impulses and accost people.

Accordingly, in various embodiments, the neurological or psychiatric disease or disorder is one or more of bipolar I disorder, bipolar II disorder, cyclothymic disorder, other specified bipolar and related disorder, or unspecified bipolar and related disorder, and bipolar I disorder or bipolar II disorder with the specifiers of anxious distress, with mixed features, with rapid cycling, with melancholic features, with atypical features, with mood-congruent psychotic features, with mood incongruent psychotic features, with catatonia, with peripartum onset, and/or with seasonal pattern. A recent article by Hu et al [*Prim Care Companion CNS Disord.* 2014; 16(2): PCC.13r01599] highlights that bipolar disorder, while commonly encountered in the primary care setting, is often misdiagnosed or undiagnosed. The DSM-5 attempts to capture the large proportion of patients with subsyndromal mixed symptoms with the inclusion of the mixed specifier.

In various embodiments, the neurological or psychiatric disease or disorder is a depressive disorder. Depressive disorders include, but are not limited to, depressive disorders including, but not limited to, unipolar depression, seasonal depression and post-partum depression, atypical depression, catatonic depression, elderly depression, endogenous depression, melancholic depression, perinatal depression, situational depression, chronic depression, bipolar depression, major depressive disorder (MDD), major depressive disorder with mixed features (MDD-MF), treatment resistant depression (TRD), and dysthymia, and are associated with depressed mood (sadness), poor concentration, insomnia, fatigue, appetite disturbances, excessive guilt and thoughts of suicide, premenstrual syndrome (PMS) and premenstrual dysphoric disorder (PDD), mood disorders due to a general medical condition, and substance-induced mood disorders.

Depression is an affective disorder, the pathogenesis of which cannot be explained by any single cause or theory. Unfortunately, treatment options for depressed patients who have suboptimal clinical responses to therapy with an antidepressant are limited. Approximately thirty percent (30%) of patients initiating antidepressant therapy show suboptimal or delayed clinical responses to the first-line antidepressant agents that are commonly used to treat depression.

Typically, if a patient exhibits suboptimal or delayed clinical response after several weeks of therapy with an antidepressant, the clinician's initial approach is to increase the dose of the antidepressant. If the patient's response remains unsatisfactory after increasing the dose, the most common approaches that many clinicians will pursue are: a) switching to another antidepressant; or b) adding a second antidepressant; or c) attempting an augmentation therapy by administering agents such as lithium carbonate, thyroid hormone (triiodothyronine), psychostimulants, modafinil, atypical antipsychotics, buspirone, or pindolol.

In its full syndromal expression, clinical depression manifests as major depressive disorder, with episodic course and varying degrees of residual manifestations between episodes. The mood is typically depressed, irritable, and/or anxious. The patient may appear miserable, with furrowed brows, downturned corners of the mouth, slumped posture, poor eye contact, and monosyllabic (or absent) speech. The morbid mood may be accompanied by preoccupation with guilt, self-denigrating ideas, decreased ability to concentrate, indecisiveness, diminished interest in usual activities, social withdrawal, helplessness, hopelessness, and recurrent thoughts of death and suicide. Sleep disorders are common. In some, the morbid mood is so deep that tears dry up; the patient complains of an inability to experience usual emotions—including grief, joy, and pleasure—and of a feeling that the world has become colorless, lifeless, and dead.

Melancholia (formerly endogenous depression) is characterized by marked psychomotor slowing (of thinking and activity) or agitation (e.g., restlessness, wringing of the hands, pressure of speech), weight loss, irrational guilt, and loss of the capacity to experience pleasure. Mood and activity vary diurnally, with a nadir in the morning. Most melancholic patients complain of difficulty falling asleep, multiple arousals, and insomnia in the middle of the night or early morning. Sexual desire is often diminished or lost. Amenorrhea can occur. Anorexia and weight loss may lead to emaciation and secondary disturbances in electrolyte balance.

In atypical depression, reverse vegetative features dominate the clinical presentation; they include anxious-phobic symptoms, evening worsening, initial insomnia, hypersomnia that often extends into the day, and hyperphagia with weight gain. Unlike patients with melancholia, those with atypical depression show mood brightening to potentially positive events but often crash into a paralyzing depression with the slightest adversity. Atypical depressive and bipolar II disorders overlap considerably.

In dysthymic disorder, depressive symptoms typically begin insidiously in childhood or adolescence and pursue an intermittent or low-grade course over many years or decades; major depressive episodes may complicate it (double depression). In pure dysthymia, depressive manifestations occur at a subthreshold level and overlap considerably with those of a depressive temperament: habitually gloomy, pessimistic, humorless, or incapable of fun; passive and lethargic; introverted; skeptical, hypercritical, or complaining; self-critical, self-reproaching, and self-derogatory; and preoccupied with inadequacy, failure, and negative events.

Thorough evaluation of many persons with depression reveals bipolar traits, and as many as one in five patients with a depressive disorder also develops frank hypomania or mania. Most switches from unipolar to bipolar disorder occur within 5 years of the onset of depressive manifestations. Predictors of a switch include early onset of depression (<25 years old), postpartum depression, frequent episodes of depression, quick brightening of mood with somatic treatments (e.g., antidepressants, phototherapy, sleep deprivation, electroconvulsive therapy), and a family history of mood disorders for three consecutive generations.

Between episodes, patients with bipolar disorder exhibit depressive moodiness and sometimes high-energy activity; disruption in developmental and social functioning in bipolar depression is more common than in unipolar disorder. In bipolar disorder, depression episodes are shorter (3 to 6 months), age of onset is younger, onset of episodes is more abrupt, and cycles (time from onset of one episode to that of the next) are shorter than in unipolar disorder. Cyclicity is particularly accentuated in rapid-cycling forms of bipolar disorder (usually defined as >=4 episodes/year). In addition depressive episodes in bipolar disorder are a difficult component of BPD to treat. For example, psychiatrists indicate that about 25% of patients across all bipolar disorders are refractory during a manic episode, while about 70% are refractory during a depressive episode.

Accordingly, in various embodiments, the neurological or psychiatric disease or disorder is one or more of bipolar depression, major depressive disorder (MDD), persistent depressive disorder (Dysthymia), premenstrual dysphoric disorder (PMDD), major depressive disorder with mixed features (MDD-MF), depressive disorder due to another medical condition, other specified depressive disorder, unspecified depressive disorder, or treatment resistant depression (TRD), and MDD with the specifiers of anxious distress, with mixed features, with melancholic features, with atypical features, with mood-congruent psychotic features, with mood-incongruent psychotic features, with catatonia, with peripartum onset, and/or with seasonal pattern, and seasonal affective disorder.

It is to be understood that TRD is a term used in clinical psychiatry to describe cases of major depressive disorder (MDD) that do not respond adequately to appropriate courses of at least two antidepressants.

In various embodiments, a depressive disorder is associated with acute suicidality or suicide ideation. The United States Food and Drug Administration has adopted a "black box" label warning indicating that antidepressants may increase the risk of suicidal thinking and behavior in some children, adolescents and young adults (up to age 24) with a depressive disorder such as MDD. In various embodiments, it is believed that the compositions and methods of the present inventions do not increase the risk of suicidal thinking and/or behavior in children, adolescents and/or young adults with a depressive disorder, e.g., with MDD. In various embodiments, the present inventions provide medicaments for and provide methods of treating one or more symptoms of a depressive disorder (e.g., MDD) in children, adolescents and/or young adults without increasing the risk of suicidal thinking and/or behavior.

In various embodiments, the neurological or psychiatric disease or disorder is schizophrenia. Schizophrenia is a disorder of unknown origin, which usually appears for the first time in early adulthood and is marked by characteristics such as psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder. Schizophrenia is classified into subgroups: the paranoid type, characterized by delusions and hallucinations and absence of thought disorder, disorganized behavior, and affective flattening; the disorganized type, also named "hebephrenic schizophrenia," in which thought disorder and flat affect are present together; the catatonic type, in which prominent psychomotor disturbances are evident, and symptoms may include catatonic stupor and waxy flexibility; and the undifferentiated type, in which psychotic symptoms are present but the criteria for paranoid, disorganized, or catatonic types have not been met. The symptoms of schizophrenia normally manifest themselves in three broad categories: positive, negative and cognitive symptoms. Positive symptoms are those which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making.

Accordingly, in various embodiments, the neurological or psychiatric disease or disorder is one or more of schizotypal (personality) disorder, delusional disorder, brief psychotic disorder, schizophreniform disorder, schizophrenia, schizoaffective disorder, substance/medication-induced psychotic disorder, psychotic disorder due to another medical condition, other specified schizophrenia spectrum and other psychotic disorder, unspecified schizophrenia spectrum, and other psychotic disorder.

It is to be understood that schizoaffective disorder includes a condition that includes aspects of both schizophrenia and a mood disorder, such as, for example, a major depressive disorder, a bipolar disorder, etc.

In various embodiments, the neurological or psychiatric disease or disorder is anxiety disorder. Anxiety disorders are characterized by fear, worry, and uneasiness, usually generalized and unfocused as an overreaction to a situation. Anxiety disorders differ in the situations or types of objects that induce fear, anxiety, or avoidance behavior, and the associated cognitive ideation. Anxiety differs from fear in that anxiety is an emotional response to a perceived future threat while fear is associated with a perceived or real immediate threat. They also differ in the content of the associated thoughts or beliefs. Examples of anxiety disorders include separation anxiety disorder, selective mutism, specific phobia, social anxiety disorder (social phobia), panic disorder, panic attack specifier, agoraphobia, generalized anxiety disorder, substance/medication-induced anxiety disorder, anxiety disorder due to another medical condition, illness anxiety disorder, social (pragmatic) communication disorder, other specified anxiety disorder, and unspecified anxiety disorder; stressor-related disorders, including reactive attachment disorder, disinhibited social engagement disorder, posttraumatic stress disorder (PTSD), acute stress disorder, and adjustment disorders.

In various embodiments, the neurological or psychiatric disease or disorder is a sleep disorder including those sleep disorders which are produced by psychiatric conditions, including, but not limited to, insomnia, disturbed sleep, jet lag, hypersomnia, cataplexy, sleep related disorder (e.g., sleep apnea, insomnia, narcolepsy, cataplexy), obstructive sleep apnea, REM sleep behavior disorder, Restless Leg Syndrome, periodic limb movement disorder, circadian rhythm sleep disorders, delayed sleep phase disorder, sleepwalking, night terrors, bed wetting, rapid eye movement sleep behavior disorder, shift work sleep disorder, excessive daytime sleepiness, non-24-hour sleep-wake disorder, sleep paralysis and narcolepsy.

Provided herein are also the following embodiments.

Embodiment 1. A formulation comprising a salt of (S)-(4,5-dihydro-7H-thieno[2,3-c]pyran-7-yl)-N-methylmethanamine and one or more excipients, wherein the amount of the salt of (S)-(4,5-dihydro-7H-thieno[2,3-c]pyran-7-yl)-N-methylmethanamine is about 2 to about 80% w/w, on a free base basis.

Embodiment 2. The formulation of embodiment 1, wherein the salt of (S)-(4,5-dihydro-7H-thieno[2,3-c]pyran-7-yl)-N-methylmethanamine is selected from:

(S)-(4,5-dihydro-7H-thieno[2,3-c]pyran-7-yl)-N-methylmethanamine hydrochloride,
(S)-(4,5-dihydro-7H-thieno[2,3-c]pyran-7-yl)-N-methylmethanamine besylate,
(S)-(4,5-dihydro-7H-thieno[2,3-c]pyran-7-yl)-N-methylmethanamine R-mandelate,
(S)-(4,5-dihydro-7H-thieno[2,3-c]pyran-7-yl)-N-methylmethanamine L-tartrate,
(S)-(4,5-dihydro-7H-thieno[2,3-c]pyran-7-yl)-N-methylmethanamine D-tartrate,
(S)-(4,5-dihydro-7H-thieno[2,3-c]pyran-7-yl)-N-methylmethanamine mesylate, and
(S)-(4,5-dihydro-7H-thieno[2,3-c]pyran-7-yl)-N-methylmethanamine L-malate.

Embodiment 3. The formulation of embodiment 2, wherein the salt of (S)-(4,5-dihydro-7H-thieno[2,3-c]pyran-7-yl)-N-methylmethanamine is crystalline.

Embodiment 4. The formulation of embodiment 3, wherein the crystalline (S)-(4,5-dihydro-7H-thieno[2,3-c]pyran-7-yl)-N-methylmethanamine hydrochloride is characterized by a powder x-ray diffraction pattern comprising peaks, in terms of 2-theta, at 9.6±0.2°, 14.9±0.2°, 20.5±0.2, and 25.1±0.2°.

Embodiment 5. The formulation of embodiment 4, wherein the crystalline (S)-(4,5-dihydro-7H-thieno[2,3-c]pyran-7-yl)-N-methylmethanamine hydrochloride is further characterized by the powder x-ray diffraction pattern further comprising a peak, in terms of 2-theta, at 20.2±0.2° and 20.8±0.2°.

Embodiment 6. The formulation of embodiment 4 or embodiment 5, wherein the crystalline (S)-(4,5-dihydro-7H-thieno[2,3-c]pyran-7-yl)-N-methylmethanamine hydrochloride is further characterized by the powder x-ray diffraction pattern further comprising a prominent peak, in terms of 2-theta, at two or more of 17.9±0.2°, 24.8±0.2° and 27.1±0.2°.

Embodiment 7. The formulation of any one of embodiments 4-6, wherein the crystalline (S)-(4,5-dihydro-7H-thieno[2,3-c]pyran-7-yl)-N-methylmethanamine hydrochloride is characterized by a powder x-ray diffraction pattern substantially in accord with FIG. 2B.

Embodiment 8. The formulation of any one of embodiments 4-7, wherein the crystalline (S)-(4,5-dihydro-7H-thieno[2,3-c]pyran-7-yl)-N-methylmethanamine hydrochloride has a differential scanning calorimetry thermogram comprising a peak at 214±2° C.

Embodiment 9. The formulation of any one of embodiments 4-8, wherein the crystalline (S)-(4,5-dihydro-7H-thieno[2,3-c]pyran-7-yl)-N-methylmethanamine hydrochloride has a differential scanning calorimetry thermogram substantially in accord with FIG. 3A.

Embodiment 10. The formulation of any one of embodiments 3-9, wherein the crystalline (S)-(4,5-dihydro-7H-thieno[2,3-c]pyran-7-yl)-N-methylmethanamine hydrochloride is characterized by monoclinic space group P21.

Embodiment 11. The formulation of any one of embodiments 3-10, wherein the crystalline (S)-(4,5-dihydro-7H-thieno[2,3-c]pyran-7-yl)-N-methylmethanamine hydrochloride has unit cell dimensions: a is about 9.2 Å, b is about 11.2 Å, c is about 10.2 Å, α is about 90°, β is about 92°, and γ is about 90°.

Embodiment 12. The formulation of any one of embodiments 3-11, wherein the crystalline (S)-(4,5-dihydro-7H-thieno[2,3-c]pyran-7-yl)-N-methylmethanamine hydrochloride has chiral purity greater than about 90% (S)-(4,5-dihydro-7H-thieno[2,3-c]pyran-7-yl)-N-methylmethanamine hydrochloride.

Embodiment 13. The formulation of any one of embodiments 3-12, wherein the crystalline (S)-(4,5-dihydro-7H-thieno[2,3-c]pyran-7-yl)-N-methylmethanamine hydrochloride has chemical purity of the substance is greater than about 99% (S)-(4,5-dihydro-7H-thieno[2,3-c]pyran-7-yl)-N-methylmethanamine hydrochloride.

Embodiment 14. The formulation of embodiment 3, wherein the crystalline (S)-(4,5-dihydro-7H-thieno[2,3-c]pyran-7-yl)-N-methylmethanamine hydrochloride is characterized by a powder x-ray diffraction pattern comprising peaks, in terms of 2-theta, at 8.6±0.2°, 17.2±0.2°, and 25.9±0.2°.

Embodiment 15. The formulation of embodiment 14, wherein the crystalline (S)-(4,5-dihydro-7H-thieno[2,3-c]pyran-7-yl)-N-methylmethanamine hydrochloride is characterized by a powder x-ray diffraction pattern substantially in accord with FIG. 2C.

Embodiment 16. The formulation of embodiment 14 or embodiment 15, wherein the crystalline (S)-(4,5-dihydro-7H-thieno[2,3-c]pyran-7-yl)-N-methylmethanamine hydrochloride has a differential scanning calorimetry thermogram comprising a peak at 215±2° C.

Embodiment 17. The formulation of any one of embodiments 14-16, wherein the crystalline (S)-(4,5-dihydro-7H-thieno[2,3-c]pyran-7-yl)-N-methylmethanamine hydrochloride has a differential scanning calorimetry thermogram substantially in accord with FIG. 3B.

Embodiment 18. The formulation of any one of embodiments 14-17, wherein the crystalline (S)-(4,5-dihydro-7H-thieno[2,3-c]pyran-7-yl)-N-methylmethanamine hydrochloride is characterized by orthorhombic space group P212121.

Embodiment 19. The formulation of any one of embodiments 3, and 14-17, wherein the crystalline (S)-(4,5-dihydro-7H-thieno[2,3-c]pyran-7-yl)-N-methylmethanamine hydrochloride has unit cell dimensions: a is about 5.1 Å, b is about 10.2 Å, c is about 20.5 Å, α is about 90°, β is about 90°, and γ is about 90°.

Embodiment 20. The formulation of embodiment 2, wherein the salt of (S)-(4,5-dihydro-7H-thieno[2,3-c]pyran-7-yl)-N-methylmethanamine is (S)-(4,5-dihydro-7H-thieno[2,3-c]pyran-7-yl)-N-methylmethanamine besylate.

Embodiment 21. The formulation of embodiment 2, wherein the salt of (S)-(4,5-dihydro-7H-thieno[2,3-c]pyran-7-yl)-N-methylmethanamine is (S)-(4,5-dihydro-7H-thieno[2,3-c]pyran-7-yl)-N-methylmethanamine R-mandelate.

Embodiment 22. The formulation of embodiment 2, wherein the salt of (S)-(4,5-dihydro-7H-thieno[2,3-c]pyran-7-yl)-N-methylmethanamine is (S)-(4,5-dihydro-7H-thieno[2,3-c]pyran-7-yl)-N-methylmethanamine L-tartrate.

Embodiment 23. The formulation of embodiment 2, wherein the salt of (S)-(4,5-dihydro-7H-thieno[2,3-c]pyran-7-yl)-N-methylmethanamine is (S)-(4,5-dihydro-7H-thieno[2,3-c]pyran-7-yl)-N-methylmethanamine D-tartrate.

Embodiment 24. The formulation of embodiment 2, wherein the salt of (S)-(4,5-dihydro-7H-thieno[2,3-c]pyran-7-yl)-N-methylmethanamine is (S)-(4,5-dihydro-7H-thieno[2,3-c]pyran-7-yl)-N-methylmethanamine mesylate.

Embodiment 25. The formulation of embodiment 2, wherein the salt of (S)-(4,5-dihydro-7H-thieno[2,3-c]pyran-7-yl)-N-methylmethanamine is (S)-(4,5-dihydro-7H-thieno[2,3-c]pyran-7-yl)-N-methylmethanamine L-malate.

Embodiment 26. The formulation of any one of embodiments 1-25, wherein the formulation is a tablet.

Embodiment 27. The formulation of any one of embodiments 1-26, wherein the amount of the salt of (S)-(4,5-dihydro-7H-thieno[2,3-c]pyran-7-yl)-N-methylmethanamine is about 50 to about 80% w/w.

Embodiment 28. The formulation of any one of embodiments 1-26, wherein the amount of the salt of (S)-(4,5-dihydro-7H-thieno[2,3-c]pyran-7-yl)-N-methylmethanamine is about 60 to about 80% w/w.

Embodiment 29. The formulation of any one of embodiments 1-26, wherein the amount of the salt of (S)-(4,5-dihydro-7H-thieno[2,3-c]pyran-7-yl)-N-methylmethanamine is about 70% w/w.

Embodiment 30. The formulation of any one of embodiments 1-29, wherein the excipient is one or more fillers.

Embodiment 31. The formulation of embodiment 30, wherein the amount of the filler is about 10 to about 50% w/w.

Embodiment 32. The formulation of embodiment 30, wherein the amount of the filler is about 20 to about 40% w/w.

Embodiment 33. The formulation of any one of embodiments 30-33, wherein the filler is microcrystalline cellulose, mannitol, or a mixture thereof.

Embodiment 34. The formulation of any one of embodiments 1-33, wherein the excipient is one or more disintegrants.

Embodiment 35. The formulation of embodiment 34, wherein the amount of the disintegrant is about 0.5 to about 10% w/w.

Embodiment 36. The formulation of embodiment 35, wherein the amount of the disintegrant is about 1 to about 5% w/w.

Embodiment 37. The formulation of embodiment 35, wherein the amount of the disintegrant is about 2% w/w.

Embodiment 38. The formulation of embodiment 37, wherein the disintegrant is sodium starch glycolate.

Embodiment 39. The formulation of any one of embodiments 1-38, wherein the excipient comprises one or more lubricants.

Embodiment 40. The formulation of embodiment 39, wherein the amount of the lubricant is about 0.1 to about 0.5% w/w.

Embodiment 41. The formulation of embodiment 39, wherein the amount of the lubricant is about 0.2% w/w.

Embodiment 42. The formulation of embodiment 41, wherein the lubricant is magnesium stearate.

Embodiment 43. The formulation of any one of embodiments 1-42 further comprises a coating.

Embodiment 44. The formulation of any one of embodiments 1-29 comprising a salt of (S)-(4,5-dihydro-7H-thieno[2,3-c]pyran-7-yl)-N-methylmethanamine, filler, disintegrant, and lubricant.

Embodiment 45. The formulation of any one of embodiments 1-19 comprising (S)-(4,5-dihydro-7H-thieno[2,3-c]pyran-7-yl)-N-methylmethanamine hydrochloride, filler, disintegrant, and lubricant.

Embodiment 46. The formulation of any one of embodiments 1-19 and 45 comprising (S)-(4,5-dihydro-7H-thieno[2,3-c]pyran-7-yl)-N-methylmethanamine hydrochloride, microcrystalline cellulose, mannitol, sodium starch glycolate, and magnesium stearate.

Embodiment 47. A method of treating a neurological disease or disorder, comprising administering to a subject a therapeutically effective amount of the formulation of any one of embodiments 1-46.

Embodiment 48. The method of embodiment 47, wherein the neurological disease or disorder is schizophrenia.

Embodiment 49. The method of embodiment 47, wherein neurological disease or disorder is the schizophrenia spectrum disorder, schizophrenia negative symptoms, attenuated psychosis syndrome, prodromal schizophrenia, delusional disorder, psychosis, attenuated psychosis syndrome, psychotic disorder, delirium, Tourette's syndrome, post-traumatic stress disorder, behavior disorder, affective disorder, depression, bipolar disorder, major depressive disorder, dysthymia, bipolar disorder, manic disorder, seasonal affective disorder, obsessive-compulsive disorder, narcolepsy, REM behavior disorder, substance abuse or dependency, Lesch-Nyhan disease, Wilson's disease, autism, Alzheimer's disease agitation and psychosis, or Huntington's chorea.

Embodiment 50. The method according to embodiment 49, wherein the schizophrenia spectrum disorder is selected from schizophrenia, attenuated psychosis syndrome, prodromal schizophrenia, schizoid personality disorder, and schizotypal personality disorder.

Embodiment 51. The method of any one of embodiments 47-49, wherein about 25 mg to about 100 mg per day of the salt of (S)-(4,5-dihydro-7H-thieno[2,3-c]pyran-7-yl)-N-methylmethanamine is administered to the subject.

Embodiment 52. A method of preparing (4,5-dihydro-7H-thieno[2,3-c]pyran-7-yl)-N-methylmethanamine, comprising:
(a) reacting 2-(thiophen-3-yl)ethan-1-ol with N-methylaminoacetaldehyde dimethylacetal and triflic acid to provide (4,5-dihydro-7H-thieno[2,3-c]pyran-7-yl)-N-methylmethanamine triflate; and
(b) reacting (4,5-dihydro-7H-thieno[2,3-c]pyran-7-yl)-N-methylmethanamine triflate with a base to provide (4,5-dihydro-7H-thieno[2,3-c]pyran-7-yl)-N-methylmethanamine.

Embodiment 53. A method of preparing (S)-(4,5-dihydro-7H-thieno[2,3-c]pyran-7-yl)-N-methylmethanamine, comprising:
(a) reacting 2-(thiophen-3-yl)ethan-1-ol with N-methylaminoacetaldehyde dimethylacetal and triflic acid to provide (4,5-dihydro-7H-thieno[2,3-c]pyran-7-yl)-N-methylmethanamine triflate;
(b) reacting (4,5-dihydro-7H-thieno[2,3-c]pyran-7-yl)-N-methylmethanamine triflate with a base to provide (4,5-dihydro-7H-thieno[2,3-c]pyran-7-yl)-N-methylmethanamine;
(c) reacting (4,5-dihydro-7H-thieno[2,3-c]pyran-7-yl)-N-methylmethanamine with (R)-mandelic acid to provide (S)-(4,5-dihydro-7H-thieno[2,3-c]pyran-7-yl)-N-methylmethanamine (R)-mandelate; and
(d) reacting (S)-(4,5-dihydro-7H-thieno[2,3-c]pyran-7-yl)-N-methylmethanamine (R)-mandelate with a base to provide (S)-(4,5-dihydro-7H-thieno[2,3-c]pyran-7-yl)-N-methylmethanamine.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

The invention claimed is:

1. A compound which is crystalline (S)-(4,5-dihydro-7H-thieno[2,3-c]pyran-7-yl)-N-methylmethanamine hydrochloride characterized by a powder x-ray diffraction pattern comprising peaks, in terms of 2-theta, at 9.6±0.2°, 14.9±0.2°, 20.5±0.2°, and 25.1±0.2°.

2. The compound of claim 1, wherein the crystalline (S)-(4,5-dihydro-7H-thieno[2,3-c]pyran-7-yl)-N-methylmethanamine hydrochloride is further characterized by the powder x-ray diffraction pattern further comprising a peak, in terms of 2-theta, at 20.2±0.2° and 20.8±0.2°.

3. The compound of claim 1 or 2, wherein the crystalline (S)-(4,5-dihydro-7H-thieno[2,3-c]pyran-7-yl)-N-methylmethanamine hydrochloride is further characterized by the powder x-ray diffraction pattern further comprising a peak, in terms of 2-theta, at two or more of 17.9±0.2°, 24.8±0.2° and 27.1±0.2°.

4. The compound of claim 1, wherein the crystalline (S)-(4,5-dihydro-7H-thieno[2,3-c]pyran-7-yl)-N-methylmethanamine hydrochloride is characterized by a powder x-ray diffraction pattern of FIG. 2B.

5. The compound of claim 1, wherein the crystalline (S)-(4,5-dihydro-7H-thieno[2,3-c]pyran-7-yl)-N-methylmethanamine hydrochloride has a differential scanning calorimetry thermogram comprising a peak at 214±2° C.

6. The compound of claim 1, wherein the crystalline (S)-(4,5-dihydro-7H-thieno[2,3-c]pyran-7-yl)-N-methylmethanamine hydrochloride has a differential scanning calorimetry thermogram of FIG. 3A.

7. The compound of claim 1, wherein the crystalline (S)-(4,5-dihydro-7H-thieno[2,3-c]pyran-7-yl)-N-methylmethanamine hydrochloride is characterized by monoclinic space group P21.

8. The compound of claim 1, wherein the crystalline (S)-(4,5-dihydro-7H-thieno[2,3-c]pyran-7-yl)-N-methylmethanamine hydrochloride has unit cell dimensions: α is about 9.2 Å, b is about 11.2 Å, c is about 10.2 Å, α is about 90°, β is about 92°, and γ is about 90°, wherein the term about means within 2% of each indicated value.

9. The compound of claim 1, wherein the crystalline (S)-(4,5-dihydro-7H-thieno[2,3-c]pyran-7-yl)-N-methylmethanamine hydrochloride has chiral purity greater than 90% (S)-(4,5-dihydro-7H-thieno[2,3-c]pyran-7-yl)-N-methylmethanamine hydrochloride.

10. The compound of claim 1, wherein the crystalline (S)-(4,5-dihydro-7H-thieno[2,3-c]pyran-7-yl)-N-methylmethanamine hydrochloride has chiral purity greater than 95% (S)-(4,5-dihydro-7H-thieno[2,3-c]pyran-7-yl)-N-methylmethanamine hydrochloride.

11. The compound of claim 1, wherein the crystalline (S)-(4,5-dihydro-7H-thieno[2,3-c]pyran-7-yl)-N-methylmethanamine hydrochloride has chemical purity greater than 95% (S)-(4,5-dihydro-7H-thieno[2,3-c]pyran-7-yl)-N-methylmethanamine hydrochloride.

12. The compound of claim 1, wherein the crystalline (S)-(4,5-dihydro-7H-thieno[2,3-c]pyran-7-yl)-N-methylmethanamine hydrochloride has chemical purity greater than 99% (S)-(4,5-dihydro-7H-thieno[2,3-c]pyran-7-yl)-N-methylmethanamine hydrochloride.

13. The compound of claim 1, wherein the crystalline (S)-(4,5-dihydro-7H-thieno[2,3-c]pyran-7-yl)-N-methylmethanamine hydrochloride has chemical purity of greater than 99.5%.

14. The compound of claim 1, wherein the crystalline (S)-(4,5-dihydro-7H-thieno[2,3-c]pyran-7-yl)-N-methylmethanamine hydrochloride has polymorph purity of greater than 95%.

15. The compound of claim 1, wherein the crystalline (S)-(4,5-dihydro-7H-thieno[2,3-c]pyran-7-yl)-N-methylmethanamine hydrochloride has a Raman spectrum of FIG. 4A.

16. The compound of claim 1, wherein the crystalline (S)-(4,5-dihydro-7H-thieno[2,3-c]pyran-7-yl)-N-methylmethanamine hydrochloride has a THz Raman spectrum of FIG. 4D.

17. The compound of claim 1, wherein the crystalline (S)-(4,5-dihydro-7H-thieno[2,3-c]pyran-7-yl)-N-methyl-methanamine hydrochloride is substantially non-hygroscopic.

18. A pharmaceutical composition comprising the compound of any one of claims 1, 10, 12, or 14 and one or more pharmaceutically acceptable excipients.

19. The pharmaceutical composition of claim 18 wherein the one or more pharmaceutically acceptable excipients are selected from the group consisting of fillers, disintegrants, and lubricants.

20. The pharmaceutical composition of claim 18 wherein the one or more pharmaceutically acceptable excipients are selected from the group consisting of mannitol, microcrystalline cellulose, sodium starch glycolate, and magnesium stearate.

21. The pharmaceutical composition of claim 18 comprising:
- (a) 10 mg to 120 mg, on a free base basis, of crystalline (S)-(4,5-dihydro-7H-thieno[2,3-c]pyran-7-yl)-N-methylmethanamine hydrochloride;
- (b) mannitol;
- (c) microcrystalline cellulose;
- (d) sodium starch glycolate; and
- (e) magnesium stearate.

\* \* \* \* \*